(12) United States Patent
Perrin et al.

(10) Patent No.: US 12,427,209 B2
(45) Date of Patent: Sep. 30, 2025

(54) DUAL MODE 18F-LABELLED THERANOSTIC COMPOUNDS AND USES THEREOF

(71) Applicants: Provincial Health Services Authority, Vancouver (CA); The University of British Columbia, Vancouver (CA)

(72) Inventors: David Perrin, Vancouver (CA); Aron Roxin, Vancouver (CA); Mathieu Lepage, L'Huisserie (FR); Sungjoon Huh, Surrey (CA); Zhibo Liu, Beijing (CN); Rajaguru Kandasamy, Tamil Nadu (IN); Francois Benard, Vancouver (CA); Kuo-Shyan Lin, Richmond (CA); Hsiou-Ting Kuo, Vancouver (CA); Chengcheng Zhang, Richmond (CA)

(73) Assignees: Provincial Health Services Authority, Vancouver (CA); The University of British Columbia, Vancouver (CA)

( * ) Notice: Subject to any disclaimer, the term of this patent is extended or adjusted under 35 U.S.C. 154(b) by 1092 days.

(21) Appl. No.: 17/415,649

(22) PCT Filed: Dec. 18, 2019

(86) PCT No.: PCT/CA2019/051853
§ 371 (c)(1),
(2) Date: Jun. 17, 2021

(87) PCT Pub. No.: WO2020/124237
PCT Pub. Date: Jun. 25, 2020

(65) Prior Publication Data
US 2022/0062446 A1    Mar. 3, 2022

Related U.S. Application Data

(60) Provisional application No. 62/781,584, filed on Dec. 18, 2018.

(51) Int. Cl.
| A61K 51/04 | (2006.01) |
| A61K 51/08 | (2006.01) |
| C07F 5/02  | (2006.01) |

(52) U.S. Cl.
CPC ........ A61K 51/0482 (2013.01); A61K 51/083 (2013.01); C07F 5/027 (2013.01)

(58) Field of Classification Search
CPC .............. A61K 51/0402; A61K 51/083; A61K 51/0482; C07F 5/027
See application file for complete search history.

(56) References Cited

U.S. PATENT DOCUMENTS

| 5,650,134 A | 7/1997 | Albert et al. |
| 6,166,226 A | 12/2000 | Buchwald et al. |
| 7,041,859 B1 | 5/2006 | Kabalka |
| 8,114,381 B2 | 2/2012 | Perrin et al. |
| 8,153,101 B2 | 4/2012 | McBride et al. |
| 8,574,546 B2 | 11/2013 | Perrin et al. |
| 8,691,761 B2 | 4/2014 | Rivier et al. |
| 10,150,804 B2 | 12/2018 | Benard et al. |
| 10,556,023 B2 | 2/2020 | Perrin et al. |
| 10,882,871 B2 | 1/2021 | Benard et al. |
| 11,207,432 B2 | 12/2021 | Perrin et al. |
| 2006/0128664 A1 | 6/2006 | Holmes-Farley et al. |
| 2009/0028791 A1 | 1/2009 | Balatoni et al. |
| 2014/0112873 A1 | 4/2014 | Gillies et al. |
| 2014/0147381 A1 | 5/2014 | Espenan |
| 2016/0333068 A1* | 11/2016 | Benard ............ A61K 51/083 |
| 2020/0222563 A1 | 7/2020 | Perrin et al. |
| 2021/0024605 A1 | 1/2021 | Perrin et al. |
| 2021/0205483 A1 | 7/2021 | Benard et al. |
| 2022/0062445 A1 | 3/2022 | Perrin et al. |

FOREIGN PATENT DOCUMENTS

| CA | 2267153 | 4/1998 |
| CA | 2710923 | 2/2010 |
| CA | 2810241 | 3/2012 |
| CA | 2931554 | 6/2015 |
| CN | 102066974 A | 5/2011 |
| CN | 105636924 A | 6/2016 |
| CN | 106967152 A | 7/2017 |
| CN | 108699087 A | 10/2018 |
| EP | 1027316 A1 | 8/2000 |
| EP | 1089305 A2 | 4/2001 |
| EP | 2226328 A1 | 9/2010 |
| EP | 2555796 A1 | 2/2013 |
| WO | WO 2005/077967 A1 | 8/2005 |

(Continued)

OTHER PUBLICATIONS http://www.merriamwebster.com/dictionary/derivative (Year: 2011).*
Antunes et al., "Influence of Different Spacers on the Biological Profile of a DOTA-Somatostatin Analogue," Bioconjugate Chemistry, 2007, vol. 18, pp. 84-92.
Bagutski et al. "Improved method for the conversion of pinacolboronic esters into trifluoroborate salts: facile synthesis of chiral secondary and tertiary trifluoroborates," Tetrahedron 2009, 65, pp. 9956-9960.
Banerjee et al., "Clinical applications of Gallium-68," Applied Radiation and Isotopes, 2013, vol. 76, pp. 2-13.
Bernard-Gauthier, V. et al., "From Unorthodox to Established: The Current Status of 18F-Trifluoroborate- and 18F-SIFA-Based Radiopharmaceuticals in PET Nuclear Imaging," Bioconjugate Chemistry, 2016, vol. 27, pp. 267-279.

(Continued)

Primary Examiner — James W Rogers
(74) Attorney, Agent, or Firm — COOLEY LLP

(57) ABSTRACT

A compound or molecular complex. The compound or molecular complex comprises: a metal chelator configured for chelation with a radioactive isotope or a non-radioactive isotope; and a trifluoroborate ($BF_3$)-containing moiety configured for $^{19}F/^{18}F$ exchange or a precursor thereof; and optionally a cell-targeting domain.

5 Claims, 45 Drawing Sheets

(56) References Cited

FOREIGN PATENT DOCUMENTS

| WO | WO 2007/032005 A2 | 3/2007 |
|---|---|---|
| WO | WO 2009/012596 A1 | 1/2009 |
| WO | WO-2009135015 A2 | 11/2009 |
| WO | WO 2011/124931 A1 | 10/2011 |
| WO | WO 2012/094334 A1 | 7/2012 |
| WO | WO 2012/118909 A1 | 9/2012 |
| WO | WO-2013028664 A1 | 2/2013 |
| WO | WO-2013028791 A1 | 2/2013 |
| WO | WO 2014/134716 A1 | 9/2014 |
| WO | WO-2015055315 A1 | 4/2015 |
| WO | WO 2015/100498 A1 | 7/2015 |
| WO | WO-2015135082 A1 | 9/2015 |
| WO | WO-2017117687 A1 | 7/2017 |

OTHER PUBLICATIONS

Boutourine et al., "Rapid Routes of Synthesis of Chemically Reactive and Highly Radioactive Labeled α- and β-Oligonucleotide Derivatives for in Vivo Studies," Bioconjungate Chemistry, 1:350-356, (1990).

Breeman et al., "Somatostatin receptor-mediated imaging and therapy: basic science, current knowledge, limitations and future perspectives," European Journal of Nuclear Medicine, Sep. 2001, vol. 28, No. 9, pp. 1421-1429.

Buchmann et al., "Comparison of 68Ga-DOTATOC PET and 111In-DTPAOC (Octreoscan)SPECT in patients with neuroendocrine tumours," Eur J Nucl Med Mol Imaging., 2007, vol. 34, pp. 1617-1626.

Cai et al., "RGD-based PET tracers for imaging receptor integrin αvβ3 expression," Journal of Labelled Compounds and Radiopharmaceuticals, 2013, vol. 56, pp. 264-279.

Chin et al., "First Experience with Clinical-Grade [18F]FP-P(RGD)2: An Automated Multi-step Radiosynthesis for Clinical PET Studies," Mol Imaging Biol., 2012, vol. 14, pp. 88-95.

Doedens et al., "Multiple N-Methylation of MT-II Backbone Amide Bonds Leads to Melanocortin Receptor Subtype hMC1R Selectivity: Pharmacological and Conformational Studies," J Am Chem Soc, 2010, vol. 132, pp. 8115-8128.

Dumas et al., "Synthesis of Acyltrifluoroborates," Organic Letters, 14:2138-2141, (2012).

Eberl et al., "High beam current operation of a PETtraceTM cyclotron for 18F production," Applied Radiation and Isotopes, 2012, vol. 70, pp. 922-930.

EP Office Action mailed Mar. 10, 2020 in corresponding European Appln No. 14759809.8 (20 page).

Extended European Search Report for EP2964658 mailed Oct. 4, 2016, 12 pages.

Extended Search Report for European Patent Application No. 15733077.0, dated Jun. 19, 2017, 6 pages.

Fani et al., "Unexpected Sensitivity of sst2 Antagonists to N-Terminal Radiometal Modifications," The Journal of Nuclear Medicine, Sep. 2012, vol. 53, No. 9, pp. 1481-1489.

Gabriel et al., "68Ga-DOTA-Tyr3-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.

Gabriel et al., "An Intrapatient Comparison of 99mTc-EDDA/HYNIC-TOC with 111In-DTPA Octreotide for Diagnosis of Somatostatin Receptor-Expressing Tumors," The Journal of Nuclear Medicine, May 2003, vol. 44, No. 5, pp. 708-716.

Ginj et al., "Design, Synthesis, and Biological Evaluation of Somatostatin-Based Radiopeptides," Chemistry & Biology, Oct. 2006, vol. 13, pp. 1081-1090.

Guo et al., "Preparation and Biological Evaluation of 64Cu Labeled Tyr3-Octreotate using a Phosphonic Acid-Based Cross-Bridged Macrocyclic Chelator," Bioconjugate Chemistry, 2012, vol. 23, pp. 1470-1477.

Harwig, C.W., et al., "Synthesis and characterization of 2,6-difluoro-4-carboxyphenylboronic acid and a biotin derivative thereof as captors of anionic aqueous [18F]-fluoride for the preparation of [18F/19F]-labeled aryltrifluoroborates with high kinetic stability," Tetrahedron Letters, 2008, vol. 49, pp. 3152-3156.

Henze et al., "PET Imaging of Somatostatin Receptors Using [68GA]DOTA-D-Phe1-Tyr3-Octreotide: First Results in Patients with Meningiomas," The Journal of Nuclear Medicine, Jul. 2001, vol. 42, No. 7, pp. 1053-1056.

Imahori et al., "Positron Emission Tomography-based Boron Neutron Capture Therapy Using Boronophenylalanine for High-Grade Gliomas: Part I," Clinical Cancer Research, vol. 4, Aug. 1998, pp. 1825-1832.

Imahori et al., "Positron Emission Tomography-based Boron Neutron Capture Therapy Using Boronophenylalanine for High-Grade Gliomas: Part II," Clinical Cancer Research, vol. 4, Aug. 1998, pp. 1833-1841.

International Search Report and Written Opinion for International (PCT) Patent Application No. PCT/CA2015/000002, mailed May 4, 2015, 10 pages.

International Search Report and Written Opinion of the International Searching Authority for International Application No. PCT/CA2019/050703, dated Jul. 17, 2019, 11 pages.

International Search Report and Written Opinion of the International Searching Authority for International Application No. PCT/CA2019/051853, dated Feb. 18, 2020, 8 pages.

International Preliminary Report Patentability, dated Aug. 14, 2006, corresponding to PCT/CA2005/000195, 6 pages.

Ishiwata et al., "4-Borono-2[18F]-D,L,phenylalanine: A Possible Tracer for Melanoma Diagnosis with PET," International Journal of Radiation Applications and Instrumentation. Part B, Nuclear Medicine and Biology, 1992, vol. 19, No. 3, pp. 311-318.

Ishiwata et al., "A unique in vivo assessment of 4-[10B] borono-L-phenylalanine in tumour tissues for boron neutron capture therapy of malignant melanomas using positron emission tomography and 4-borono-2-[18F]fluoro-L-phenylalanine," Melanoma Research, 1992, vol. 2, pp. 171-179.

Kabalka, G., et al., "Evaluation of Fluorine-18-BPA-Fructose for Boron Neutron Capture Treatment Planning," The Journal of Nuclear Medicine, vol. 38, No. 11, Nov. 1997, pp. 1762-1767.

Kabalka, G., et al., "The Development of Boron Neutron Capture Agents Utilizing Positron Emission Tomography," Special publication Royal Society of Chemistry (Great Britain), vol. 253, (2000), Contemporary Boron Chemistry—Medicinal Applications, pp. 120-126.

Kayani "A Comparison of 68Ga-DOTATATE and 18F-FDG PET/CT in Pulmonary Neuroendocrine Tumors," The Journal of Nuclear Medicine, Dec. 2009, vol. 50, No. 12, pp. 1927-1932.

Kemerink et al., Effect of the positron range of 18F, 68Ga and 124I on PET/CT in lung equivalent materials, Eur J Nucl Med Mol Imaging, 2011, vol. 38, pp. 940-948.

Kirkham et al. "Synthesis of Ynone Trifluoroborates toward Functionalized Pyrazoles," Org. Letters, 2012, vol. 14, No. 20, pp. 5354-5357.

Krausz et al., "SPECT/CT hybrid imaging with 111In-pentetreotide in assessment of neuroendocrine tumours," Clinical Endocrinology, 2003, vol. 59, pp. 565-573.

Kwekkeboom et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.

Kwekkeboom et al. "Somatostatin receptor-based imaging and therapy of gastroenteropancreatic neuroendocrine tumors," Endocr Relat Cancer., 2010, vol. 17, pp. R53-R73.

Laforest et al. "Image quality with non-standard nuclides in PET," QJ Nucl Med Mol Imaging, 2008, vol. 52, pp. 151-158.

Laverman et al., "A Novel Facile Method of Labeling Octreotide with $^{18}$F-Fluorine," The Journal of Nuclear Medicine, Mar. 2010, vol. 51(3), pp. 454-461.

Laverman et al., "Optimized labeling of NOTA-conjugated octreotide with F-18," Tumor Biol., 2012, vol. 33, pp. 427-434.

Lawrence et al. "Regiospecific Functionalized of Methyl C—H Bonds of Alkyl Groups in Reagents with Heteroatom Functionality," J. Am. Chem. Soc., 2004, vol. 126, pp. 15334-15335.

(56) References Cited

OTHER PUBLICATIONS

Lennox et al., "Organotrifluoroborate Hydrolysis: Boronic Acid Release Mechanism and an Acid-Base Paradox in Cross-Coupling," J. Am. Chem. Soc., 134:7431-7441, (2012).
Leyton et al., "Targeting Somatostatin Receptors: Preclinical Evaluation of Novel $^{18}$F-Fluoroethyltriazole-Tyr$^3$-Octreotate Analogs for PET," The Journal of Nuclear Medicine, Sep. 2011, vol. 52(9), pp. 1441-1448.
Li et al. "Hydrolytic stability of nitrogenous-heteroaryltrifluoroborates under aqueous conditions at near neutral pH," Journal of Fluorine Chemistry, 130:377-382, (2009).
Li et al., "One-step and one-pot-two-step radiosynthesis of cyclo-RGD-$^{18}$F-aryltrifluoroboronate conjugates for functional imaging," Am. J. Nucl. Med. Mol. Imaging, 2013, vol. 3(1), pp. 44-56.
Liu et al., ""Kit-like" radiosynthesis and biological evaluation of an F-labeled 4-(2-Aminoethyl)-benzenesulfonamide (AEBS) trimer for imaging carbonic anhydrase IX expression with positron emission tomography," World Molecular Imaging Congress, Sep. 19, 2013—poster, 1 page.
Liu et al., "(18)F-trifluoroborate derivatives of [des-arg(10)]kallidin for imaging bradykinin b1 receptor expression with positron emission tomography," Molecular Pharmaceutics, 2015, vol. 12, No. 3, pp. 974-982.
Liu et al., "An Organotrifluoroborate for Broadly Applicable One-Step 18F-Labeling," Angew Chem Int Ed., 2014, vol. 53, pp. 11876-11880.
Liu et al., "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.
Liu et al., "Kit-like 18F-labeling of RGD-19F-Arytrifluroborate in high yield and at extraordinarily high specific activity with preliminary in vivo tumor imaging," Nuclear Medicine and Biology, vol. 40, 2013, pp. 841-849.
Liu et al., "Preclinical evaluation of a high affinity 18F-trifluoroborate octreotate derivative for somatostatin receptor imaging-poster," University of British Columbia, 2014, 1 page.
Liu et al., "Preclinical Evaluation of a High-Affinity $^{18}$F-Trifluoroborate Octreotate Derivative for Somatostatin Receptor Imaging," Journal of Nuclear Medicine, Sep. 2014, vol. 55(9), pp. 1499-1505.
Liu et al., "Preclinical Evaluation of a Novel 18F-Labelled Somatostatin Receptor-Binding Peptide—Abstract Proof," ScholarOne, Inc., 2014, Control ID: 1931699, 4 pages.
Liu et al., "Preclinical evaluation of a novel F-labelled somatostatin receptor-binding peptide," The Journal of Nuclear Medicine, 2014, vol. 55 (Supplement 1):1089, 1 page.
Liu et al., "Rapid, one-step, high yielding 18F-labeling of an aryltrifluoroborate bioconjugate by isotope exchange at very high specific activity," Journal of Labelled Compounds and Radiopharmaceuticals, 2012, vol. 55, pp. 491-496.
Liu et al., "Stoichiometric Leverage: Rapid 18F-Aryltrifluoroborate Radiosynthesis at High Specific Activity for Click Conjugation," Angew. Chem. Int. Ed., 2013, vol. 52, pp. 2303-2307.
Matteson et al., "Iodomethaneboronic Esters and Aminomethaneboronic Esters," Journal of Organometallic Chemistry, 1979, vol. 170, pp. 259-264.
Means et al. "Chemical Modifications of Proteins: History and Applications," Bioconjugate Chemistry, 1990, vol. 1, No. 1, pp. 2-12.
Molander et al., "Functionalization of Organotrifluoroborates: Reductive Amination," J. Org. Chem., 2008, vol. 73, pp. 3885-3891.
Molander et al., "Synthesis of an Acyltrifluoroborate and its Fusion with Azides to Form Amides," J. Org. Chem., 75: 4304-4306, (2010).
Molander et al., "Synthesis of Functionalized Organotriflurorborates via the 1,3- Dipolar Cycloaddition of Azides," Organic Letters, 8:2031-2034, (2006).

Na Sun et al., "Biorelevant pKa (37° C) predicted from the 2D structure of the molecule and its pKa at 25 ° C," Journal of Pharmaceutical and Biomedical Analysis, vol. 56, No. 2, 2011, pp. 173-182.
Nichols, T., et al., "Improved treatment planning for boron neutron capture therapy for glioblastoma multiforme using fluorine-18 labeled boronophenylalanine and positron tomography," Med. Phys., vol. 29, No. 10, Oct. 2002, pp. 2351-2358.
Office Action for European Application No. 14759809.8 dated Oct. 10, 2018, 17 pages.
Okarvi, "Recent Progress in Fluorine-18 labelled peptide radiopharmaceuticals," European Journal of Nuclear Medicine, (2001), vol. 28, pp. 929-938.
Onufriev et al., "A Novel View of pH Titration in Biomolecules," Biochemistry, vol. 40, No. 12. Mar. 27, 2001 (7 pages).
Poeppel et al., "$^{68}$GA-DOTATOC Versus $^{68}$Ga-DOTATATE PET/CT in Functional Imaging of Neuroendocrine Tumors," The Journal of Nuclear Medicine, Dec. 2011, vol. 52(12), pp. 1864-1870.
Poethko et al., "Two-Step Methodology for High-Yield Routine Radiohalogenation of Peptides: 18F-Labeled RGD and Octreotide Analogs," The Journal of Nuclear Medicine, May 2004, vol. 45 No. 5, pp. 892-902.
Poole et al., "Radiotracers in Fluorine Chemistry. Part IV. Fluorine-18 Exchange between labelled Alkyfluorosilanes and Fluorides or Fluoride Methoxides, of Tungsten(vi), Molybdenum,(vi), Tellurium(vi), and Iodine(v)," J. Chem. Soc., Dalton, (1976), pp. 1557-1560.
Pourghisian et al., "(18)F-AmBF3-MJ9: a novel radiofluorinated bombesin derivative for prostate cancer imaging," Bioorganic & Medicinal Chemistry, 2015, vol. 23, No. 7, pp. 1500-1506.
Raushel et al. "Reinvestigation of Aminomethyltrifluoroborates and Their Application in Suzuki-Miyaura Cross-Coupling Reactions," J. Org. Chem, 2011, vol. 76, pp. 2762-2769.
Reubi et al., "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.
Roxin et al. "Preliminary evaluation of 18F-labeled LLP2A-trifluoroborate conjugates as VLA-4 (α4β1 integrin) specific radiotracers for PET imaging of melanoma" Nuclear Medicine and Biology 61 (2018) 11-20.
Roxin et al., "A metal-free DOTA-conjugated $^{18}$F-labeledradiotracer: [$^{18}$F]DOTA-AMBF3 LLP2A for imaging VLA-4 Over-expression in murine melanoma with improved tumor uptake and greatly enhanced renal clearance," Bioconjugate Chem. 2019, 30, 1210-1219.
Schirrmacher et al., "18F-labeling of peptides by means of an organisilicon-based fluoride acceptor," Angew. Chem. Int. Ed., 2006, vol. 45, pp. 1-5.
Shoup et al., "Synthesis of Fluorine-18-Labeled Biotin Derivatives: Biodistribution and Infection Localization," The Journal of Nuclear Medicine, (1994), vol. 35, pp. 1685-1690.
Smith, M. et al., "March's Advanced Organic Chemistry: Reactions, Mechanisms, and Structure," 7th ed., Jun. 13, 2013, John Wiley & Sons, vol. 116, pp. 334-346.
Sprague et al., "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.
Storch et al., "Evaluation of [99mTc/EDDA/HYNIC0]Octreotide Derivatives Compared with [111In-DOTA0, Tyr3, Thr8]Octreotide and [111In-DTPA0]Octreotide: Does Tumor or Pancreas Uptake Correlate with the Rate of Internalization?" The Journal of Nuclear Medicine, Sep. 2005, vol. 46, No. 9, pp. 1561-1569.
Supplemental European Search Report dated Mar. 26, 2010, for EP05706491.7, 4 pages.
Ting et al. "Capturing aqueous [18F]-fluoride with an arylboronic ester for PET: Synthesis and aqueous stability of a fluorescent [18F]-labeled aryltrifluoroborate, "Journal of Fluorine Chemistry, 129:349-358, (2008).

(56) References Cited

OTHER PUBLICATIONS

Ting et al. "Toward [18F]-Labeled Aryltrifluoroborate Radiotracers: In Vivo Positron Emission Tomography Imaging of Stable Aryltrifluoroborate Clearance in Mice," J. Am. Chem. Soc., 130:12045-12055, (2008).

Ting et al., "Arylfluoroborates and Alkylfluorosilicates as Potential PET Imaging Agents: High-Yielding Aqueous Biomolecular 18F-Labeling," J. Am. Chem. Soc., 127:13094-13095, (2005).

Ting et al., "Substituent effects on aryitrifluoroborate solvolysis in water: Implications for Suzuki-Miyaura coupling and the design of stable 18F-labeled aryitrifluoroborates for use in PET imaging," J. Org. Chem., 73:4662-4670, (2008).

Toyokuni et al., "Synthesis of a New Heterobiofunctional Linker, N-[4-(Aminooxy)butyl] maleimide, for Facile Access to a Thiol-Reactive 18F-Labeling Agent," Bioconjugate Chem, 2003, vol. 14, pp. 1253-1259.

Vallabhajosula et al., "Preclinical Evaluation of Technetium-99m-Labeled Somatostatin Receptor-Binding Peptides," The Journal of Nuclear Medicine, Jun. 1996, vol. 37, No. 6, pp. 1016-1022.

Virgolini et al. "Somatostatin Receptor Subtype Specificity and in Vivo Binding of a Novel Tumor Tracer. 99mTc-P8291," Cancer Research, May 1998, vol. 58, pp. 1850-1859.

Wängler et al., "One-Step $^{18}$F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography," Bioconjugate Chem., 2010, vol. 21(12), pp. 2289-2296.

Wester et al., "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.

International Preliminary Report on Patentability for International Application No. PCT/CA2014/000200, issued Sep. 8, 2015, 5 pages.

International Search Report for International Application No. PCT/CA2014/000200, mailed Jun. 11, 2014, 5 pages.

Written Opinion of the International Searching Authority for International Application No. PCT/CA2014/000200, mailed Jun. 11, 2014, 4 pages.

Zhan et al., "Hydration of the Fluoride Anion: Structures and Absolute Hydration Free Energy from First-Principles Electronic Structure Calculations," J Phys Chem A., 2004, vol. 108, pp. 2020-2029.

Zhang et al., "Preclinical Melanoma Imaging with $^{68}$Ga-labeled α-Melanocyte-Stimulating Hormone Derivatives Using PET," Theranostics, 2017, vol. 7, Issue 4, pp. 805-813.

Zhang et al., "Selectively targeting the melanocortin-1 receptor with N-methylation of an αMSH derivative for PET imaging of melanoma," Journal of Nuclear Medicine, May 2018, 59 (Supplement 1): 611.

Zhang et al., "Targeting the melanocortin-1 receptor with $^{177}$Lu-labeled alpha-melanocyte stimulating hormone derivatives: increased tumor uptake using an albumin binder," Journal of Nuclear Medicine, May 2018, 59 (Supplement 1): 1106.

Banerjee, S.R. et al., "Effect of Chelators on the Pharmacokinetics of 99mTc-Labeled Imaging Agents for the Prostate-Specific Membrane Antigen (PSMA)" J Med Chem, 2013, vol. 56, pp. 6108-6121.

Clayden et al., "The definition of pKa" Organic Chemistry. Oxford University Press, 2001, pp. 185-188.

Dumas, A.M. et al., "Amide-Forming Ligation of Acyltrifluorborates and Hydroxylamines in Water," Angew Chem Int Ed Engl, 51:5683-5686 (Jun. 2012).

Extended European Search Report for Application No. 17735797.7, dated Aug. 13, 2019, 8 pages.

Extended European Search Report for Application No. 19900988.7, dated Oct. 31, 2022, 7 pages.

International Preliminary Report on Patentability for International Application No. PCT/CA2008/001368, mailed on Feb. 4, 2010, 8 pages.

International Search Report and Written Opinion prepared by the Canadian Intellectual Property Office dated Mar. 31, 2017, for International Application No. PCT/CA2017/050026, 10 pages.

Kopka, K. et al. "Glu-Ureido-Based Inhibitors of Prostate-Specific Membrane Antigen: Lessons Learned During the Development of a Novel Class of Low-Molecular-Weight Theranostic Radiotracers," The Journal of Nuclear Medicine, Sep. 2017, vol. 58, No. 9(Suppl), pp. 17S-26S.

Lepage, M., et al., "Toward 18 F-Labeled Theranostics: A Single Agent that Can Be Labeled with 18F, 64Cu, or 177Lu," Chembiochem, 2020, vol. 21, No. 7, pp. 943-947.

Liu, Z. et al., "From Minutes to Years: Predicting Organotrifluoroborate Solvolysis Rates," Chemistry—A European Journal, Mar. 2015, vol. 21, No. 10, pp. 3924-3928.

Maresca, K.P. et al., "Small molecule inhibitors of PSMA incorporating technetium-99m for imaging prostate cancer: Effects of chelate design on pharmacokinetics", Inorganica Chimica Acta, 2012, 389, 168-175.

Molander, G.A. et al., "Synthesis of Functionalized Organotriflurorborates via Halomethyltrifluoroborates", Organic Letters, 8(10):2031-2034 (May 2006).

Molander, G.A. et al., "Synthesis of Functionalized Organotriflurorborates via the 1,3-Dipolar Cycloaddition of Azides," Organic Letters, 8(13):2767-2770 (Jun. 2006).

Sprik and Ciccotti, "Free energy from constrained molecular dynamics," J Chem Phys, 109(18):7737-7744, (1998).

Walsh, J.C. et al., "Application of Silicon-Fluoride Chemistry to Fluorine-18 Labeling Agents for Biomolecules: A Preliminary Note," J. Labelled Cpd. Radiopharm., 1999, vol. 42 (Suppl. 1), pp. S1-S3.

Roxin et al., "The case for DOTA as a pharmacokinetic modulator for 18F-labeled peptides: DOTA-[18F]AMBF3-LLP2A for improved PET imaging of VLA-4 over-expression in murine melanoma," Journal of Nuclear Medicine. May 2019; 60 (supplement 1):1008, 2 pages.

* cited by examiner

DUAL MODE 18F-LABELLED THERANOSTIC COMPOUNDS AND USES THEREOF

CROSS REFERENCE TO RELATED APPLICATIONS

This application is a U.S. national stage entry under 35 U.S.C. § 371 of International Application No. PCT/CA2019/051853 filed Dec. 18, 2019, entitled "DUAL MODE $^{18}$F-LABELLED THERANOSTIC COMPOUNDS AND USES THEREOF," which claims priority to, and the benefit of, U.S. Provisional Patent Application No. 62/781,584, filed on Dec. 18, 2018. Each of the foregoing applications are hereby incorporated by reference in their entirety (except for any subject matter disclaimers or disavowals, and except to the extent of any conflict with the disclosure of the present application, in which case the disclosure of the present application shall control).

FIELD OF INVENTION

The present invention relates to compounds/complexes for imaging and/or treatment. In particular, the invention relates to dual mode compounds/complexes configured for imaging when $^{18}$F-labelled and for therapy when chelated with a radiometal.

BACKGROUND OF THE INVENTION

PET imaging is playing an increasingly important role in non-invasive clinical diagnosis.[1-7] In comparison to MRI or SPECT, PET combines very high sensitivity[10] with dynamic spatio-temporal resolution to examine biodistribution and clearance.[11, 12] $^{18}$F-Deoxyglucose (FDG) and $^{18}$F-thymidine (FLT)[13] provide images based on heightened metabolism characteristic of most but not all cancers.[4] Cancer subtypes are increasingly distinguished by peptides,[4,14-19] that distinguish pathologically distinct cell types and assess the presence of specific molecular targets, a feat that is impossible with FDG.[20-23] Clinical peptidic tracers and drugs include octreotate,[24-28] bombesin,[29] and RGD,[30-32] Lupron™ and Sandostatin™.[33,34]

Radiometal (e.g. $^{68}$Ga, $^{64}$Cu, $^{99m}$Tc) chelation offers ease of labelling, but $^{18}$F-fluoride offers scalability at lower cost. Thus $^{18}$F-fluoride is preferred: it decays cleanly (>97% β+), can be produced in high isotopic purity and at much lower cost than $^{68}$Ga (>1 Ci for $400)[35], and affords optimal imaging properties.[36,37] Its short half-life minimizes radiation doses while high specific activity ensures that the tracer meets microdose requirements.[38] Nevertheless, its short half-life (109.8 min) also challenges labeling peptides. Previous work on $^{18}$F-labeled organotrifluoroborates (RBF3s) now makes $^{18}$F-labeling as easy as radiometal chelation.[39] Though certain $^{18}$F-RBF3-peptides show high tumor uptake,[40] a clear advantage of radiometallated peptides is generally higher tumor uptake.[41]

Nevertheless, radiotoxic metallopeptides are used to treat certain cancers where few treatment options exist. For example, an octreotate-chelator was complexed with $^{90}$Y to treat pancreatic cancer.[42] Several peptides are emerging as targeting agents for radiotherapy.[43,44] Nevertheless, not all patients respond to such therapy. Ideally, patients should be imaged with the same peptide prior to treatment. Yet PET imaging of radiotherapeutic peptides is limited to metals with pairs of isotopes (e.g. $^{86}$Y/$^{90}$Y, $^{64}$Cu/$^{67}$Cu, $^{203}$Pb/$^{212}$Pb), one for imaging and the other for treatment.[45,46]

Sadly, the production of diagnostic PET metals is limited and expensive. Worse yet, for some radiometals e.g. $^{177}$Lu, there is no readily available or useful isotope for PET (there is one report of PET with β+-emitting $^{167}$Lu). Typically, different metals are used for imaging.

Thus current practice poses significant problems when one radiometal is used for imaging and a different one is used for therapy. For example, TATE was labeled with $^{111}$In (for imaging) and $^{90}$Y (for therapy). Significant differences in uptake led to the conclusion that TATE should be evaluated with the same isotope, i.e., the β+-emitting $^{86}$Y.[45,46] Sadly, $^{86}$Y is very expensive and gives lower resolution than $^{18}$F.[47] Similar problems extend to SPECT imaging: DOTA-TATE chelates of $^{111}$In, $^{67}$Ga, $^{177}$Lu, and $^{90}$Y all show different affinities, making it difficult to correlate images between different metallo-peptides because the radiometal affects both affinity and imaging signal.[43,48] Similar differences are seen with bombesin-NOTA; the $^{68}$Ga-chelate shows much lower affinity than the $^{111}$In-chelate: 1.2 nM vs. 23 pM respectively.[49] Variations in affinities thwart image correlation and prediction of radiotherapeutic uptake. In addition, there are only a few instances where two metal isotopes can be identified to provide for a theranostic pair of isotopologs. There is therefore an unmet need in the field for theranostic dual-function PET imaging tracers/radiotherapeutics which facilitate improved treatment planning based on PET imaging results.

No admission is necessarily intended, nor should it be construed, that any of the preceding information constitutes prior art against the present invention.

SUMMARY

Various embodiments relate to a compound or molecular complex, the compound or molecular complex comprising: a metal chelator configured for chelation with a radioactive metal isotope or a non-radioactive metal isotope; and a trifluoroborate (BF$_3$)-containing moiety configured for $^{19}$F/$^{18}$F exchange or a boronate prescursor that is capable of conversion to an $^{18}$F-labeled trifluoroborate.

Various embodiments relate to a compound or molecular complex, the compound or molecular complex comprising: a cell-targeting domain; a metal chelator configured for chelation with a metal radioactive isotope or a non-radioactive metal isotope; and a trifluoroborate (BF$_3$)-containing moiety configured for $^{19}$F/$^{18}$F exchange or a boronate prescursor that is capable of conversion to an $^{18}$F-labeled trifluoroborate. In some such embodiments, the cell-targeting domain may comprise a peptide, a polypeptide or protein, a peptidomimetic, or a nucleic acid aptamer, a macrocycle, a steroid, or a small-molecule, wherein the cell-targeting domain specifically binds a cellular marker. In other such embodiments, the cell-targeting domain comprises LLP2A, PSMA-617, TATE, or peptide D-Phe-Gln-Trp-Ala-Val-Gly-His-Sta-Leu-NH$_2$. In other such embodiments, the cell-targeting domain comprises (i) an antibody or an antibody derivative or fragment that specifically binds an antigen of a target cell or (ii) a protein domain that specifically binds to an antibody or an antibody derivative or fragment that specifically binds the antigen.

In some embodiments, the metal chelator may be linked to the cell-targeting domain by a linker containing the BF$_3$-containing moiety. The linker may contain multiple BF$_3$-containing moieties. The linker may be a peptide linker. The linker may comprise Lys(AMBF$_3$).

In some embodiments, the compound or molecular complex the metal chelator is either unchelated or chelated with a non-radioactive metal isotope and the $BF_3$-containing moiety is $^{18}F$-labelled.

In some embodiments, the metal chelator is chelated with a radioactive metal isotope and the $BF_3$-containing moiety is $^{19}F$-labelled.

In some embodiments, the metal chelator is chelated with a radioactive metal isotope and the $BF_3$-containing moiety is $^{18}F$-labelled.

In some embodiments, the radioactive metal isotope is an alpha emitter, a beta emitter or an auger emitter.

In some embodiments, the metal chelator is a chelator selected from the chelators selected from the group consisting of: DOTA and derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; H2dedpa, H4octapa, H4py4pa, H4Pypa, H2azapa, H5decapa, and other picolinic acid derivatives; CP256; PCTA; DOTP; HEHA; C-NETA; C-NE3TA; HBED; SHBED; BCPA; CP256; YM103; cyclam; DiamSar; desferrioxamine (DFO) and DFO derivatives; H6phospa; a trithiol chelate; mercaptoacetyl; hydrazinonicotinamide; dimercaptosuccinic acid; 1,2-ethylenediyl-bis-L-cysteine diethyl ester; methylenediphosphonate; hexamethylpropyleneamineoxime; and hexakis(methoxy isobutyl isonitrile); a porphyrin, a chlorin, a texaphrin, a phthalocyanine. In some embodiments, the metal chelator is selected from DOTA and DOTA derivatives. In some embodiments, the metal chelator is DOTA.

In some embodiments, the $BF_3$-containing moiety is:

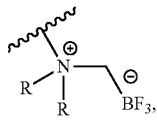

or a group shown in Table 3 or 4, wherein each R is independently a $C_1$-$C_5$ linear or branched alkyl group.

In some embodiments, the compound is selected from the group consisting of: DOTA-AMBF3-PEG2-LLP2A; PSMA-617-LysAMBF3-DOTA; DOTA-Lys(AMBF3)-TATE; and DOTA-Lys-AMBF3-Pip-D-Phe-Gln-Trp-Ala-Val-Gly-His-Sta-Leu-NH$_2$.

In some embodiments, the compound or molecular complex further comprises a fluorophore or other light emitting moiety.

In some embodiments, the compound or molecular complex comprises Lys(AMBF$_3$).

In some embodiments, the compound comprises DOTA-Bn-NH-Lys-(AMBF3).

In some embodiments where the compound or molecular complex comprises both the $BF_3$-containing moiety and the cell targeting domain, the compound or molecular complex is for use in: imaging a subject to confirm the presence of a cellular marker of a disease or condition using the compound or molecular complex labelled with $^{18}F$; and treating the disease or condition using the compound or molecular complex chelated with a therapeutic radioactive isotope.

In some embodiments where the compound or molecular complex is a compound comprising the $BF_3$-containing moiety and does not comprise the cell-targeting domain, the compound or molecular complex is for use in combination with a bispecific antibody to image and/or treat a disease or condition in a subject, wherein the bispecific antibody is specific for (i) a cellular marker of the disease or condition and (ii) the metal chelator. In some such embodiments, the compound or molecular complex may be for administration to the subject as a complex with the bispecific antibody. In other such embodiments, the bispecific antibody may be for administration to the subject prior to administration of the compound or molecular complex to the subject in a pre-targeting step during which the bispecific antibody binds to the cellular marker.

BRIEF DESCRIPTION OF THE DRAWINGS

The features of the invention will become apparent from the following description in which reference is made to the appended drawings wherein:

FIG. 52 provides the MALDI-TOF of the peptide 10, depicting the predicted isotope pattern, at [M+Na+]$^+$=1807.02.

DETAILED DESCRIPTION

Figure 1:
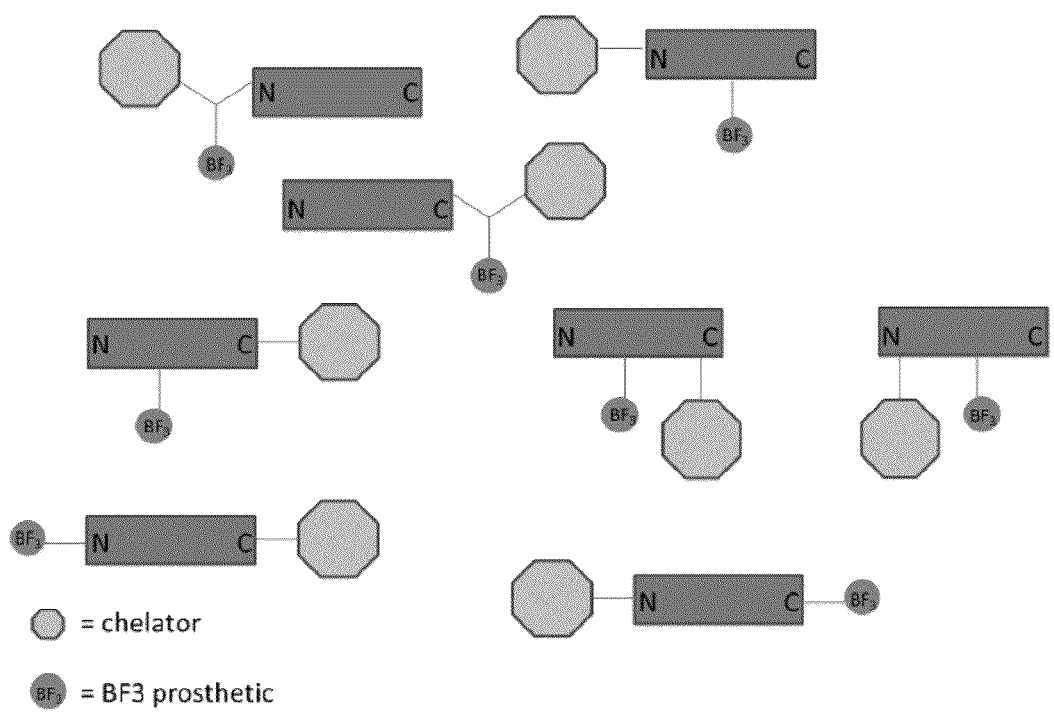
FIG. 1 shows a schematic representation of various relative configurations of the functional domains of certain dual-mode PET imaging radiotherapeutics.

As used herein, the terms "comprising," "having", "including" and "containing," and grammatical variations thereof, are inclusive or open-ended and do not exclude additional, unrecited elements and/or method steps, even if a feature/component defined as a part thereof consists or consists essentially of specified feature(s)/component(s). The term "consisting essentially of" if used herein in connection with a compound, composition, use or method, denotes that additional elements and/or method steps may be present, but that these additions do not materially affect the manner in which the recited compound, composition, method or use functions. The term "consisting of" if used herein in connection with a feature of a compound, composition, use or method, excludes the presence of additional elements and/or method steps in that feature. A compound, composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the context clearly dictates otherwise. The use of the word "a" or "an" when used herein in conjunction with the term "comprising" may mean "one," but it is also consistent with the meaning of "one or more," "at least one" and "one or more than one."

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, et cetera.

As used herein, the terms "treat", "treatment", "therapeutic" and the like includes ameliorating symptoms, reducing disease progression, improving prognosis and reducing recurrence.

As used herein, the term "diagnostic agent" includes an "imaging agent". As such, a "diagnostic radionuclide" includes radionuclides that are suitable for use in imaging agents.

The term "subject" refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include base-free forms, solvates, salts or pharmaceutically acceptable salts thereof. Unless otherwise specified or indicated, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g. protonated) state or may be shown without specifying formal charges. As will be appreciated by the person of skill in the art, the ionization state of certain groups within a compound (e.g. without limitation, $CO_2H$, $PO_3H_2$, $SO_2H$, $SO_3H$, $SO_4H$, $OPO_3H_2$ and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized. Likewise, $OSO_3H$ (i.e. $SO_4H$) groups, $SO_2H$ groups, $SO_3H$ groups, $OPO_3H_2$ (i.e. $PO_4H_2$) groups and $PO_3H$ groups would generally be deprotonated (and negatively charged) at neutral and physiological pH values.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, for administration to a subject. As used herein, "pharmaceutically acceptable" means suitable for in vivo use in a subject, and is not necessarily restricted to therapeutic use, but also includes diagnostic use. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (*J. Pharm Sci.* 66:1-19), or Remington—The Science and Practice of Pharmacy, 21st edition (Gennaro et al editors. Lippincott Williams & Wilkins Philadelphia), each of which is incorporated by reference in its entirety.

As used herein, the expression "Cy-Cz", where y and z are integers (e.g. $C_1$-$C_{15}$, $C_1$-$C_{30}$, $C_1$-$C_{100}$, and the like), refers to the number of carbons (e.g. in alkyl, alkenyl or alkynyl groups) in a compound, R-group or substituent, or refers to the number of carbons plus heteroatoms where the expression is further defined as having, or optionally having, one or more heteroatoms. In latter case, the expression "Xy-Xz" may be used (e.g. $X_3$-$X_{15}$ and the like), where y and z are integers referring to the number of carbons plus heteroatoms. Heteroatoms may include any, some or all possible heteroatoms. For example, in some embodiments, the heteroatoms are selected from N, O, S, P and Se. In some embodiments, the heteroatoms are selected from N, O, S and P. Such embodiments are non-limiting.

Unless explicitly stated otherwise, the term "alkyl" refers to an alkane missing a hydrogen atom, and includes any one or more of the following: linear alkyls, branched alkyls, acyclic alkyls, cylcoalkyls including mono-cyclic and multi-cyclic cycloalkyls (e.g. fused rings, multiple non-fused rings or a combination thereof), and/or unsubstituted or substituted. For example, an alkyl may be both branched and cyclic. If unspecified, the size of the alkyl is what would be considered reasonable to the person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100 or more than 100 carbons in length, subject to the common general knowledge of the person of skill in the art. As used herein, the term "alkylenyl" refers to a divalent analog of an alkyl group.

As used herein in the context of an alkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

Non-limiting examples of a $C_1$-$C_{20}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, I-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl, t-decyl, cyclopropanyl, cyclobutanyl, cyclopentanyl, cyclohexanyl, cycloheptanyl, cyclooctanyl, cyclononanyl, cyclodecanyl, and the like. Unless otherwise specified, a $C_1$-$C_{20}$ alkylenyl therefore encompasses, without limitation, all divalent analogs of the above-listed saturated alkyl groups.

As used herein, the terms "alkenyl" and "alkynyl" refer to an alkene and alkyne, respectively, that is missing a hydrogen atom, and may include linear, branched, and/or cyclic groups, and may be unsubstituted or substituted. Non-limiting examples of a $C_2$-$C_{20}$ alkenyl group may include vinyl, allyl, isopropenyl, I-propene-2-yl, 1-butene-1-yl, 1-butene-2-yl, 1-butene-3-yl, 2-butene-1-yl, 2-butene-2-yl, octenyl, decenyl, cyclopropenyl, cyclobutenyl, cyclopentenyl, cyclohexenyl, cycloheptenyl, cyclooctenyl, cyclononanenyl, cyclodecanenyl, and the like. Unless otherwise specified, a $C_1$-$C_{20}$ alkenylenyl therefore encompasses, without limitation, all divalent analogs of the above-listed alkenyl groups. Non-limiting examples of a $C_2$-$C_{20}$ alkynyl group may include ethynyl, propynyl, butynyl, pentynyl, hexynyl, heptynyl, octynyl, nonynyl, decynyl, and the like. Unless otherwise specified, a $C_1$-$C_{20}$ alkynylenyl therefore encompasses, without limitation, all divalent analogs of the above-listed alkynyl groups.

Non-limiting examples of non-aromatic heterocyclic groups include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, oxathiolanyl, and the like. Unless further specified, an "aryl" group includes both single aromatic rings as well as fused rings containing at least one aromatic ring. Non-limiting examples of $C_3$-$C_{20}$ aryl groups include phenyl (Ph), pentalenyl, indenyl, naphthyl and azulenyl. Non-limiting examples of $X_3$-$X_{20}$ aromatic heterocyclic groups include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, isoxazolyl, and the like.

As used herein, the term "substituted" is used as it would normally be understood to a person of skill in the art and generally refers to a compound or chemical entity that has one chemical group replaced with a different chemical group. Unless otherwise specified, a substituted alkyl is an alkyl in which one or more hydrogen atom(s) are independently each replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, aryl, and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amine, amide, oxo, hydroxyl, thiol, phosphate, phosphonate, sulfate, $SO_2H$, $SO_3H$, alkyls, aryls, ketones, carboxaldehyde, carboxylates, carboxamides, nitriles, monohalomethyl, dihalomethyl or trihalomethyl.

As used herein, the term "unsubstituted" is used as it would normally be understood to a person of skill in the art. Non-limiting examples of unsubstituted alkyls include methyl, ethyl, tert-butyl, pentyl and the like. The expression "optionally substituted" is used interchangeably with the expression "unsubstituted or substituted".

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

The wavy line " ⌇ " symbol shown through or at the end of a bond in a chemical formula (e.g. in the groups listed in Tables 3 and 4) is intended to define the R group on one side of the wavy line, without modifying the definition of the structure on the opposite side of the wavy line. Where an R group is bonded on two or more sides (e.g. $R^2$), any atoms shown outside the wavy lines are intended to clarify orientation of the R group. As such, only the atoms between the two wavy lines constitute the definition of the R group. When atoms are not shown outside the wavy lines, or for a chemical group shown without wavy lines but does have bonds on multiple sides (e.g. —C(O)NH—, and the like.), the chemical group should be read from left to right matching the orientation in the formula that the group relates to (e.g. for formula —$R^a$—$R^b$—$R^c$—, the definition of $R^b$ as —C(O)NH—would be incorporated into the formula as —$R^a$—C(O)NH—$R^c$— not as —$R^a$—NHC(O)—$R^c$—) unless another orientation is clearly intended.

This disclosure refers to radioisotopes and non-radioactive isotopes, as well as compounds, complexes or molecular compositions that are isotopologs. When an isotopolog is identified as containing a particular isotope, it will be understood that the compound/complex/composition may in practical reality be obtained in a mixture of isotopologs that heavily favours the identified isotope. For example, a preparation of a compound/complex/composition identified as hot-F or the $^{18}F$ isotopolog may in actuality contain a minimal quantity of the corresponding $^{19}F$ isotopolog. Vice versa, a preparation of a compound/complex/composition identified as hot-M or the radiometallated isotopolog (e.g. $^{177}Lu$) may contain a minimal quantity of the corresponding non-radioactive isotopolog (e.g. $^{174}Lu$, $^{nat}Lu$).

The term "Xaa" refers to an amino acid residue in a peptide chain or an amino acid that is otherwise part of a compound. Amino acids have both an amino group and a carboxylic acid group, either or both of which can be used for covalent attachment. In attaching to the remainder of the compound, the amino group and/or the carboxylic acid group may be converted to an amide or other structure; e.g. a carboxylic acid group of a first amino acid is converted to an amide (i.e. a peptide bond) when bonded to the amino group of a second amino acid. As such, Xaa may have the formula —N($R^a$)$R^b$C(O)—, where $R^a$ and $R^b$ are R-groups. $R^a$ will typically be hydrogen or methyl, or $R^a$ and $R^b$ may form a cyclic structure. The amino acid residues of a peptide may comprise typical peptide (amide) bonds and may further comprise bonds between side chain functional groups and the side chain or main chain functional group of another amino acid. For example, the side chain carboxylate of one amino acid residue in the peptide (e.g. Asp, Glu, etc.) may be bonded to the amine of another amino acid residue in the peptide (e.g. Dap, Dab, Orn, Lys). Further details are provided below. Unless otherwise indicated, "Xaa" may be any amino acid, including a proteinogenic or nonproteinogenic amino acid. Non-limiting examples of nonproteinogenic amino acids are shown in Table 1 and include: D-amino acids (including without limitation any D-form of the following amino acids), ornithine (Orn), 3-(1-naphtyl)alanine (Nal), 3-(2-naphtyl)alanine (2-Nal), α-aminobutyric acid, norvaline, norleucine (Nle), homonorleucine, beta-(1,2,3-triazol-4-yl)-L-alanine, 1,2,4-triazole-3-alanine, Phe(4-F), Phe(4-Cl), Phe(4-Br), Phe(4-I), Phe(4-$NH_2$), Phe(4-$NO_2$), homoarginine (hArg), 2-amino-4-guanidinobutyric acid (Agb), 2-amino-3-guanidinopropionic acid (Agp), B-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl)propanoic acid, 2-amino-3-(anthracen-9-yl)propanoic acid, 2-amino-3-(pyren-1-yl) propanoic acid, Trp(5-Br), Trp(5-$OCH_3$), Trp (6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys($N_3$)), azido-ornithine (Orn($N_3$)), 2-amino-4-azidobutanoic acid Dab($N_3$), Dap($N_3$), 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp), and tranexamic acid. If not specified as an L- or D-amino acid, an amino acid shall be understood to an L-amino acid.

TABLE 1

| List of non-limiting examples of non-proteinogenic amino acids. | |
| --- | --- |
| p-aminomethylaniline-diglycolic acid (pABzA-DIG) | 10-aminodecanoic acid |
| ornithine (Orn) | 2-aminooctanoic acid |
| 3-(1-naphtyl)alanine (Nal) | 2-amino-3-(anthracen-2-yl)propanoic acid |
| 3-(2-naphtyl)alanine (2-Nal) | 2-amino-3-(anthracen-9-yl)propanoic acid |
| α-aminobutyric acid | 2-amino-3-(pyren-1-yl)propanoic acid |
| norvaline | Trp(5-Br), |
| norleucine (Nle) | Trp(5-$OCH_3$), |
| homonorleucine | Trp(6-F), |
| beta-(1,2,3-triazol-4-yl)-L-alanine | Trp(5-OH) |
| 1,2,4-triazole-3-alanine | Trp(CHO), |
| Phe(4-F), | 2-aminoadipic acid (2-Aad) |
| Phe(4-Cl), | 3-aminoadipic acid (3-Aad) |
| Phe(4-Br), | propargylglycine (Pra) |
| Phe(4-I), | homopropargylglycine (Hpg) |
| Phe(4-$NH_2$), | beta-homopropargylglycine (Bpg) |
| Phe(4-$NO_2$), | 2,3-diaminopropionic acid (Dap) |
| homoarginine (hArg) | 2,4-diaminobutyric acid (Dab) |
| 4-(2-aminoethyl)-1-carboxymethyl-piperazine (Acp) | azidolysine (Lys($N_3$)) |
| 2-(5'-azidopentyl)alanine, 2-(6'-azidohexyl)alanine | azido-ornithine (Orn($N_3$)) |
| 2-amino-4-guanidinobutyric acid (Agb) | amino-4-azidobutanoic acid Dab($N_3$) |
| 2-amino-3-guanidinopropionic acid (Agp) | tranexamic acid |
| β-alanine | 4-amino-1-carboxymethyl-piperidine (Pip) |
| 4-aminobutyric acid | $NH_2(CH_2)_2O(CH_2)_2C(O)OH$ |
| 5-aminovaleric acid | $NH_2(CH_2)_2[O(CH_2)_2]_2C(O)OH$ (dPEG2) |
| 6-aminohexanoic acid | $NH_2(CH_2)_2[O(CH_2)_2]_3C(O)OH$ |
| 7-aminoheptanoic acid | $NH_2(CH_2)_2[O(CH_2)_2]_4C(O)OH$ |
| 8-aminooctanoic acid | $NH_2(CH_2)_2[O(CH_2)_2]_5C(O)OH$ |
| 9-aminononanoic acid | $NH_2(CH_2)_2[O(CH_2)_2]_6C(O)OH$ |

TABLE 1-continued

List of non-limiting examples of non-proteinogenic amino acids.

| | |
|---|---|
| $N^\epsilon, N^\epsilon, N^\epsilon$-trimethyl-lysine<br>cysteic acid | any D-amino acid of a proteinogenic amino acid or any D-amino acid of a non-proteinogrenic amino acid in this Table |

As used herein, the term "molecular composition" will be understood to mean a molecular complex in which two or more molecules are held together by non-covalent interactions (e.g. hydrophobic, ionic, electrostatic, and the like), such as in a multi-chain protein.

Various aspects of the invention relate to a compound or molecular complex comprising:
  a metal chelator configured for chelation optionally with a radioactive isotope or a non-radioactive isotope or no metal;
  a trifluoroborate ($BF_3$)-containing moiety configured for radiofluorination by $^{19}F/^{18}F$ exchange or a boronate prescursor that is capable of conversion to an $^{18}F$-labeled trifluoroborate; and optionally
  a cell-targeting domain.

Such compounds/complexes are dual-mode in that they are suitable for imaging or radiotherapy, or may be used for both applications. For example, the compounds/complexes may be used as imaging/diagnostic agents when $^{18}F$-labelled ("hot-F"), or may be used as therapeutic agents when chelated with a therapeutic radioactive metal isotope ("hot-M"). This provides the advantage of using the same compound for imaging and therapy; i.e. an $^{18}F$-labelled companion diagnostic (optimized for imaging using hot-F) is provided that is chemically identical to the radiotherapeutic agent (optimized for therapy using hot-M).

In some embodiments, the metal chelator is unchelated or is chelated with a non-radioactive metal isotope ("cold-M"). As used herein, both unchelated and chelated with a non-radioactive metal isotope are considered to be "cold-M". When the $BF_3$-containing moiety of such embodiments is $^{18}F$-labelled, the hot-F/cold-M compounds/complexes are useful as imaging or diagnostic agents without causing any negative effects from a radioactive metal isotope.

If imaging reveals that a subject is a candidate for therapeutic treatment, then the same compound/complex can be administered (either as cold-F/hot-M or hot-F/hot-M). As such, the hot-F/cold-M compound/complex is useful as a companion diagnostic to the hot-M therapeutic agent. In other cases, it is conceivable that an unchelated compound/complex can be used equally well and in other embodiments it is recognized that a surrogate metal cation may be used in lieu of a hot metal cation. For example, in some embodiments, a hot-F compound chelated with non-radioactive $Zn^{2+}$ may be used even though radioactive $Zn^{2+}$ is not commonly used therapeutically or diagnostically. Accordingly, in some embodiments the metal chelator is chelated with a radioactive isotope and the $BF_3$-containing moiety is $^{19}F$-labelled, and in other embodiments the metal chelator is chelated with a radioactive isotope and the $BF_3$-containing moiety is also $^{18}F$-labelled.

The term "BF3" and "$BF_3$" (i.e. subscript "3") have the same meaning and are used interchangeably in this application.

The term "cell-targeting domain" (also referred to as a "cellular antigen targeting module") has a broad meaning, and includes any compound or complex that specifically binds to a cellular marker, for example but without limitation peptides, polypeptides, proteins, peptidomimetics, nucleic acids, steroids, aptamers, affibodies, minibodies, vitamins, small molecules, macrocycles, and the like. The term "cellular marker" includes, without limitation, cell surface antigens such as cluster of differentiation (CD) molecules. Unless otherwise indicated, the term "antigen" as used herein would be understood as not necessarily requiring an immune response to be elicited by the binding of the cell-targeting domain to the cellular marker (or antigen); various embodiments only require specific binding to the cellular marker under physiological conditions (e.g. in vivo). In some embodiments, the cell-targeting domain targets a human cellular marker, or a human CD molecule. Various cell-targeting domains of each of the above-listed categories have been produced and many are commercially available. For example, antibodies have been generated for a broad range of human CD molecules.

As used herein, the phrase "specifically binds" refers a preferred association (e.g. formation of a non-covalent complex) in contrast to a background association with a heterogeneous population of proteins and/or other macromolecules. Thus, under designated conditions (e.g. immunoassay conditions), the cell-targeting domain "specifically binds" to the cellular marker when they associate at least two times the background level of association with other macromolecules present in a sample (in vitro) or organism (in vivo). A variety of immunoassay formats or other binding assays may be used to select cell-targeting domains which specifically bind with a particular target marker. For example, solid-phase ELISA immunoassays are routinely used to select antibodies which specifically bind with a protein. In some embodiments, the cell-targeting domain will produce a binding signal at least twice over the background signal and in some cases at least 10 to 100 times over the background. Unless otherwise specified, the association of the cell-targeting domain to the target marker will generally have an equilibrium dissociation constant ($K_D$) of about $10^{-4}$ M to $10^{-15}$ M. In some embodiments, the association is less than about $10^{-4}$ M. In some embodiments, the association is less than about $10^{-5}$ M. In some embodiments, the association is less than about $10^{-6}$ M. In some embodiments, the association is less than about $10^{-7}$ M. In some embodiments, the association is less than about $10^{-8}$ M. In some embodiments, the association is less than about $10^{-9}$ M. In some embodiments, the association is less than about $10^{-10}$ M. In some embodiments, the association is less than about $10^{-11}$ M. In some embodiments, the association is less than about $10^{-12}$ M. In some embodiments, the association is less than about $10^{-13}$ M. In some embodiments, the association is less than about $10^{-14}$ M. Equilibrium dissociation constants can be measured using any known method in the art.

In some embodiments, the cell-targeting domain is a peptide, polypeptide, or protein. Peptides and polypeptides may be synthesized using standard methods, non-limiting examples of which are described in further detail below. Proteins may be prepared using standard molecular biology methods.

Various peptides, polypeptides and peptidomimetics are known that specifically bind a target cellular marker. Non-limiting examples include: LLP2A, PSMA-617, TATE, bombesin or derivatives (e.g. D-Phe-Gln-Trp-Ala-Val-Gly-His-Sta-Leu-NH$_2$, and the like), RGD, cholecystokinin. LLP2A targets the transcellular very-late antigen 4 (VLA-4). PSMA-617 targets the prostate-specific membrane antigen (PSMA). TATE targets the somatostatin receptor. Bombesin and derivatives targets gastrin-releasing peptide receptor (GRPR). Bradykinin (BK) and derivatives target bradykinin-1-receptor. Any other peptide ligand of a receptor may be used.

In some embodiments, the cell-targeting domain is a peptidomimetic. Peptidomimetics may be produced by substituting peptide/polypeptide groups with non-peptide groups. For example, but without limitation, the peptide bond amide (—C(O)—NH—) may be replaced by pseudo-peptide bond (—CH$_2$—NH—), carbon-carbon bond (—CH$_2$—CH$_2$—) or urea bond (—NH—C(O)—NH—) to increase peptide half-life in vivo.

Various types of polypeptide/protein domains are known that are capable of specifically targeting a cellular marker. In some embodiments, the cell-targeting domain is or comprises an antibody, or an antibody derivative/fragment comprising an antibody variable domain, that specifically binds to the cellular marker. For antibodies and antibody derivatives, the cellular marker would be considered an antigen which contained an epitope that is specifically bound by the antibody variable domain. In general, an "epitope" may be a peptide, protein, nucleic acid, carbohydrate, polysaccharide, lipid, organic compound, and the like, as well as complexes thereof, which forms contacts with an antibody variable domain. An epitope may be continuous or discontinuous. The area of an epitope that contacts the antibody variable domain is typically between about 4 and 10 nm$^2$. Methods for attached antibodies or antibody derivatives/fragments to the remainder of the compound/complex, with or without a linker, are known. For example, compounds have been attached to antibodies at its N-termini, C-termini, cysteine residues, lysine residues, or elsewhere by chemical or enzymatic conjugation (e.g. as is well documented for antibody-drug conjugates).

The heavy chain of an antibody is composed of a variable domain ($V_H$) and multiple constant domains (e.g. for IgG1: $C_H^1$, $C_H^2$ and $C_H^3$). The light chain of an antibody is composed of a variable domain ($V_L$) and a constant domain ($C_L$). Each of $V_L$ and $V_H$ includes three complementarity determining regions (CDRs) apiece as well as framework regions. The six CDRs may all contribute to epitope binding, but their relative contributions vary, and in certain cases, not all six CDRs are necessary for binding. For example, the CDR3 of the heavy chain tends to contribute disproportionately more to epitope binding. Furthermore, single domain antibodies, nanobodies, and the like are known which only have three CDRs (e.g. a single domain antibody obtained or derived from the heavy chain variable domain of dromedaries, camels, llamas, alpacas, sharks, or similar animals, or engineered from the heavy chain of conventional antibodies, including but not limited to human and murine antibodies). Unless otherwise specified, the phrase "antibody variable domain" as used herein refers to any protein comprising $V_H$, both $V_H$ and $V_L$, a single domain antibody, a nanobody, or any antibody-derived protein which suitably positions the required CDR(s) (e.g. 1, 2, 3, 4, 5 or 6 CDRs) for specific binding of the epitope portion of an antigen. Methods for producing proteins comprising an antibody variable domain which binds a target epitope are known, including (without limitation): isolation of antibodies from an immunized animal, from the modification of whole antibodies, from de novo synthesis using recombinant DNA methodologies or solid phase peptide/polypeptide synthesis, or selected from display libraries and the like.

In some embodiments, the cell-targeting domain comprises an antibody. The antibody may be of any species or may be chimeric or artificial or genetically engineered. For example, but without limitation, the antibody may be non-human (e.g.: a camelid, such as camel, dromedary, alpaca, llama and the like; cartilaginous fish, such as shark and the like; mouse, rat, monkey or other), primatized, humanized or fully human. A chimeric antibody contains amino acid sequences from multiple species, e.g. from human and non-human or from two non-human species. Methods for humanizing or primatizing non-human antibodies are well known in the art, e.g. by substituting non-human (or non-primate) constant domains for those of a human antibody (creating a chimeric antibody) or by substituting one or more (e.g. 1, 2, 3, 4, 5 or 6) of the CDRs of a human (or primate) antibody with a non-human antibody. The antibody may be comprised of two heavy chains and two light chains. The antibody may be a single-chain antibody with the heavy chain and light chain separated by a linker. The antibody may be a heavy chain only antibody (e.g. a camel, dromedary, alpaca, llama, or shark antibody which lacks light chains, or a human heavy chain). The antibody may be a single-domain antibody (sdAb).

In some embodiments, the cell-targeting domain comprises an antibody derivative. As used herein, the term "antibody derivative" includes antibody fragments which retain antigen-binding functionality, as well as artificial antibodies. Antibody derivatives comprise an antibody variable domain. Antigen binding fragments may comprise both $V_L$ and $V_H$, or $V_H$ without $V_L$. In some embodiments, the antibody derivative comprises: a Fab, a Fab', a F(ab')2, an scFv (i.e. single chain Fv), a scFv-Fc, an sdAb, a minibody, nanobody, a diabody or a tri(a)body.

In some embodiments, the antibody or antibody derivative is a IgA, a IgM, a IgG, a IgE, a IgD, a sdAb, a Fab, a Fab', a F(ab')2, a scFv, a scFv-Fc, a minibody, a nanobody, a diabodies or a tri(a)body. In some embodiments, the antibody is an IgG antibody.

Many antibodies have a $K_D$ value in the low micromolar to nanomolar range, with high affinity antibodies having low nanomolar $K_D$ values and very high affinity antibodies having picomolar $K_D$ values. In some embodiments, the antibody or antibody derivative binds the cellular antigen with a $K_D$ of less than 500 nM, less than 400 nM, less than 300 nM, less than 200 nM, less than 100 nM, less than 50 nM, less than 10 nM, less than 5 nM, or less than 1 nM. In some embodiments, the antibody or antibody derivative may bind the binding substrate with a picomolar $K_D$ ($10^{-10}$ M to $10^{-12}$ M). Such binding affinities are obtainable using known display technologies, such as mRNA display, phage display, ribosome display, and yeast display, to screen libraries by selecting for specific and high-affinity for the desired target, and in some cases affinity maturation methods.

In some embodiments, the cell-targeting domain is a nucleic acid aptamer that specifically binds the cellular marker. Aptamers are single stranded oligonucleotides (DNA or RNA) that can bind a wide range of cellular targets. Aptamers can be produced to bind a desired target with high affinity, e.g. subnanomolar $K_D$, using various methods such as selection from random libraries and sequence optimization. Aptamers may be synthesized by standard oligonucleotide synthetic methods/instruments and attached to the remainder of the compound/complex using chemical conjugation, with or without a linker.

In some embodiments, a cell-targeting domain may be used in a pre-targeting context where it is first conjugated to a reactive group that reacts with a chelator-$BF_3$ either prior to or after injection. For example, but without limitation, an antibody or aptamer is conjugated to a cyclooctene. This may be injected, allowed to associate with targets, and then the same animal or patient is injected with a chelator-BF3 that is linked to a tetrazine such that it reacts in vivo with the cyclooctene conjugate via $N_2$-extruding cycloaddition reaction. In other cases, the $N_2$-extruding cycloaddition reaction is performed prior to injection.

The metal chelator may be any chelator suitable for binding a radiometal. Many suitable radiometal chelators are known, e.g. as summarized in Price and Orvig, *Chem. Soc. Rev.*, 2014, 43, 260-290, and an extensive variety of metal chelators are commercially available (e.g. from Macrocyclics™) or are described in the literature and are too numerous to list here.

In some embodiments, but without limitation, the metal chelator is selected from the group consisting of: DOTA and derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; H2dedpa, H4octapa, H4py4pa, H4Pypa, H2azapa, H5decapa, and other picolinic acid derivatives; CP256; PCTA; DOTP; HEHA; C-NETA; C-NE3TA; HBED; SHBED; BCPA; CP256; YM103; cyclam; DiamSar; desferrioxamine (DFO) and DFO derivatives; H6phospa; a trithiol chelate; mercaptoacetyl; hydrazinonicotinamide; dimercaptosuccinic acid; 1,2-ethylenediylbis-L-cysteine diethyl ester; methylenediphosphonate; hexamethylpropyleneamineoxime; and hexakis(methoxy isobutyl isonitrile); a porphyrin, a chlorin, a texaphrin, a phthalocyanine. In some embodiments, the metal chelator is DOTA or a DOTA derivative. Notably, one skilled in the art could replace any of the chelators listed herein with another chelator in the art.

Exemplary non-limiting examples of metal chelators and example radiometals that may be chelated by these chelators are shown in Table 2. In alternative embodiments, the metal chelator is or comprises a metal chelator selected Table 2.

TABLE 2

Exemplary metal chelators and exemplary radionuclides which bind said chelators

| Chelator | Radionuclide |
|---|---|
| DOTA, 1,4,7,10-tetraazacyclododecane-1,4,7,10-tetraacetic acid | Cu-64/67<br>Ga-67/68<br>In-111<br>Lu-177<br>Y-86/90<br>Bi-203/212/213<br>Pb-212<br>Ac-225<br>Gd-159<br>Yb-175<br>Ho-166<br>As-211<br>Sc-44/47<br>Pm-149<br>Pr-142<br>Sn-117m<br>Sm-153<br>Tb-149/152/155/161<br>Er-165<br>Ra-223/224<br>Th-227 |
| CB-DO2A, 4,10-bis(carboxymethyl)-1,4,7,10-tetraazabicyclo[5.5.2]tetradecane | Cu-64/67 |
| TCMC, 1,4,7,10-tetrakis(carbamoylmethyl)-1,4,7, 0-tetraazacyclododecane | Pb-212 |

TABLE 2-continued
Exemplary metal chelators and exemplary radionuclides which bind said chelators
| Chelator | Radionuclide |
|---|---|
| 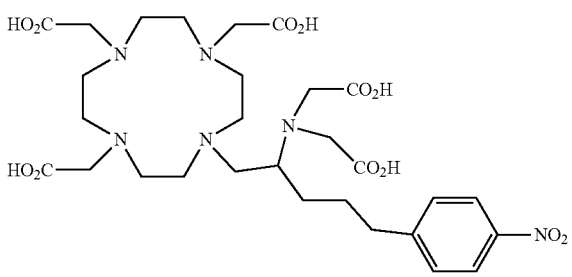 [SMILES: O=C(O)CN1CCN(CC(=O)O)CCN(CC(CCCc2ccc([N+](=O)[O-])cc2)N(CC(=O)O)CC(=O)O)CCN(CC(=O)O)CC1]<br>3p-C-DEPA | Bi-212/213 |
| 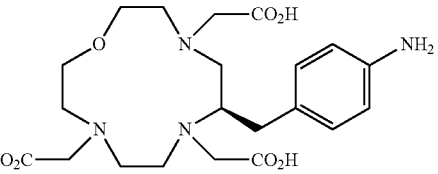<br>p-NH$_2$-Bn-Oxo-DO3A | Cu-64/67 |
| 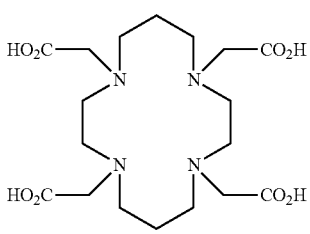 [SMILES: O=C(O)CN1CCCN(CC(=O)O)CCN(CC(=O)O)CCCN(CC(=O)O)CC1]<br>TETA, 1,4,8,11-tetraazacyclotetradecane-1,4,8,11-tetraacetic acid | Cu-64/67 |
| 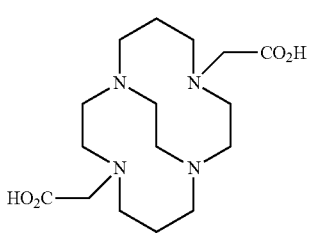 [SMILES: O=C(O)CN1CCCN2CCN(CCCN(CC(=O)O)CC2)CC1]<br>CB-TE2A, 4,11-bis-(carboxymethyl)-1,4,8,11-tetraazabicyclo[6.6.2]-hexadecane | Cu-64/67 |
| 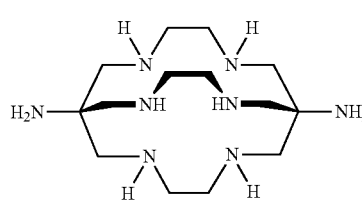<br>Diamsar | Cu-64/67 |

TABLE 2-continued

Exemplary metal chelators and exemplary radionuclides which bind said chelators

| Chelator | Radionuclide |
|---|---|
| 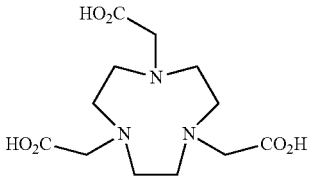 [SMILES: O=C(O)CN1CCN(CC(=O)O)CCN(CC(=O)O)CC1]<br>NOTA, 1,4,7-triazacyclononane-1,4,7-triacetic acid | Cu-64/67<br>Ga-68<br>In-111<br>Sc-44/47 |
| 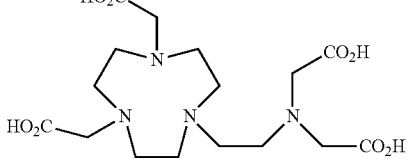<br>NETA, {4-[2-(bis-carboxymethylamino)-ethyl]-7-carboxymethyl-[1,4,7]triazonan-1-yl}-acetic acid | Cu-64/67<br>Ga-68<br>Lu-177<br>Y-86/90<br>Bi-213<br>Pb-212 |
| 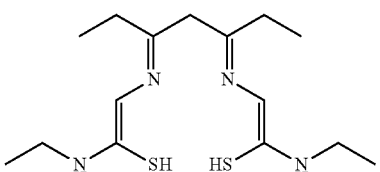<br>HxTSE | Au-198/199 |
| 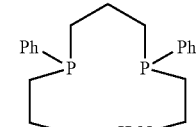<br>$P_2N_2Ph_2$ | Rh-105 |
| 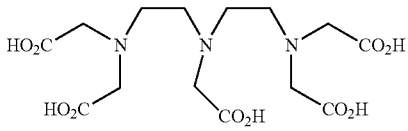 [SMILES: O=C(O)CN(CCN(CC(=O)O)CC(=O)O)CCN(CC(=O)O)CC(=O)O]<br>DTPA, diethylenetriaminepentaacetic acid | In-111<br>Sc-44/47<br>Lu-177<br>Y-86/90<br>Sn-117m<br>Pd-109 |
| 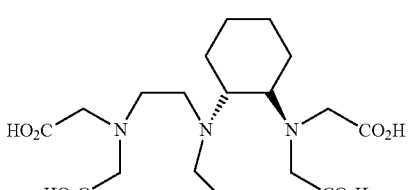<br>CHX-A00-DTPA, 2-(p-isothiocyanatobenzyl)-cyclohexyldiethylenetriaminepentaacetic acid | In-111<br>Lu-177<br>Y-86/90<br>Bi-212/213 |

TABLE 2-continued

Exemplary metal chelators and exemplary radionuclides which bind said chelators

| Chelator | Radionuclide |
| --- | --- |
| H₂dedpa, 1,2-[[6-(carboxy)-pyridin-2-yl]-methylamino]ethane | Cu-64/67 |
| H₂azapa, N,N'-[1-benzyl-1,2,3-triazole-4-yl]methyl-N,N'-[6-(carboxy)pyridin-2-yl]-1,2-diaminoethane | Cu-64/67 |
| H₄octapa | In-111<br>Lu-177<br>Y-86/90<br>Ac-225 |
| H₆phospa | Ac-225 |

TABLE 2-continued
Exemplary metal chelators and exemplary radionuclides which bind said chelators
| Chelator | Radionuclide |
|---|---|
| 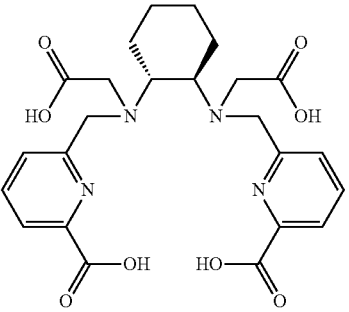 [SMILES: O=C(O)CN(Cc1cccc(C(=O)O)n1)[C@@H]1CCCC[C@H]1N(CC(=O)O)Cc1cccc(C(=O)O)n1]<br>H₄CHXoctapa | In-111<br>Ac-225 |
| 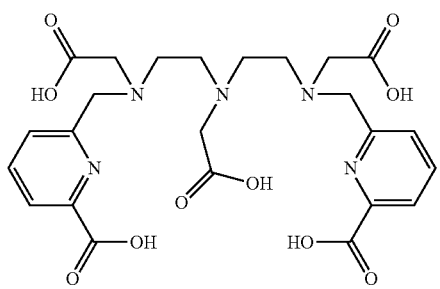 [SMILES: O=C(O)CN(CCN(CC(=O)O)Cc1cccc(C(=O)O)n1)CCN(CC(=O)O)Cc1cccc(C(=O)O)n1]<br>H₅decapa | In-111<br>Lu-177<br>Ac-225 |
| 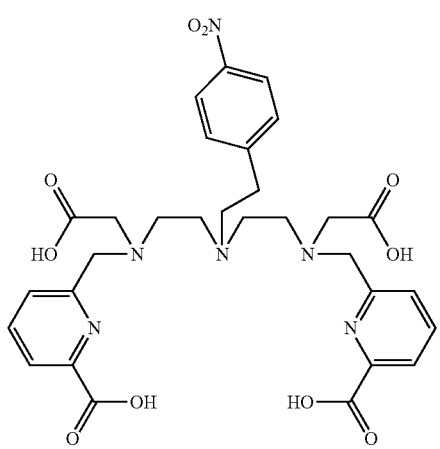 [SMILES: O=C(O)CN(CCN(CCc1ccc([N+](=O)[O-])cc1)CCN(CC(=O)O)Cc1cccc(C(=O)O)n1)Cc1cccc(C(=O)O)n1]<br>H₄neunpa-p-Bn-NO₂ | In-111<br>Lu-177<br>Ac-225 |
| 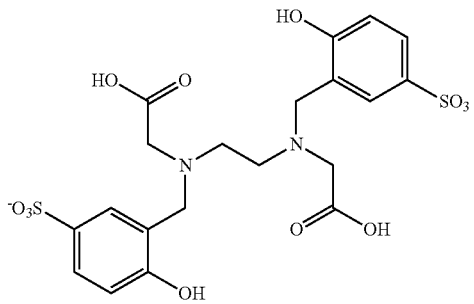<br>SHBED, N,N'-bis(2-hydroxy-5-sulfobenzyl)-ethylenediamine-N,N'-diacetic acid | In-111<br>Ga-68 |

TABLE 2-continued

Exemplary metal chelators and exemplary radionuclides which bind said chelators

| Chelator | Radionuclide |
|---|---|
| BPCA | In-111 |
| PCTA, 3,6,9,15-tetraazabicyclo[9.3.1]-pentadeca-1(15),11,13-triene-3,6,9,-triacetic acid | Cu-64/67 |
| H2-MACROPA (N,N'-bis[(6-carboxy-2-pyridil)methyl]-4,13-diaza-18-crown-6) | Ac-225 |

In some embodiments, the metal chelator is unchelated (i.e. unmetallated).

In some embodiments, the metal chelator is chelated/complexed to a metal, either a radioactive metal isotope (radiometal) or a non-radioactive metal isotope. In some embodiments, the chelated metal is non-radioactive. In some embodiments, the chelated metal is a radiometal. In some embodiments, the radiometal is a therapeutic radiometal, meaning it is radiotoxic (also referred to herein as a "radiotoxin"). In some embodiments, the radiometal is a therapeutic alpha emitter. In some embodiments, the radiometal is a beta emitter. In some embodiments, the radiometal is an auger emitter. In some embodiments, the therapeutic radiometal is $^{64}$Cu, $^{67}$Ga, $^{111}$In, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr or $^{114m}$In.

In some embodiments, the radiometal: $^{68}$Ga, $^{61}$Cu, $^{64}$Cu, $^{67}$Cu, $^{67}$Ga, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{72}$As, $^{77}$As, $^{211}$At, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{114m}$In, $^{94m}$Tc, $^{99m}$Tc, $^{149}$Tb, $^{152}$Tb, $^{155}$Tb, or $^{161}$Tb. In other embodiments, the radiometal, the radionuclide-bound metal, or the radionuclide-bound metal-containing moiety or prosthetic group is: $^{68}$Ga, $^{61}$Cu, $^{64}$Cu, $^{67}$Cu, $^{67}$Ga, $^{111}$In, $^{44}$Sc, $^{86}$Y, $^{177}$Lu, $^{90}$Y, $^{225}$Ac, $^{213}$Bi, or $^{212}$Bi. In some embodiments, the chelator is a chelator from Table 2 and the chelated radiometal/radionuclide is a radionuclide indicated in Table 2 as a binder of the chelator.

In some embodiments, the chelator is: DOTA or a derivative thereof, chelated with $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y $^{86}$Y, $^{225}$Ac, $^{117m}$Sn, $^{153}$Sm, $^{149}$Tb, $^{152}$Tb, $^{155}$Tb, $^{161}$Tb, $^{165}$Er, $^{213}$Bi, $^{224}$Ra, $^{212}$Bi, $^{212}$Pb, $^{225}$Ac, $^{227}$Th, $^{223}$Ra, $^{47}$Sc, $^{64}$Cu or $^{67}$Cu; H2-MACROPA conjugated with $^{225}$Ac; Me-3,2-HOPO chelated with $^{227}$Th; H$_4$py4pa chelated with $^{225}$Ac, $^{227}$Th or $^{177}$Lu; H$_4$pypa chelated with $^{177}$Lu; NODAGA chelated with $^{68}$Ga; DTPA chelated with $^{111}$In; or DFO chelated with $^{89}$Zr.

In some embodiments, the chelator is TETA (1,4,8,11-tetraazacyclotetradecane-1,4,8,11-tetraacetic acid), SarAr (1-N-(4-Aminobenzyl)-3,6,10,13,16,19-hexaazabicyclo [6.6.6]-eicosane-1,8-diamine), NOTA (1,4,7-triazacyclononane-1,4,7-triacetic acid), TRAP (1,4,7-triazacyclononane-1,4,7-tris[methyl(2-carboxyethyl)phosphinic acid), HBED (N,N0-bis(2-hydroxybenzyl)-ethylenediamine-N, N0-diacetic acid), 2,3-HOPO (3-hydroxypyridin-2-one), PCTA (3,6,9,15-tetraazabicyclo[9.3.1]-pentadeca-1(15),11, 13-triene-3,6,9,-triacetic acid), DFO (desferrioxamine), DTPA (diethylenetriaminepentaacetic acid), OCTAPA (N,N0-bis(6-carboxy-2-pyridylmethyl)-ethylenediamine-N, N0-diacetic acid) or another picolinic acid derivative.

In some embodiments, the chelator is a chelator for radiolabelling with $^{99m}$Tc, $^{94m}$Tc, $^{186}$Re, or $^{188}$Re, such as mercaptoacetyl, hydrazinonicotinamide, dimercaptosuccinic acid, 1,2-ethylenediylbis-L-cysteine diethyl ester, methylenediphosphonate, hexamethylpropyleneamineoxime and hexakis(methoxy isobutyl isonitrile), and the like. In some embodiments, In some embodiments, the chelator is mercaptoacetyl, hydrazinonicotinamide, dimercaptosuccinic acid, 1,2-ethylenediylbis-L-cysteine diethyl ester, methylenediphosphonate, hexamethylpropyleneamineoxime or hexakis(methoxy isobutyl isonitrile). In some of these embodiments, the chelator is bound by a radiometal. In some such embodiments, the radiometal is $^{99m}$Tc, $^{94m}$Tc, $^{186}$Re, or $^{188}$Re.

In some embodiments, the chelator is a chelator capable of binding $^{72}$As or $^{77}$As, such as a trithiol chelate and the like. In some embodiments, the chelator is a trithiol chelate. In some embodiments, the chelator is conjugated to $^{72}$As. In some embodiments, the chelator is conjugated to $^{77}$As.

Non-radioactive metals suitable for chelation to the above metal chelators are well known, e.g. $^{89}$Y, $^{174}$Lu, $^{208}$Pb, and the like including known stable or meta-stable isotopes that are commonly known in transition metals, lanthanides and actinides as would be typically used by those familiar with the art of metal chelation.

The BF$_3$-containing moiety (also referred to as a "BF$_3$-containing prosthetic group") may be any such group that is capable of $^{18}$F/$^{19}$F exchange radiolabeling.

In some embodiments, the BF$_3$-containing moiety is

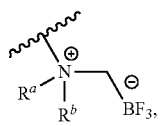

wherein each of $R^a$ and $R^b$ is independently a $C_1$-$C_5$ linear or branched alkyl group. In some embodiments, $R^a$ is methyl. In some embodiments, $R^a$ is ethyl. In some embodiments, $R^a$ is propyl. In some embodiments, $R^a$ is isopropyl. In some embodiments, $R^a$ is n-butyl. In some embodiments, $R^b$ is methyl. In some embodiments, $R^b$ is ethyl. In some embodiments, $R^b$ is propyl. In some embodiments, $R^b$ is isopropyl. In some embodiments, $R^b$ is n-butyl. In some embodiments, $R^a$ and $R^b$ are the same. In some embodiments, $R^a$ and $R^b$ are different.

In some embodiments, the BF$_3$-containing moiety is a group shown in Table 3 (below), wherein each R (when present), e.g. in the pyridine substituted with —OR, —SR, —NR—, —NHR or —NR$_2$ groups, is independently a $C_1$-$C_5$ linear or branched alkyl. In some embodiments, R is methyl. In some embodiments, R is ethyl. In some embodiments, R is propyl. In some embodiments, R is isopropyl. In some embodiments, R is n-butyl. In some embodiments, In some embodiments, the BF$_3$-containing moiety is

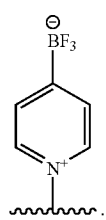

TABLE 3

Non-limiting examples of BF$_3$-containing groups.

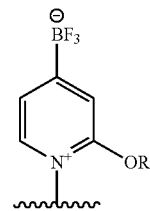

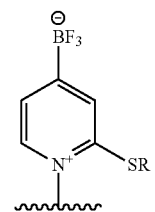

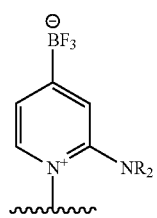

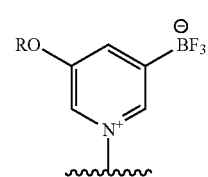

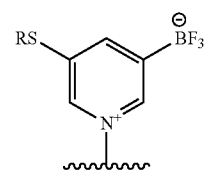

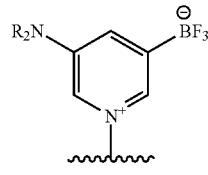

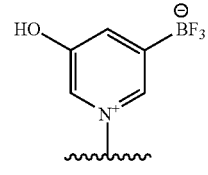

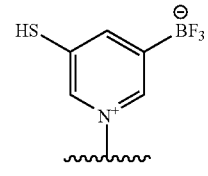

TABLE 3-continued
Non-limiting examples of BF$_3$-containing groups.
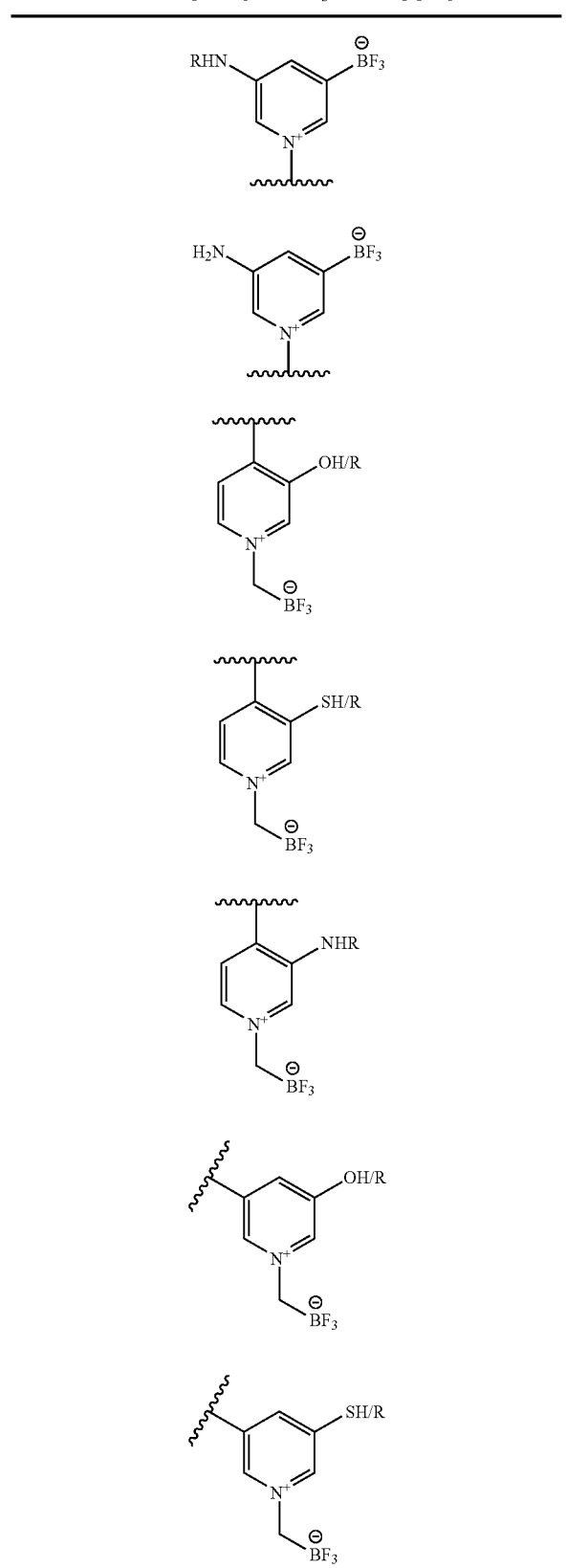

TABLE 3-continued
Non-limiting examples of BF₃-containing groups.
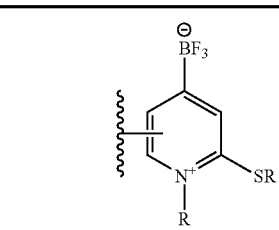
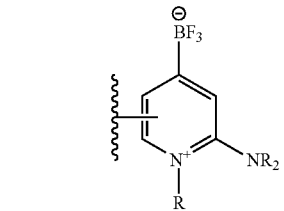
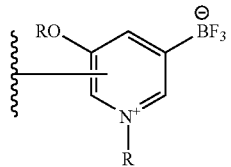
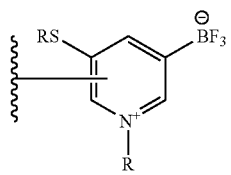
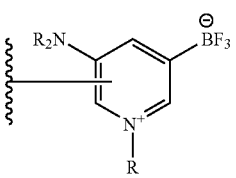
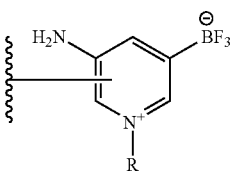
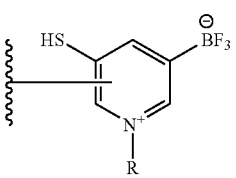
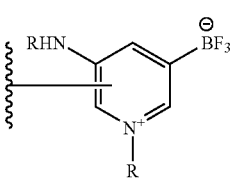
TABLE 3-continued
Non-limiting examples of BF₃-containing groups.
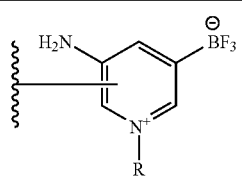
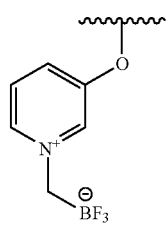
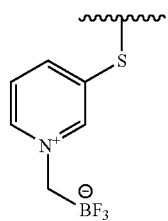
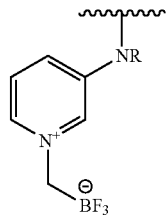
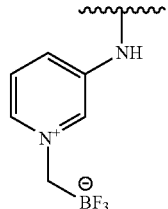
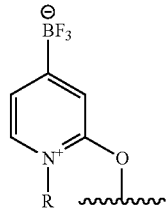
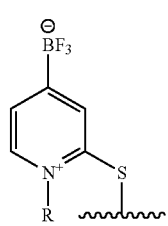

TABLE 3-continued

Non-limiting examples of BF₃-containing groups.

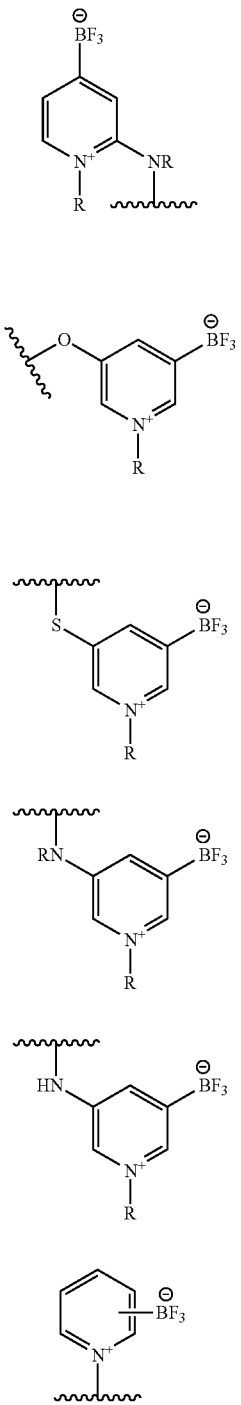

TABLE 4

Further non-limiting examples of BF₃-containing groups.

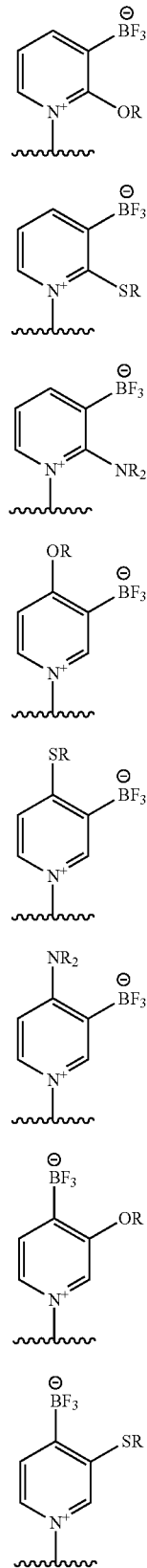

In some embodiments, the BF₃-containing moiety is a group shown in Table 4 (below), wherein each R (when present), e.g. in the pyridine substituted with —OR, —SR, —NR—, —NHR or —NR₂ groups, is independently a $C_1$-$C_5$ linear or branched alkyl. In some embodiments, R is methyl. In some embodiments, R is ethyl. In some embodiments, R is propyl. In some embodiments, R is isopropyl.

TABLE 4-continued
Further non-limiting examples of BF₃-containing groups.
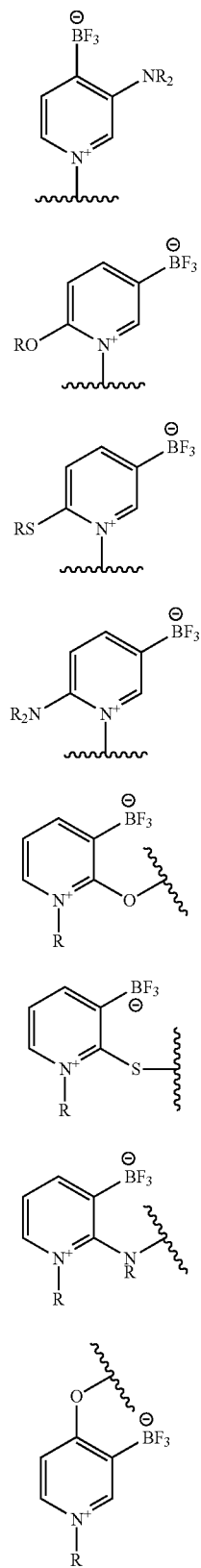
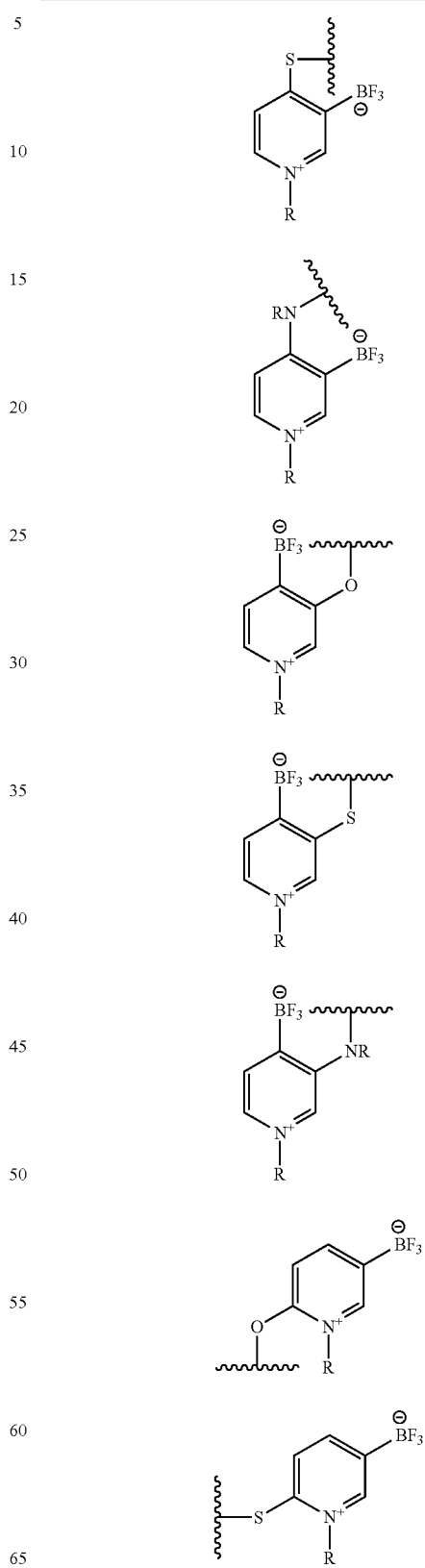

TABLE 4-continued
Further non-limiting examples of BF$_3$-containing groups.
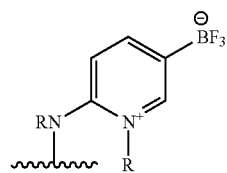
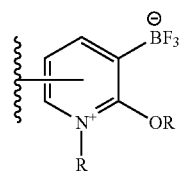
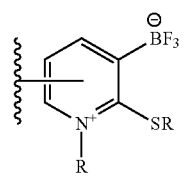
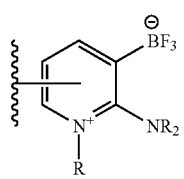
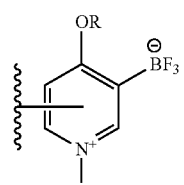
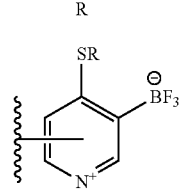
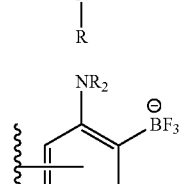
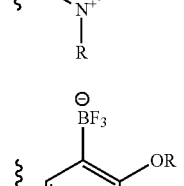
TABLE 4-continued
Further non-limiting examples of BF$_3$-containing groups.
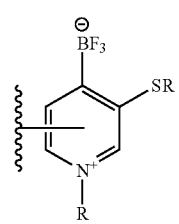
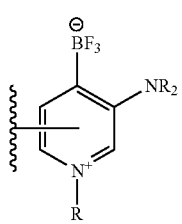
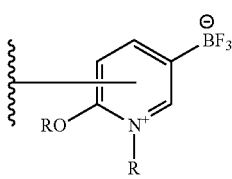
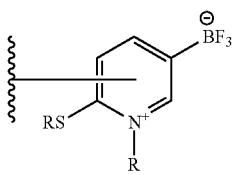
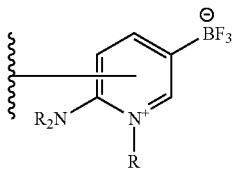
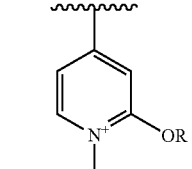
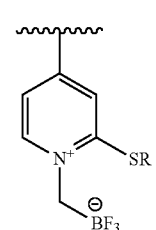

TABLE 4-continued

Further non-limiting examples of BF$_3$-containing groups.

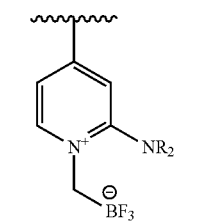
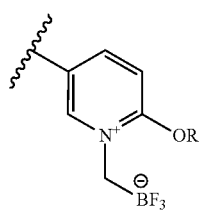
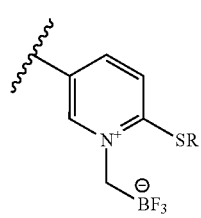
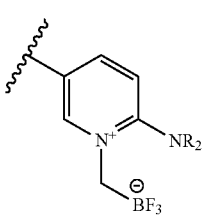
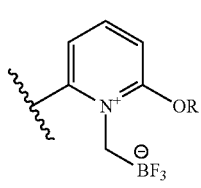
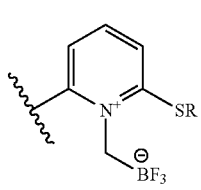
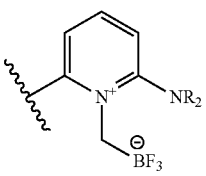

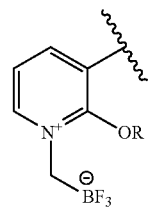
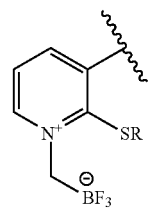
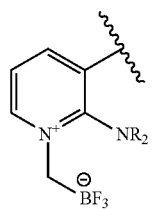
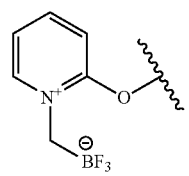
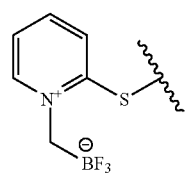
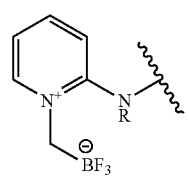
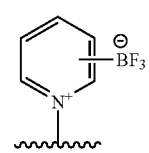

In some embodiments, the BF$_3$-containing moiety comprises $^{18}$F. In some embodiments, one fluorine in the BF$_3$-containing moiety is $^{18}$F. In some embodiments, all three fluorines are $^{18}$F. In some embodiments, all three fluorines in the BF$_3$-containing moiety are $^{19}$F.

In some embodiments, the compound or complex comprises a plurality of BF$_3$-containing moieties, each of which may be the same or different or a combination thereof. Some embodiments comprise two BF$_3$-containing moieties, each of which is independently selected from those listed above. Some embodiments comprise three BF$_3$-containing moieties, each of which is independently selected from those listed above. Some embodiments comprise four BF$_3$-containing moieties, each of which is independently selected from those listed above. In some embodiments, the BF$_3$-containing moieties are attached to a linker positioned between the metal chelator and the cell-targeting domain.

It is appreciated that while $^{18}$F-labeling by isotope exchange may be a preferred method of labeling, conversion of other sp2/sp3 hybridized boronate species may in certain cases be favorable. Examples of such boronates include pinacolates, di-, tri-, tetra-arylated pinacolates, neopentyl-diolates, catecholates, diolates in general, MIDA-boronates, complexes based on anthranilamides, even possibly borohydrides. Such boronate complexes are known or easily known to those trained in the art of organoboron chemistry and such complexes are optionally of interest when they can be readily converted to the corresponding trifluoroborates. Accordingly, in some embodiments, the compound/complex comprises a boronate prescursor capable of conversion to an $^{18}$F-labeled trifluoroborate instead of a BF$_3$-containing moiety.

The compound or molecular complex may further comprise a linker. For example, but without limitation, the metal chelator may be linked to the cell-targeting domain by a linker containing the BF$_3$-containing moiety. In some embodiments, the linker comprises two (or more) BF$_3$-containing moieties. However, the components of the compound/complex may have any configuration. For example, the BF$_3$-containing moiety (or moieties) may be attached directly to the metal chelator and/or to the cell-targeting domain. A non-limiting example of a linker is a peptide linker.

The linker may be any linker including for example, but without limitation, an amino acid linker, a peptide linker, a polyethylene glycol (PEG) linker, an alkylene linker (e.g. C$_1$-C$_{30}$), an ether, an ester, a thioether, a disulfide, a thioester, an amide, a carbamate, ureido, a phosphodiester. In some embodiments, the linker is or comprises —N(H)—(CH$_2$)n-C(O)— in which n is 1, 2, 3, 4, 5, 6, 7, 8, 9, 10, 11, 12, 13, 14, 15 or more than 15.

In some embodiments, the linker is a linear or branched peptide linker (Xaa$^1$)$_n$ wherein n is 1 to 8 and each Xaa$^1$ is the same or different or is a combination thereof. In some embodiments, the peptide linker is a linear peptide linker. In some embodiments, the peptide linker is a branched peptide linker. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, each Xaa$^1$ is independently selected from proteinogenic amino acids and the non-proteinogenic amino acids listed in Table 1. In some embodiments, each peptide backbone amino group in the linker is optionally methylated.

In some embodiments, the linker comprises Lys(AMBF$_3$). In some embodiments, including for example (but without limitation) in embodiments comprising a PEG linker or a peptide linker (Xaa$^1$)$_{1-8}$, the linker comprises amino acid residue Xaa$^2$ defined as —N(H)—C(R$^1$R$^2$R$^3$)(H)—C(O)—

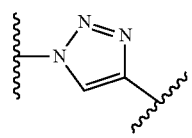

wherein R$^1$ is a C$_1$-C$_5$ alkylenyl group, R$^2$ is

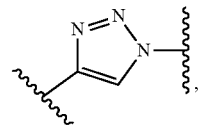

and R$^3$ is

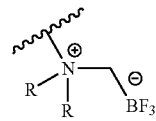

or a group shown in Table 1 or Table 2 wherein each R is independently a C$_1$-C$_5$ linear or branched alkyl group. In some embodiments R$^1$ is —CH$_2$—. In some embodiments R$^1$ is —(CH$_2$)$_2$—. In some embodiments R$^1$ is —(CH$_2$)$_3$—. In some embodiments R$^1$ is —(CH$_2$)$_4$—. In some embodiments R$^1$ is —(CH$_2$)$_5$—. In some embodiments, R$^2$ is

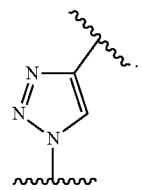

In some embodiments, R$^2$ is

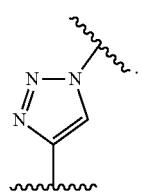 [SMILES: *c1cn(*)nn1]

In some embodiments, R$^3$ is

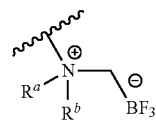

wherein each of R$^a$ and R$^b$ is independently a C$_1$-C$_5$ linear or branched alkyl group. In some embodiments, R$^a$ is methyl. In some embodiments, R$^a$ is ethyl. In some embodiments, R$^a$ is propyl. In some embodiments, R$^a$ is isopropyl. In some embodiments, R$^a$ is n-butyl. In some embodiments, R$^b$ is methyl. In some embodiments, R$^b$ is ethyl. In some embodiments, R$^b$ is propyl. In some embodiments, R$^b$ is isopropyl. In some embodiments, R$^b$ is n-butyl. In some embodiments, R$^a$ and R$^b$ are the same. In some embodiments, R$^a$ and R$^b$ are different. In some embodiments, R$^3$ is

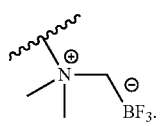

In some embodiments, R³ is

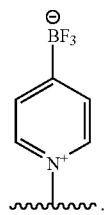

In some embodiments, the linker comprises two Xaa² residues each of which is independently as defined above (i.e. the same or different).

In some embodiments, the metal chelator attaches to the linker or to the cell-targeting domain by forming an amide bond (between an amino group and a carboxylic acid group) or a 1,2,3-triazole (reaction between an azide and an alkyne), or by reaction between a maleimide and a thiol group.

In some embodiments, the chelator is attached (with or without a linker) to the N-terminus of a peptide/polypeptide/protein cell-targeting domain and the BF₃-containing moiety (or precursor) is attached (with or without a linker) to the C-terminus of the cell-targeting domain. In some embodiments, the chelator is attached (with or without a linker) to the C-terminus of a peptide/polypeptide/protein cell-targeting domain and the BF₃-containing moiety (or precursor) is attached (with or without a linker) to the N-terminus of the cell-targeting domain. In some embodiments, the chelator is attached (with or without a linker) to the N-terminus of a peptide/polypeptide/protein cell-targeting domain and the BF₃-containing moiety (or precursor) is attached (with or without a linker) to a side chain of the cell-targeting domain. In some embodiments, the chelator is attached (with or without a linker) to the C-terminus of a peptide/polypeptide/protein cell-targeting domain and the BF₃-containing moiety (or precursor) is attached (with or without a linker) to a side chain of the cell-targeting domain. In some embodiments, both the chelator and the BF₃-containing moiety are attached (with or without linkers) to separate side chains of a peptide/polypeptide/protein cell-targeting domain. In some embodiments, the chelator is attached to the N-terminus or the C-terminus of a peptide/polypeptide/protein cell-targeting domain via a linker and the BF₃-containing moiety (or precursor) is attached to the linker. In some embodiments, the chelator is attached to a side chain of a peptide/polypeptide/protein cell-targeting domain via a linker and the BF₃-containing moiety (or precursor) is attached to the linker. For illustrative purposes, FIG. 1 shows various non-limiting configurations of the compound or complex.

In some embodiments, the compound or molecular complex has Formula I or is a salt or solvate of Formula I:

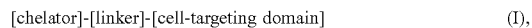

[chelator]-[linker]-[cell-targeting domain]   (I), wherein: the chelator is any chelator described above; the cell-targeting domain is any cell-targeting domain described above; and the linker comprises one or a plurality of any BF₃-containing moiety independently selected from those described above. In some embodiments, the linker is any peptide linker defined above.

In some embodiments, the compound or molecular complex is or comprises DOTA-AMBF3-PEG2-LLP2A.

In some embodiments, the compound or molecular complex is or comprises PSMA-617-LysAMBF3-DOTA.

In some embodiments, the compound or molecular complex is or comprises DOTA-Lys(AMBF3)-TATE.

In some embodiments, the compound or molecular complex is or comprises DOTA-Lys-AMBF3-Pip-D-Phe-Gln-Trp-Ala-Val-Gly-His-Sta-Leu-NH₂.

In some embodiments the composition contains a [chelator]-[linker]-BF₃.

In some embodiments, the compound or molecular complex further comprises a fluorophore or other light emitting moiety, such as (but without limitation) Cy3, Cy5, Cy7, other near-IR dyes, or fluorescein.

Various embodiments of the compound or molecular complex relate to a dual-mode compound or molecular composition suitable for imaging and radiotherapy comprising: a) a cellular antigen targeting module; b) a BF₃-containing moiety/prosthetic that is readily labelled with ¹⁸F; and c) a radiotoxin-containing moiety that is readily formulated with a radioactive therapeutic isotope or a non-radioactive isotope. As noted above, in the diagnostic imaging mode/format the BF₃ moiety contains at least one 'hot' radioactive fluorine (i.e. ¹⁸F) whereas the radiotoxin-containing moiety contains non-radioactive ('cold') isotope/metal atom (or alternatively, none at all). Accordingly, in some embodiments, the BF₃-containing moiety/prosthetic is labelled with ¹⁸F and the radiotoxin-containing moiety contains a radioactive therapeutic isotope. In the targeted radiotherapeutic mode/format the BF₃ moiety may contain 'cold' fluorine (i.e. ¹⁹F) whereas the radiotoxin-containing moiety contains radioactive/radiotoxic 'hot' isotope/metal atom (suitably efficacious for radiotherapy). Accordingly, in some embodiments, the BF₃-containing moiety/prosthetic is labelled with ¹⁹F and the radiotoxin-containing moiety contains a non-radioactive isotope or does not contain a radioactive isotope. Such compounds therefore comprise useful theranostic pairs whereby disease detection/diagnosis is effected by using compositions in the diagnostic imaging mode (i.e. with ¹⁸F) and disease treatment/therapy is effected by subsequent use of the same compositions in targeted radiotherapeutic mode (i.e. without ¹⁸F and with a radiotherapeutic isotope). The former then constitutes a 'companion diagnostic' to the latter.

As noted above, in various embodiments, the functional domains of the dual-mode (imaging/radiotherapy) compounds of the invention may be separated by various linkers/intervening groups of varying size/length that are well known to those skilled in the art. In some embodiments, the cellular antigen binding module, BF₃-containing prosthetic and radiotoxin-containing moiety may be positioned relative to one another in a plurality of different configurations to obtain the desired properties of the theranostic pair (companion diagnostic for imaging and targeted radiotherapeutic of the same chemical composition). FIG. 1 shows a non-limiting representation of some configurations of the dual-mode PET imaging agent/radiotherapeutic.

In some embodiments, the cellular antigen-binding module may comprise i) a peptide/polypeptide, ii) a non-peptide/non-protein ligand capable of binding to the cellular antigen being targeted, iii) an antibody or antibody fragment, iv) scFv domains/fragments, v) nucleic acid aptamers or vi) bi-specific antibody or fragment thereof. Accordingly, the modification with both a trifluoroborate and a chelator may be applied to non-peptidic small molecules, drugs, or other compositions with diverse properties or larger molecules e.g. antibodies, aptamers, and the like. In some embodiments, the cellular antigen being targeted is the integrin known as transcellular very-late antigen 4 (VLA-4) and the compound is or comprises DOTA-AMBF$_3$-PEG2-LLP2A. In some embodiments, the cellular antigen/protein being targeted is prostate-specific membrane antigen (PSMA) and the compound is or comprises PSMA-617-LysAMBF$_3$-DOTA. In some embodiments, the cellular antigen being targeted is a somatostatin receptor (i.e. SSTR) and the compound is or comprises DOTA-Lys(AMBF$_3$)-TATE. In some embodiments, the cellular antigen being targeted is the gastrin-releasing peptide receptor (GRPR) and the compound is or comprises DOTA-Lys(AMBF$_3$)-RM2 (DOTA-Lys-AMBF$_3$-4-amino-1-carboxymethyl-piperidine-D-Phe-Gln-Trp-Ala-Val-Gly-His-Sta-Leu-NH$_2$). In some embodiments, the cellular antigen being targeted is a bradykinin receptor (e.g. the bradykinin-1-receptor; B1R) and the compound is or comprises DOTA-Lys(AMBF3)-BK. In some embodiments, the BF$_3$-containing moiety/prosthetic that is readily labelled with $^{18}$F is as disclosed in the following patent application(s): WO/2005/077967, WO/2009/012596A1, and WO/2014/134716, which claimed priority to U.S. 61/775,280, each of which is incorporated by reference in its entirety.

In some embodiments, but without limitation, the radiotoxin-chelating moiety may include a metal ion chelator (e.g. DOTA, NOTA, NODAGA, Octapa, Macropa, and the like). In other embodiments, chelators could be used to chelate metals for fluorescent, MRI applications, and other applications that involve metals be they therapeutic, diagnostic, or emissive in ways that use metals and chelators for applications that would be considered bimodal or multimodal. In some embodiments, but without limitation, the therapeutic radiotoxin/metal includes $^{177}$Lu or $^{210}$Bi or $^{212}$Pb. Other suitable radiometals are known or obtainable that would be useful for practicing the therapeutic mode of the invention. In some embodiments, the chelator is used without a metal or chelates a nonradioactive metal, e.g. Zn$^{2+}$, Ca$^{2+}$, Ni$^{2+}$, Gd$^{3+}$, and the like. Such compounds may be useful for imaging (e.g. PET imaging). In some embodiments, the compound may comprise both $^{18}$F and a radiometal (e.g. $^{225}$Ac). Such compounds may be used for imaging (e.g. PET) to identify patients who would respond to targeted therapy with $^{225}$Ac with the knowledge that there is no stable isotope of $^{225}$Ac. For therapy one would use the $^{19}$F-isotopolog while retaining the radiotoxic $^{225}$Ac. In some embodiments, one or more trifluoroborates may be linked to the tracer that includes at least one chelator. Accordingly, in some embodiments, the compound/composition contains more than one trifluoroborate group. It is also possible that one may use limiting amounts of $^{18}$F-fluoride to prepare a doubly labeled radiotracer for imaging applications in which the radiometal is also desired.

The compounds presented herein incorporate peptides, which may be synthesized by any of a variety of methods established in the art. This includes but is not limited to liquid-phase as well as solid-phase peptide synthesis using methods employing 9-fluorenylmethoxycarbonyl (Fmoc) and/or t-butyloxycarbonyl (Boc) chemistries, and/or other synthetic approaches.

Solid-phase peptide synthesis methods and technology are well-established in the art. For example, peptides may be synthesized by sequential incorporation of the amino acid residues of interest one at a time. In such methods, peptide synthesis is typically initiated by attaching the C-terminal amino acid of the peptide of interest to a suitable resin. Prior to this, reactive side chain and alpha amino groups of the amino acids are protected from reaction by suitable protecting groups, allowing only the alpha carboxyl group to react with a functional group such as an amine group, a hydroxyl group, or an alkyl halide group on the solid support. Following coupling of the C-terminal amino acid to the support, the protecting group on the side chain and/or the alpha amino group of the amino acid is selectively removed, allowing the coupling of the next amino acid of interest. This process is repeated until the desired peptide is fully synthesized, at which point the peptide can be cleaved from the support and purified. A non-limiting example of an instrument for solid-phase peptide synthesis is the Aapptec Endeavor 90 peptide synthesizer.

To allow coupling of additional amino acids, Fmoc protecting groups may be removed from the amino acid on the solid support, e.g. under mild basic conditions, such as piperidine (20-50% v/v) in DMF. The amino acid to be added must also have been activated for coupling (e.g. at the alpha carboxylate). Non-limiting examples of activating reagents include without limitation 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-azabenzotriazole (HOAt). Coupling may be performed in the presence of a suitable base, such as N,N-diisopropylethylamine (DIPEA/DIEA) and the like. For long peptides or if desired, peptide synthesis and ligation may be used.

Apart from forming typical peptide bonds to elongate a peptide, peptides may be elongated in a branched fashion by attaching to side chain functional groups (e.g. carboxylic acid groups or amino groups), either: side chain to side chain; or side chain to backbone amino or carboxylate. Coupling to amino acid side chains may be performed by any known method, and may be performed on-resin or off-resin. Non-limiting examples include: forming an amide between an amino acid side chain containing a carboxyl group (e.g. Asp, D-Asp, Glu, D-Glu, and the like) and an amino acid side chain containing an amino group (e.g. Lys, D-Lys, Orn, D-Orn, Dab, D-Dab, Dap, D-Dap, and the like) or the peptide N-terminus; forming an amide between an amino acid side chain containing an amino group (e.g. Lys, D-Lys, Orn, D-Orn, Dab, D-Dab, Dap, D-Dap, and the like) and either an amino acid side chain containing a carboxyl group (e.g. Asp, D-Asp, Glu, D-Glu, and the like) or the peptide C-terminus; and forming a 1, 2, 3-triazole via click chemistry between an amino acid side chain containing an azide group (e.g. Lys(N$_3$), D-Lys(N$_3$), and the like) and an alkyne group (e.g. Pra, D-Pra, and the like). The protecting groups on the appropriate functional groups must be selectively removed before amide bond formation, whereas the reaction between an alkyne and an azido groups via the click reaction to form an 1,2,3-triazole does not require selective deprotection. Non-limiting examples of selectively removable protecting groups include 2-phenylisopropyl esters (O-2-PhiPr) (e.g. on Asp/Glu) as well as 4-methyltrityl (Mtt), allyloxycarbonyl (alloc), 1-(4,4-dimethyl-2,6-dioxocyclohex-1-ylidene))ethyl (Dde), and 1-(4,4-dimethyl-2,6-dioxocyclohex-1-ylidene)-3-methylbutyl (ivDde) (e.g. on Lys/Orn/Dab/Dap). O-2-PhiPr and Mtt protecting groups can be selectively deprotected under mild acidic conditions, such as 2.5% trifluoroacetic acid (TFA) in DCM. Alloc protecting groups can be selectively deprotected using tetrakis(triphenylphosphine)palladium(0) and phenyl silane in DCM. Dde and ivDde protecting groups can be selectively deprotected using 2-5% of hydrazine in DMF. Deprotected side chains of Asp/Glu (L- or D-forms) and Lys/Orn/Dab/Dap (L- or D-forms) can then be coupled, e.g. by using the coupling reaction conditions described above.

Peptide backbone amides may be N-methylated (i.e. alpha amino methylated). This may be achieved by directly using Fmoc-N-methylated amino acids during peptide synthesis. Alternatively, N-methylation under Mitsunobu conditions may be performed. First, a free primary amine group is protected using a solution of 4-nitrobenzenesulfonyl chloride (Ns-Cl) and 2,4,6-trimethylpyridine (collidine) in NMP. N-methylation may then be achieved in the presence of triphenylphosphine, diisopropyl azodicarboxylate (DIAD) and methanol. Subsequently, N-deprotection may be performed using mercaptoethanol and 1,8-diazabicyclo[5.4.0]undec-7-ene (DBU) in NMP. For coupling protected amino acids to N-methylated alpha amino groups, HATU, HOAt and DIEA may be used.

Coupling between the linker and different components of the compounds/complexes of the invention may require the formation of thioether (—S—) or ether (—O—) linkages; this can be achieved either on solid phase or in solution phase. For example, the formation of thioether (—S—) linkage can be achieved by coupling between a thiol-containing compound (such as the thiol group on cysteine side chain) and an alkyl halide (such as 3-(Fmoc-amino)propyl bromide and the like) in an appropriate solvent (such as N,N-dimethylformamide and the like) in the presence of base (such as N,N-diisopropylethylamine and the like). The formation of an ether (—O—) linkage can be achieved via the Mitsunobu reaction between an alcohol (such as the hydroxyl group on the side chain of serine or threonine, for example) and a phenol group (such as the side chain of tyrosine, for example) in the presence of triphenylphosphine and diisopropyl azidicarboxylate (DIAD) in an aprotic solvent (such as 1,4-dioxane and the like). If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

Non-peptide moieties (e.g. radiolabeling groups, albumin-binding groups and/or linkers) may be coupled to the peptide N-terminus while the peptide is attached to the solid support. This is facile when the non-peptide moiety comprises an activated carboxylate (and protected groups if necessary) so that coupling can be performed on resin. For example, but without limitation, a bifunctional chelator, such as 1,4,7,10-tetraazacyclododecane-1,4,7,10-tetraacetic acid (DOTA) tris(tert-butyl ester) may be activated in the presence of N-hydroxysuccinimide (NHS) and N,N'-dicyclohexylcarbodiimide (DCC) for coupling to a peptide. Alternatively, a non-peptide moiety may be incorporated into the compound via a copper-catalyzed click reaction under either liquid or solid phase conditions. Copper-catalyzed click reactions are well established in the art. For example, 2-azidoacetic acid is first activated by NHS and DCC and coupled to a peptide. Then, an alkyne-containing non-peptide moeity may be clicked to the azide-containing peptide in the presence of $Cu^{2+}$ and sodium ascorbate in water and organic solvent, such as acetonitrile (ACN) and DMF and the like.

The synthesis of radiometal chelators is well-known and many chelators are commercially available (e.g. from Sigma-Aldrich™/Milipore Sigma™ and others). Protocols for conjugation of radiometals to the chelators is also well known (e.g. see Example 1, below).

Generally, the $BF_3$-containing motif can be coupled to the linker via click chemistry by forming a 1,2,3-triazole ring between a $BF_3$-containing azido (or alkynyl) group and an alkynyl (or azido) group on the linker, or by forming an amide linkage between a $BF_3$-containing carboxylate and an amino group on the linker. To make the $BF_3$-containing azide, alkyne or carboxylate, a boronic acid ester-containing azide, alkyne or carboxylate is first prepared following by the conversion of the boronic acid ester to $BF_3$ in a mixture of HCl, DMF and $KHF_2$. For alkyl $BF_3$, the boronic acid ester-containing azide, alkyne or carboxylate can be prepared by coupling boronic acid ester-containing alkyl halide (such as iodomethylboronic acid pinacol ester) with an amine-containing azide, alkyne or carboxylate (such as N,N-dimethylpropargylamine). For aryl $BF_3$, the boronic acid ester can be prepared via Suzuki coupling using aryl halide (iodine or bromide) and bis(pinacolato)diboron.

$^{18}F$-Fluorination of the $BF_3$-containing moiety via $^{18}F$-$^{19}F$ isotope exchange reaction can be achieved following previously published procedures (Liu et al. Nat Protoc 2015 10:1423-1432, incorporated by reference in its entirety). Generally, ~100 nmol of a $BF_3$-containing compound is dissolved in a mixture of 15 μl of pyridazine-HCl buffer (pH=2.0-2.5, 1 M), 15 μl of DMF and 1 μl of a 7.5 mM $KHF_2$ aqueous solution. $^{18}F$-Fluoride solution (in saline, 60 μl) is added to the reaction mixture, and the resulting solution is heated at 80° C. for 20 min. At the end of the reaction, the desired product can be purified by solid phase extraction or by reversed high performance liquid chromatography (HPLC) using a mixture of water and acetonitrile as the mobile phase.

When the peptide has been fully synthesized on the solid support, the desired peptide/compound may be cleaved from the solid support using suitable reagents, such as TFA, tri-isopropylsilane (TIS) and water. Side chain protecting groups, such as Boc, pentamethyldihydrobenzofuran-5-sulfonyl (Pbf), trityl (Trt) and tert-butyl (tBu) are simultaneously removed (i.e. deprotection). The crude peptide/compound may be precipitated and collected from the solution by adding cold ether followed by centrifugation. Purification and characterization of the peptides may be performed by standard separation techniques, such as high performance liquid chromatography (HPLC) based on the size, charge and polarity of the peptides. The identity of the purified peptides may be confirmed by mass spectrometry or other similar approaches.

Examples of synthetic schemes are provided in the Examples.

As discussed, the compounds/complexes disclosed herein are dual-mode in that they are suitable for imaging or radiotherapy, or may be used for both applications. For example, the compounds/complexes may be used as imaging/diagnostic agents when $^{18}F$-labelled ("hot-F"), or may be used as therapeutic agents when chelated with a therapeutic radioactive metal isotope ("hot-M").

Accordingly, in some embodiments, the metal chelator is hot-F/cold-M, i.e. $^{18}$F-labelled (preferred for PET) and either unchelated or is chelated with a non-radioactive metal isotope. Such embodiments are useful as imaging or diagnostic agents without causing the negative effects from a radioactive metal isotope. If imaging reveals that a subject is a candidate for therapeutic treatment, then the same compound/complex can be administered (either as cold-F/hot-M or hot-F/hot-M). As such, the hot-F/cold-M compound/complex is useful as a companion diagnostic to the hot-M therapeutic agent. Hence, $^{18}$F is used to image bound compounds/complexes that are chelated to nonradioactive metal isotopes, e.g., $^{89}$Y, $^{174}$Lu, $^{208}$Pb. Patients who show positive images with the hot-F/cold-M isotopolog can be treated with the radiotoxic isotopolog comprising cold-F/hot-M.

When the BF$_3$-containing moeity group is $^{18}$F-labelled (i.e. hot-F), there is disclosed use of the compound/complex for preparation of a radiolabelled tracer for imaging tissues expressing the cellular marker/antigen in a subject. There is also disclosed a method of imaging tissues expressing the cellular marker/antigen in a subject, in which the method comprises: administering to the subject a composition comprising the compound/complex and a suitable excipient; and imaging tissue of the subject, e.g. using PET or SPECT. When the tissue is a diseased tissue, targeted treatment using the hot-M version may then be selected for treating the subject.

When the metal chelator is chelated to a therapeutic radioisotope, there is disclosed use of the compound/complex (or a pharmaceutical composition thereof) for the treatment in a subject of conditions or diseases associated with expression of cellular marker/antigen. Accordingly, there is provided use of the compound in preparation of a medicament for treating a subject a condition or disease associated with expression of the cellular marker/antigen. There is also provided a method of treating the condition or disease in a subject, in which the method comprises: administering to the subject a composition comprising the compound/complex and a pharmaceutically acceptable excipient.

Various embodiments of the compound or molecular complex may be used for: imaging a subject to confirm the presence of a cellular marker of a disease or condition using the compound or molecular complex labelled with $^{18}$F; and treating the disease or condition using the compound or molecular complex chelated with a therapeutic radioactive isotope. There is therefore disclosed a method that comprises: administering the $^{18}$F-labelled compound or molecular complex of a theranostic pair to the subject; imaging the subject to confirm the presence of a cellular marker of a disease or condition using the compound or molecular complex labelled with $^{18}$F; and treating the disease or condition by administering the radiometallated compound or molecular complex of the theranostic pair. In some embodiments, the method/use further comprises performing an $^{18}$F/$^{19}$F-isotope exchange reaction to prepare the radiofluorinated compound/complex. In some embodiments, the method/use further comprises performing the chelation reaction to prepare the radiometallated compound/complex. In some embodiments, the compound/complex used for the diagnostic step is metallated with a non-therapeutic isotopolog of the therapeutic metal chelated to the compound/complex used in the treatment step.

For example, but without limitation, the cell-targeting domain may be LLP2A and the tissue to be imaged may be a VLA-4-expressing tissue. For example, but without limitation, the cell-targeting domain may be LLP2A and the condition or disease may be a VLA-4-expressing condition or disease, such as multiple myeloma, leukemia and other hematological malignancies, and melanoma, multiple sclerosis, asthma, Crohns disease, inflammatory bowel disease, and the like. For example, but without limitation, the compound may be DOTA-AMBF3-PEG2-LLP2A.

For example, but without limitation, the cell-targeting domain may be PSMA-617 and tissue to be imaged may be a PSMA-expressing tissue. For example, but without limitation, the cell-targeting domain may be PSMA-617 and the disease may be a PSMA-expressing cancer. For example, but without limitation, the compound may be PSMA-617-LysAMBF$_3$-DOTA. PSMA expression has been detected in various cancers (e.g. Rowe et al., 2015, *Annals of Nuclear Medicine* 29:877-882; Sathekge et al., 2015, *Eur J Nucl Med Mol Imaging* 42:1482-1483; Verburg et al., 2015, *Eur J Nucl Med Mol Imaging* 42:1622-1623; and Pyka et al., J Nucl Med Nov. 19, 2015 jnumed.115.164442). Accordingly, without limitation, the PSMA-expressing cancer may be prostate cancer, renal cancer, breast cancer, thyroid cancer, gastric cancer, colorectal cancer, bladder cancer, pancreatic cancer, lung cancer, liver cancer, brain tumor, melanoma, neuroendocrine tumor, ovarian cancer or sarcoma. In some embodiments, the cancer is prostate cancer.

For example, but without limitation, the cell-targeting domain may be TATE and the tissue to be imaged may be a somatostatin receptor-expressing tissue. For example, but without limitation, the cell-targeting domain may be TATE and the condition or disease may be a somatostatin receptor-expressing condition or disease, such as neuroendocrine tumours, breast cancers, small cell lung cancer, lymphomas, meningiomas, pituitary adenomas and pancreatic cancer. For example, but without limitation, the compound may be DOTA-Lys(AMBF$_3$)-TATE.

For example, but without limitation, the cell-targeting domain may be bombesin or a bombesin derivative (e.g. D-Phe-Gln-Trp-Ala-Val-Gly-His-Sta-Leu-NH$_2$) and the tissue to be imaged may be a GRPR-expressing tissue. For example, but without limitation, the cell-targeting domain may be bombesin or a bombesin derivative (e.g. D-Phe-Gln-Trp-Ala-Val-Gly-His-Sta-Leu-NH$_2$) and the condition or disease may be a GRPR-expressing condition or disease. Aberrant or ectopic GRPR expression has been detected in various conditions and diseases, including psychiatric/neurological disorders, inflammatory disease, and cancer. Accordingly, without limitation, the GRPR-expressing condition or disease may be psychiatric disorder, neurological disorder, inflammatory disease, prostate cancer, lung cancer, head and neck cancer, colon cancer, kidney cancer, ovarian cancer, liver cancer, pancreatic cancer, breast cancer, glioma or neuroblastoma. In some embodiments, the cancer is prostate cancer. For example, but without limitation, the compound may be DOTA-Lys(AMBF$_3$)-Pip-D-Phe-Gln-Trp-Ala-Val-Gly-His-Sta-Leu-NH$_2$.

REFERENCES NOT CITED INLINE (1) Tsien, R. Y. *Nat. Cell Biol.* 2003, Ss16-Ss21.
(2) Edwards, B. S.; Oprea, T.; Prossnitz, E. R.; Sklar, L. A. *Curr. Opin. Chem. Biol.* 2004, 8, 392-398.
(3) Aina, O. H.; Liu, R. W.; Sutcliffe, J. L.; Marik, J.; Pan, C. X.; Lam, K. S. *Mol. Pharm.* 2007, 4, 631-651.

(4) Gagnon, M. K. J.; Hausner, S. H.; Marik, J.; Abbey, C. K.; Marshall, J. F.; Sutcliffe, J. L. *Proc. Natl. Acad. Sci. USA* 2009, 106, 17904-17909.

(5) Lee, S.; Xie, J.; Chen, X. Y. *Chem. Rev.* 2010, 110, 3087-3111.

(6) Lee, S.; Xie, J.; Chen, X. Y. *Biochemistry* 2009, 49, 1364-1376.

(7) Liu, S. *Bioconjugate Chem.* 2009, 20, 2199-2213.

(8) Worsley, D. F.; Wilson, D. C.; Powe, J. E.; Benard, F. *Canadian Association of Radiologists Journal—Journal De L Association Canadienne Des Radiologistes* 2010, 61, 13-18.

(9) Newswire, P. *MarketsandMarkets:* 2011, http://www.prnewswire.com/news-releases/marketsandmarkets-radiopharmaceuticals-for-therapy-and-petspect-imaging-market-to-reach-4734-million-by-2015-127441573.html.

(10) Chen, E. Q.; Macintyre, W. J.; Go, R. T.; Brunken, R. C.; Saha, G. B.; Wong, C. Y. O.; Neumann, D. R.; Cook, S. A.; Khandekar, S. P. *J. Nucl. Med.* 1997, 38, 582-586.

(11) Rahmim, A.; Zaidi, H. *Nucl. Med. Commun.* 2008, 29, 193-207.

(12) Hicks, R. J.; Hofman, M. S. *Nat. Rev. Clin. Oncol.* 2012, 9, 712-720.

(13) Rischin, D.; Hicks, R. J.; Fisher, R.; Binns, D.; Corry, J.; Porceddu, S.; Peters, L. *J. Journal of Clinical Oncology* 2006, 24, 2098-2104.

(14) Newton-Northup, J. R.; Figueroa, S. D.; Deutscher, S. L. *Combinatorial Chem. High Throughput Screening* 2011, 14, 9-21.

(15) Xiao, W. W.; Wang, Y.; Lau, E. Y.; Luo, J. T.; Yao, N. H.; Shi, C. Y.; Meza, L.; Tseng, H.; Maeda, Y.; Kumaresan, P.; Liu, R. W.; Lightstone, F. C.; Takada, Y.; Lam, K. S. *Mol. Cancer Ther.* 2010, 9, 2714-2723.

(16) Lee, S.; Xie, J.; Chen, X. Y. *Biochemistry* 2010, 49, 1364-1376.

(17) Hong, H.; Goel, S.; Zhang, Y.; Cai, W. *Curr. Med. Chem.* 2011, 18, 4195-4205.

(18) Gong, P.; Shi, B. H.; Zheng, M. B.; Wang, B.; Zhang, P. F.; Hu, D. H.; Gao, D. Y.; Sheng, Z. H.; Zheng, C. F.; Ma, Y. F.; Cai, L. T. *Biomaterials* 2012, 33, 7810-7817.

(19) Mansi, L.; Virgolini, I. *Eur. J. Nucl. Med.* Mol. Imag. 2011, 38, 605-612.

(20) Banerjee, S. R.; Pomper, M. G. *Appl. Radiat. Isot.* 2013, 76, 2-13.

(21) Avril, N.; Menzel, M.; Dose, J.; Schelling, M.; Weber, W.; Janicke, F.; Nathrath, W.; Schwaiger, M. *J. Nucl. Med.* 2001, 42, 9-16.

(22) Alberini, J. L.; Edeline, V.; Giraudet, A. L.; Champion, L.; Paulmier, B.; Madar, O.; Poinsignon, A.; Bellet, D.; Pecking, A. P. *Journal of Surgical Oncology* 2011, 103, 602-606.

(23) Pecking, A. P.; Bellet, D.; Alberini, J. L. *Clin. Exp. Metastasis* 2012, 29, 847-852.

(24) Oberg, K. *Clinics* 2012, 67, 109-112.

(25) Kwekkeboom, D. J.; Kam, B. L.; van Essen, M.; Teunissen, J. J. M.; van Eijck, C. H. J.; Valkema, R.; de Jong, M.; de Herder, W. W.; Krenning, E. P. *Endocrine-Related Cancer* 2010, 17, R53-R73.

(26) Walker, R. C.; Smith, G. T.; Liu, E.; Moore, B.; Clanton, J.; Stabin, M. *J. Nucl. Med.* 2013, 54, 855-860.

(27) van Vliet, E. I.; Teunissen, J. J. M.; Kam, B. L. R.; de Jong, M.; Krenning, E. P.; Kwekkeboom, D. J. *Neuroendocrinology* 2013, 97, 74-85.

(28) Singla, S.; Gupta, S.; Reddy, R. M.; Durgapal, P.; Bal, C. S. Jap. *J. Clin. Oncol.* 2012, 42, 1202-1206.

(29) Yu, Z. L.; Ananias, H. J. K.; Carlucci, G.; Hoving, H. D.; Helfrich, W.; Dierckx, R.; Wang, F.; de Jong, I. J.; Elsinga, P. H. *Curr. Pharm. Des.* 2013, 19, 3329-3341.

(30) Wan, W.; Guo, N.; Pan, D.; Yu, C.; Weng, Y.; Luo, S.; Ding, H.; Xu, Y.; Wang, L.; Lang, L.; Xie, Q.; Yang, M.; Chen, X. *J. Nucl. Med.* 2013, 54, 691-698.

(31) Choi, H.; Phi, J. H.; Paeng, J. C.; Kim, S.-K.; Lee, Y.-S.; Jeong, J. M.; Chung, J.-K.; Lee, D. S.; Wang, K.-C. *Molecular imaging* 2013, 12, 213-217.

(32) Beer, A. J.; Haubner, R.; Sarbia, M.; Goebel, M.; Luderschmidt, S.; Grosu, A. L.; Schnell, O.; Niemeyer, M.; Kessler, H.; Wester, H. J.; Weber, W. A.; Schwaiger, M. *Clin. Cancer. Res.* 2006, 12, 3942-3949.

(33) Pozsgai, E.; Schally, A. V.; Halmos, G.; Rick, F.; Bellyei, S. *Hormone and Metabolic Research* 2010, 42, 781-786.

(34) Hohla, F.; Buchholz, S.; Schally, A. V.; Krishan, A.; Rick, F. G.; Szalontay, L.; Papadia, A.; Halmos, G.; Koster, F.; Aigner, E.; Datz, C.; Seitz, S. *Cancer Lett.* 2010, 294, 35-42.

(35) Okarvi, S. M. *Eur. J. Nucl. Med.* 2001, 28, 929-938.

(36) Laforest, R.; Liu, X. Quarterly *Journal of Nuclear Medicine and Molecular Imaging* 2008, 52, 151-158.

(37) Kemerink, G. J.; Visser, M. G. W.; Franssen, R.; Beijer, E.; Zamburlini, M.; Halders, S.; Brans, B.; Mottaghy, F. M.; Teule, G. J. *J. Eur. J. Nucl. Med.* Mol. Imag. 2011, 38, 940-948.

(38) Rowland, M. *J. Pharm. Sci.* 2012, 101, 4067-4074.

(39) Liu, Z. B.; Pourghiasian, M.; Radtke, M. A.; Lau, J.; Pan, J. H.; Dias, G. M.; Yapp, D.; Lin, K. S.; Benard, F.; Perrin, D. M. *Angew. Chem.—Int. Edit.* 2014, 53, 11876-11880.

(40) Liu, Z.; Pourghiasian, M.; Benard, F.; Pan, J.; Lin, K.-S.; Perrin, D. M. *Journal of nuclear medicine: official publication, Society of Nuclear Medicine* 2014, 55, 1499-1505.

(41) Zhang, H. W.; Abiraj, K.; Thorek, D. L. J.; Waser, B.; Smith-Jones, P. M.; Honer, M.; Reubi, J. C.; Maecke, H. R. *PLoS One* 2012, 7.

(42) Kwekkeboom, D.; Krenning, E. P.; de Jong, M. *J. Nucl. Med.* 2000, 41, 1704-1713.

(43) Ramogida, C. F.; Orvig, C. *Chem. Commun.* 2013, 49, 4720-4739.

(44) Kim, Y. S.; Brechbiel, M. W. *Tumor Biol.* 2012, 33, 573-590.

(45) Forster, G. J.; Engelbach, M.; Brockmann, J.; Reber, H.; Buchholz, H. G.; Macke, H. R.; Rosch, F.; Herzog, H.; Bartenstein, P. *Eur. J. Nucl. Med.* 2001, 28, 1743-1750.

(46) Walrand, S.; Flux, G. D.; Konijnenberg, M. W.; Valkema, R.; Krenning, E. P.; Lhommel, R.; Pauwels, S.; Jamar, F. *Eur. J. Nucl. Med.* Mol. Imag. 2011, 38, 57-68.

(47) Neesse, A.; Griesmann, H.; Gress, T. M.; Michl, P. *Arch. Biochem. Biophys.* 2012, 524, 64-70.

(48) Garmestani, K.; Milenic, D. E.; Brady, E. D.; Plascjak, P. S.; Brechbiel, M. W. *Nucl. Med. Biol.* 2005, 32, 301-305.

(49) Varasteh, Z.; Velikyan, I.; Lindeberg, G.; Sorensen, J.; Larhed, M.; Sandstrom, M.; Selvaraju, R. K.; Malmberg, J.; Tolmachev, V.; Orlova, A. *Bioconjugate Chem.* 2013, 24, 1144-1153.

(50) Hijnen, N. M.; de Vries, A.; Nicolay, K.; Grull, H. *Contrast Media & Molecular Imaging* 2012, 7, 214-222.

(51) Wienhoff, B. E.; Prasanphanich, A. F.; Lane, S. R.; Nanda, P. K.; Bandari, R. P.; Sieckman, G. L.; Smith, C. J. *Synthesis and Reactivity in Inorganic Metal—Organic and Nano-Metal Chemistry* 2013, 43, 178-184.

The present invention will be further illustrated in the following examples.

EXAMPLES $^{18}$F-labeled companion diagnostics are chemically identical to radiotherapeutic agents. Since $^{18}$F is preferred for PET, a hot-F/cold-M isotopolog for imaging is prepared, which serves as the companion diagnostic for a cold-F/hot-M isotopolog that may be used for treatment. Hence, $^{18}$F may be used to image peptides that are chelated to nonradioactive metal isotopes, e.g., $^{89}$Y $^{174}$Lu, $^{208}$Pb. Patients who show positive images with the hot-F/cold-M isotopolog may then be treated with the radiotoxic isotopolog comprising cold-F/hot-M.

For therapy, a radiotoxic metal (e.g. $^{90}$Y or $^{177}$Lu[50,51] and the like) may be used. For pre-treatment imaging, a different diagnostic metal would typically be used, e.g. $^{111}$In for SPECT or $^{64}$Cu for PET. This practice poses problems in correlating images with potential therapeutic outcomes. For example, DOTA-TATE is labeled with $^{111}$In for SPECT imaging and then with $^{90}$Y for therapy yet there are clear differences in uptake. Using the same tracer with the PET isotope $^{86}$Y is expensive and not readily available.[45,46] Hence, there is an advantage to peptides that contain both a metal chelator, e.g. DOTA, as well as a pendant organotrifluroboroate for labeling with $^{18}$F-fluoride. While eventually the chelator could be used for metal chelation—either to a radiotoxic metal for therapeutic use or to a non-radioactive metal that might be used as a surrogate for the radiotoxin (i.e. the radiotoxic metal) or for other purposes including changing the PKPC of the F-18 labeled tracer—a compound/complex (tracer) with both a chelator and a $BF_3$ prosthetic could be a superior PET imaging agent.

Figure 2:
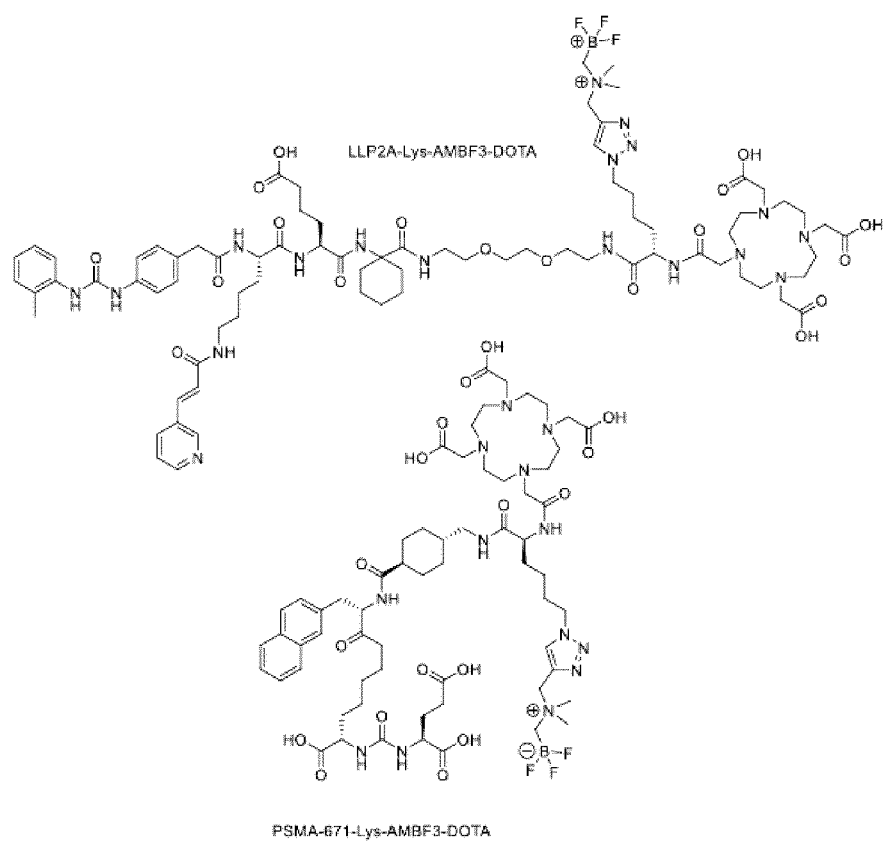
FIG. 2 shows the chemical structures of DOTA-AMBF3-PEG2-LLP2A (also called LLP2A-LysAMBF3-DOTA) and PSMA-617-LysAMBF3-DOTA.
Figure 3:
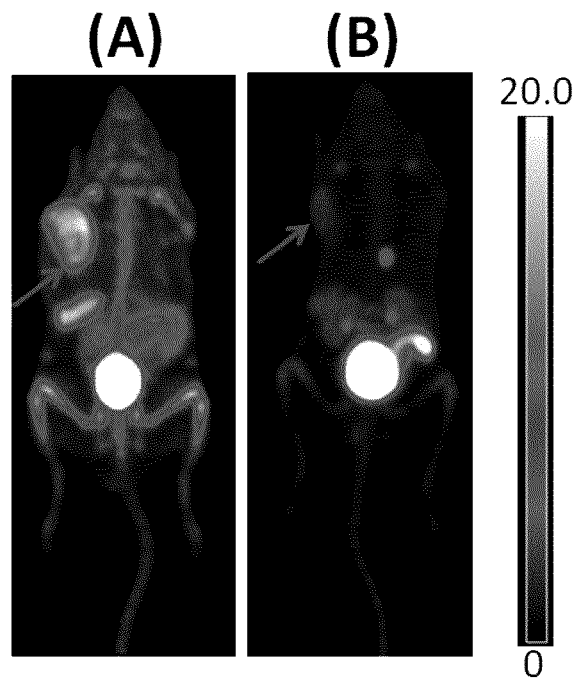
FIG. 3 shows maximum intensity projection images (1 h post-injection) of F-18 labeled LLP2A-Lys-AMBF3-DOTA in B16F10 melanoma xenograft-bearing mice (A) without and (B) with co-injection of nonradioactive LLP2A-Lys-AMBF3-DOTA (100 μg).

Two compositions were initially prepared based on a PSMA-targeting urea and an integrin-targeting peptidic ligand, LLP2A (see FIG. 2). Surprisingly, when labeled with $^{18}$F-fluoride through isotope exchange, these nonmetallated compositions give excellent tumor uptake values along with extraordinary tumor:non-tumor ratios (see Tables 5, 6, 7 and FIGS. 3 and 4).

Cell Culture Methods

The B16F10 melanoma cell line (*Mus musculus*) was obtained commercially from ATTC (CRL-6475). The cell line was confirmed pathogen-free by the IMPACT 1 mouse profile test (IDEXX BioResearch). Cells were cultured in Dulbecco's Modified Eagle's Medium (DMEM, StemCell Technologies) supplemented by 10% FBS, 100 U/mL penicillin and 100 μg/mL streptomycin at 37° C. in a humidified incubator containing 5% $CO_2$. Cells grown to approximately 90% confluence were washed with sterile 1×PBS (pH 7.4), followed by trypsinization.

The LNCap cell line was obtained from ATCC (LNCaP clone FGC, CRL-1740). It was established from a metastatic site of left supraclavicular lymph node of human prostatic adenocarcinoma. Cells were cultured in PRMI 1640 medium supplemented with 10% FBS, penicillin (100 U/mL) and streptomycin (100 μg/mL) at 37° C. in humidified incubator containing 5% $CO_2$. Cells grown to 80-90% confluence were then washed with sterile phosphate-buffered saline (1×PBS pH 7.4) and trypsinization.

In Vivo Biodistribution and PET/CT Imaging Studies of F-18 LLP2A-Lys-AMBF3-DOTA

All animal experiments were conducted according to the guidelines established by Canadian Council on Animal Care and approved by Animal Ethics Committee of the University of British Columbia. Mice were housed under pathogen-free conditions and kept on twelve-hour light and dark cycles in the Animal Resource Centre of BC Cancer Research Centre, Vancouver, Canada. PET imaging and biodistribution studies were performed using male C57BL/6J mice. For tumor implantation, mice were anesthetized by inhalation with 2% isoflurane in 2.0 L/min of oxygen, and 1×10$^6$ B16F10 cells were implanted subcutaneously on the right back at the level of the forelimbs. Mice were imaged or used in biodistribution studies once the tumor grew to reach 8-10 mm in diameter in 8-10 days.

PET/CT imaging studies were carried out on a microPET/CT scanner (Inveon, Siemens). Briefly, for static PET scans, each tumor bearing mouse was injected with 4-6 MBq of F-18 labeled LLP2A-Lys-AMBF3-DOTA via the caudal lateral tail vein under isoflurane sedation. For blocking study, mice were co-injected with 100 μg of non-radioactive LLP2A-Lys-AMBF3-DOTA. After injection, the mice were allowed to recover and roam freely in their cages. After 50 min, the mice were sedated again and positioned in the scanner. A baseline CT scan was obtained for localization and attenuation correction. This was followed by a 10 min static PET scan. The mice were kept warm by a heating pad during acquisition. The mice were euthanized using $CO_2$ inhalation after static PET imaging followed by biodistribution. The PET images were reconstructed using the ordered subset expectation maximization and maximum a posteriori algorithm (OSEM3D/MAP), using 2 OSEM3D iterations followed by 18 MAP iterations, with a requested resolution of 1.5 mm.

Mice for biodistribution study only were anesthetized by 2% isoflurane inhalation, and injected with 1-2 MBq of F-18 labeled LLP2A-Lys-AMBF3-DOTA. For blocking studies, 100 μg of non-radioactive LLP2A-Lys-AMBF3-DOTA was co-injected with the radioactive compound. After injection, the mice were allowed to recover and roam freely in their cages, and euthanized by $CO_2$ inhalation 1 h later. Blood was promptly withdrawn, and the organs of interest were harvested, rinsed with 1×PBS (pH 7.4), and blotted dry. Each organ was weighed and the radioactivity of the collected tissue was measured using a WIZARD 2480 (PerkinElmer), normalized to the injected dose using a standard curve and expressed as the percentage of the injected dose per gram of tissue (% ID/g).

In Vivo Biodistribution and PET/CT Imaging Studies of F-18 PSMA-Lys-AMBF3-DOTA

Imaging and biodistribution experiments were performed using NODSCID 1L2RγKO male mice. The mice were maintained and the experiments were conducted in according to the guidelines established by Canadian Council on Animal Care and approved by Animal Ethics Committee of the University of British Columbia. Mice were anesthetized by inhalation with 2% isoflurane in oxygen, and implanted subcutaneously with 1×10$^7$ LNCaP cells behind left shoulder. Mice were imaged or used in biodistribution studies when the tumor grew up to reach 5-8 mm in diameter during 5-6 weeks.

PET imaging experiments were conducted using Siemens Inveon (Erlanger, Germany) micro PET/CT scanner. Each tumor bearing mouse was injected 6-8 MBq of F-18 labeled PSMA-Lys-AMBF3-DOTA through the tail vein under anesthesia (2% isoflurane in oxygen). For blocking, the mice were co-injected with non-radioactive DCFPyL (0.5 mg). The mice were allowed to recover and roam freely in their cage. After 50 min, the mice were sedated again with 2% isoflurane in oxygen inhalation and positioned in the scanner. A 10-min CT scan was conducted first for localization and attenuation correction after segmentation for reconstructing the PET images. Then, a 10-min static PET imaging was performed to determined uptake in tumor and other organs. The mice were kept warm by a heating pad during acquisition.

For biodistribution studies, the mice were injected with the radiotracer as described above. For blocking, the mice were co-injected with non-radioactive DCFPyL (0.5 mg). After 1 hour, the mice were anesthetized with 2% isoflurane inhalation, and euthanized by $CO_2$ inhalation. Blood was withdrawn immediately from the heart, and the organs/tissues of interest were collected. The collected organs/tissues were weighed and counted using an automatic gamma counter. The uptake in each organ/tissue was normalized to the injected dose using a standard curve, and expressed as % ID/g.

Example 1: Tuned Biodistribution of $^{18}$F-LLP2A Trifluoroborate Radiotracer by DOTA Conjugation for VLA-4 Targeted PET Imaging of Melanoma 1.1 Abstract The transcellular very-late antigen 4 (VLA-4) is linked to tumor metastasis, drug resistance and is overexpressed by many cancers. Previous reports have shown successful PET imaging of VLA-4 expressing melanoma tumors using $^{64}$Cu and $^{68}$Ga chelated to LLP2A conjugates and more recently with $^{18}$F using [$^{18}$F]RBF$_3$ radioprosthetics. Yet, these antecedent [$^{18}$F]RBF$_3$-PEG$_2$-LLP2A derivatives showed modest tumor uptake values and significant accumulation in the GI tract. To address this, we designed a new RBF$_3$-LLP2A bioconjugate with an appended DOTA moiety, which increased tumor uptake and reduced GI accumulation. Methods: Herein, we describe the synthesis of a modified LLP2A-PEG$_2$-NH$_2$ (1) conjugate equipped with an $^{18}$F-trifluoroborate radioprosthetic, AMBF$_3$, and a DOTA moiety. The precursor, DOTA-AMBF$_3$-PEG$_2$-LLP2A (6) was radiolabeled by isotope exchange and was purified by semi-prep HPLC and C18 cartridge elution. Male C57BL/6J mice bearing B16-F10 melanoma tumors that overexpress the VLA-4 target were used to evaluate DOTA-[$^{18}$F]AMBF$_3$-PEG$_2$-LLP2A ([$^{18}$F]6) using a combination of static and dynamic PET scans, biodistribution studies and blocking by co-injecting 1 in excess to [$^{18}$F]6 at 1 h post injection (p.i.). Results: Precursor, 6, was synthesized and $^{18}$F-labeled to provide formulations of [$^{18}$F]6 with mean (±SD) radiochemical purities of 95.9±1.8%, in radiochemical yields of 4.8±2.9% having molar activities of 131.72±50.32 GBq/μmol. In vivo static PET images of [$^{18}$F]6 provided clear tumor visualization, and biodistribution studies showed that tumor uptake was 9.46±2.19 percent injected dose per gram of tissue (% ID/g) with high tumor:muscle and tumor:blood contrast ratios of ~8 and ~10, respectively. Blocking confirmed the specificity of [$^{18}$F]6 to VLA-4 in the tumor and the bone marrow. Dynamic PET showed clearance of [$^{18}$F]6 mainly via the renal pathway, wherein accumulation in the intestines was reduced ~10-fold compared to our previously investigated [$^{18}$F]RBF$_3$-PEG$_2$-LLP2A's, while spleen uptake was enhanced to levels similar to previously reported LLP2A-chelator radiotracers. Conclusions: This study highlights [$^{18}$F]6 as a promising VLA-4 radiotracer and demonstrates how biodistribution of LLP2A radiotracers can be rerouted from the GI tract to the spleen and bladder.

1.2 Introduction

The transcellular very-late antigen 4 (VLA-4) receptor is overexpressed in several cancers (1-15), and has been correlated with tumor metastasis (11, 16-18) and resistance to chemotherapy (19). Thus, it represents a versatile biomarker for imaging by the high-affinity peptidomimetic ligand, LLP2A. Since its initial development by Lam et al. (20), the LLP2A pharmacophore has been validated for in vivo VLA-4 targeting by NIR fluorescence imaging (21), single-photon emission computed tomography (SPECT) using $^{111}$In (22) and $^{99m}$Tc (23), and extensively by positron emission tomography (PET) with $^{68}$Ga and $^{64}$Cu. (23-27) Yet to date, there has been only one report of PET imaging with $^{18}$F; LLP2A-PEG$_2$-NH$_2$ (1) was appended to one of two radiprosthetic groups, ammoniumdimethyl-trifluoroborate (AMBF$_3$) and N-pyridinyl-para-trifluoroborate (N-Pyr-p-BF$_3$), then successfully $^{18}$F-labeled in a single step and PET imaged in mice with B16-F10 melanoma tumors. (28) At 1 h post injection (p.i.) the tumor uptake values of these two [$^{18}$F]RBF$_3$-PEG$_2$-LLP2A's were modest (2.8 and 4.4% ID/g) while high intestinal accumulation (~52% ID/g) was observed.

In contrast, LLP2A conjugates to chelated radiometals consistently exhibit tumor uptake values in the range of 10-15% ID/g at 1 h to 2 h p.i. using the same murine melanoma tumor model.(23-27) Nevertheless, radiometal-lated LLP2A-chelator conjugates are consistently sequestered in the spleen due to partial clearance by the reticuloendothelial system (RES). Since the aforementioned [$^{18}$F]RBF$_3$-PEG$_2$-LLP2A's displayed hydrophobic properties that led to sub-optimal images, we hypothesized that the incorporation of a hydrophilic chelator, DOTA, onto an RBF$_3$-PEG$_2$-LLP2A bioconjugate, would favor renal clearance. Hence, to test this hypothesis, we conjugated 1,4,7,10-tetraazacyclododecane-1,4,7,10-tetraacetic acid (DOTA) to a nearly identical AMBF$_3$-PEG$_2$-LLP2A precursor scaffold. To this end, we also designed a new amino acid, Fmoc-Lys-(AMBF$_3$), that was grafted and deprotected to enable further appendage of the DOTA moiety. The resulting conjugate DOTA-[$^{18}$F]AMBF$_3$-LLP2A (6) was labeled by $^{18}$F/$^{19}$F-isotope exchange (IEX) (28, 29) and investigated by in vivo PET imaging (static and dynamic scans), biodistribution studies, and VLA-4 blocking studies using 1 as the validated blocking agent. To the best of our knowledge, this report represents the first investigation of any $^{18}$F-labeled peptidic radiotracer with an appended DOTA-chelator that is used to tune biodistribution in favor of renal clearance.

1.3 Materials and Methods

Figure 9:
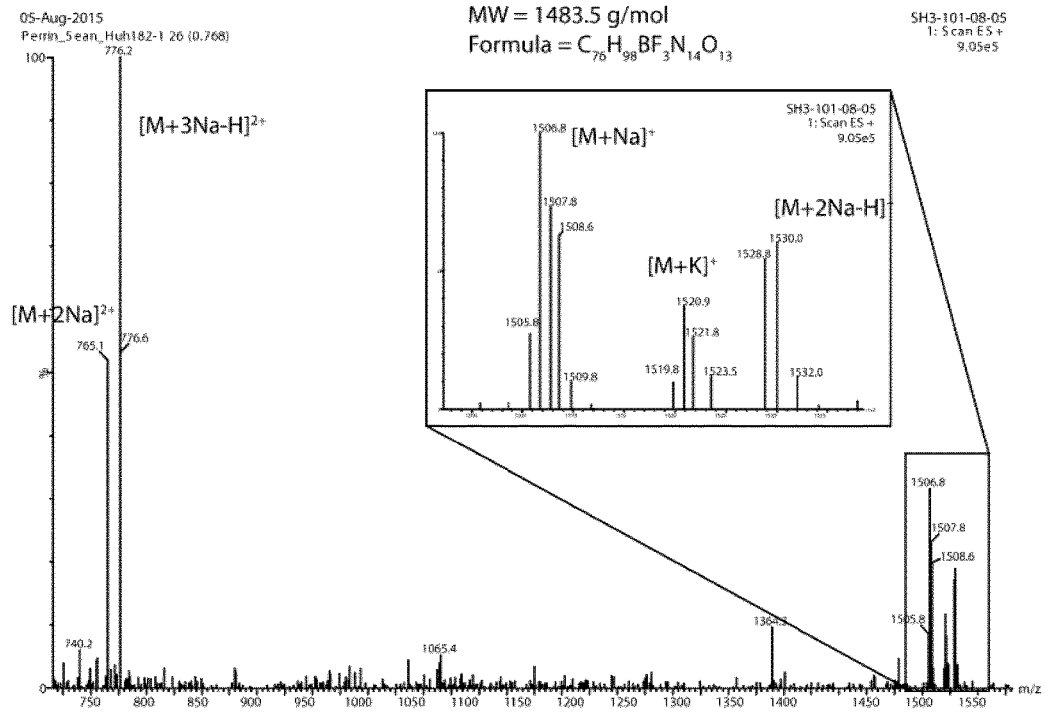
FIG. 9 shows ESI-MS(+) spectrum of LLP2A-PEG$_2$-AMBF$_3$—Fmoc (3): calculated for $C_{76}H_{98}BF_3N_{14}O_{13}$, 1483.5 m/z; found, [M+Na]$^+$=1506.8 m/z, [M+K]$^+$=1520.9 m/z.
Figure 10:
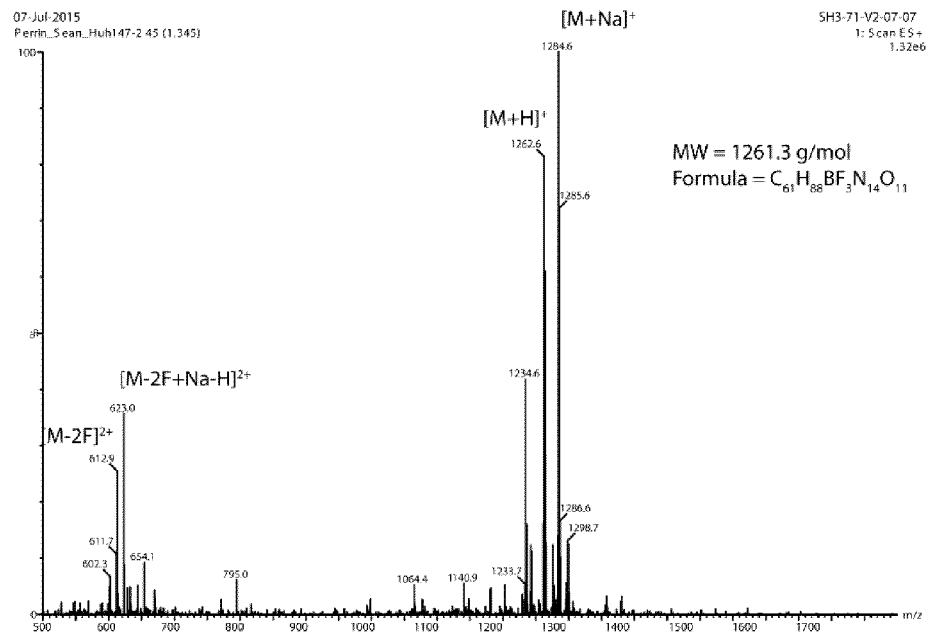
FIG. 10 shows ESI-MS(+) spectrum of AMBF$_3$-PEG$_2$-LLP2A-NH$_2$ (4): calculated for $C_{61}H_{88}BF_3N_{14}O_{11}$, 1261.3 m/z; found, [M+H]$^+$=1262.6 m/z, [M+Na]$^+$=1284.6 m/z.
Figure 11:
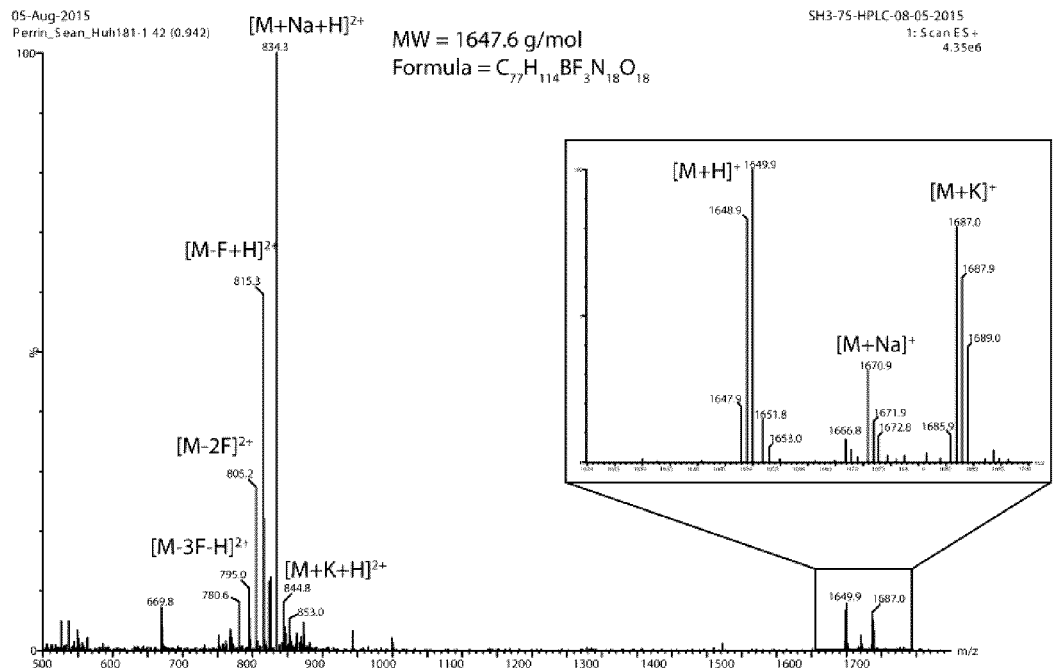
FIG. 11 shows ESI-MS(+) spectrum of DOTA-AMBF$_3$-PEG$_2$-LLP2A (6): calculated for $C_{77}H_{114}BF_3N_{138}O_{18}$, 1647.6 m/z; found, [M+H]$^+$=1648.9 m/z, [M+Na]$^+$=1670.9 m/z, [M+K]$^+$=1687.0 m/z.
Figure 12:
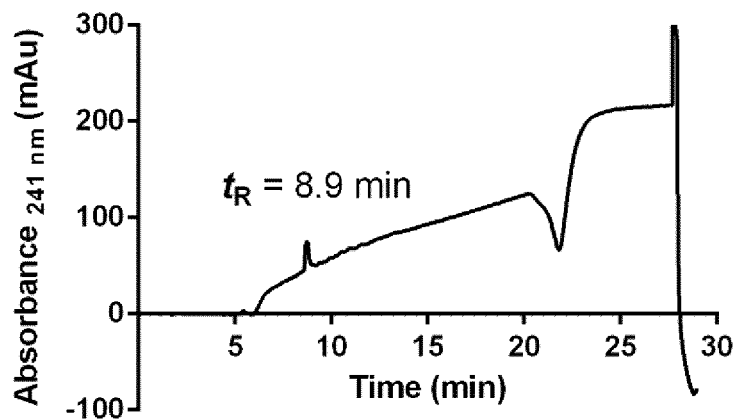
FIG. 12 shows an analytical HPLC chromatogram ($A_{Abs}$=241 nm) of 6 ($t_R$=8.9 min) after semi-prep HPLC purification (>95% purity) performed using HPLC method A.

Synthesis of DOTA-AMBF$_3$-PEG$_2$-LLP2A (6). The LLP2A peptidomimetic was synthesized on the solid phase as previously described, (20), while using a 0-bis-(aminoethyl)ethyleneglycol trityl resin for anchoring a PEG$_2$ spacer and an —NH$_2$ conjugation handle, as previously reported (28, 30). LLP2A-PEG$_2$-NH$_2$ (1) (4.2 mg, 4.46 μmol, 1 eq.) was dissolved in 200 μL of (1:19) DIPEA:DMF (v/v) and was subsequently used to dissolve Fmoc-Lys-(AMBF$_3$)—NHS (2) (5.85 mg, 8.91 μmol, 2 eq.), the synthesis of which is given in the supplementary information (Scheme 2). The conjugation proceeded at r.t. for 2 h. The mixture was concentrated by speed-vac (~50 μL-100 μL), precipitated with 1.0 mL Et$_2$O and centrifuged. The supernatant was removed and the product was redissolved in 50 μL DMF. The described Et$_2$O precipitation/centrifugation methods were repeated, and the final pellet was dried by speed-vac. These methods gave 6.5 mg (~4.3 μmol) of product in near quantitative yield of LLP2A-PEG$_2$-AMBF$_3$—Fmoc (3). ESI-MS(+): calculated for $C_{76}H_{98}BF_3N_{14}O_{13}$, 1483.5 m/z; found, [M+Na]$^+$=1506.8 m/z, [M+2Na–H]$^+$=1528.8 m/z (FIG. 9). TLC: [(1:19) NH$_4$OH:EtOH, v/v], $R_f$=0.46 (visible with 254 nm). The intermediate, 3 (1.5 mg, 1 μmol, 1 eq.), was dissolved with 200 μL of (1:4) piperidine:DMF (v/v), and Fmoc-removal was achieved within 2 h at rt. The mixture was concentrated and subjected to two rounds of the described Et$_2$O precipitation/centrifugation methods. The final pellet was dried by speed-vac to provide ~1.3 mg (~1 µmol) of AMBF$_3$-PEG$_2$-LLP2A-NH$_2$ (4) with a quantitative yield. ESI-MS(+): calculated for C$_{61}$H$_{88}$BF$_3$N$_{14}$O$_{11}$, 1261.3 m/z; found, [M+H]$^+$=1262.6 m/z, [M+Na]$^+$=1284.6 m/z (FIG. 10). TLC: [(1:19) NH$_4$OH:EtOH, v/v], R$_f$=0.18 (visible with 254 nm, stained with ninhydrin). The intermediate, (1.9 µmol) of the purified (>95% purity) radiotracer precursor, 6 (characterized by ESI-MS, FIG. 11 and HPLC, FIG. 12), for a 7.4% yield. ESI-MS(+): calculated for C$_{77}$H$_{114}$BF$_3$N$_{18}$O$_{18}$, 1647.6 m/z; found, [M+H]$^+$=1648.9 m/z, [M+Na]$^+$=1670.9 m/z [M+K]$^+$=1687.0 m/z. TLC: [(1:19) NH$_4$OH:MeOH], R$_f$=0.67 (visible with 254 nm, stained with light blue with bromocresol green).

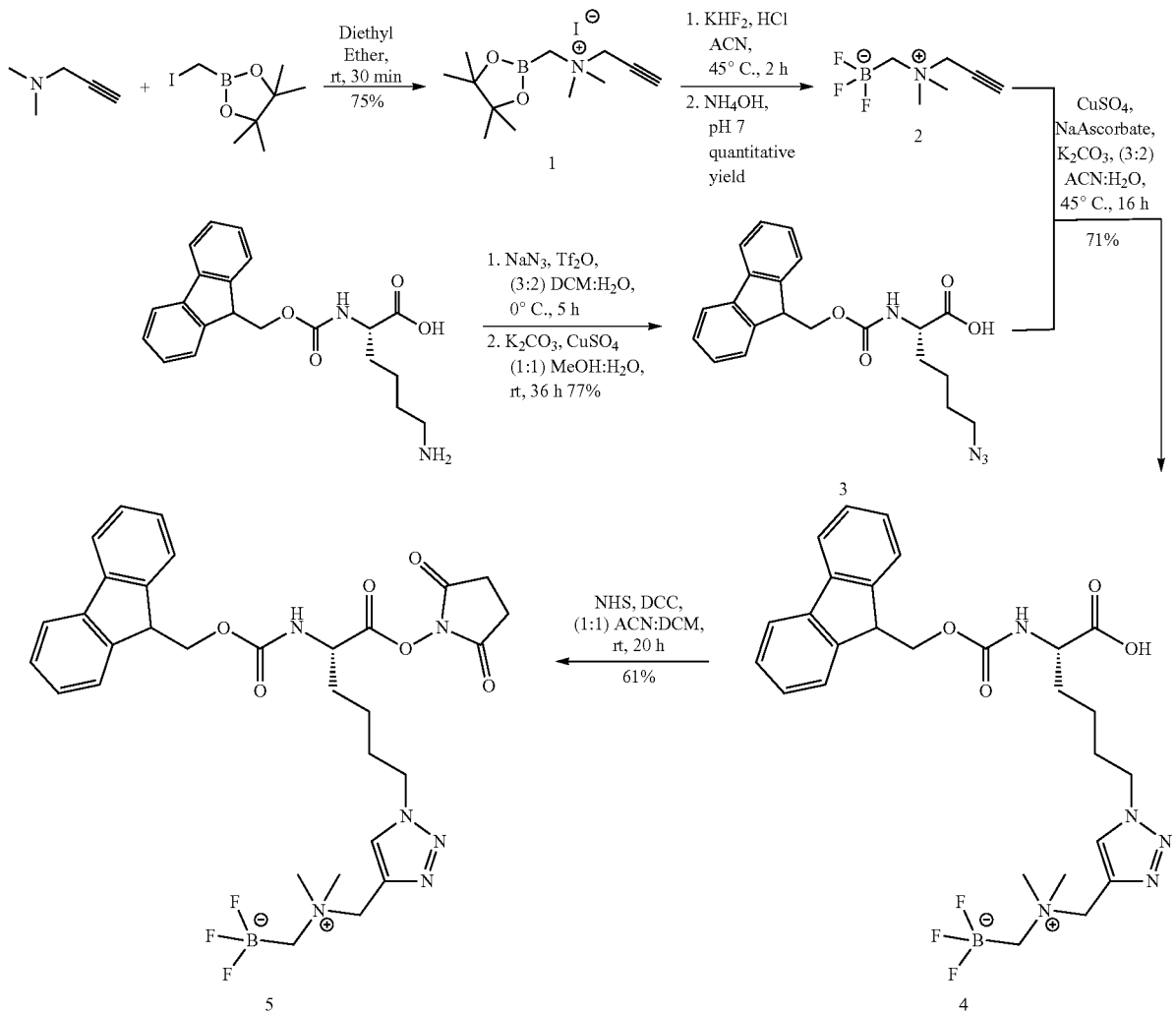

Scheme 2: Synthetic scheme for Fmoc-Lys(AMBF$_3$)-O-NHS.

4 (1.8 mg, 1.4 µmol, 1 eq.), was dissolved in 100 µL of (1:19) DIPEA:DMF (v/v) and conjugated to DOTA-NHS (5) (1.6 mg, 2.1 µmol, 1.5 eq.) within 2 h at rt. The mixture was concentrated and subjected to two rounds of the described Et$_2$O precipitation/centrifugation methods. The final pellet was dried by speed-vac to provide 2.4 mg (~1.4 µmol) of crude DOTA-AMBF$_3$-PEG$_2$-LLP2A (6). The aforementioned procedures were repeated to obtain 42.1 mg of crude 6 for HPLC purification. These combined samples were dissolved in 1.0 mL of (1:1) MeCN with 0.1% formic acid: H$_2$O with 0.1% formic acid (v/v) and purified by HPLC method A. The product (6) was collected at t$_R$=8.9 min and diluted with an equivalent volume of H$_2$O before freezing with dry ice and lyophilisation. These methods gave 3.1 mg ESI-MS characterization. Mass spectra were acquired using a Waters ZQ spectrometer with either MeOH or CH$_3$CN as the mobile phase.

HPLC methods and characterizations. The Agilent 1100 HPLC (auto-sampler unit and multi-channel PDA detector) was used to purify the precursors, 6, by HPLC method A. The Chromatographic Specialties Inc. Knauer Smartline pump 100 and Bioscan radiation detector was to purify the $^{18}$F-radiotracers, 7, by HPLC method B. The Agilent Technologies 1200 HPLC (single-channel 1200 Series PDA detector and Bioscan radiation detector, linked by Agilent Interface 35900E) was used to develop standard curves for the precursors, 6, and for QC of 7 formulations prior to animal injections by HPLC method C.

HPLC method A: for the purification and analysis of 6. Agilent Eclipse XDB-C18, 9.4 mm×250 mm, 5 μm column; solvent A=MeCN with 0.1% formic acid (v/v) and solvent B=$H_2O$ with 0.1% formic acid (v/v); flow rate=2.0 mL/min; absorbance channels=257 nm (purification) and 241 nm (analysis). Gradient: i) 25% to 80% solvent A over 15 min, ii) 80% to 100% solvent A over 1 min, iii) 100% solvent A for 6 min, iv) 100% to 25% solvent A over 1 min, v) 25% solvent A for 6 min.

HPLC method B: for the purification of [$^{18}$F]6. Phenomenex Luna C18-100A, 10 mm×250 mm, 5 μM column; solvent A=$H_2O$ with 0.1% TFA (v/v) and solvent B=MeOH with 0.1% TFA (v/v); flow rate=4.5 mL/min; absorbance channel=257 nm. Initially, used an isocratic mixture containing 40% solvent B (v/v) for 12 min, then switched to 100% solvent B (v/v) for another 12 min. The $^{18}$F-radiotracer, [$^{18}$F]6, was collected at ~21 min to 23 min.

HPLC method C: for the analysis of [$^{18}$F]6. Phenomenex Jupiter C18-300A, 4.6 mm×250 mm, 10 μm column, solvent A=$H_2O$ with 0.1% TFA (v/v), solvent B=MeCN with 0.1% TFA (v/v); flow rate=2.0 mL/min; absorbance channel=257 nm. Gradient: i) 0% solvent B for 4 min, ii) 0% to 40% solvent B over 2 min, iii) 40% solvent B for 4 min, iv) 40% to 80% solvent B over 4 min, v) 80% solvent B for 11 min, vi) 80% to 0% solvent B over 3 min, and vii) 0% solvent B for 4 min.

Synthesis of Fmoc-Lys-AMBF$_3$—NHS

Chemicals, Solvents, Hardware. 3-Dimethylamino-1-propyne and trifluoromethylsulfonyl anhydride were purchased from Sigma-Aldrich. Iodomethylboronic acid pinacol ester was purchased from Frontier Scientific. Potassium bifluoride (KHF$_2$) was purchased from Acros Organics. Sodium azide was purchased from Honeywell Riedel-de Haen. Fmoc-Lys-OH was purchased from Novabiochem. Cupric sulfate, ascorbic acid, sodium hydroxide, and potassium carbonate were purchased from Fisher Scientific. N-Hydroxysuccinimide and N,N'-dicyclohexylcarbodiimide were purchased from Alfa Aesar. Flash chromatography was performed using silica gel (230-400 mesh) purchased from Silicycle. Thin layer chromatography (TLC) was performed on silica gel 60 F$_{254}$ that was purchased from EMD Chemicals. $^1$H, $^{19}$F and $^{13}$C NMR spectra were recorded at room temperature on a Bruker AV300 instrument. The deuterated solvents acetonitrile-d$_3$, chloroform-d, and acetone-d$_6$ were purchase from Sigma-Aldrich. Electrospray-ionization mass spectrometry (ESI-MS) was performed using a Micromass LCT instrument. HRMS was performed using a Waters-Micromass LCT with a time-of-flight (TOF) detector.

N-Propargyl-N,N-dimethylammoniomethylboronylpinacolate. To a flamed dried round bottom flask under Ar$_{(g)}$, 1.5 mL of 3-dimethylamino-1-propyne (13.8 mmol, 1.01 eq) was loaded and dissolved in 28 mL of Et$_2$O. A 3.67 g sample of iodomethylboronic acid pinacol ester (13.7 mmol, 1 eq) was added dropwise and the reaction was stirred for 30 min at RT. The product precipitated as a white solid and was collected via vacuum filtration. The crude was washed with cold Et$_2$O. The crude was transferred to a pre-weighed scintillation vial and was dried in vacuo. This gave 3.4 g (9.81 mmol) of 1 as a light beige powder for a 72% yield. $^1$H NMR (300 MHz, acetone-d$_6$) δ ppm: 1.35 (s, 12H), 3.56 (s, 6H), 3.67 (t, J=2.4 Hz, 1H), 3.74 (s, 2H), 4.90 (d, J=2.3 Hz, 2H). $^{13}$C NMR (75 MHz, acetone-d$_6$) δ ppm: 25.04, 53.61, 57.75, 73.01, 82.88, 86.48. ESI-MS(+): calculated for C$_{12}$H$_{23}$BNO$_2$+=224.1 m/z; found [M]$^+$=224.6 m/z.

N-Propargyl-N,N-dimethylammoniomethyl-trifluoroborate. Stock solutions of 3 M KHF$_{2\ (aq)}$ and 4 M HCl$_{(aq)}$ were prepared. Compound 1 (1.87 g, 5.33 mmol, 1 eq) was loaded into a 50 mL falcon tube with 10 mL of CH$_3$CN. A 9 mL volume of 3 M KHF$_{2\ (aq)}$ (27 mmol, 5.1 eq) and 8 mL of 4 M HCl$_{(aq)}$ (32 mmol, 6 eq) were added and the solution was stirred for 2 h while heating at 45° C. The solution was then neutralized with conc. NH$_4$OH$_{(aq)}$ until pH~7 which creates a biphasic layer of CH$_3$CN and the aqueous layer. The layer on the top (the organic CH$_3$CN layer) was collected into a 250 mL round bottom flask and the aqueous layer was washed with CH$_3$CN (3×10 mL). The crude product was dried by rotary evaporation. A 20 mL volume of acetone was used to precipitate additional salts from the crude product sample and the mixture was filtered using a glass sintered funnel. The filtrate was collected in a round bottom flask, was concentrated by rotary evaporation, and further dried in vacuo. The crude was then washed with 20 mL of diethyl ether and then with 20 mL of chloroform to dissolve any remaining excess pinacol. The crude sample was dissolved with minimal acetone and column chromatography (silica gel, 43-60 μm, 230-400 mesh, ~40 g; isocratic acetone) was performed while monitoring the eluting fractions by TLC (acetone, R$_f$=0.41, stained with I$_2$). The fractions containing purified 2 were pooled, concentrated by rotary evaporation and further dried in vacuo. The solid product was collected in a pre-weighed vial and dried in vacuo. This gave 911 mg (5.52 mmol) of 2 as a light orange solid for a quantitative yield. $^1$H NMR (300 MHz, acetone-d$_6$) δ ppm: 2.54 (br. s, 2H), 3.24 (s, 6H), 3.47 (t, J=2.4 Hz, 1H), 4.40 (d, J=2.3 Hz, 2H). $^{13}$C NMR (75 MHz, acetone-d$_6$) δ ppm: 52.21, 56.57, 73.13, 80.48. $^{19}$F NMR (282 MHz, acetone-d$_6$) δ ppm: −138.66 (q, 3F). ESI-MS(+): calculated for C$_6$H$_{11}$BF$_3$N, 165.0 m/z; found [M+Na]$^+$=188.4 m/z.

Fmoc-Lys(N$_3$)—OH. Trifluoromethylsulfonyl azide was used for a diazo-transfer of the primary amine of Fmoc-Lys-OH. A 2.94 g sample of NaN$_3$ (45.2 mmol, 8.63 eq) was loaded to a round bottom flask and dissolved in 20 mL of (2:3) H$_2$O:CH$_2$Cl$_2$ (v/v). As the mixture was stirred, 1.02 mL of triflic anhydride (Tf$_2$O) (6 mmol, 1.15 eq) was added dropwise over 30 min. The reaction was stirred for 5 h in an ice water bath at −0° C. The organic layer was extracted with CH$_2$Cl$_2$ (2×20 mL) and the collected organic layers were subsequently washed with sat. NaHCO$_{3\ (aq)}$ (20 mL). Trifluoromethylsulfonyl azide was dissolved in the described collected organic layer. A 1.93 g sample of Fmoc-Lys-OH (5.24 mmol, 1 eq) was loaded to a round bottom flask charged with 2.32 g of K$_2$CO$_3$ (16.8 mmol, 3 eq) and 15 mg of Cu(II)SO$_4$ (94.0 μmol, 0.39 mol %), and was dissolved in 15 mL of (1:1) MeOH:H$_2$O (v/v). The organic layer containing triflic azide was added dropwise over 30 min. The solution was stirred for 21 h at RT and the reaction was quenched with 60 mL of 2.5 M HCl$_{(aq)}$. The organic layer was extracted with CH$_2$Cl$_2$ (3×20 mL) and was washed with brine (2×50 mL). The collected organic layer was dried with anhydrous Na$_2$SO$_4$ and the salt was removed by vacuum filtration. The collected solution was concentrated by rotary evaporation. Column chromatography (silica gel, 43-60 μm, 230-400 mesh, ~80 g; solvent gradient of (0.5:99.5) MeOH:CH$_2$Cl$_2$ (v/v) to (1:99) MeOH:CH$_2$Cl$_2$ (v/v)) was performed while monitoring the eluting fractions by TLC ((1:9) MeOH:CH$_2$Cl$_2$ (v/v), R$_f$=0.37, visible with 254 nm, stained with I$_2$ and bromocresol green). The pure fractions were concentrated by rotary evaporation and further dried in vacuo. This gave 1.60 g (4.06 mmol) of 3 as a white waxy solid for a 77% yield. $^1$H NMR (300 MHz, CDCl$_3$) δ ppm: 1.05-2.21 (m, 6H), 3.05-3.36 (m, 2H), 4.23 (t, J=6.9 Hz, 1H), 4.39-4.74 (m, 3H), 5.57 (d, J=8.2 Hz, 1H), 7.32 (t, J=7.32 Hz, 2H), 7.41 (t, J=7.4 Hz, 2H), 7.51-7.67 (m, J=7.5 Hz, 2H), 7.77 (d, J=7.5 Hz, 2H), 9.76 (s, 1H). $^{13}$C NMR (75 MHz, CDCl$_3$) δ ppm: 22.48, 28.36, 31.86, 47.16, 51.07, 53.59, 67.22, 120.09, 125.10, 127.14, 127.83, 141.37, 143.67, 156.27, 176.84. ESI-MS(−): calculated for C$_{21}$H$_{22}$N$_4$O$_4$, 394.4 m/z; found [M−H]$^-$=393.4 m/z and [2M−H]$^-$=787.7 m/z.

Fmoc-Lys(AMBF$_3$)—OH. A fresh stock solution of 1 M sodium ascorbate was prepared by dissolving 1.98 g of sodium ascorbate (0.01 mol) in 10 mL of DI H$_2$O. A stock solution of 1 M Cu(II)SO$_4$ $_{(aq)}$ was then prepared by dissolving 1.60 g of anhydrous Cu(II)SO$_4$ (0.01 mol) in 10 mL of DI H$_2$O. A 414.6 mg sample of compound 2 (2.513 mmol, 5.24 eq) was loaded into a round-bottom flask and dissolved in 2.5 mL of (3:2) CH$_3$CN:H$_2$O (v/v). A 1.5 mL volume of 1 M Cu(II)SO$_4$ $_{(aq)}$ (1.5 mmol, 3.1 eq) was added first, followed by the addition of 3 mL of 1 M sodium ascorbate (3 mmol, 6.2 eq). A 189 mg sample of compound 3 (479 µmol, 1 eq) was then added to the solution. The solution was then neutralized to pH ~7 with the addition of 101 mg of K$_2$CO$_3$ (732 µmol, 1.5 eq) and then was stirred for 16 h at 45° C. The mixture was vacuum filtered to remove precipitates and the filtrate was concentrated by rotary evaporation. The dried crude was resuspended in (1:1) MeOH:CH$_2$Cl$_2$ (v/v) (5×10 mL), vacuum filtered to remove precipitates, and the filtrate was dried by rotary evaporation. The dried crude was then resuspended in (5:95) MeOH:CH$_2$Cl$_2$ (v/v) (5×10 mL), vacuum filtered to remove precipitates, and the filtrate was again dried by rotary evaporation. Column chromatography (silica gel, 230-400 mesh, ~50 g; solvent of (1:4:95) AcOH:MeOH:CH$_2$Cl$_2$ (v/v/v)) was performed while monitoring eluting fractions by TLC (1:10:89 AcOH:MeOH:CH$_2$Cl$_2$ (v/v/v), R$_f$=0.21, visible with 254 nm light, stained with I$_2$). The fractions containing pure 4 were pooled, concentrated by rotary evaporation and further dried in vacuo. This gave 192 mg (343 µmol) of 4 as dark yellow oil for a 71% yield. $^1$H NMR (300 MHz, CD$_3$CN) δ ppm: 1.27-1.91 (m, 6H), 2.29 (d, J=4.57 Hz, 2H), 2.95 (s, 6H), 4.08 (br s, 1H), 4.22 (t, J=6.90 Hz, 1H), 4.32 (d, J=7.08 Hz, 2H), 4.38 (t, J=6.97 Hz, 1H), 4.43 (s, 2H), 6.01 (d, J=5.94 Hz, 1H), 7.33 (t, J=7.30 Hz, 2H), 7.42 (t, J=7.50 Hz, 2H), 7.66 (d, J=4.34 Hz, 2H), 7.83 (d, J=7.54 Hz, 2H), 8.02 (s, 1H). $^{13}$C NMR (75 MHz, CD$_3$CN) δ ppm: 23.22, 30.19, 31.56, 47.97, 50.79, 53.45, 54.73, 61.28, 67.20, 120.93, 126.16, 128.07, 128.43, 128.65, 137.30, 142.07, 145.08, 157.09. $^{19}$F NMR (282 MHz, CD$_3$CN) δ ppm: −138.16 (d, 3F). ESI-MS(−): calculated for C$_{27}$H$_{33}$BF$_3$N$_5$O$_4$, 559.4 m/z; found [M−H]$^-$=558.5 m/z and [M+I]$^-$=686.4 m/z.

Fmoc-Lys(AMBF$_3$)—O—NHS. A 163.3 mg sample of 4 (291.7 µmol, 1 eq) was added to a round-bottom flask and dissolved with 8 mL of (1:1) CH$_2$Cl$_2$:CH$_3$CN (v/v). A 305 mg sample of DCC (1.48 mmol, 5.07 eq) was added to the solution; follow by the addition of 170 mg of NHS (1.48 mmol, 5.07 eq), and the solution was stirred at RT for 21 hours. The reaction mixture was vacuum filtered using a sintered funnel, and the collected filtrate was concentrated by rotary evaporation. Column chromatography (column diameter=0.5 cm; silica gel (230-400 mesh), ~10 g; gradient from CH$_2$Cl$_2$ increasing by 10% CH$_3$CN (v/v) per 50 mL to (1:1) CH$_2$Cl$_2$:CH$_3$CN (v/v)) was performed while monitoring eluting fractions by TLC (1:1) CH$_2$Cl$_2$:CH$_3$CN (v/v), R$_f$=0.52, visible with 254 nm, stained with I$_2$). The fractions containing pure 5 were pooled, concentrated rotary evaporation and further dried in vacuo. This gave 118 mg (180 µmol) of 5 as yellow oil for a 61% yield. $^1$H NMR (300 MHz, CD$_3$CN) δ ppm: 1.47-1.53 (m, 1H), 1.86-1.98 (m, 5H), 2.33 (d, J=4.1 Hz, 2H), 2.79 (s, 4H), 2.98 (s, 6H), 4.26 (t, J=6.9 Hz, 1H), 4.38 (d, J=7.5 Hz, 2H), 4.42 (d, J=7.0 Hz, 2H), 4.46 (d, J=4.3 Hz, 2H), 4.49-4.56 (m, 1H), 6.33 (d, J=7.8 Hz, 1H), 7.36 (t, J=7.4 Hz, 2H), 7.45 (t, J=7.4 Hz, 2H), 7.68 (d, J=7.3 Hz, 2H), 7.86 (d, J=7.5 Hz, 2H), 8.06 (s, 1H). $^{13}$C NMR (75 MHz, CD$_3$CN) δ ppm: 22.04. 25.16, 25.24, 25.40, 29.10, 30.55, 46.95, 49.83, 52.31, 52.55, 54.34, 60.27, 66.63, 117.34, 120.02, 125.21, 127.16, 127.54, 127.76, 136.42, 141.14, 144.02, 155.99, 168.64, 169.83. $^{19}$F NMR (282 MHz, CD$_3$CN) δ ppm: −138.21 (d, 3F). ESI-MS(+): calculated for C$_{31}$H$_{36}$BF$_3$N$_6$O$_6$, 656.5 m/z; found, [M+Na]$^+$=679.8 m/z. HRMS: calculated for C$_{31}$H$_{36}$BF$_3$N$_6$O$_6$, 656.4702 m/z; found [M+Na]$^+$=679.2618 m/z.

Structural characterization of Lys-AMBF$_3$ is shown in accompanying FIGS. 15 to 33.

Saturation binding assay. In vitro binding saturation assays were performed on B16-F10 cells following published procedures (n=3).(28) Cells were grown to near-confluence on 24 well poly-D-lysine plates. Growth media was removed, and reaction media (RPMI, 1% BSA, 100 U/mL penicillin/streptomycin) was added and allowed to incubate for at least 1 h at 37° C. Increasing concentrations (5 pM to 20 nM) of [$^{18}$F]6 were added to the cells and incubated for 1 h at 25° C. with mild agitation. Non-specific binding was determined by repeating the described incubations with [$^{18}$F]6 while simultaneously adding 1 (10 µM). After incubation, cells were washed twice with ice-cold PBS, harvested following incubation with trypsin, and measured for radioactivity using a WIZARD 2480 gamma counter (PerkinElmer). Values from the non-specific binding assays were subtracted from the respective values of the specific binding assays. Dissociation constants (K$_d$'S) were determined using GraphPad PRISM 7 with a one-site specific binding model.

Figure 13:
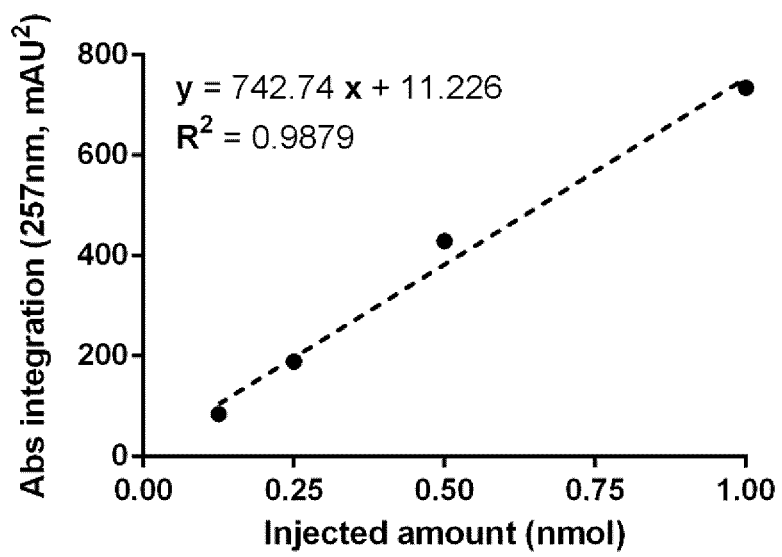
FIG. 13 shows a standard curve used for characterizing [$^{18}$F]6 (post HPLC-purification and formulation) based on the UV-vis absorption ($\lambda$=257 nm) of 6 and obtained using HPLC method C.

Radiolabeling of DOTA-AMBF$_3$-PEG$_2$-LLP2A (6) with [$^{18}$F]fluoride anion. Precursor 6 (80 nmol) was dissolved in 15 µL of 1 M pyridazine-HCl (pH=2), 10 µL of DMF, 15 µL of MeOH and 4 µL of 5 mM KHF$_2$ $_{(aq)}$ (50 mol % $^{19}$F$^-$ carrier) with a final pH of ~2.0 (Scheme 1). The $^{18}$F/H$_2$$^{18}$O (~1 Ci) was passed through an activated 9 mg QMA cartridge (pre-conditioned with 1.7 mL brine then rinsed with 2.5 mL water and dried with 3 mL air) to trap $^{18}$F (>95% efficiency), which was then eluted into a septum-sealed reaction vessel containing the precursor using ~80-100 µL of 0.9% saline (>90% efficiency). The solution was heated at 82-84° C. for 5 min and then heated in vacuo for 15 min. After quenching with 2 mL of 40 mM NH$_4$HCO$_2$ $_{(aq)}$ (pH=6.8), the solution was purified by semi-preparative HPLC with two successive isocratic solvent conditions (HPLC method B). The radiotracer [$^{18}$F]6, was collected and directly diluted into 50 mL of H$_2$O. By applying a small pressure of He$_{(g)}$ to the container, the resulting solution was passed through a Sep-Pak Light C18 cartridge (pre-washed successively with 9 mL EtOH, 9 mL H$_2$O and 10 mL air). The trapped [$^{18}$F]6 was eluted into a septum-sealed vial with 0.5 mL of (9:1) EtOH: 0.9% saline (v/v), and was finally formulated with 4 mL PBS to provide [$^{18}$F]6 in (1:9) EtOH:PBS (v/v) at pH ~7 for animal injections. All purified formulations of [$^{18}$F]6 were characterized by analytical HPLC (method C) to quantify the radiochemical purity, radiochemical yield, and molar activity based on a standard curve, (FIG. 13) prior to animal injections.

Scheme 1. Synthesis of 4 and precursor 6 for the production of [$^{18}$F]6.
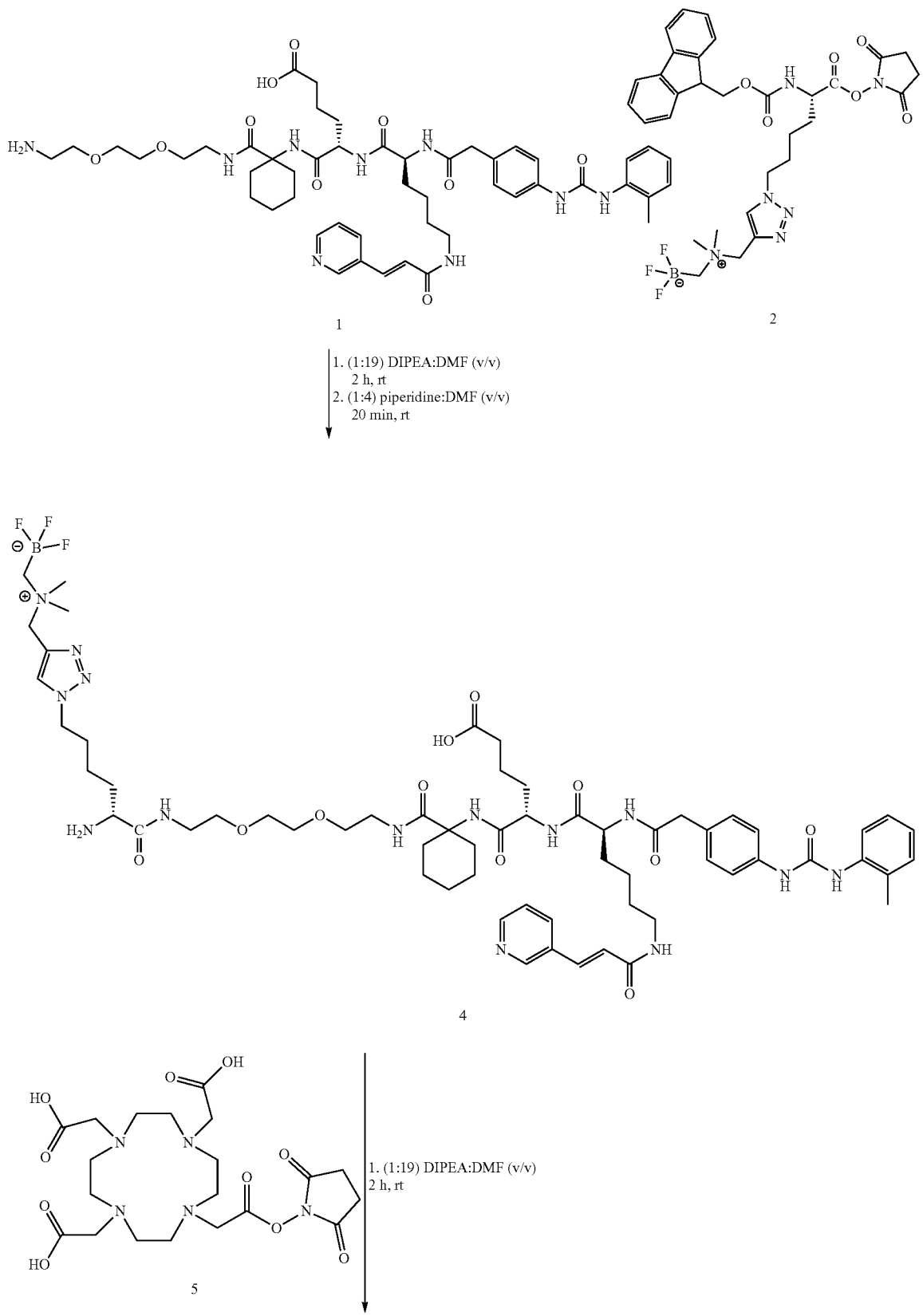

-continued

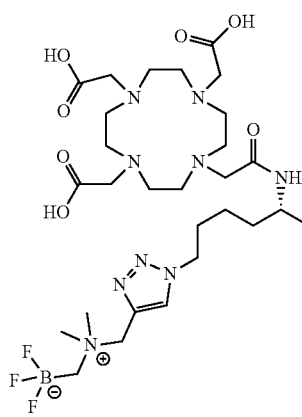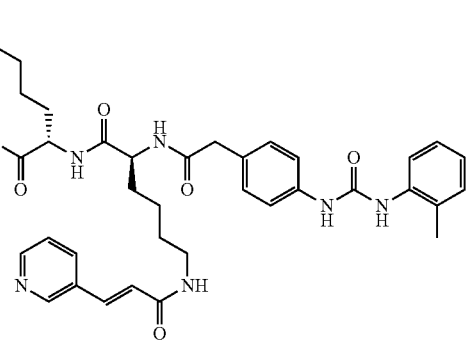

6

PET imaging of DOTA-[$^{18}$F]AMBF$_3$-PEG$_2$-LLP2A ([$^{18}$F]6) in B16-F10 tumor-bearing mice. B16-F10 cells (ATTC, CRL-6475) were cultured in DMEM with 10% FBS (v/v), 100 U/mL penicillin and 100 µg/mL streptomycin at 37° C. under 5% CO$_{2\ (g)}$. All animal experiments were conducted following the guidelines of the Canadian Council on Animal Care and were approved by Animal Ethics Committee of the University of British Columbia. Male C57BL/6J mice were anesthetized with 2% isoflurane, and were injected with 1×10$^6$ B16-F10 cells subcutaneously at the right shoulder. Tumors were allowed to grow until reaching diameters of 7-9 mm. PET and CT imaging studies involved a microPET/CT scanner (Inveon, Siemens) as previously reported (28, 31-33). For static PET scans (recorded for 10 min), mice were first injected with 4-6 MBq of ([$^{18}$F]6) via the tail vein while anesthetized with 2% isoflurane and were subjected to baseline CT scans (recorded for 10 min) prior to PET imaging. For static PET images involving competitive VLA-4 blocking, 200 µg of 1 was co-injected with 4-6 MBq of [$^{18}$F]6, and the described methods were used to obtain both baseline CT and PET images at 1 h p.i. Dynamic PET scans involved the described anesthesia, injection of 4-6 MBq of [$^{18}$F]6, baseline CT scans, and PET scans recorded from 5 sec. to 52.5 min p.i. (28 time points). Mice were finally euthanized using CO$_{2\ (g)}$ inhalation after each static PET imaging study and their organs were harvested for biodistribution measurements.

Biodistribution of DOTA-[$^{18}$F]AMBF$_3$-PEG$_2$-LLP2A ([$^{18}$F]6) in B16-F10 tumor-bearing mice. Mice were anesthetized using 2% isoflurane and injected with 2-3 MBq of [$^{18}$F]6 via the tail vein. For competitive VLA-4 blocking studies, 200 µg of 1 was co-injected with 2-3 MBq of [$^{18}$F]6. At 1 h p.i., mice were euthanized by CO$_{2\ (g)}$ inhalation, blood was collected, and the organs were excised. After rinsing and drying the samples, organs were weighed, their radioactivity was recorded using a Wallac WIZARD2 gamma counter (PerkinElmer), and values were expressed as % ID/g for each organ. Two-tailed ANOVA Sidak's multiple comparison tests (GraphPad PRISM) were used to evaluate statistical significance between the biodistribution of [$^{18}$F]6 alone compared with competitive blocking of VLA-4 by co-injections of 1.

Additional details are provided in Lepage et al., ChemBioChem 10.1002/cbic.201900632.

1.4 Results

Figure 8:
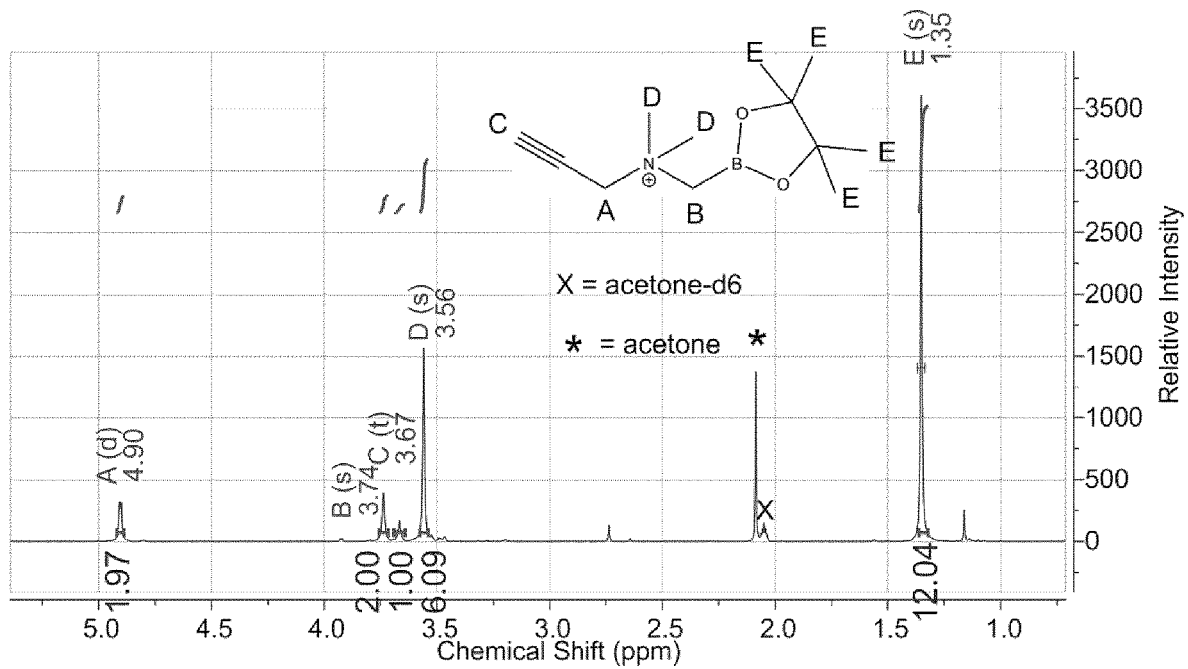
FIG. 8 shows $^1H$ NMR (acetone-$d_6$, 300 MHz, RT) spectrum of 1.
Figure 14:
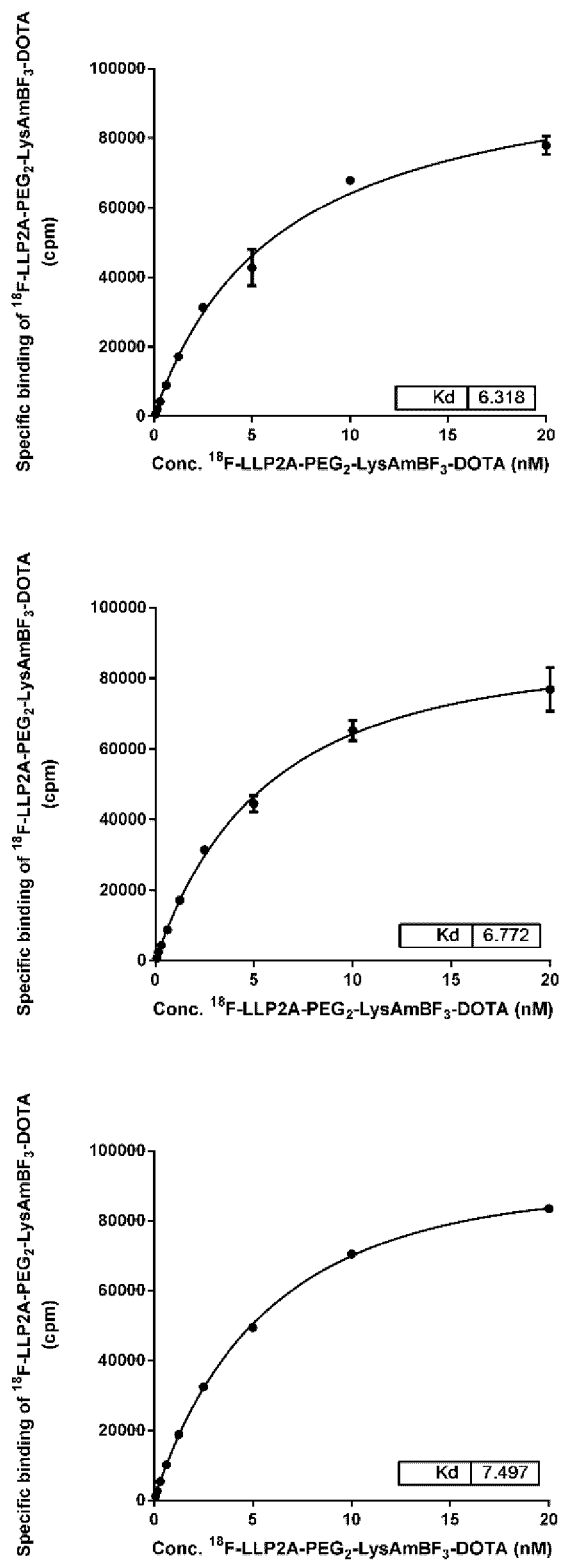
FIG. 14 shows in vitro binding saturation assays for the $^{18}$F-radiotracer, [$^{18}$F]6, with VLA-4 expressing B16-F10 cells (each in duplication, error bars showing±SD) giving a calculated $K_d$ value of 6.9±0.59 nM (n=3).
Figure 15:
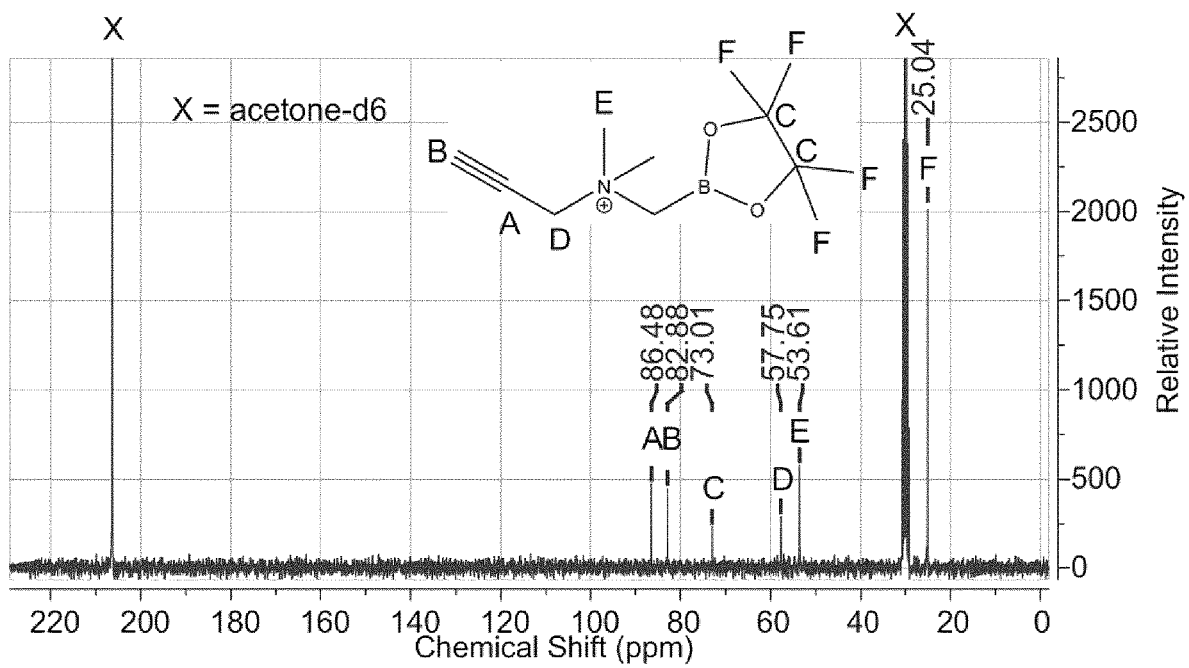
FIG. 15 shows $^{13}$C{$^1$H}NMR (acetone-$d_6$, 75 MHz, RT) spectrum of 1.
Figure 16:
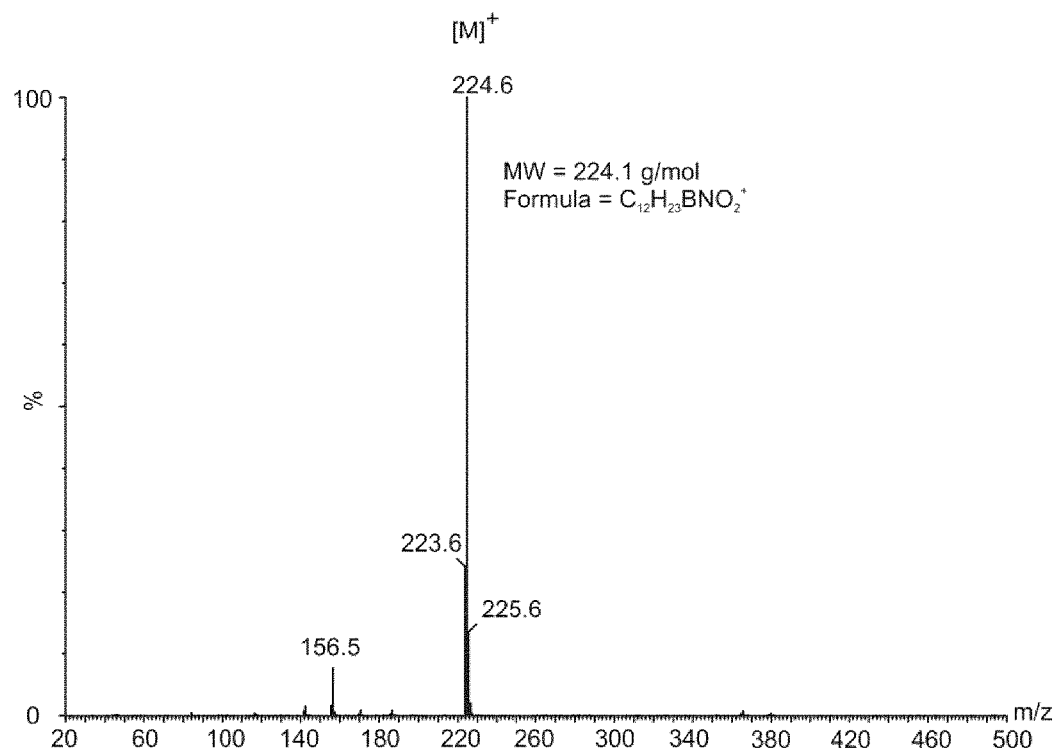
FIG. 16 shows ESI-MS(+) spectrum of 1: calculated for $C_{12}H_{23}BNO_2{}^+$=224.1 m/z; found, [M]$^+$=224.6 m/z.
Figure 17:
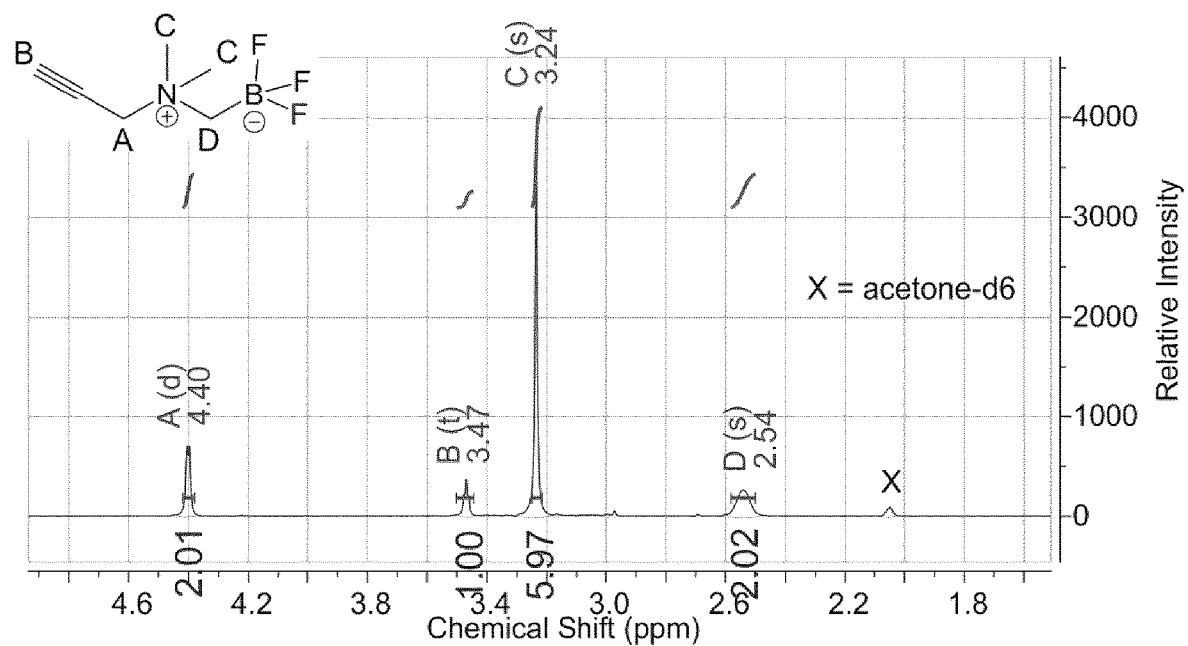
FIG. 17 shows $^1$H NMR (acetone-$d_6$, 300 MHz, RT) of 2.
Figure 18:
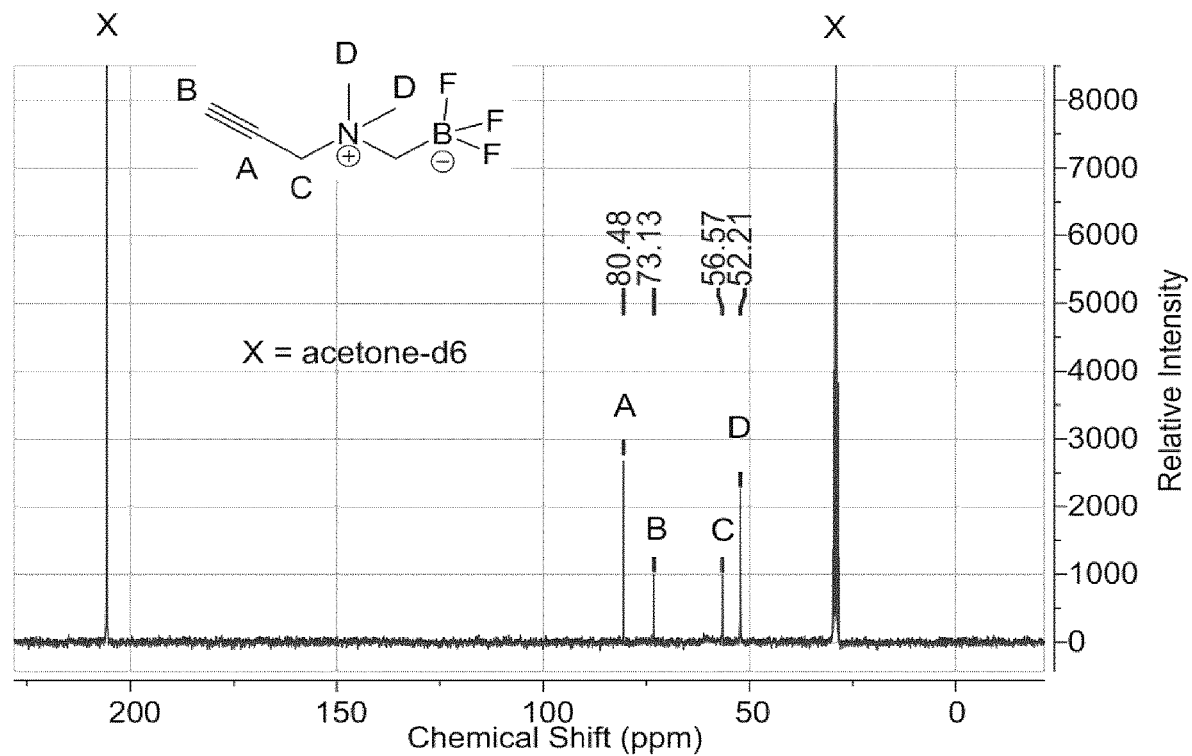
FIG. 18 shows $^{13}$C{$^1$H}NMR (acetone-$d_6$, 75 MHz, RT) spectrum of 2.
Figure 19:
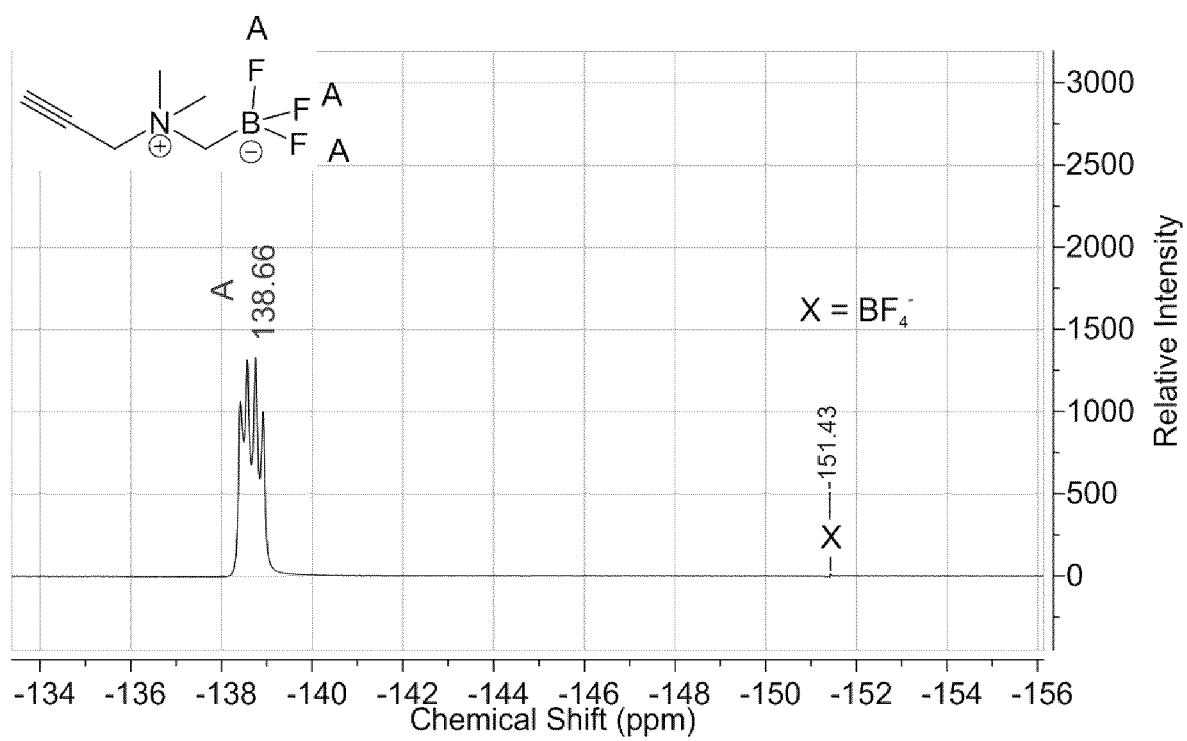
FIG. 19 shows $^{19}$F{$^1$H}NMR (acetone-$d_6$, 282 MHz, RT) spectrum of 2.
Figure 20:
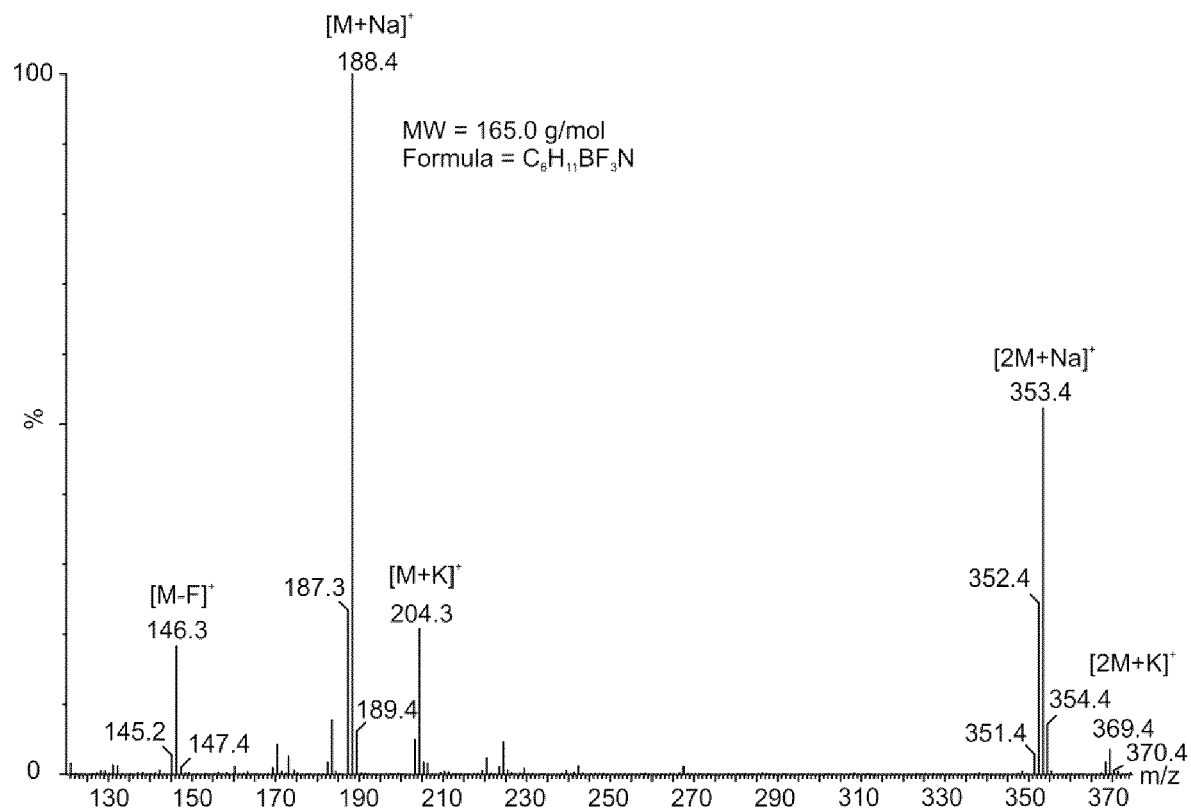
FIG. 20 shows ESI-MS(+) spectrum of 2: calculated for $C_6H_{11}BF_3N$, 165.0 m/z; found, [M+Na]$^+$=188.4 m/z.
Figure 21:
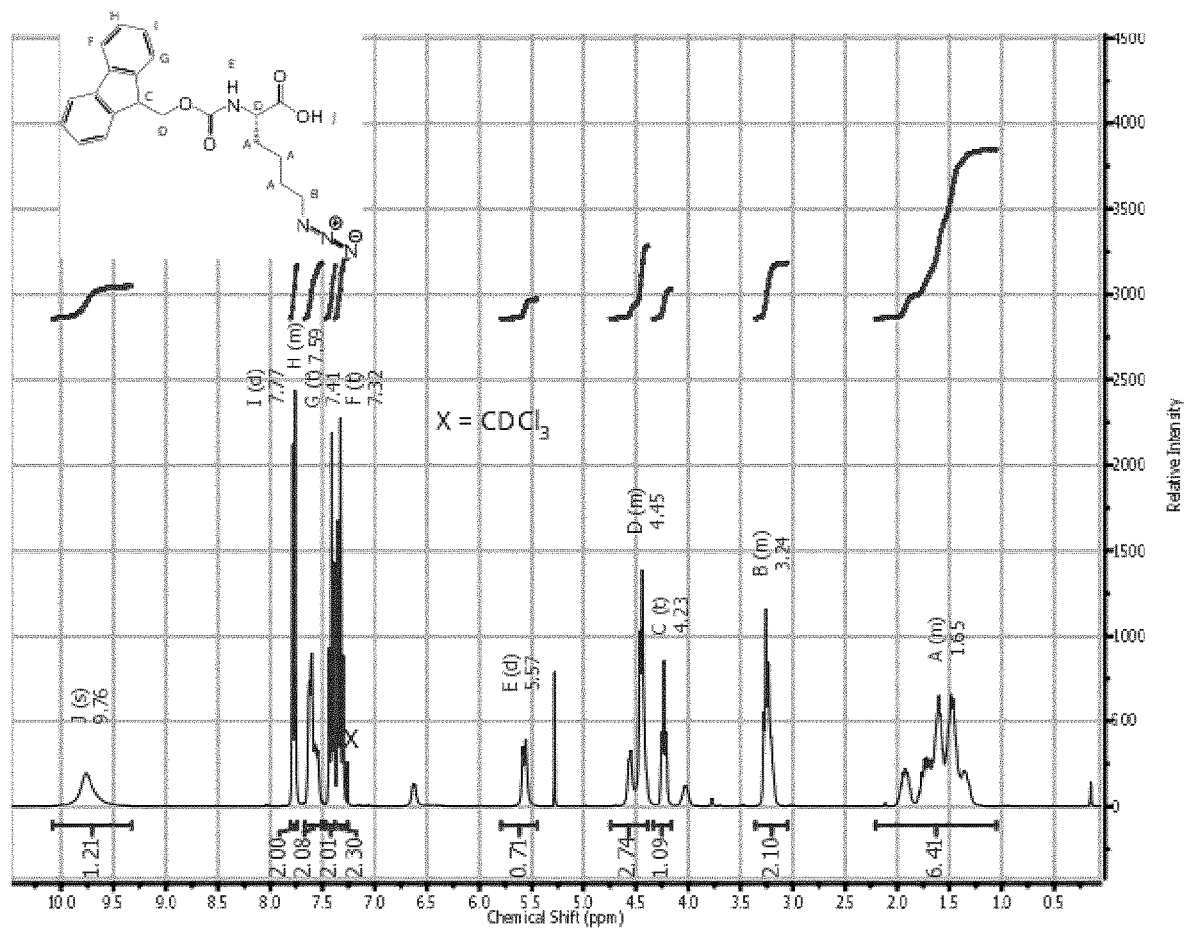
FIG. 21 shows $^1$H NMR (CDCl$_3$, 300 MHz, RT) spectrum of 3.
Figure 22:
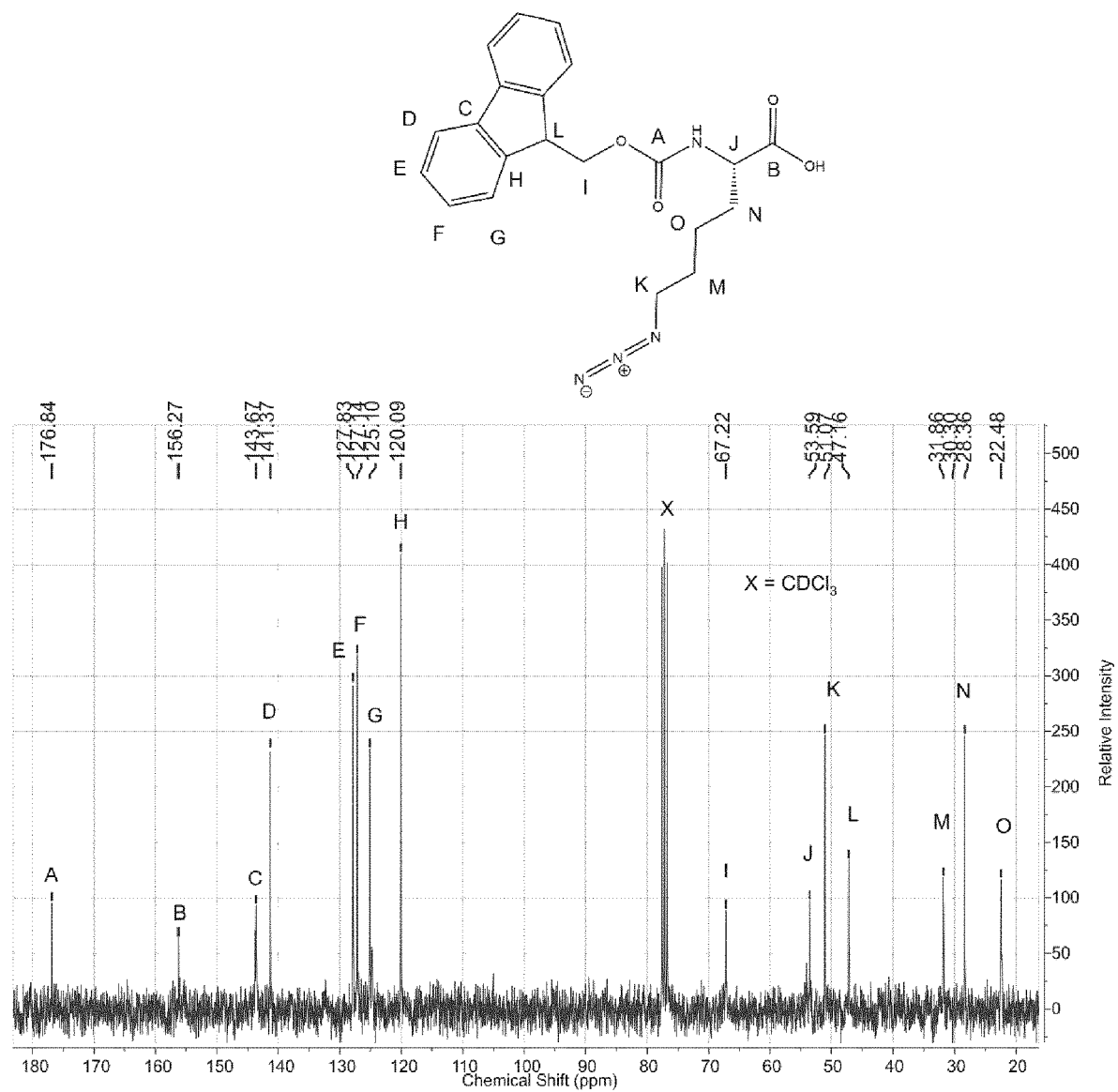
FIG. 22 shows $^{13}$C{$^1$H}NMR (CDCl$_3$, 75 MHz, RT) spectrum of 3.
Figure 23:
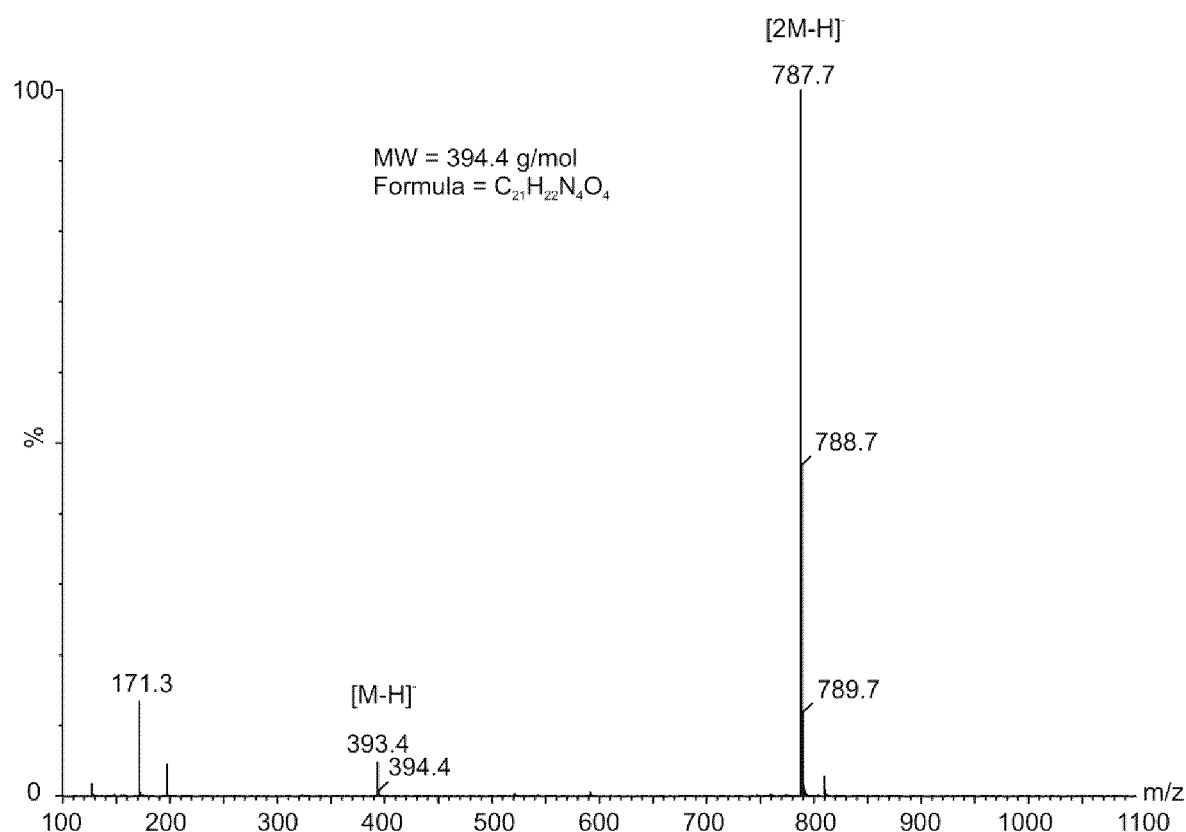
FIG. 23 shows ESI-MS(−) spectrum of 3: calculated for $C_{21}H_{22}N_4O_4$, 394.4 m/z; found, [M−H]$^-$=393.4 m/z and [2M−H]$^-$=787.7 m/z.
Figure 24:
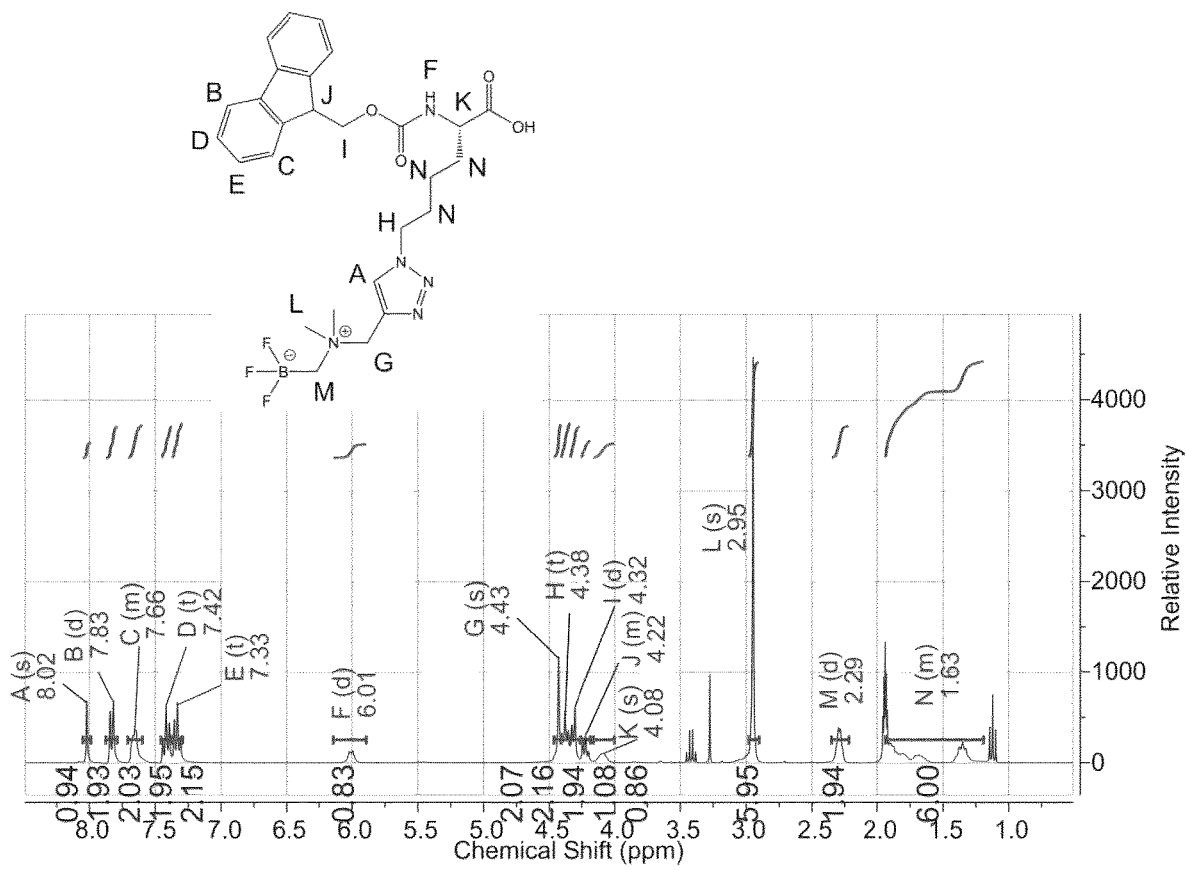
FIG. 24 shows $^1$H NMR (CD$_3$CN, 300 MHz, RT) spectrum of 4.
Figure 25:
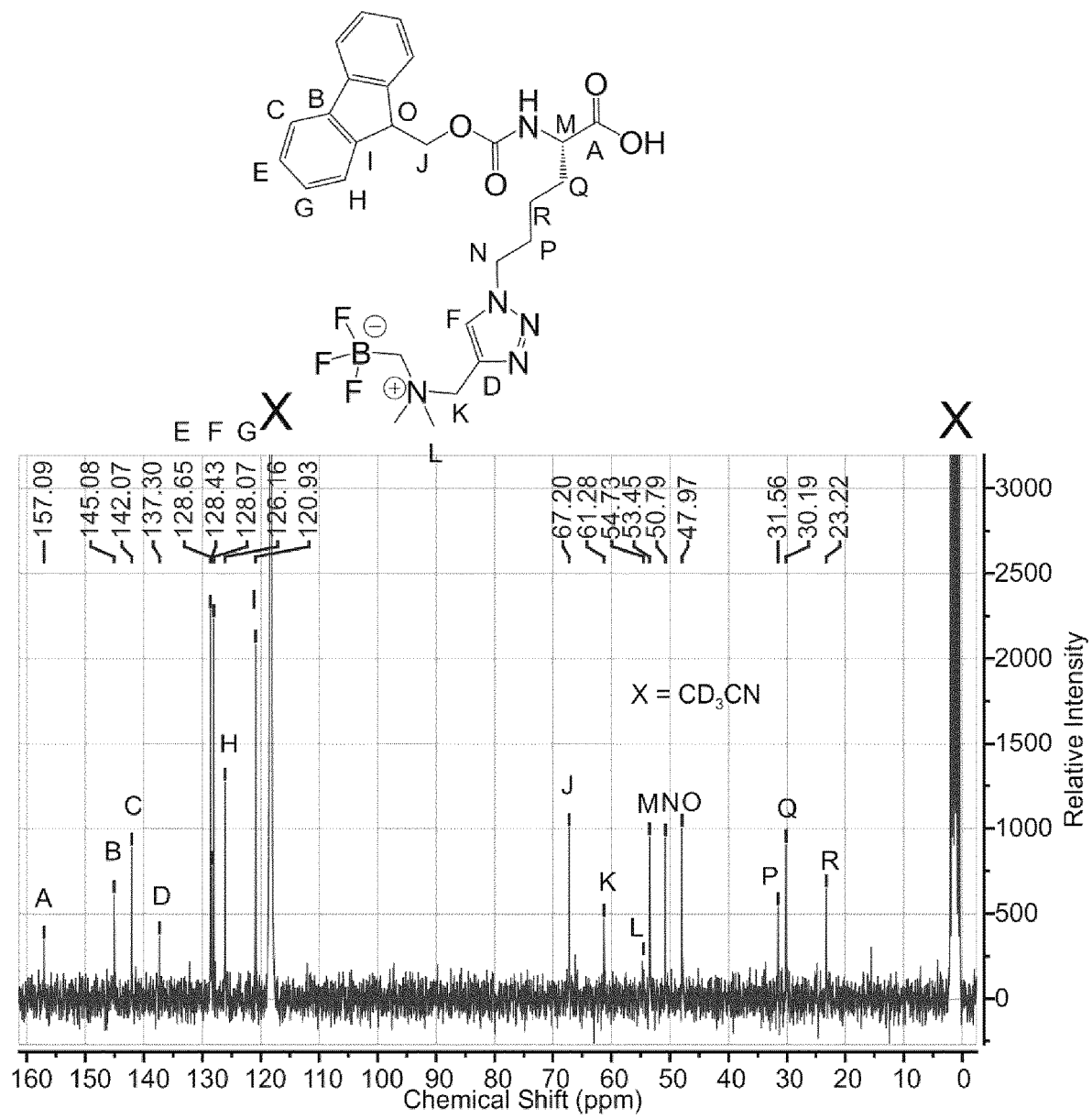
FIG. 25 shows $^{13}$C{$^1$H}NMR (CD$_3$CN, 75 MHz, RT) spectrum of 4.
Figure 26:
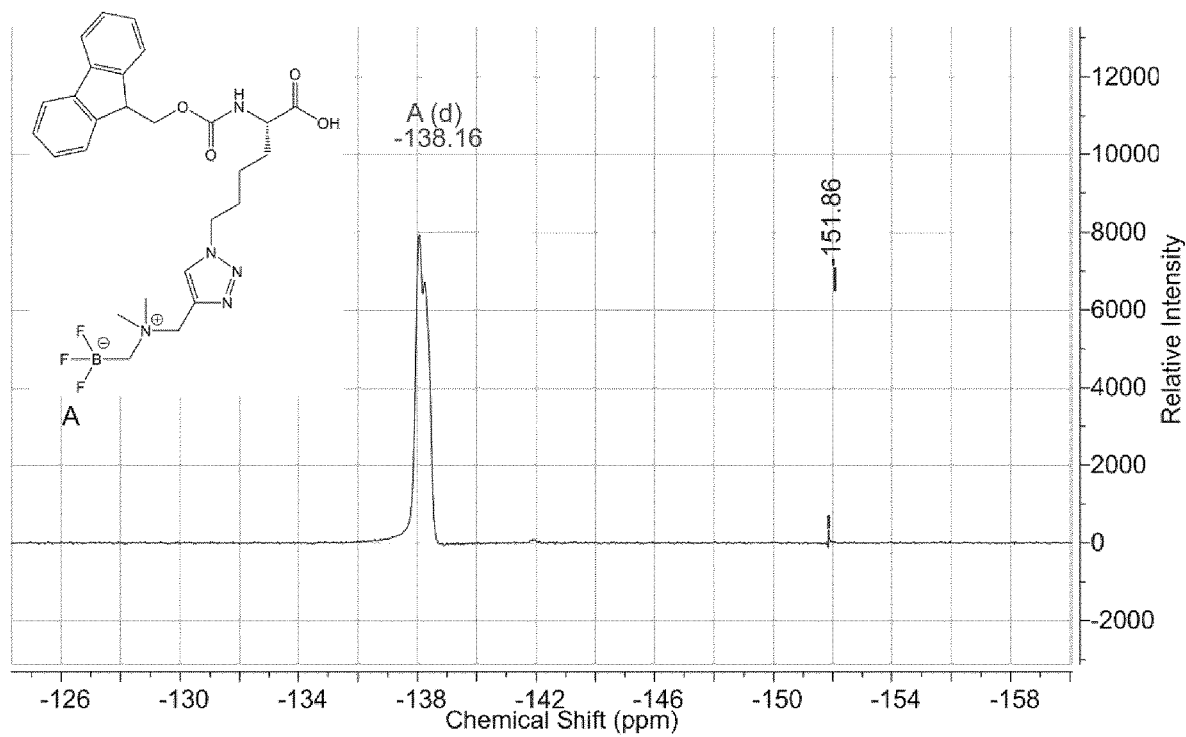
FIG. 26 shows $^{19}$F{$^1$H}NMR (CD$_3$CN, 282 MHz, RT) spectrum of 4.
Figure 27:
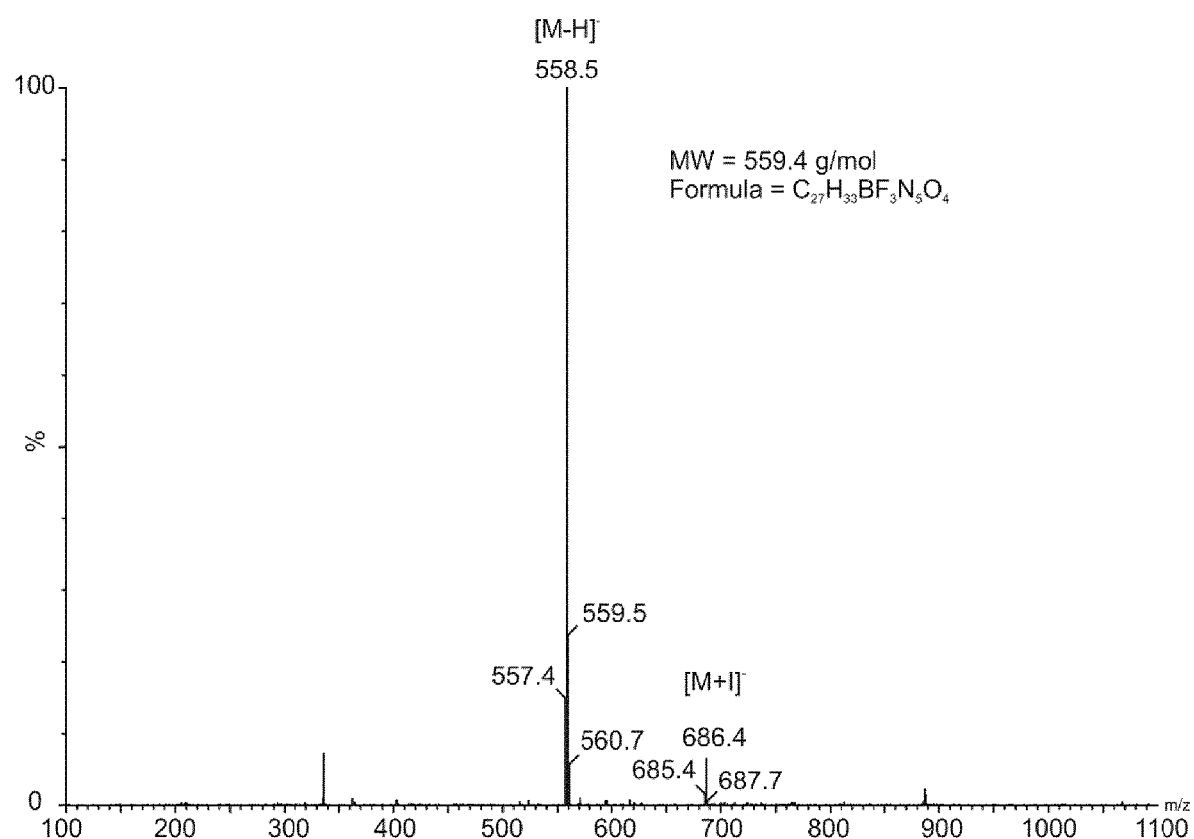
FIG. 27 shows ESI-MS(−) spectrum of 4: calculated for $C_{27}H_{33}BF_3N_5O_4$, 559.4 m/z; found, [M−H]$^-$=558.5 m/z and [M+I]$^-$=686.4 m/z.
Figure 28:
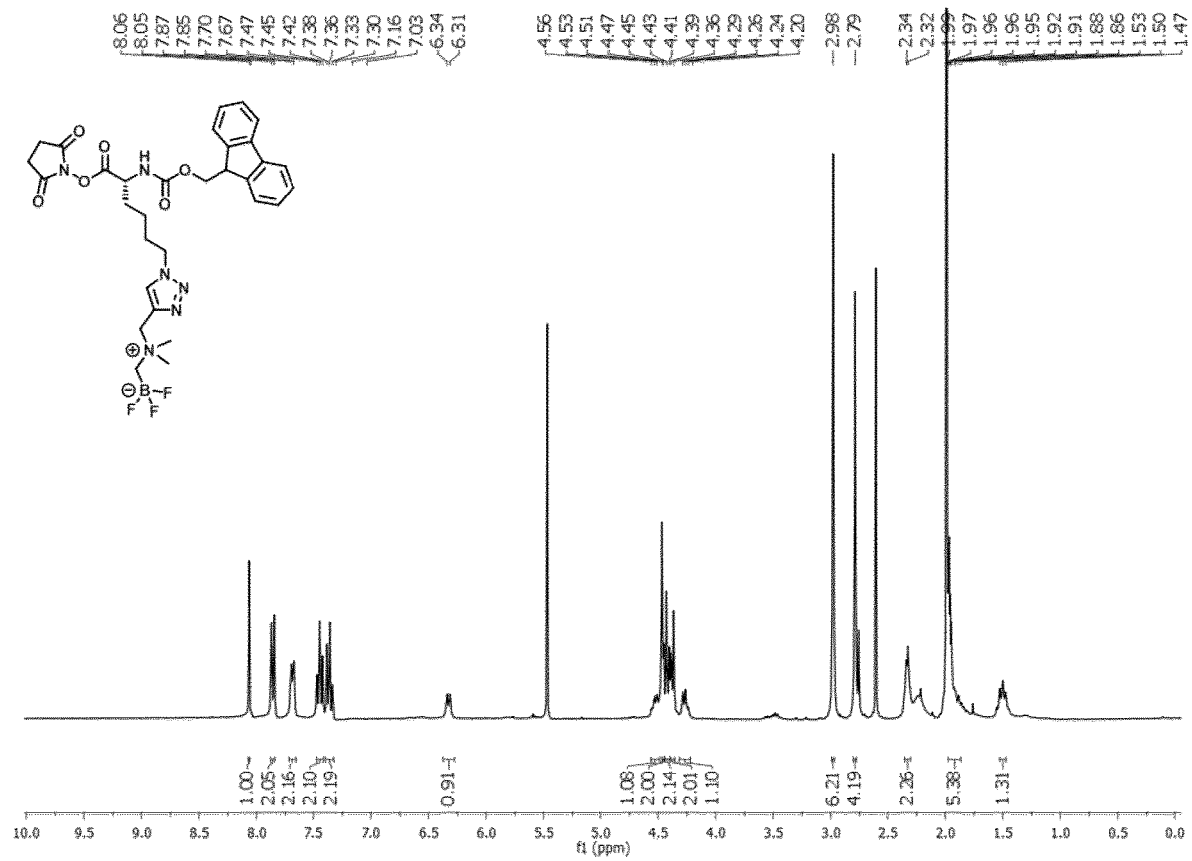
FIG. 28 shows $^1$H NMR (CD$_3$CN, 300 MHz, RT) spectrum of 5.
Figure 29:
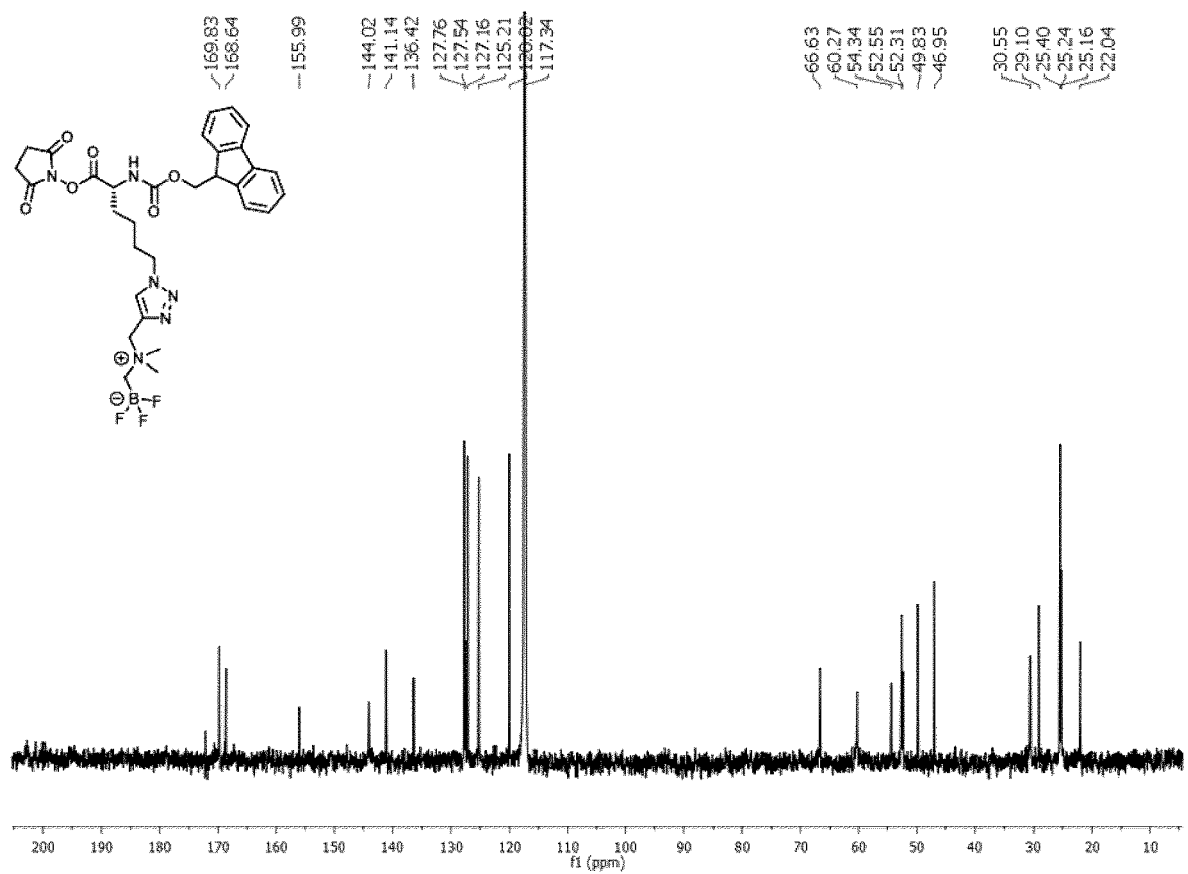
FIG. 29 shows $^{13}$C{$^1$H}NMR (CD$_3$CN, 75 MHz, RT) spectrum of 5.
Figure 30:
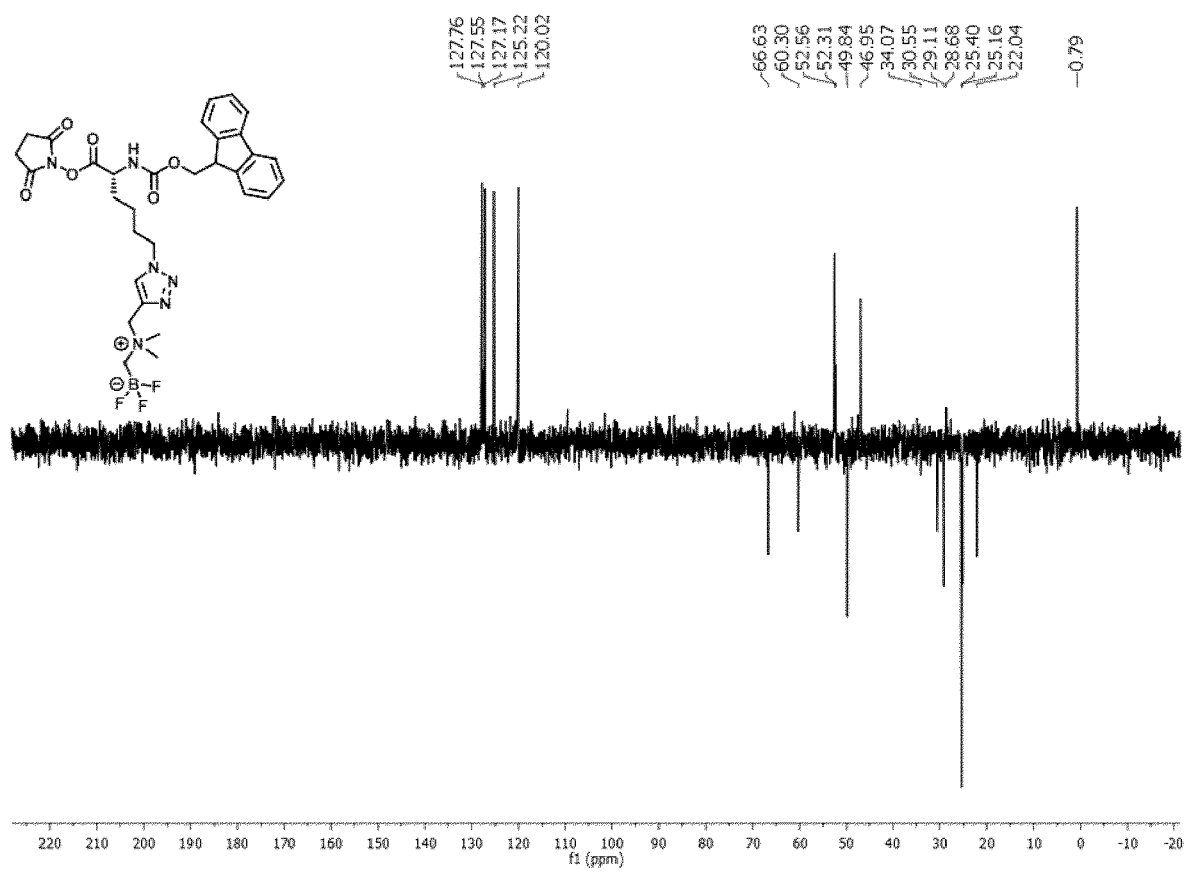
FIG. 30 shows $^{13}$C DEPT-135 NMR (CD$_3$CN, 75 MHz, RT) spectrum of 5.
Figure 31:
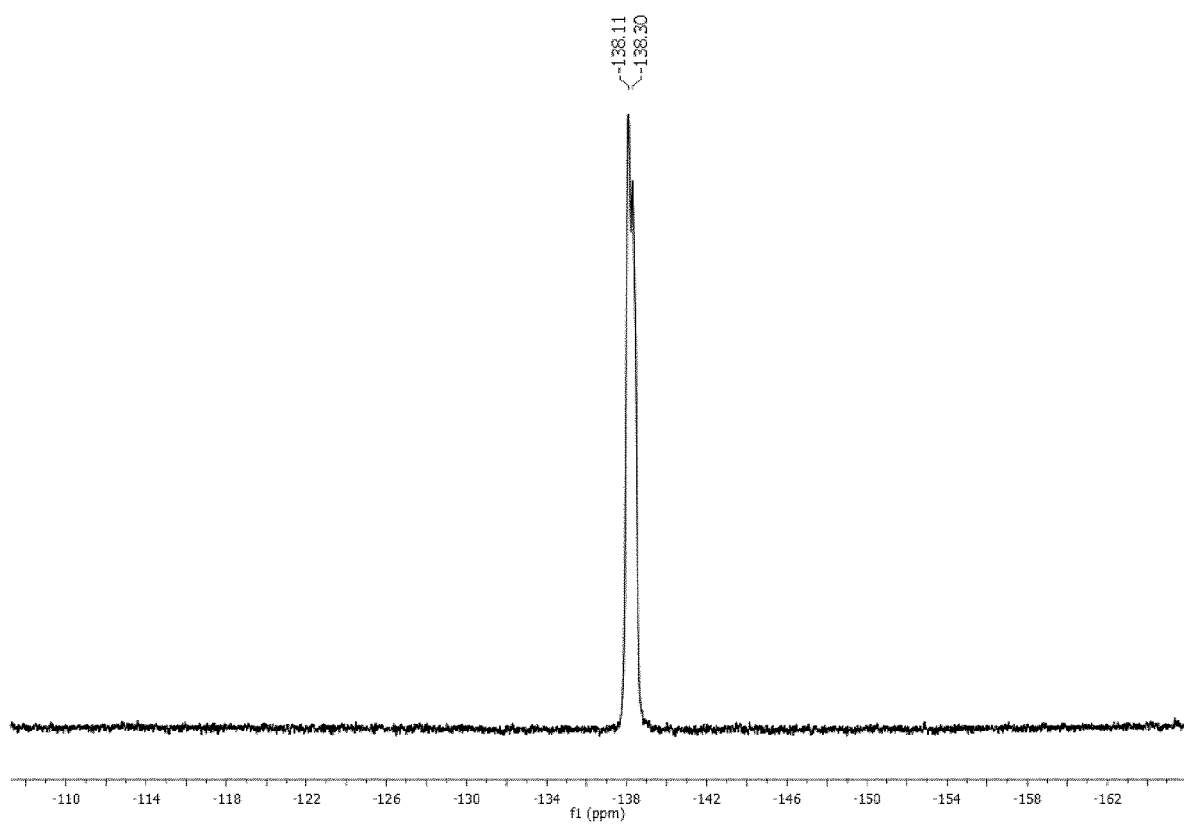
FIG. 31 shows $^{19}$F{$^1$H}NMR (CD$_3$CN, 282 MHz, RT) spectrum of 5.
Figure 32:
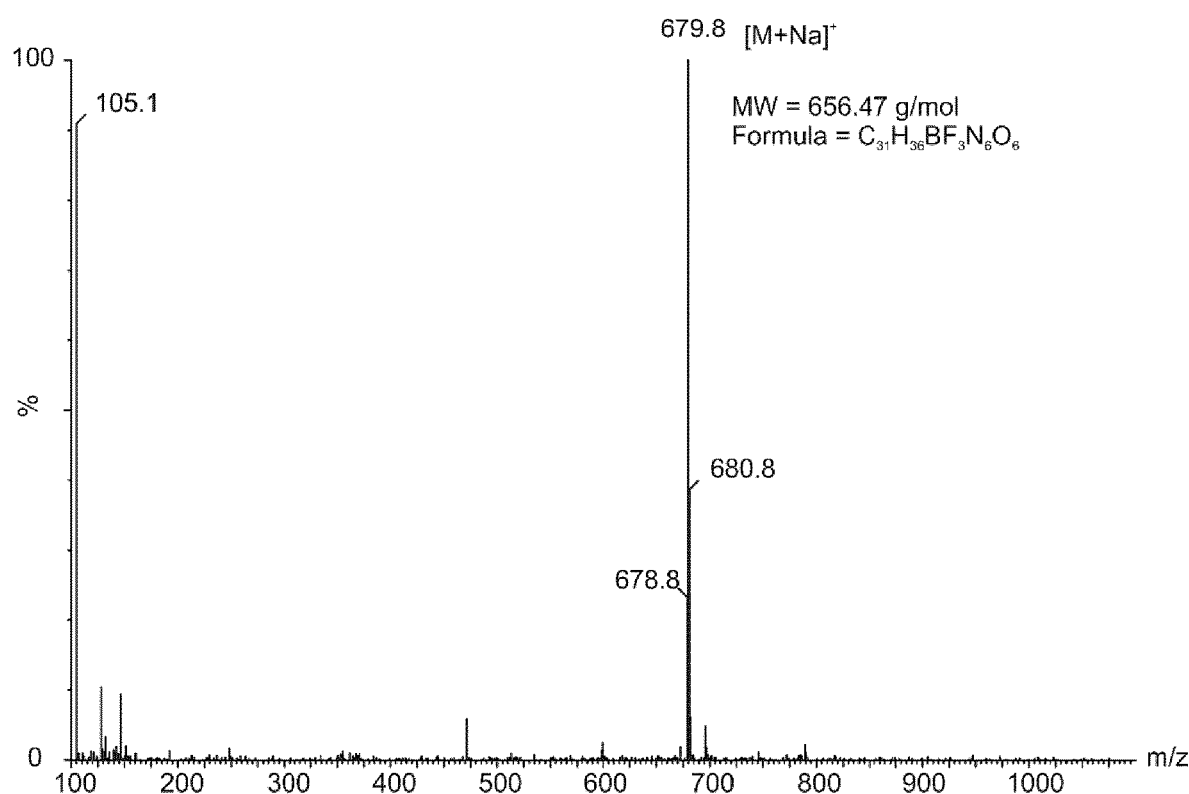
FIG. 32 shows ESI-MS(+) spectrum of 5: calculated for $C_{31}H_{36}BF_3N_6O_6$, 656.5 m/z; found, [M+Na]$^+$=679.8 m/z.
Figure 33:
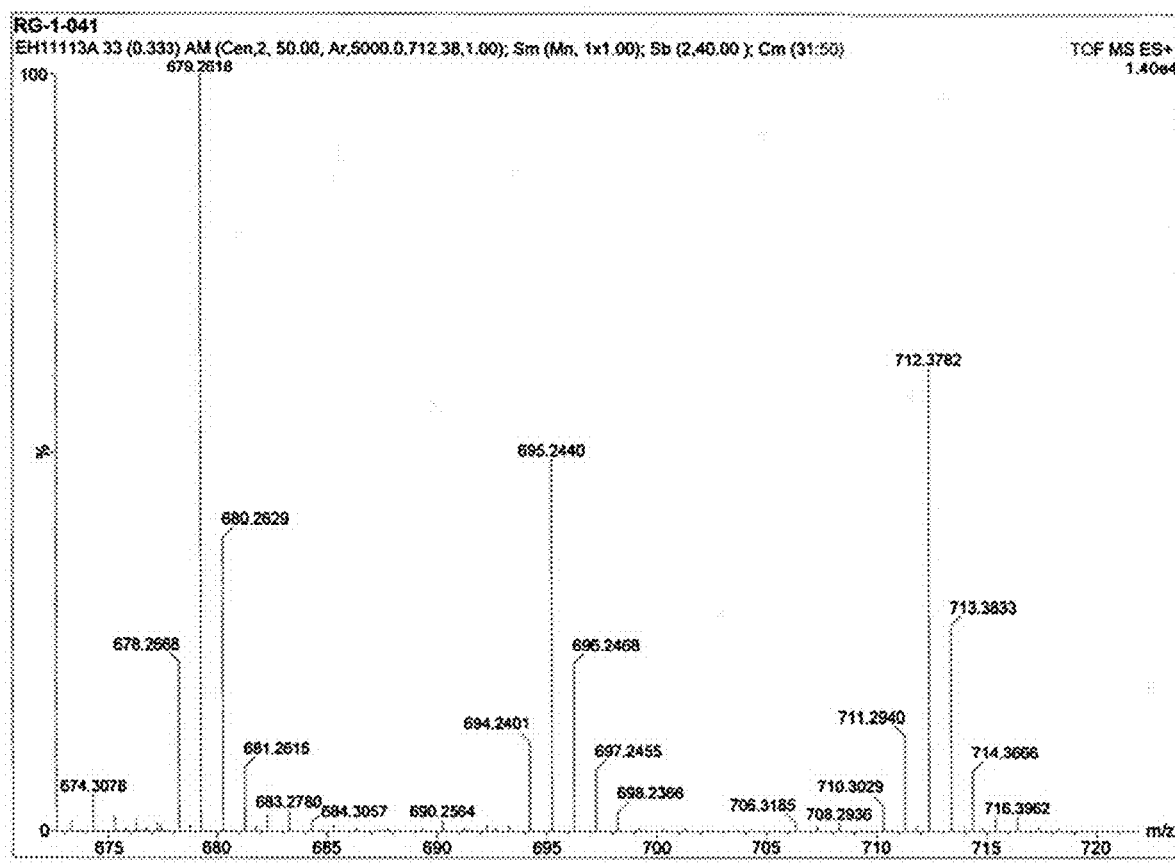
FIG. 33 shows HRMS of spectrum of 5: calculated for $C_{31}H_{36}BF_3N_6O_6$, 656.4702 m/z; found [M+Na]$^+$=679.2618 m/z.
Figure 34:
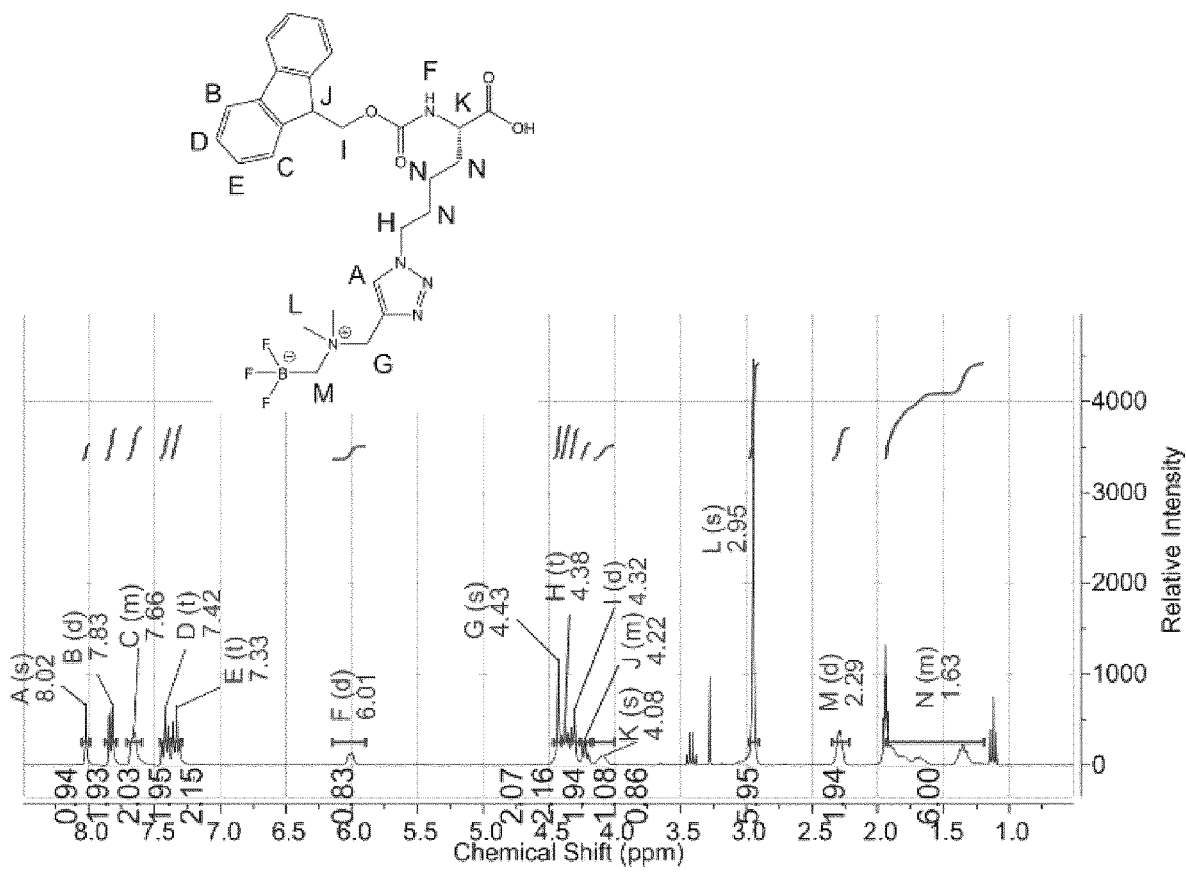
FIG. 34 shows $^1$H NMR (CD$_3$CN, 300 MHz, RT) spectrum of Fmoc-LysAMBF$_3$—OH.
Figure 35:
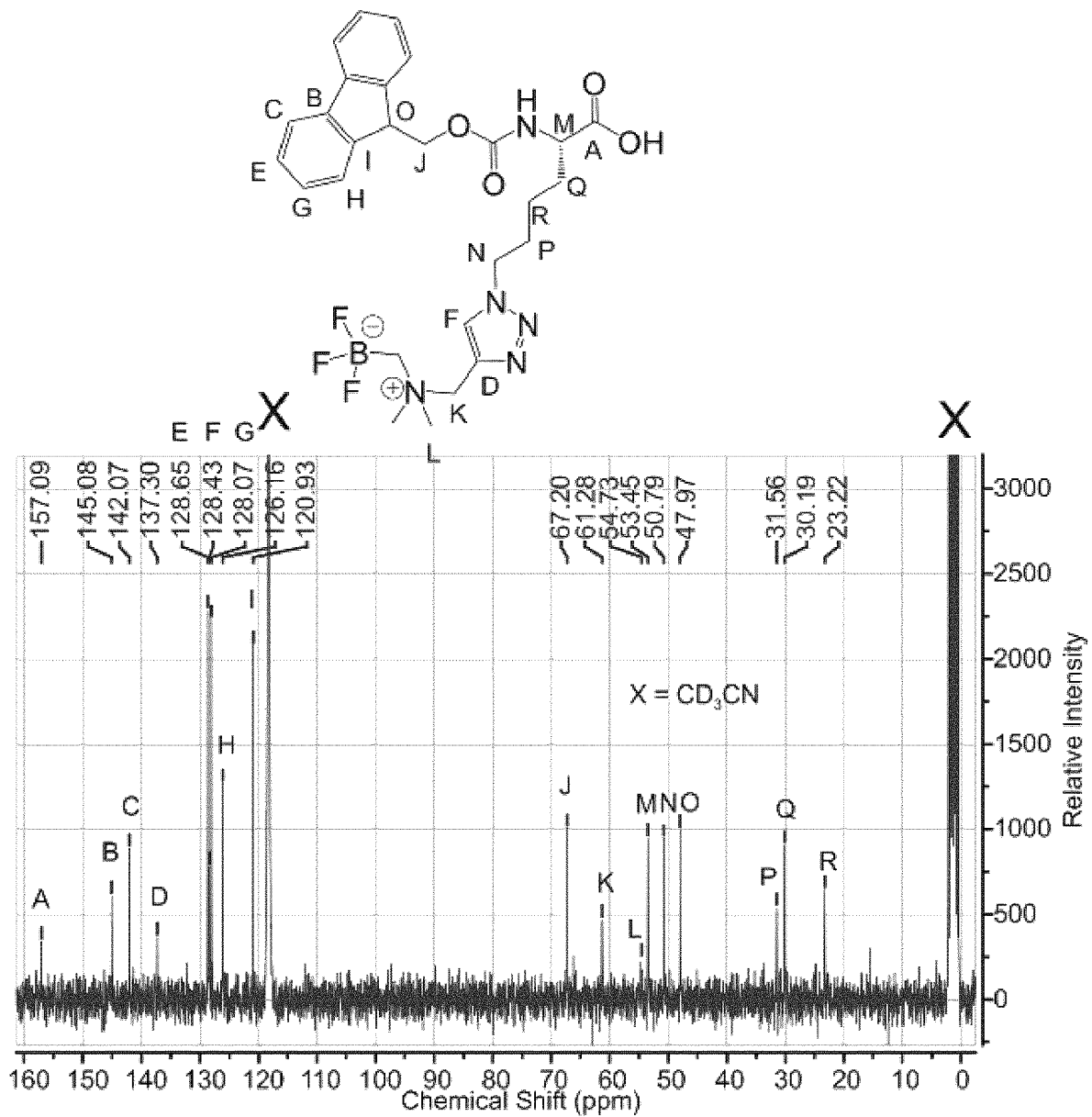
FIG. 35 shows $^{13}$C{$^1$H}NMR (CD$_3$CN, 75 MHz, RT) spectrum of Fmoc-LysAMBF$_3$—OH.
Figure 36:
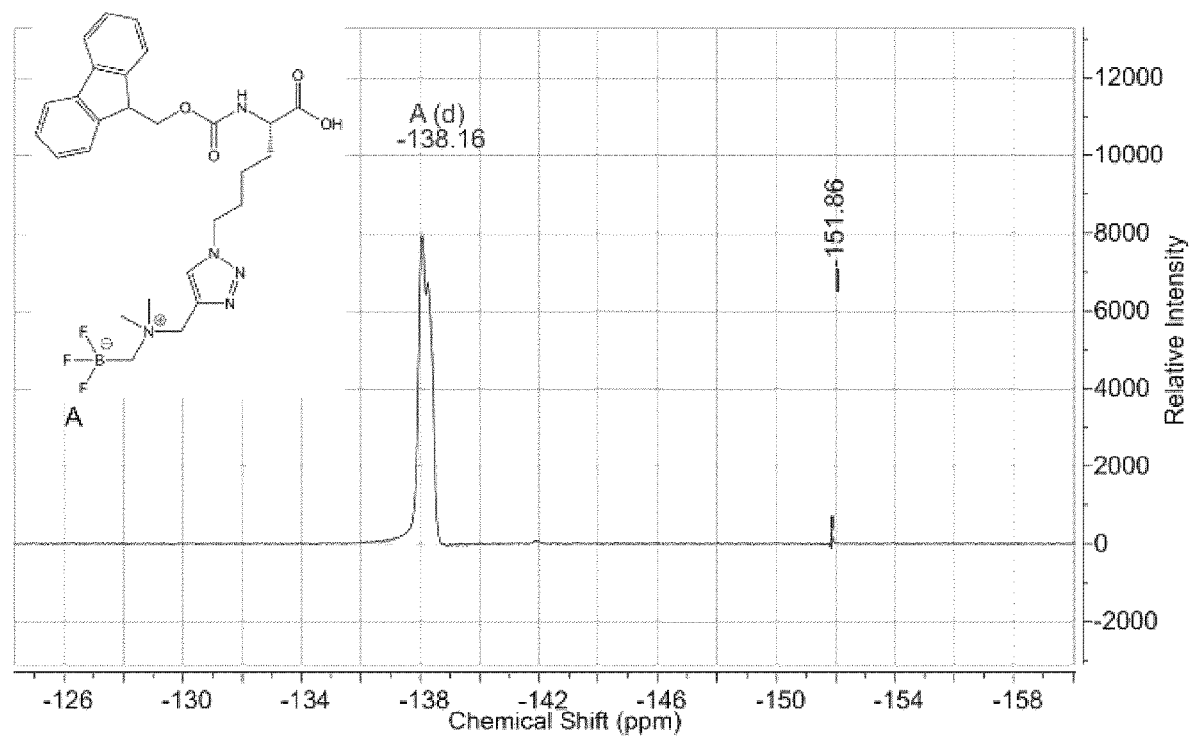
FIG. 36 shows $^{19}$F{$^1$H}NMR (CD$_3$CN, 282 MHz, RT) spectrum of Fmoc-LysAMBF$_3$—OH.
Figure 37:
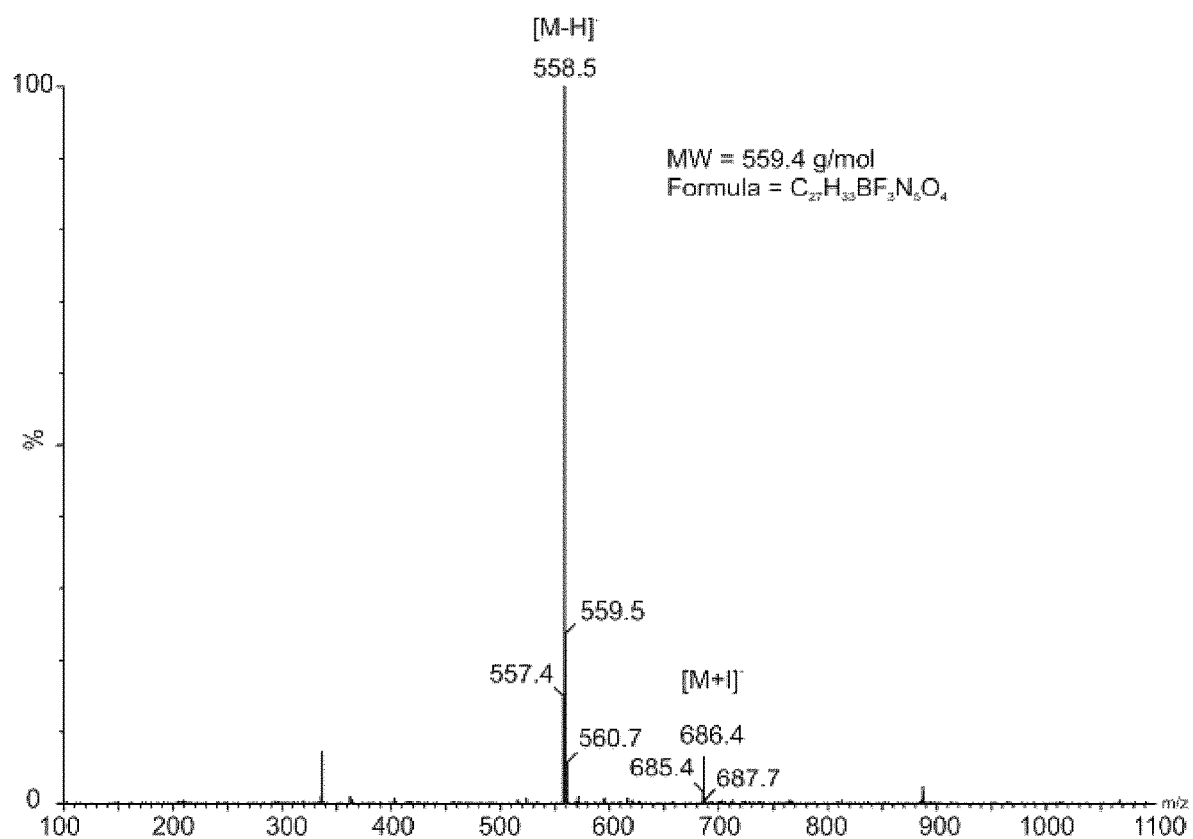
FIG. 37 shows ESI-MS(−) spectrum of Fmoc-Lys(AMBF$_3$)—OH: calculated for $C_{27}H_{33}BF_3N_5O_4$, 559.4 m/z; found, [M−H]$^-$=558.5 m/z and [M+I]$^-$=686.4 m/z.
Figure 38:
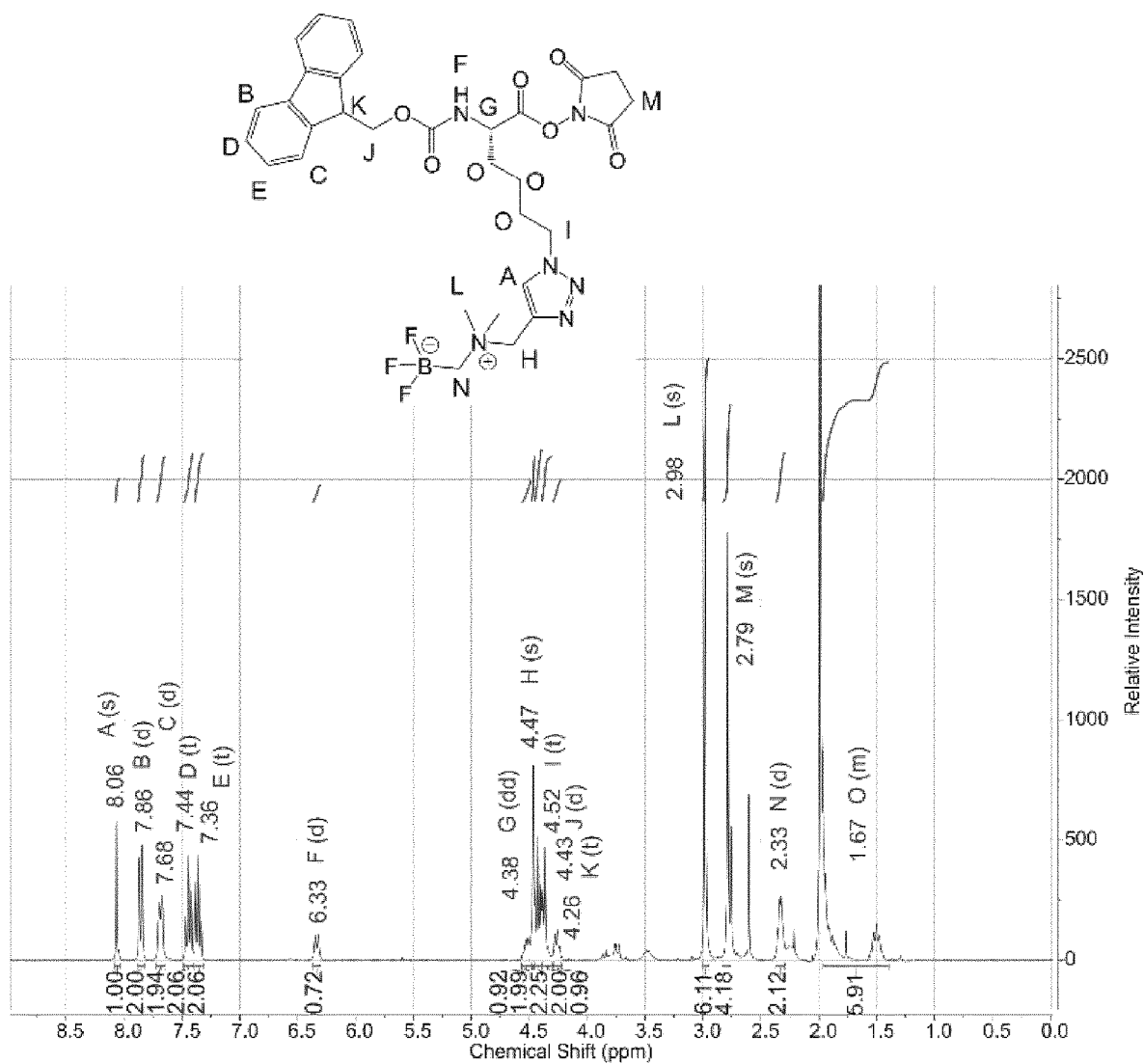
FIG. 38 shows structural characterization of Fmoc-LysAMBF$_3$—O—NHS by $^1$H NMR (CD$_3$CN, 300 MHz, RT).
Figure 39:
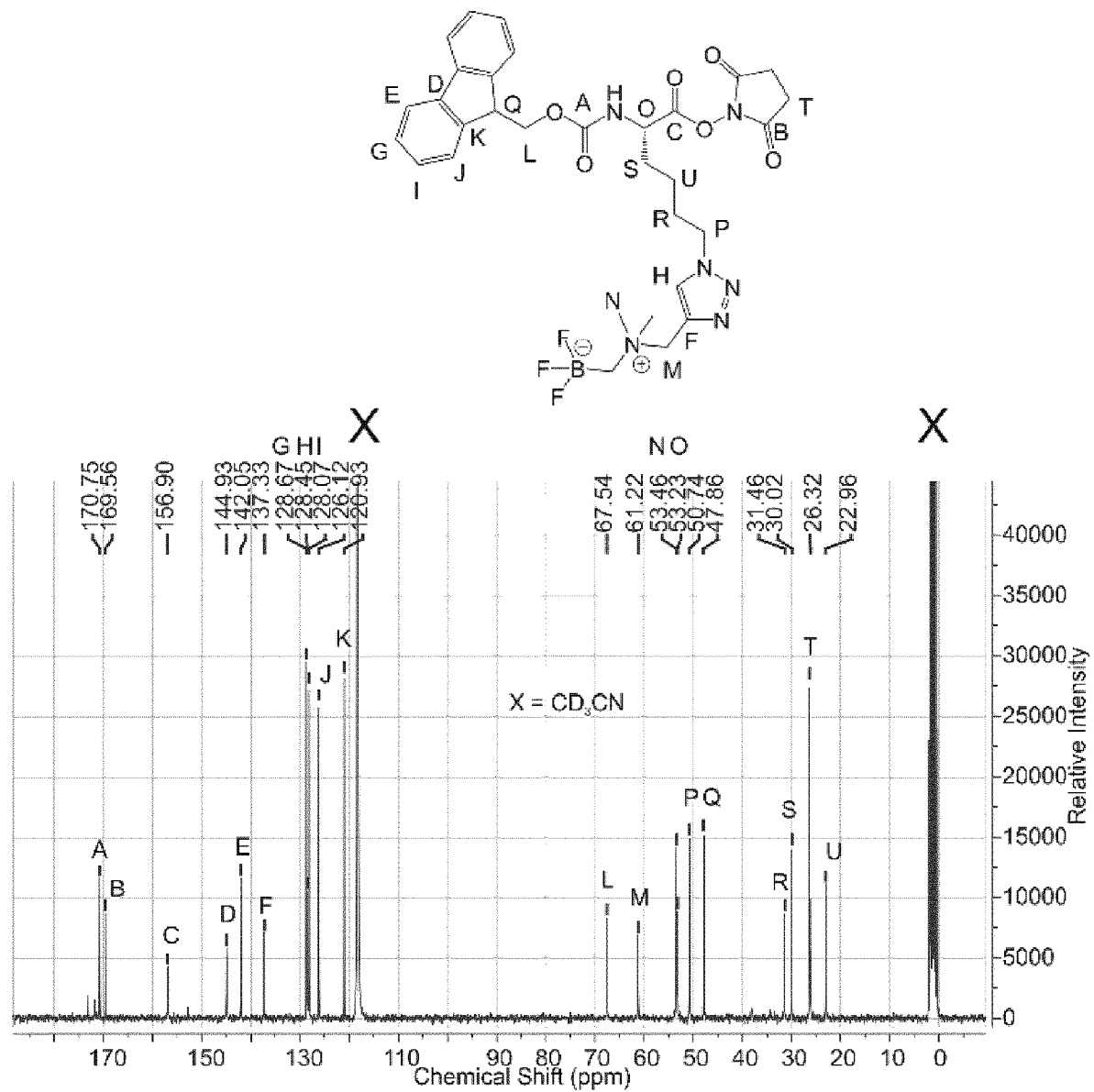
FIG. 39 shows structural characterization of Fmoc-LysAMBF$_3$—O—NHS by $^{13}$C{$^1$H}NMR (CD$_3$CN, 75 MHz, RT).
Figure 40:
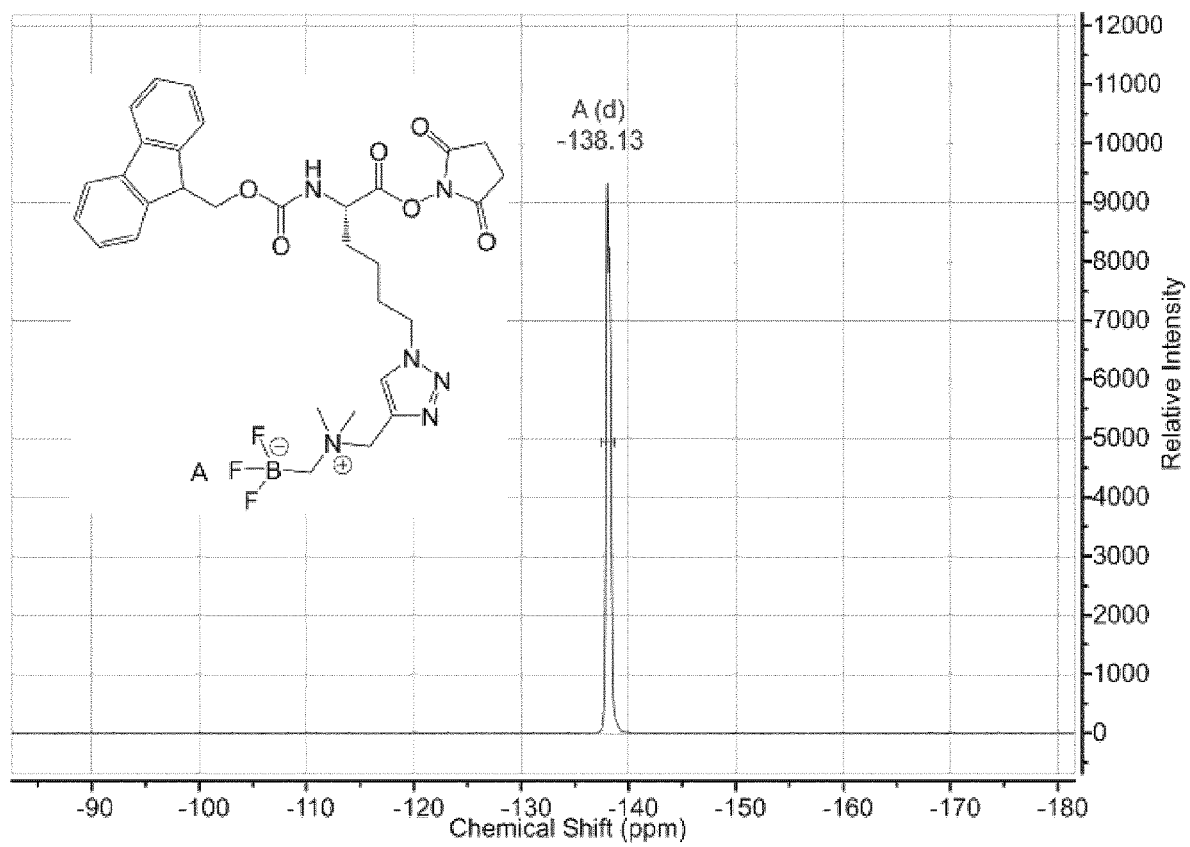
FIG. 40 shows $^{19}$F{$^1$H}NMR (CD$_3$CN, 282 MHz, RT) spectrum of Fmoc-LysAMBF$_3$—O—NHS.
Figure 41:
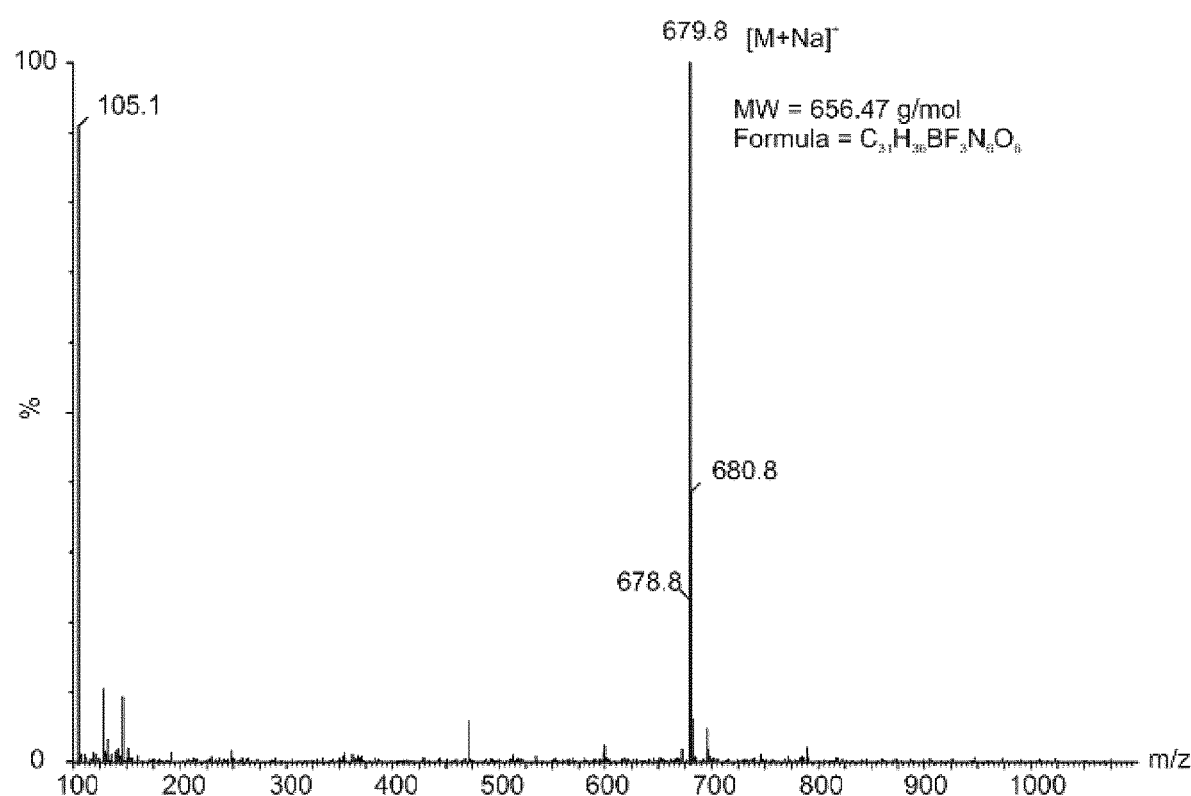
FIG. 41 shows ESI-MS(+) spectrum of Fmoc-LysAMBF$_3$—O—NHS: calculated for $C_{31}H_{36}BF_3N_6O_6$, 656.5 m/z; found, [M+Na]$^+$=679.8 m/z.

Synthesis of DOTA-AMBF$_3$-PEG$_2$-LLP2A (6) and VLA-4 affinity. The LLP2A peptidomimetic was synthesized as previously described by others (20) with modifications (PEG$_2$-NH$_2$ incorporation upon resin cleavage) reported by our lab (28). The terminal primary amine of intermediate, 1, was coupled to the Fmoc-protected lysine-AMBF$_3$ conjugate, 2, via NHS-chemistry in quantitative yields. The subsequent intermediate, 3, was subjected to efficient Fmoc-removal (intermediate 4) and was coupled to unprotected DOTA-NHS (5) under basic conditions. These methods were repeated to provide a substantial crude sample (42.1 mg) of 6 for HPLC purification. This strategy gave 3.1 mg (1.9 µmol) of the lyophilised precursor, 6, with a high purity (>95% by HPLC) for subsequent $^{18}$F-radiolabelings. A $K_d$ value of 6.9±0.59 nM (n=3) was calculated (FIG. 14), and was at least 5-fold higher than the $K_d$ values found for other [$^{18}$F]RBF$_3$-PEG$_2$-LLP2A conjugates (FIG. 8).

Figure 5:
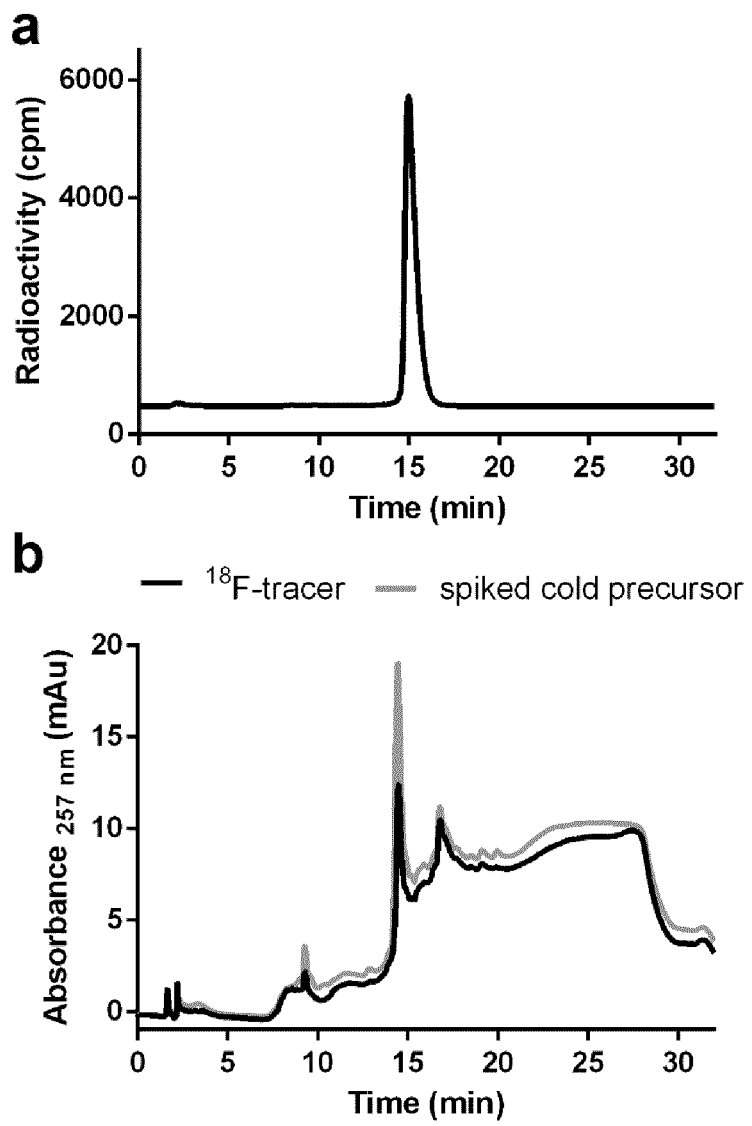
FIG. 5 shows a representative HPLC chromatogram of the purified $^{18}F$-radiotracer, 7, (post prep-HPLC purification and C18 Sep-Pak elution) formulated in (1:9) EtOH: 0.9% saline (v/v) showing the a) radiochromatogram with 7 at $t_R$=14.97 min showing a 98.5% radiochemical purity, 1.1% of $^{18}F^-$ ($t_R$=2.30 min) and a 0.4% impurity ($t_R$=8.26 min) using HPLC method B and b) the absorbance chromatograms of the 7 alone ($t_R$=14.44 min) and co-injected with 0.1 nmol of the cold precursor, 6 ($t_R$=14.49 min).

Radiosynthesis of DOTA-[$^{18}$F]AMBF$_3$-PEG$_2$-LLP2A ([$^{18}$F]6). The precursor, 6 (80 nmol), was radiolabeled with [$^{18}$F]fluoride via IEX in acidic aqueous pyridazine buffer in 71.8±1.0 min (±SD) ($^{18}$F/H$_2$$^{18}$O-delivery to formulation, n=4). The mean radiochemical purity of [$^{18}$F]6 was calculated to be 95.9±1.8% (±SD) (FIG. 5a) after confirming the identity of the sample as the $^{18}$F-labeled derivative of 6 by HPLC (FIG. 5b). The mean radiochemical yield of [$^{18}$F]6 was 4.8±2.9%, and the mean molar activity (A$_m$) was calculated to be 131.72±50.32 GBq/pmol (3.56±1.36 Ci/pmol).

PET Imaging of DOTA-[$^{18}$F]AMBF$_3$-PEG$_2$-LLP2A ([$^{18}$F]6) in B16-F10 Tumor-Bearing Mice.

Figure 6:
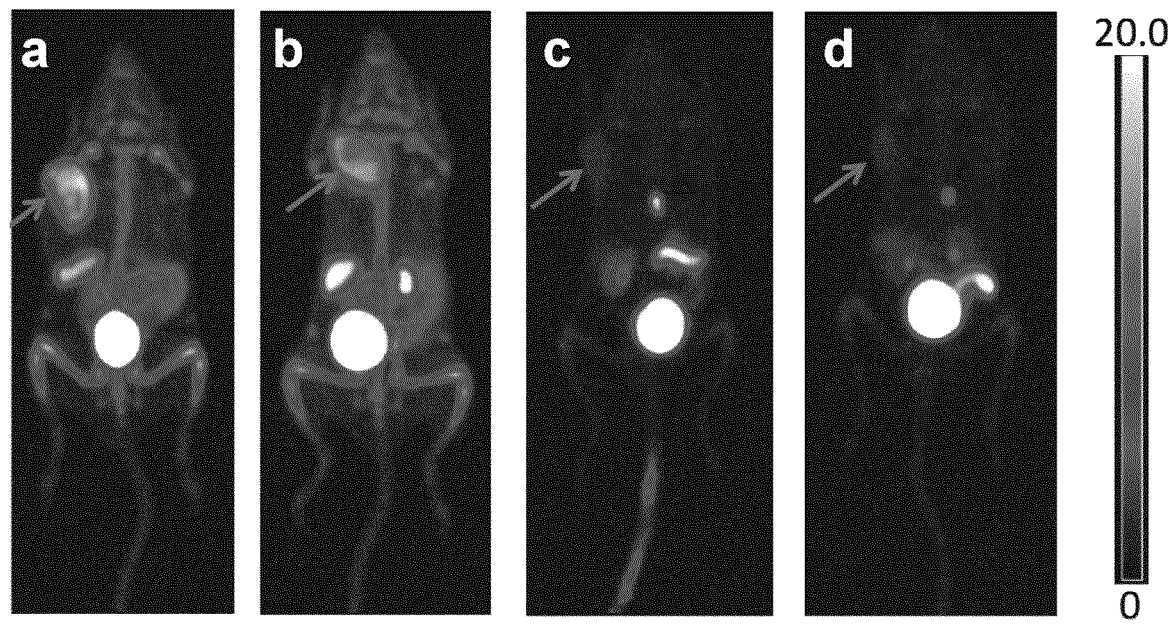
FIG. 6 shows PET images at 1 h p.i. of 7 alone (a and b; 4-6 MBq injected) and from co-injections of 7 (4-6 MBq injected) with the blocking agent, 1 (200 μg) (c and d) in B16-F10 tumor (arrows) bearing mice, scale bar is 0-20% ID/g.

The static PET images of [$^{18}$F]6 showed preferential tracer uptake at 1 h p.i. (n=2) in the tumors, spleen, kidneys and bone marrow of B16-F10 tumor-bearing mice (FIGS. 6a and 6b). Blocking studies, involving co-injections of [$^{18}$F]6 with 1 (n=2), reduced tracer uptake values in tumors and in bone marrow to near-baseline levels while activity remained visible in the spleen (FIGS. 6c and 6d). All images indicated substantial activity in the bladder, confirming the renal clearance of [$^{18}$F]6 via the kidneys.

Figure 7:
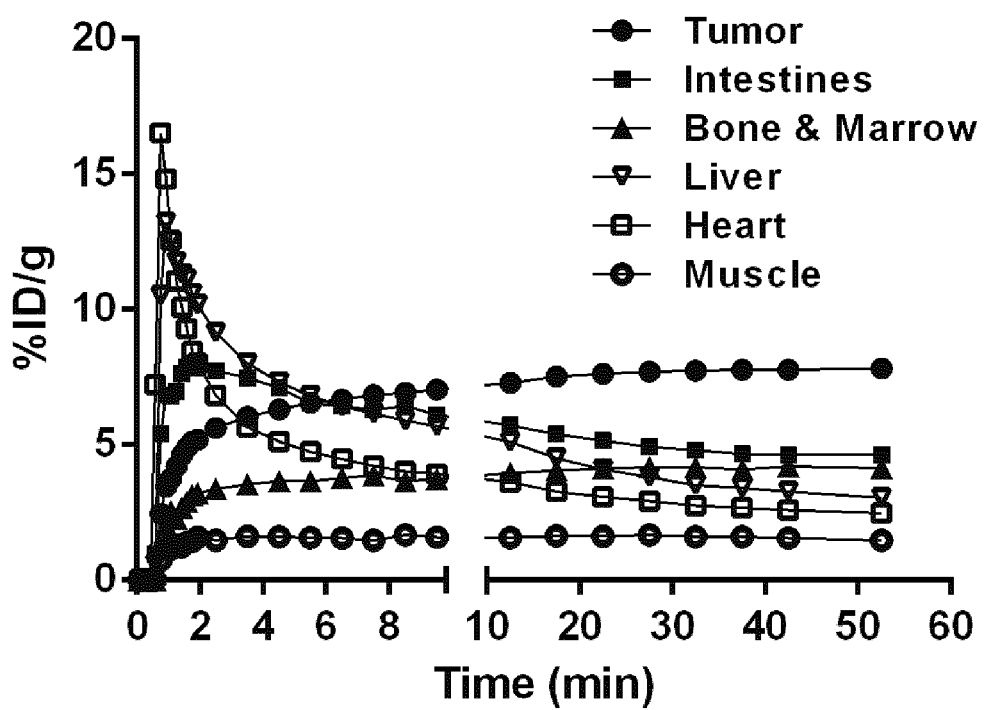
FIG. 7 shows dynamic PET scans (5 sec. to 52.5 min p.i., 28 time points) of [$^{18}F$]6 (5 MBq injected) in a B16-F10 tumor-bearing mouse.

Dynamic PET scans showed initial perfusion of [$^{18}$F]6 through circulation and a first pass through the liver within 4 min p.i. (FIG. 7). The radiotracer exhibited efficient uptake in the tumor within 1.9 min p.i. and steady accumulation therein until 52.5 min p.i. VLA-4 targeting was also observed by radiotracer accumulation in the bone marrow. These scans identified the initial presence of [$^{18}$F]6 in the intestines and retention within the gut during the scan period. Dynamic PET scans also recapitulated the high contrast static PET images as the accumulation of [$^{18}$F]6 remained low in the background muscle tissue.

Biodistribution studies revealed high accumulation of [$^{18}$F]6 in the spleen, with substantial uptake in the lungs and intestines at 1 h p.i. (Table 5). Specific VLA-4 binding was evidenced by high uptake of [$^{18}$F]6 in the tumor and bone marrow. Co-injections of 1 reduced the accumulation of [$^{18}$F]6 in the spleen (88% lower, p<0.0001), intestines (43% lower, p<0.05), the lungs (85% lower, p<0.0001), bone & marrow (78% lower, p<0.0001) and in the tumor (75% lower, p<0.0001). The contrast ratios (Table 6) showed relatively high tumor uptake of [$^{18}$F]6 compared to the background muscle (~7-fold higher) and the blood pool (~9-fold higher). VLA-4 blocking resulted in lowering these tumor-to-muscle (92% lower, p<0.0001) and tumor-to-blood (85% lower, p<0.0001) contrasts for [$^{18}$F]6 while the tumor-to-kidney and tumor-to-bone & marrow contrasts were not significantly (p>0.05) affected.

TABLE 5

Biodistribution of [$^{18}$F]6 at 1 h p.i. in B16-F10 tumor-bearing mice and with co-injection (200 μg) of the blocking agent, 1 (mean % ID/g with ±SD).

| Tissue | [$^{18}$F]6 (n = 6) | [$^{18}$F]6 with blocking (n = 5) |
|---|---|---|
| Blood | 0.94 ± 0.05 | 0.72 ± 0.09 |
| Fat | 0.31 ± 0.08 | 0.08 ± 0.01 |
| Seminal | 0.92 ± 0.24 | 0.27 ± 0.16 |
| Testes | 0.31 ± 0.02 | 0.22 ± 0.04 |
| Intestine | 4.55 ± 0.80 | 2.6 ± 0.55 |
| Spleen | 28.33 ± 4.28 | 3.49 ± 0.61 |
| Pancreas | 0.86 ± 0.14 | 0.22 ± 0.01 |
| Stomach | 1.20 ± 0.20 | 1.24 ± 1.82 [a] |
| Liver | 1.61 ± 0.21 | 0.63 ± 0.06 |
| Adrenal glands | 1.51 ± 0.31 | 0.47 ± 0.17 |
| Kidney | 4.32 ± 0.50 | 3.70 ± 0.56 |
| Heart | 0.66 ± 0.09 | 0.26 ± 0.03 |
| Lungs | 6.86 ± 0.46 | 1.06 ± 0.03 |
| Tumor | 9.46 ± 2.19 | 2.37 ± 0.34 |
| Bone & Marrow | 8.23 ± 0.84 | 1.80 ± 0.17 |
| Muscle | 1.30 ± 0.33 | 0.27 ± 0.05 |
| Brain | 0.07 ± 0.02 | 0.04 ± 0.01 |
| Tail | 1.84 ± 0.41 | 1.10 ± 0.85 |

[a] Includes one mouse with 4.45% ID/g.

TABLE 6

Tumor-to-tissue ratios of [$^{18}$F]6 after 1 h p.i. in B16-F10 tumor-bearing mice and with co-injection (200 μg) of the blocking agent, 1 (mean ratio and ±SD).

| Ratios | [$^{18}$F]6 (n = 6) | [$^{18}$F]6 with blocking (n = 5) |
|---|---|---|
| Tumor: Bone & Marrow | 1.98 ± 0.78 | 0.46 ± 0.07 |
| Tumor: Muscle | 7.96 ± 3.37 | 0.60 ± 0.05 |
| Tumor: Blood | 10.08 ± 2.17 | 1.50 ± 0.18 |
| Tumor: Kidney | 2.22 ± 0.60 | 2.55 ± 0.95 |

1.5 Discussion $^{18}$F-labeled LLP2A radiotracers were previously produced, each of which was labeled by isotope exchange on two structurally related yet relatively hydrophobic [$^{18}$F]RBF$_3$-PEG$_2$-LLP2A tracers. While several approaches exist to increase the polarity of radiotracers (e.g. adding glutamates, increasing the length of the PEG linker), this disclosure presents a novel approach that introduces a DOTA moiety as a means of increasing hydrophilicity and thereby modulating tracer clearance. High intestinal uptake was previously observed for [$^{18}$F]RBF$_3$-PEG$_2$-LLP2A conjugates. To test the LLP2A class of ligand as a peptidic scaffold, compound 6 was designed such that the DOTA would be appended on an otherwise nearly-identical LLP2A conjugate to minimize all differences save the DOTA moiety (see comparison of structures in FIG. 8). The synthesis of the DOTA-modified LLP2A derivative, 6, proceeded in an efficient, step-wise manner with nearly quantitative yields for most chemical reactions. The relatively low recovery yield of 6 in the final step was attributed to sample loss as a result of stringent HPLC purification conditions. Yet, the collected material had high purity and was obtained in sufficient quantities for all described $^{18}$F-radiolabelings and in vivo studies.

Radiosynthesis of [$^{18}$F]6 was achieved in a single aqueous step by $^{18}$F-IEX under aqueous conditions as previously demonstrated for the AMBF$_3$ radioprosthetic group and other trifluoroborates evaluated by our lab. The radiosynthesis time, radiochemical yields, purities and molar activities were suitable for in vivo studies, and were similar to antecedent [$^{18}$F]AMBF$_3$-PEG$_2$-LLP2A and [$^{18}$F]N-Pyr-p-BF$_3$-PEG$_2$-LLP2A (28). While yields were relatively low, sufficient activities of [$^{18}$F]6, 0.37-1.85 GBq (10-50 mCi), were consistently obtained for each in vivo study (n>6). As both the labeling and recovery methods are unoptimized, we are confident that these yields may be augmented by using alternate solutions during HPLC purification (ex. buffered, aqueous, isotonic ethanol solutions) for direct formulation and collection of [$^{18}$F]6. This would circumvent the need for C$_{18}$ cartridge isolation of [$^{18}$F]6 post-labeling, wherein, this hydrophilic tracer was likely lost during the initial trapping step.

The standard murine melanoma model, B16-F10, was imaged, which expresses the target VLA-4. [$^{18}$F]6 displayed preferential accumulation in the spleen, tumor, and bone marrow at 1 h p.i. Gratifyingly, the uptake of [$^{18}$F]6 in B16-F10 melanoma tumors and the corresponding tumor-to-muscle and tumor-to-blood ratios were similar to those observed for [$^{64}$Cu]Cu-CB-TE1A1P-PEG$_4$-LLP2A, [$^{64}$Cu]Cu-CB-TE2A-LLP2A, [$^{64}$Cu]Cu-NODAGA-PEG$_4$-LLP2A and [$^{68}$Ga]Ga-NODAGA-PEG$_4$-LLP2A with the same tumor model at similar time points (1 h-2 h p.i.) (23, 25-27). Blocking confirmed the specificity of [$^{18}$F]6 to VLA-4 in the tumor and the bone marrow and is consistent with the well-known VLA-4 expression in B16-F10 tumors and haematopoietic stem cells found in bone marrow (2, 9, 10, 34-37). While the high accumulation of [$^{18}$F]6 in the spleen is undesirable, sequestering of LLP2A radiotracers to the RES has been observed for the aforementioned $^{64}$Cu- and $^{68}$Ga-labeled LLP2A derivatives (23, 25-27). Our results also confirmed that the clearance route of [$^{18}$F]6 was via the kidneys and bladder, as with all previously reported in vivo studies with LLP2A radiotracers (22, 24, 26, 38-40). [00245] [$^{18}$F]6 was labeled at higher molar activities than those reported previously for $^{64}$Cu-labeled LLP2A derivatives. (24, 26, 27) Although high molar activity may have contributed to the high contrast static PET images for [$^{18}$F]6, similarly high molar activities were also achieved for two previously reported [$^{18}$F]RBF$_3$-PEG$_2$-LLP2A tracers that exhibited 4.6- and 23-fold higher in vitro binding affinity to VLA-4. Yet in both antecedent cases, tumor uptake values were 2-3 fold lower than the values shown herein.

Notably, the only appreciable difference between 6 and the antecedent AMBF$_3$-PEG$_2$-LLP2A conjugate (FIG. 8) is the DOTA moiety, which we suggest is largely responsible for higher tumor uptake values and favorable renal clearance. By contrast, our previously reported [$^{18}$F]RBF$_3$-PEG$_2$-

LLP2A's were more hydrophobic (as evidenced by HPLC retention differences) compared to [18F]6; as such, these derivatives exhibited ~3- to ~5-fold lower spleen retention and ~11-fold higher accumulation in the GI tract. In general, these results along with others', support the appendage of highly hydrophilic moieties, (previously used phosphate and carboxylate groups, here DOTA), as a means of influencing the route of clearance (i.e. renal vs. hepatobiliary) of LLP2A bioconjugates. Unlike other chemical functionalities that have been installed to favor renal clearance, DOTA may provide further advantages as it can be chelated to various non-radioactive metals (e.g. $Zn^{2+}$, $Ca^{2+}$) to further study their effects on in vivo PK/PC via $^{18}F$-PET imaging. In addition, the potential for developing companion dual-isotope "hot-cold/cold-hot" isotopologous theranostics (e.g. $^{18}F/^{174}Lu$ and $^{19}F/^{177}Lu$), which would rely respectively on F-18 for PET imaging and radiometals for therapy, is readily contemplated.

This Example shows that tumor uptake of an $^{18}F$-labeled $RBF_3$-$PEG_2$-LLP2A can be enhanced by using a hydrophilic metal-free DOTA that can be introduced in a simple synthetic approach while $^{18}F$-labeling proceeds by isotope exchange at high molar activity. In vivo PET imaging and biodistribution studies demonstrate that the DOTA moiety diverts radiotracer accumulation from the GI tract to the RES, most notably in the spleen. As we have presented a greatly improved $^{18}F$-labeled LLP2A radiotracer for VLA-4 targeted imaging, an appended DOTA appears to serve as a new and useful group for modulating tracer clearance. Such may find use with other $^{18}F$-labeled radioprosthetic groups as well.

Example 2: PSMA-617-LysAMBF3-DOTA $AMBF_3$ and Fmoc-LysN$_3$—OH were prepared following reported procedures. Perrin et al., Angew. Chem. Int. Ed. 2014, 53, 11876-11880. Nakahara et al., *Tetrahedron Lett.* 2008, 49, 5492-5494.

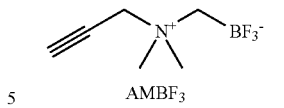

AMBF$_3$

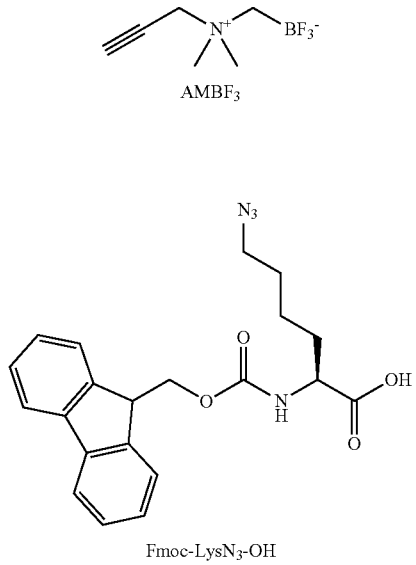

Fmoc-LysN$_3$-OH

I. Fmoc-LysAMBF$_3$—OH

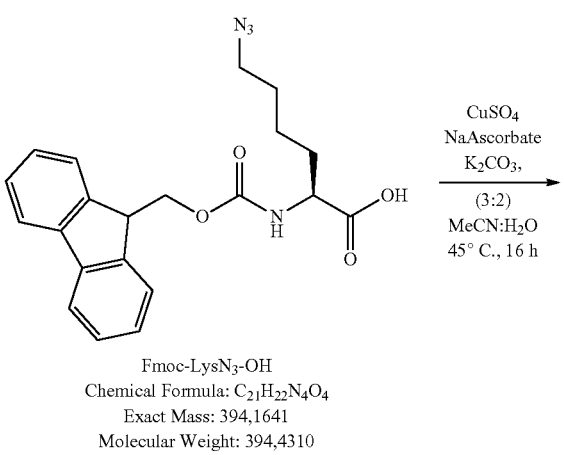

AMBF$_3$
Chemical Formula: C$_6$H$_{11}$BF$_3$N
Exact Mass: 165.0937
Molecular Weight: 164.9662

Fmoc-LysN$_3$-OH
Chemical Formula: C$_{21}$H$_{22}$N$_4$O$_4$
Exact Mass: 394.1641
Molecular Weight: 394.4310

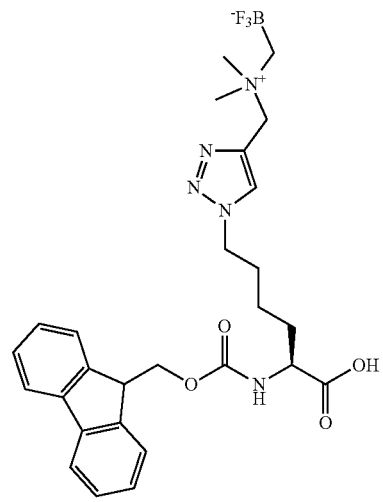

Fmoc-LysAMBF$_3$-OH
71%
Chemical Formula: C$_{27}$H$_{33}$BF$_3$N$_5$O$_4$
Exact Mass: 559.2578
Molecular Weight: 559.3972

A fresh stock solution of 1 M sodium ascorbate was prepared by dissolving 1.98 g of sodium ascorbate (0.01 mol) in 10 mL of deionized water. A stock solution of 1 M Cu(II)SO$_4$ $_{(aq)}$ was then prepared by dissolving 1.60 g of anhydrous Cu(II)SO$_4$ (0.01 mol) in 10 mL of deionized water. AMBF$_3$ (414.6 mg, 2.513 mmol, 5.24 equiv.) was loaded into an flask and dissolved in (3:2) MeCN:H$_2$O (v/v) (2.5 mL). A 1.5 mL volume of 1 M Cu(II)SO$_4$ $_{(aq)}$ (1.5 mmol, 3.1 equiv.) was added first, followed by the addition of 3 mL of 1 M sodium ascorbate (3 mmol, 6.2 equiv.). Fmoc-LysN$_3$—OH (189.1 mg, 0.479 mmol, 1 equiv.) was then added to the solution. The solution was then neutralized to pH 7 with the addition of K$_2$CO$_3$ (101.1 mg, 0.732 mmol, 1.5 equiv.). The solution was stirred for 16 h at 45° C. The mixture was vacuum filtered to remove precipitates and the filtrate was concentrated by rotary evaporation. The dried crude was resuspended in (1:1) MeOH:DCM (v/v) (5×10 mL), vacuum filtered to remove precipitates, and the filtrate was dried by rotary evaporation. The dried crude was then resuspended in (5:95) MeOH:DCM (v/v) (5×10 mL), vacuum filtered to remove precipitates, and the filtrate was again dried by rotary evaporation. Column chromatography (silica gel, 230-400 mesh, 50 g; solvent of (1:4:95) AcOH:MeOH:DCM (v/v) was performed while monitoring eluting fractions by TLC (1:10:90 AcOH:MeOH:DCM (v/v), R$_f$ of product=0.21, visible under 254 nm UV lamp, stains with I$_2$/Silica). The pure fractions were concentrated by rotary evaporator and further dried in vacuo. This gave Fmoc-LysAMBF$_3$—OH (192.0 mg, 0.343 mmol) as a dark yellow oil with 71% yield. $^1$H NMR (300 MHz, CD$_3$CN) δ (ppm): 1.27-1.91 (m, 6H), 2.30 (d, J=4.57 Hz, 2H), 2.95 (s, 6H), 4.11 (q, J=5.00 Hz, 1H), 4.22 (t, J=6.90 Hz, 1H), 4.32 (d, J=7.08 Hz, 2H), 4.38 (t, J=6.97 Hz, 2H), 4.44 (s, 2H), 6.02 (d, J=5.94 Hz, 1H), 7.33 (t, J=7.30 Hz, 2H), 7.42 (t, J=7.50 Hz, 2H), 7.66 (d, J=4.34 Hz, 2H), 7.83 (d, J=7.54 Hz, 2H), 8.02 (s, 1H). $^{13}$C NMR (75 MHz, CD$_3$CN) δ (ppm): 23.22, 30.19, 31.56, 47.97, 50.79, 53.45, 54.73, 61.28, 67.20, 120.93, 126.16, 128.07, 128.43, 128.65, 137.30, 142.07, 145.08, 157.09. $^{19}$F NMR (282 MHz, CD$_3$CN) δ (ppm): −138.16 (m, 3F). ESI-MS(−): calculated for C$_{27}$H$_{33}$BF$_3$N$_5$O$_4$, 559.4 m/z; found, [M−H]$^-$=558.5 m/z and [M+I]$^-$=686.4 m/z. See FIGS. 33-37 for spectral characterization.

II. Fmoc-LysAMBF$_3$—O—NHS

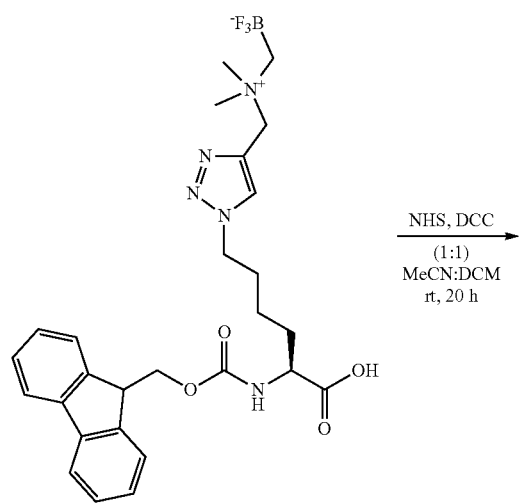

Fmoc-LysAMBF$_3$-OH
Chemical Formula: C$_{27}$H$_{33}$BF$_3$N$_5$O$_4$
Exact Mass: 559.2578
Molecular Weight: 559.3972

NHS, DCC
(1:1)
MeCN:DCM
rt, 20 h

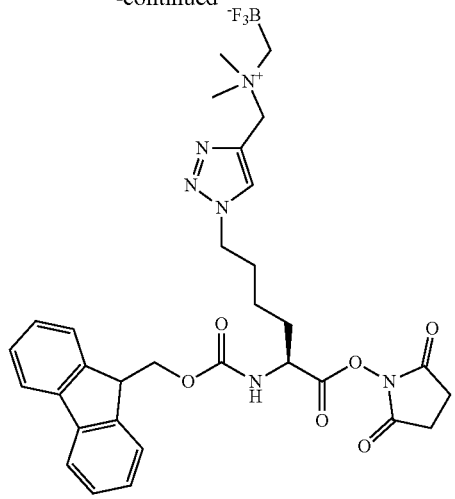

Fmoc-LysAMBF$_3$-O-NHS
61%
Chemical Formula: C$_{31}$H$_{36}$BF$_3$N$_6$O$_6$
Exact Mass: 656.2741
Molecular Weight: 656.4702

Fmoc-LysAMBF$_3$—OH (163.3 mg, 295.5 μmol, 1 equiv.) was added to an flask and dissolved in 8 mL of (1:1) DCM:MeCN (v/v). Dicyclohexylcarbodiimide (DCC) (305 mg, 1.48 mmol, 5 equiv.) was added to the solution, followed by the addition of N-hydroxysuccinimide (NHS) (170 mg, 1.48 mmol, 5 equiv.). The solution was stirred at RT for 21 hours. The reaction mixture was vacuum filtered using a sintered funnel, and the collected filtrate was concentrated by rotary evaporator. Column chromatography (column diameter=0.5 cm; silica gel (230-400 mesh), 10 g; gradient from DCM increasing by 10% CH$_3$CN (v/v) per 50 mL to (1:1) DCM:MeCN (v/v)) was performed while monitoring eluting fractions by TLC (1:1 DCM:CH$_3$CN, R$_f$ of product=0.52, visible under 254 nm UV lamp, stains with I$_2$/Silica). The pure fractions were pooled, concentrated rotary evaporator and further dried in vacuo. This gave Fmoc-LysAMBF$_3$—O—NHS (118.3 mg, 180.2 mmol) as a yellow oil in 61% yield. $^1$H NMR (300 MHz, CD$_3$CN) δ (ppm): 1.36-1.91 (m, 6H), 2.24-2.34 (m, 2H), 2.74 (s, 4H), 2.93 (s, 6H), 4.21 (m, J=6.85 Hz, 1H), 4.30-4.34 (m, 2H), 4.38 (t, J=7.08 Hz, 2H), 4.43 (s, 2H), 4.43-4.52 (m, 1H), 7.31 (t, J=7.30 Hz, 2H), 7.40 (t, J=7.30 Hz, 2H), 7.63 (d, J=7.31 Hz, 2H), 7.81 (d, J=7.54 Hz, 2H), 8.01 (s, 1H). $^{13}$C NMR (75 MHz, CD$_3$CN) δ (ppm): 22.96, 26.32, 30.02, 31.46, 47.86, 50.74, 53.23, 53.46, 61.22, 67.54, 120.93, 126.12, 128.07, 128.45, 128.67, 137.33, 142.05, 144.93, 156.90 169.56, 170.75. $^{19}$F NMR (282 MHz, CD$_3$CN) δ (ppm): −138.13 (m, 3F). ESI-MS(+): calculated for C$_{31}$H$_{36}$BF$_3$N$_6$O$_6$, 656.5 m/z; found, [M+Na]$^+$=679.8 m/z. See FIGS. 38-41.

III. PSMA-617-NH2

PSMA-617-Fmoc on resin was synthesized by SPPS following reported procedures. Eder et al., *J. Nucl. Med.* 2015, 56, 914-920.

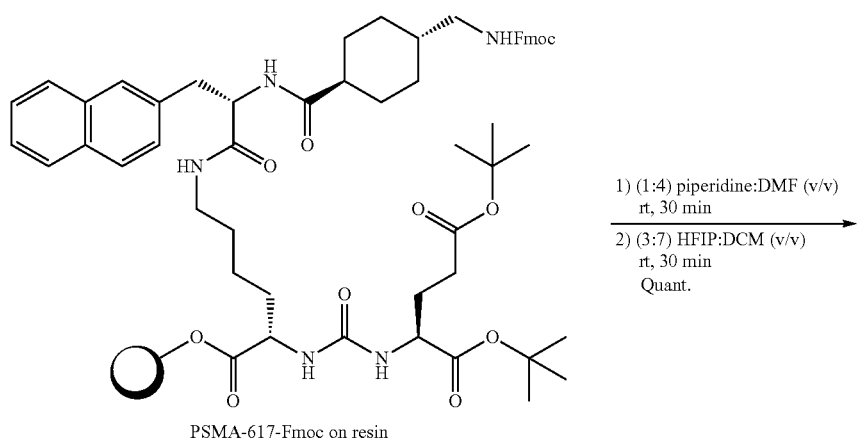

PSMA-617-Fmoc on resin 1) (1:4) piperidine:DMF (v/v) rt, 30 min
2) (3:7) HFIP:DCM (v/v) rt, 30 min Quant.

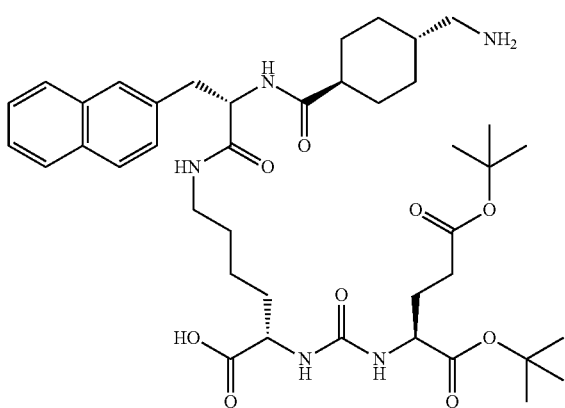

PSMA-617-NH$_2$
Chemical Formula: C$_{41}$H$_{61}$N$_5$O$_9$
Exact Mass: 767,4469
Molecular Weight: 767,9650

Figure 42:
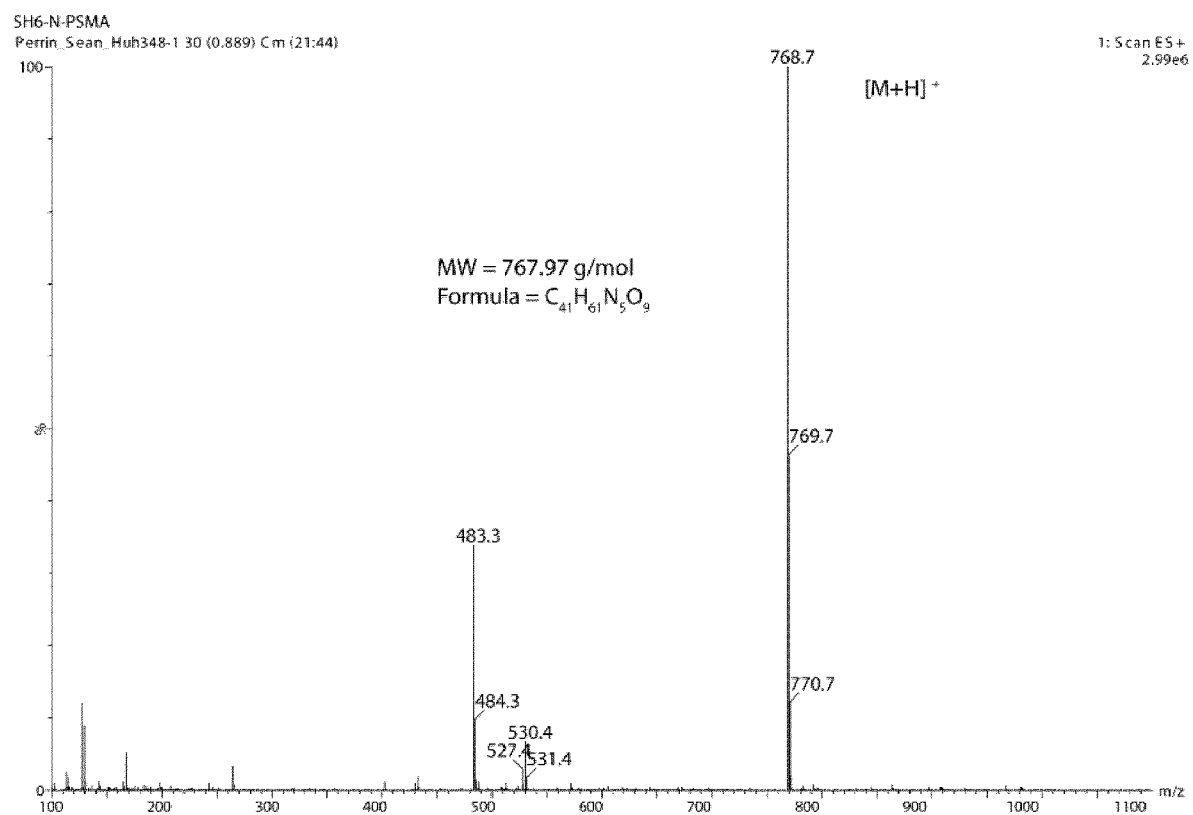
FIG. 42 shows ESI-MS(+) spectrum of PSMA-617-NH$_2$: calculated for $C_{41}H_{61}N_5O_9$, 767.97 m/z; found, [M+H]$^+$=768.7 m/z.

PSMA-617-Fmoc on resin (45.6 mg, 15.1 µmol) was placed in an Eppendorf tube. DMF (400 µL) was added to swell the resin for 30 min by placing sample in rotisserie shaker. The mixture was centrifuged down and the supernatant was removed. (1:4) piperidine:DMF (200 µL) was added to the resin and the mixture was stirred for 30 min at RT with a rotisserie shaker. The mixture was then centrifuged down and the supernatant was removed. DMF (3×200 µL) was used to wash the resin by vortexing, centrifuging, and removing the supernatant. (3:7) HFIP:DCM (200 µL) was added to cleave product off the resin and the mixture was stirred in a rotisserie shaker for 30 min. The product mixture was filtered through in 1 mL pipette filter tip to remove the resin and filtrate was collected in a separate Eppendorf tube. The mixture was concentrated down by blowing gentle air until the volume was ca. 50 to 100 µL. Cold diethyl ether (1 mL) was then added to crash out the product. The product was vortexed and centrifuged down. The supernatant was then removed, and the product was dissolved in 50 µL of DMF. Diethyl ether (1 mL) was added for additional washes and the mixture was vortexed and centrifuged. The supernatant was removed, and the mixture was dried down by speed-vac to yield expected PSMA-617-NH$_2$ in quantitative yield (11.6 mg, 15.1 µmol). ESI-MS(+): calculated for C$_{41}$H$_{61}$N$_5$O$_9$, 767.97 m/z; found, [M+H]$^+$= 768.7 m/z. TLC (2:98) MeOH, R$_f$ of product=0.29, visible under a 254 nm UV lamp). See FIG. 42 for data.

IV. PSMA-617-LysAMBF$_3$—NH$_2$

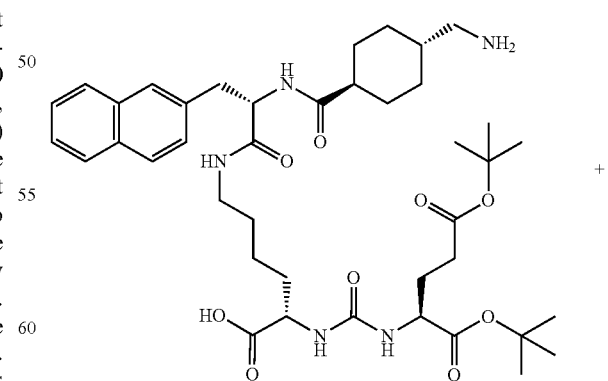

Chemical Formula: C$_{41}$H$_{61}$N$_5$O$_9$
Exact Mass: 767, 4469
Molecular Weight: 767, 9650
PSMA-617-NH$_2$

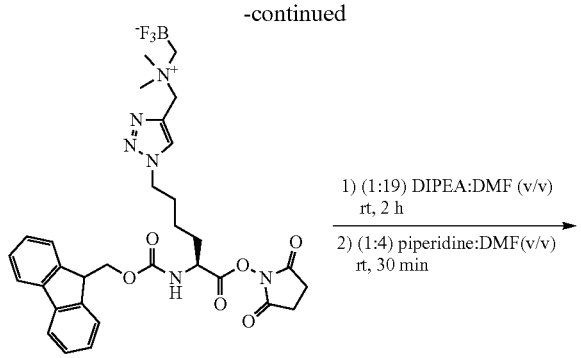

Chemical Formula: C₃₁H₃₆BF₃N₆O₆
Exact Mass: 656, 2741
Molecular Weight: 656, 4702
Fmoc-LysAMBF₃-O-NHS 1) (1:19) DIPEA:DMF (v/v) rt, 2 h
2) (1:4) piperidine:DMF(v/v) rt, 30 min

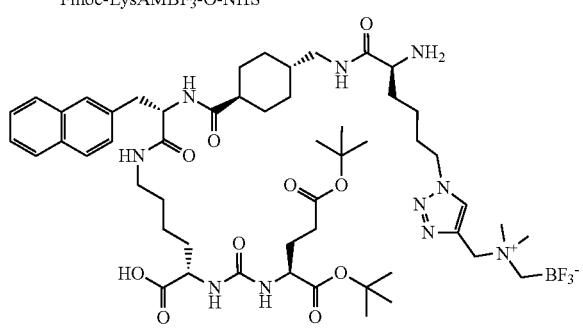

Chemical Formula: C₅₃H₈₂BF₃N₁₀O₁₀
Exact Mass: 1086, 6261
Molecular Weight: 1087, 1042
PSMA-617-LysAMBF₃-NH₂

Figure 43:
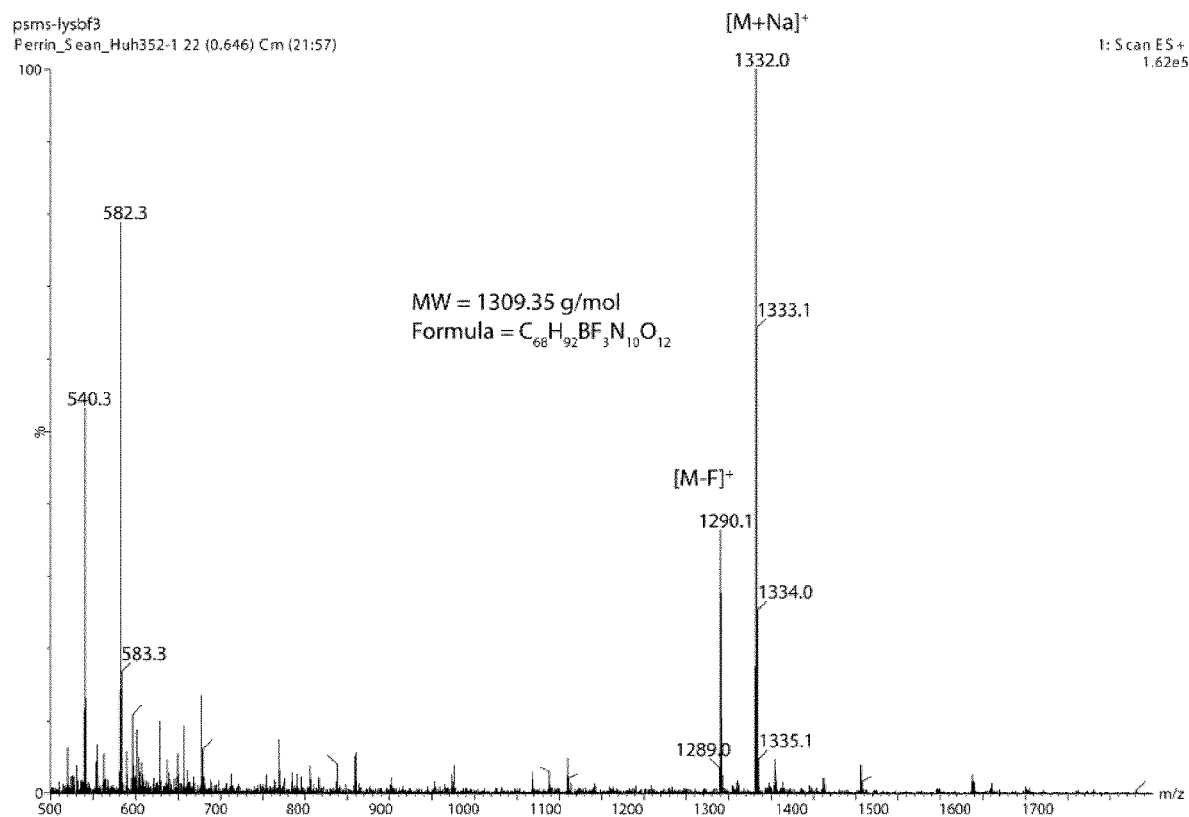
FIG. 43 shows ESI-MS(+) spectrum of PSMA-617-LysAMBF$_3$—Fmoc: calculated for $C_{68}H_{92}BF_3N_{10}O_{12}$, 1309.35 m/z; found, [M−F]$^+$=1290.1 m/z, [M+Na]$^+$=1332.0 m/z.

PSMA-617-NH₂ (12.2 mg, 9.3 µmol, 1 eq.) in an Eppendorf tube was dissolved in (1:19) DIPEA:DMF (200 µL) and was transferred to a separate Eppendorf tube containing Fmoc-LysAMBF₃—O—NHS (25.2 mg, 38.4 µmol, 4.1 eq.). The mixture was stirred for 2 h at room temperature using a rotisserie stirrer. The mixture was concentrated down by speed-vac until volume was ca. 50 to 100 µL. Cold diethyl ether (1 mL) was added to precipitate the product. The mixture was then vortexed and centrifuged to remove the supernatant. Minimal DMF (50 µL) was added to the product to dissolve the product and diethyl ether (1 mL) was added to wash crude. The mixture was vortexed and centrifuged to remove supernatant. The product was then dried by speed-vac. MeCN (500 µL) was then added to dissolve and remove excess Fmoc-LysAMBF₃—O—NHS. The mixture was centrifuged down and the supernatant containing excess reagent was removed. The product was dried once more in speed-vac. A small sample of the product PSMA-617-LysAMBF₃-Fmoc was dissolved in MeOH for MS. ESI-MS (+): calculated for C₆₈H₉₂BF₃N₁₀O₁₂, 1309.35 m/z; found, [M−F]⁺=1290.1 m/z, [M+Na]⁺=1332.0 m/z. TLC (1:19 NH₄OH:EtOH, R$_f$ of Product=0.42, visible with 254 nm). See FIG. 43.

Figure 44:
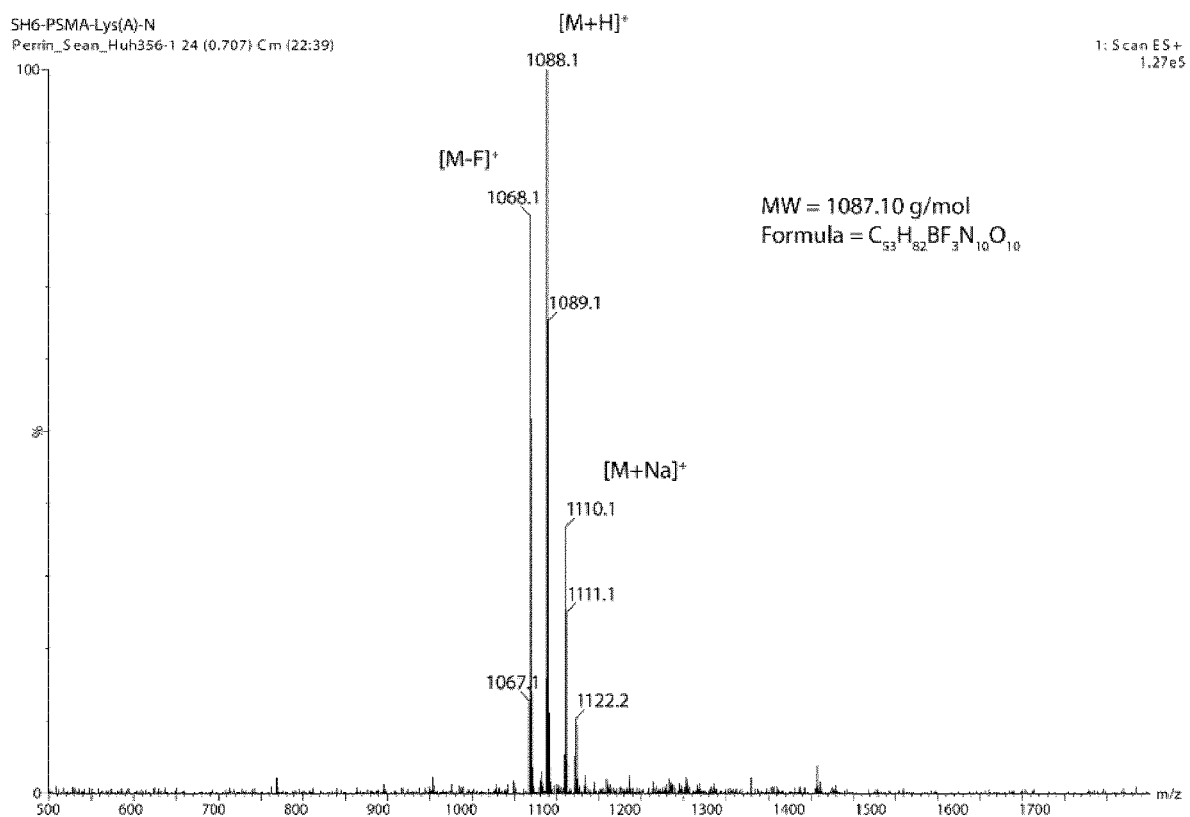
FIG. 44 shows ESI-MS(+) spectrum of PSMA-617-LysAMBF$_3$—NH$_2$: calculated for $C_{53}H_{82}BF_3N_{10}O_{10}$, 1087.10 m/z; found, [M−F]$^+$=1068.1 m/z, [M+H]$^+$=1088.1 m/z, [M+Na]$^+$=1110.1 m/z.

PSMA-617-LysAMBF₃—Fmoc was then dissolved in (1:4) piperidine:DMF (200 µL) to remove Fmoc. Reaction was carried out for 30 minutes at RT by mixing it in rotisserie stirrer. The mixture was concentrated down using speed-vac until volume was ca. 50 to 100 µL. Cold diethyl ether (1 mL) was added to precipitate the product. This was then vortexed and centrifuged to remove the supernatant. Minimal DMF (50 µL) was added to the product to dissolve so that diethyl ether wash was done once more. The mixture was vortexed and centrifuged. The supernatant was removed, and the product was then dried by speed-vac to afford a crude mixture containing PSMA-617-LysAMBF₃—NH₂. ESI-MS(+): calculated for C₅₃H₈₂BF₃N₁₀O₁₀, 1087.10 m/z; found, [M−F]⁺=1068.1 m/z, [M+H]⁺=1088.1 m/z, [M+Na]⁺=1110.1 m/z. TLC (1:19 NH₄OH:MeOH, R$_f$ of product=0.23, visible under a 254 nm UV lamp, stains with ninhydrin). See FIG. 44.

V. PSMA-617-LysAMBF₃-DOTA

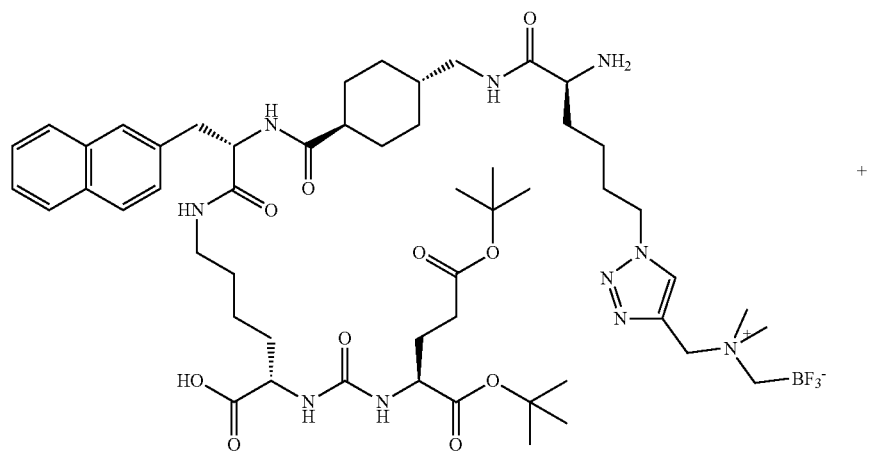

Chemical Formula: C₅₃H₈₂BF₃N₁₀O₁₀
Exact Mass: 1086.6261
Molecular Weight: 1087.1042
PSMA-617-LysAMBF₃-NH₂

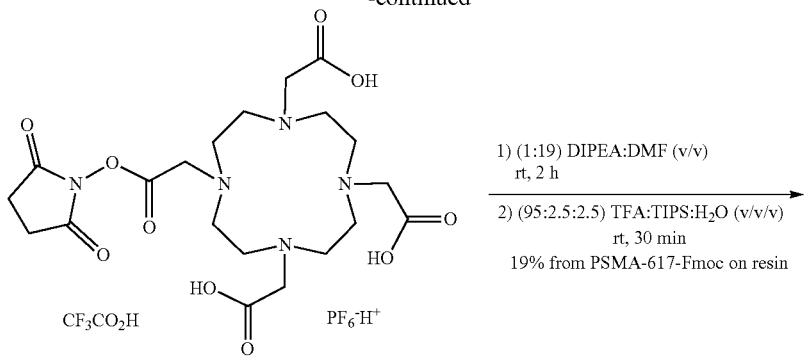

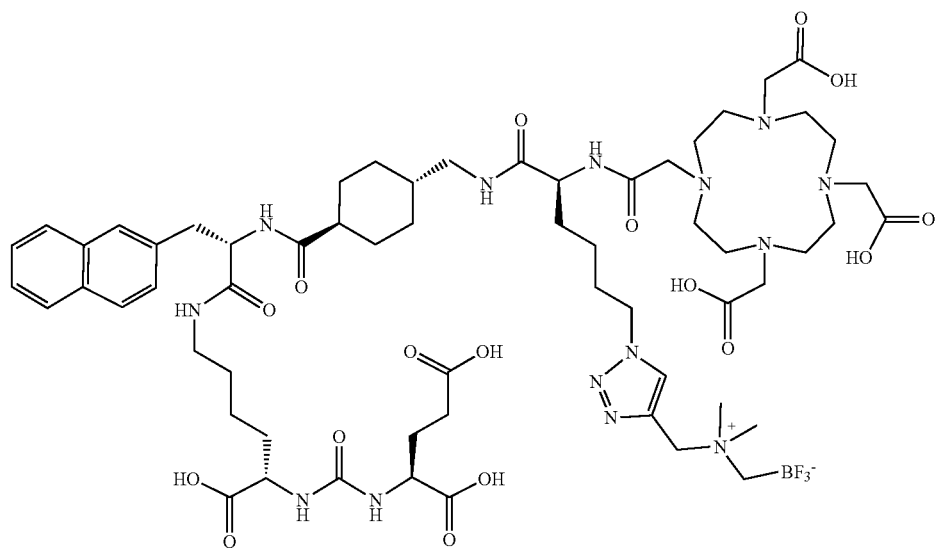

Figure 45:
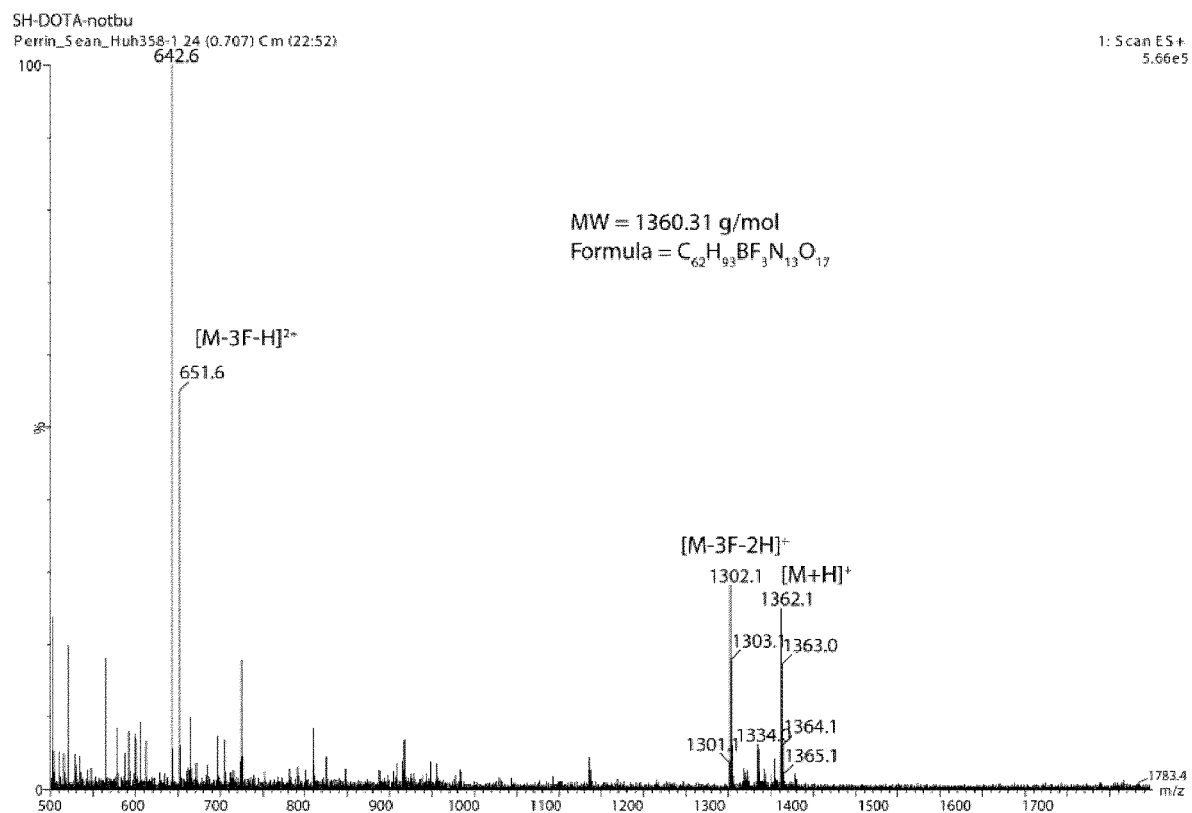
FIG. 45 shows ESI-MS(+) spectrum of PSMA-617-LysAMBF$_3$-DOTA: calculated for $C_{61}H_{93}BF_3N_{13}O_{17}$, 1360.31 m/z; found, [M−3F−2H]$^+$=1302.1 m/z, [M+H]$^+$=1362.1 m/z.

DOTA-NHS—HPF$_6$-TFA (20.2 mg, 26.2 µmol, 2.8 eq.) was weighed out and added to crude PSMA-617-LysAMBF$_3$—NH$_2$ (max. 9.3 µmol, 1 eq.) in an Eppendorf tube. (1:19) DIPEA:DMF (v/v) was added to the mixture and stirred for 2 hours at RT using rotisserie stirrer. The mixture was concentrated by speed-vac until minimal volume (50 to 100 µL) and mixture was precipitated by diethyl ether (1 mL). The mixture was vortexed and centrifuged. The supernatant was removed and the product was then dried by speed-vac. Tert-butyl was deprotected by adding (95:2.5:2.5) TFA:TIPS:H$_2$O (v/v/v) (200 µL) and the mixture was stirred for 1 h at room temperature. The mixture was then concentrated down by blowing gentle air until volume is 50 to 100 µL. Diethyl ether (1 mL) was added to precipitate the product and the mixture was vortexed and centrifuged. Supernatant was removed, and the mixture was then dried down by speed-vac to provide a crude residue (33 mg) containing PSMA-617-LysAMBF$_3$-DOTA. ESI-MS (+): calculated for C$_{61}$H$_{93}$BF$_3$N$_{13}$O$_7$, 1360.31 m/z; found, [M−3F-2H]$^+$=1302.1 m/z, [M+H]$^+$=1362.1 m/z. See FIG. 45.

The crude residue (33 mg) was dissolved in (1:1) MeCN:H$_2$O (+0.1% formic acid) (1 mL) and purified on HPLC (Column: Agilent Eclipse XDB-C18, 5 µm, 9.4 mm×250 mm; Flow rate: 2 mL/min; UV-vis detector: 276 nm; Gradient: 15% to 65% MeCN:H$_2$O (+0.1% formic acid) over 19 min). Peaks were collected at 9.25 min. Product was collected in a 50 mL falcon tube and was frozen on dry ice. Once completely frozen, the collected fraction was lyophilized to provide pure PSMA-617-LysAMBF$_3$-DOTA (2.5 mg, 1.8 µmol, 19%).

VI. PSMA-617-LysAMBF$_3$-DOTA(Cu)

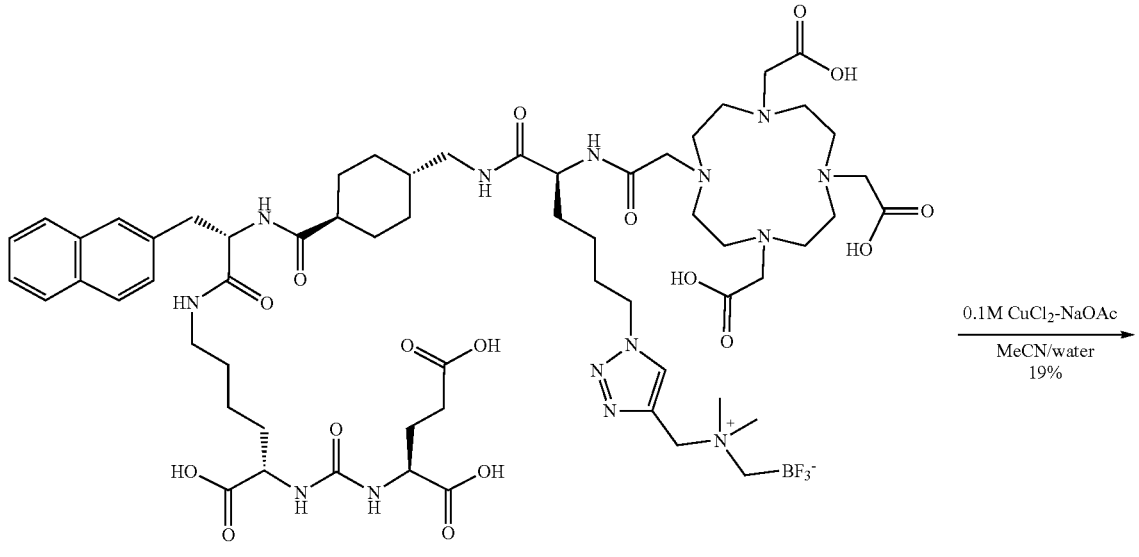

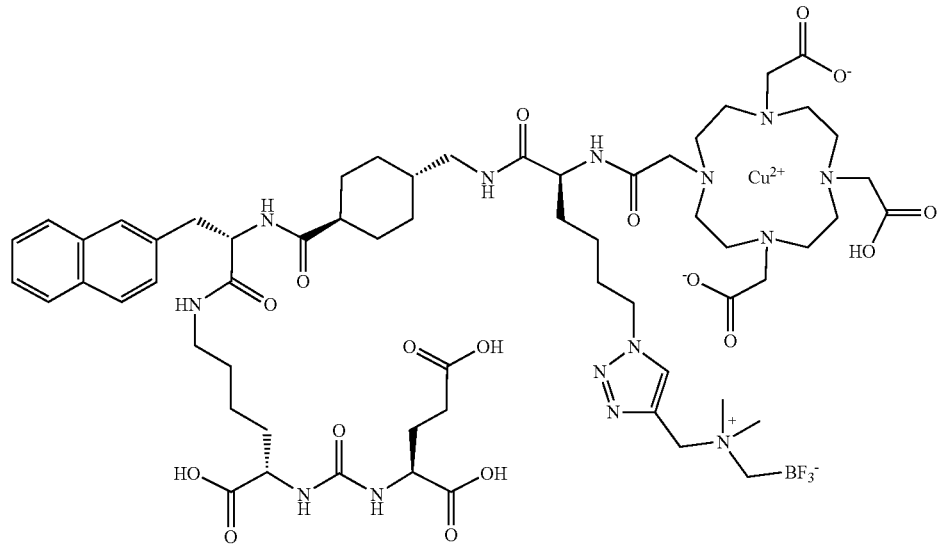

PSMA-617-LysAMBF$_3$-DOTA(Cu) was synthesized by treating PSMA-617-LysAMBF$_3$-DOTA (44.2 mg, 31.1 µmol) with a 0.1M CuCl$_2$—NaOAc (1.55 mL, pH=4) along with MeCN (1.5 mL). The mixture was placed in 65° C. hotplate for 30 minutes. Then the mixture was concentrated using the Speed-vac to afford a crude residue containing expected copper-chelate. ESI-MS(+): calculated for C$_{61}$H$_{90}$BCuF$_3$N$_{10}$O$_{10}$, 1422.8 m/z; found, [M−3F-2H]$^+$= 1362.8 m/z, [M−F]$^+$=1402.8 m/z, [M+H]$^+$=1423.8 m/z, [M+Na]$^+$=1444.8 m/z.

Figure 46:
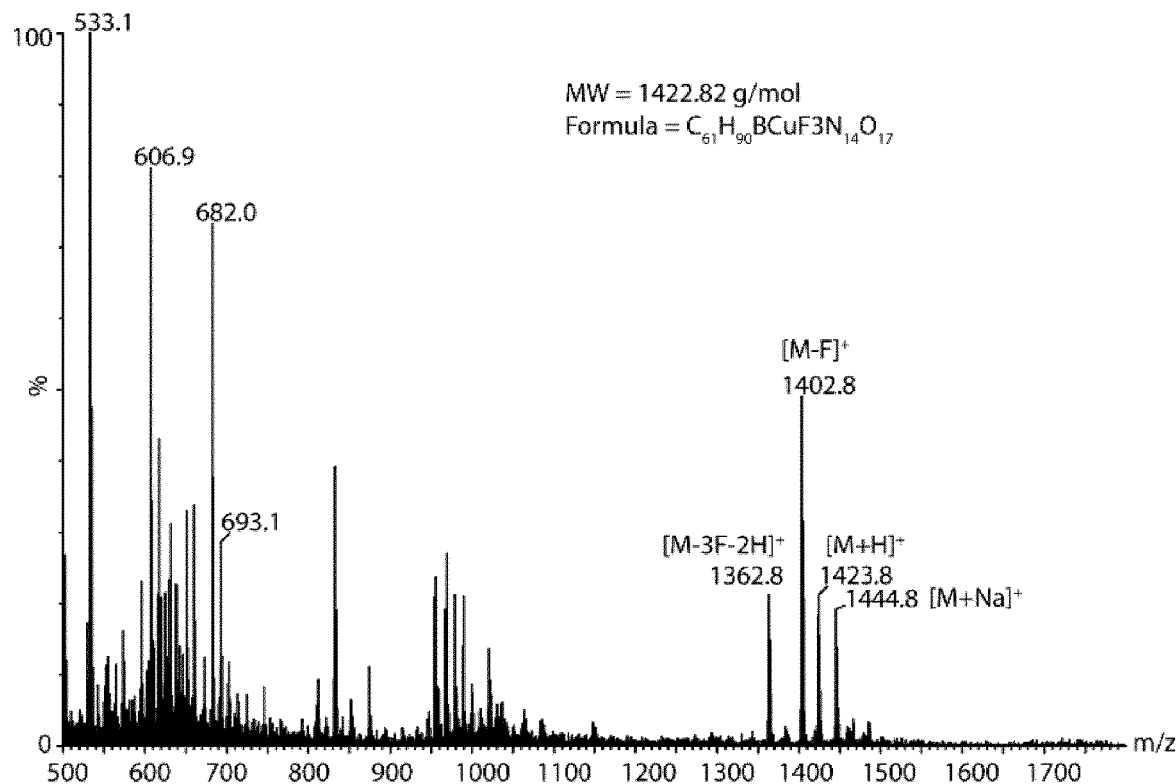
FIG. 46 shows ESI-MS(+) spectrum of PSMA-617-LysAMBF$_3$-DOTA(Cu): calculated for $C_{61}H_{90}BCuF_3N_{10}O_{10}$, 1422.8 m/z; found, [M−3F−2H]$^+$=1362.8 m/z, [M−F]$^+$=1402.8 m/z, [M+H]$^+$=1423.8 m/z, [M+Na]$^+$=1444.8 m/z.

The crude residue (44.2 mg) was dissolved in (1:1) MeCN:H$_2$O (+0.1% formic acid) (1 mL). and purified on HPLC (Column: Agilent Eclipse XDB-C18, 5 µm, 9.4 mm×250 mm; Flow rate: 2 mL/min; UV-vis detector: 276 nm; Gradient: 15% to 40% MeCN:H$_2$O (+0.1% formic acid) over 23 min). Product was collected in a 50 mL falcon tube and was frozen on dry ice. Once completely frozen, the collected fraction was lyophilized to provide pure PSMA-617-LysAMBF$_3$-DOTA(Cu) (8.5 mg, 6.0 µmol, 19%). See FIG. 46.

VII. $^{18}$F-labeling of PSMA-617-LysAMBF$_3$-DOTA or PSMA-617-LysAMBF$_3$-DOTA(Cu)

80 nmol of $^{19}$F-PSMA-617-LysAMBF$_3$-DOTA or $^{19}$F-PSMA-617-LysAMBF$_3$-DOTA(Cu) were resuspended in aqueous pyridazine-HCl buffer (15 µL, 1M, pH=2), DMF (15 µL) and aqueous KHF$_2$ (4 µL, 5 mM) in a polypropylene tube. No carrier-added $^{18}$F-fluoride was obtained by bombardment of H$_2$$^{18}$O with 18 MeV protons, followed by trapping on an anion exchange column (9 mg, QMA, chloride form). The $^{18}$F-fluoride was eluted off with saline (100 μL) into the reaction tube. The reaction mixture was heated at 80° C. for 20 min under vacuum and diluted with 40 mM aqueous ammonium formate (2 mL). The solution was purified by HPLC using the semi-preparative column, eluted with (30:70) MeN/water (+0.1% TFA) (v/v) at a flow rate of 4.5 mL/min. The retention time was around 10 m for both chelated and non-chelated tracer. The decay-corrected radiochemical yield was 1.0±0.3% (n=3) or 2.7±0.7% (n=3) for $^{18}$F-PSMA-617-LysAMBF$_3$-DOTA or $^{18}$F-PSMA-617-LysAMBF$_3$-DOTA(Cu), respectively. Radiochemical purity of >99% was achieved for the both of labeled tracers as determined by radio HPLC. The specific activity was measured using the analytical HPLC system. It was calculated by dividing the injected radioactivity (1.5 to 3 mCi) in final product solution by the mass in the injected solution. The mass of injected product was estimated by comparing the UV absorbance obtained from the injection with a previously prepared standard curve. The specific activity was 3.7±2.5 Ci/μmol (n=3) or 4.8±2.2 Ci/μmol (n=3) for $^{18}$F-PSMA-617-LysAMBF$_3$-DOTA or $^{18}$F-PSMA-617-LysAMBF$_3$-DOTA(Cu), respectively.

Results

Figure 4:
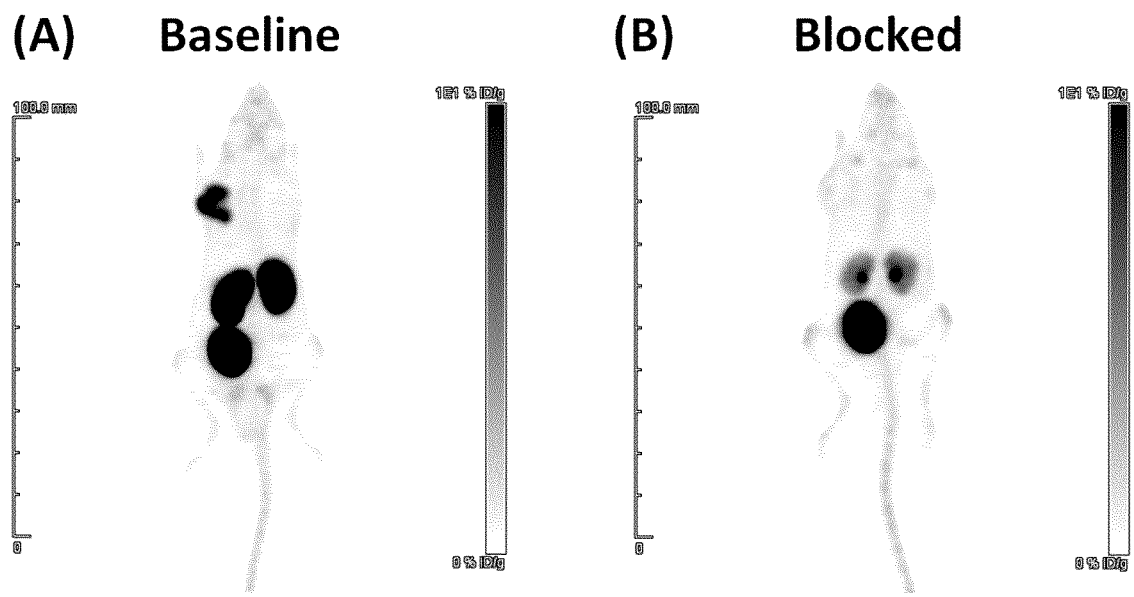
FIG. 4 shows maximum intensity projection images (1 h post-injection) of F-18 labeled PSMA-617-Lys-AMBF3-DOTA in LNCaP prostate cancer xenograft-bearing mice (A) without and (B) with co-injection of DCFPyL (0.5 mg).

Table 7 shows the biodistribution (1 h post-injection) of F-18 labeled PSMA-617-Lys-AMBF3-DOTA in mice bearing PSMA-expressing LNCaP prostate cancer xenografts. The structure of PSMA-617-LysAMBF3-DOTA is shown in FIG. 2. FIG. 4 shows maximum intensity projection PET images (1 h post-injection) of F-18 labeled PSMA-617-Lys-AMBF3-DOTA in LNCaP prostate cancer xenograft-bearing mice.

TABLE 7

Biodistribution (1 h post-inejection) of F-18 labeled PSMA-617-Lys-AMBF3-DOTA in mice bearing PSMA-expressing LNCaP prostate cancer xenografts.

| Organ/tissue | Uptake (% ID/g) | |
| --- | --- | --- |
| | Baseline (n = 5) | Blocking (n = 5) |
| blood | 0.76 ± 0.25 | 0.82 ± 0.43 |
| urine | 270.38 ± 148.78 | 1093.02 ± 468.46 |
| fat | 0.93 ± 0.20 | 0.18 ± 0.08 |
| seminal | 6.60 ± 8.78 | 1.32 ± 2.04 |
| testes | 0.56 ± 0.11 | 0.31 ± 0.18 |
| intestine | 0.48 ± 0.10 | 0.76 ± 0.24 |
| stomach | 0.14 ± 0.06 | 0.22 ± 0.23 |
| spleen | 4.14 ± 2.35 | 0.27 ± 0.06 |
| liver | 0.29 ± 0.07 | 0.40 ± 0.11 |
| pancreas | 0.36 ± 0.09 | 0.17 ± 0.06 |
| adrenal | 2.77 ± 0.94 | 0.28 ± 0.18 |
| kidney | 131.54 ± 56.67 | 6.70 ± 4.19 |
| lung | 1.81 ± 0.40 | 0.74 ± 0.28 |
| heart | 0.34 ± 0.09 | 0.30 ± 0.14 |
| tumour | 10.64 ± 4.00 | 0.78 ± 0.26 |
| muscle | 0.25 ± 0.06 | 0.40 ± 0.35 |
| bone | 0.57 ± 0.05 | 1.73 ± 0.70 |
| brain | 0.03 ± 0.01 | 0.03 ± 0.01 |
| tail | 0.98 ± 0.18 | 1.85 ± 0.33 |
| thyroid | 0.68 ± 0.23 | 0.28 ± 0.12 |
| salivary | 1.70 ± 0.58 | 0.28 ± 0.09 |
| lacrimal | 0.16 ± 0.10 | 0.19 ± 0.26 |
| Tumor/Muscle | 41.55 ± 10.83 | 2.91 ± 1.65 |
| Tumor/Blood | 14.19 ± 3.85 | 1.01 ± 0.23 |
| Tumor/Kidney | 0.09 ± 0.03 | 0.13 ± 0.04 |

REFERENCES FOR EXAMPLE 2

1. Marco R A, Díaz-Montero C M, Wygant J N, Kleinerman E S, McIntyre B W. α4 integrin increases anoikis of human osteosarcoma cells. J Cell Biochem. 2003; 88(5): 1038-1047.
2. Michigami T, Shimizu N, Williams P J, et al. Cell-cell contact between marrow stromal cells and myeloma cells via VCAM-1 and α4β1-integrin enhances production of osteoclast-stimulating activity. Blood. 2000; 96(5):1953-1960.
3. Hatano K, Kikuchi J, Takatoku M, et al. Bortezomib overcomes cell adhesion-mediated drug resistance through downregulation of VLA-4 expression in multiple myeloma. Oncogene. 2009; 28(2):231-242.
4. Olson D L, Burkly L C, Leone D R, Dolinski B M, Lobb R R. Anti-α4 integrin monoclonal antibody inhibits multiple myeloma growth in a murine model. Mol Cancer Ther. 2005; 4(1):91-99.
5. Sanz-rodríguez F, Teixidó J. VLA-4-dependent myeloma cell adhesion. Leuk Lymphoma. 2001; 41(3-4):239-245.
6. Drillenburg P, Pals S T. Cell adhesion receptors in lymphoma dissemination. Blood. 2000; 95(6):1900-1910.
7. Baldini L, Cro L, Calori R, Nobili L, Silvestris I, Maiolo A. Differential expression of very late activation antigen-3 (VLA-3)NLA-4 in B-cell non-Hodgkin lymphoma and B-cell chronic lymphocytic leukemia. Blood. 1992; 79(10):2688-2693.
8. Finn W G, Singleton T P, Schnitzer B, Ross C W, Stoolman L M. Adhesion molecule expression in CD5-negative/CD10-negative chronic B-cell leukemias: Comparison with non-Hodgkin's lymphomas and CD5-positive B-cell chronic lymphocytic leukemia. Hum Pathol. 2001; 32(1):66-73.
9. Matsunaga T, Takemoto N, Sato T, et al. Interaction between leukemic-cell VLA-4 and stromal fibronectin is a decisive factor for minimal residual disease of acute myelogenous leukemia. Nat Med. 2003; 9(9):1158-1165.
10. Vincent A, Cawley J, Burthem J. Integrin function in chronic lymphocytic leukemia. Blood. 1996; 87(11): 4780-4788.
11. Hart I R, Birch M, Marshall J F. Cell adhesion receptor expression during melanoma progression and metastasis. Cancer and Metastasis Reviews. 1991; 10(2):115-128.
12. Klemke M, Weschenfelder T, Konstandin M H, Samstag Y. High affinity interaction of integrin α4β1 (VLA-4) and vascular cell adhesion molecule 1 (VCAM-1) enhances migration of human melanoma cells across activated endothelial cell layers. J Cell Physiol. 2007; 212(2):368-374.
13. Kuphal S, Bauer R, Bosserhoff A-K. Integrin signaling in malignant melanoma. Cancer and Metastasis Reviews. 2005; 24(2):195-222.
14. Schadendorf D, Gawlik C, Haney U, Ostmeier H, Suter L, Czarnetzki B M. Tumour progression and metastatic behaviour in vivo correlates with integrin expression on melanocytic tumours. J. Pathol. 1993; 170(4):429-434.
15. Schadendorf D, Heidel J, Gawlik C, Suter L, Czarnetzki B M. Association With Clinical Outcome of Expression of VLA-4 in Primary Cutaneous Malignant Melanoma as Well as P-selection and E-selectin on Intratumoral Vessels. J Natl Cancer Inst. 1995; 87(5):366-371.
16. Garmy-Susini B, Avraamides C J, Schmid M C, et al. Integrin α4β1 signaling is required for lymphangiogenesis and tumor metastasis. Cancer Res. 2010; 70(8):3042-3051.

17. Jin H, Su J, Garmy-Susini B, Kleeman J, Varner J. Integrin α4β1 promotes monocyte trafficking and angiogenesis in tumors. Cancer Res. 2006; 66(4):2146-2152.
18. Garmy-Susini B, Jin H, Zhu Y, Sung R-J, Hwang R, Varner J. Integrin α4β1-VCAM-1-mediated adhesion between endothelial and mural cells is required for blood vessel maturation. J Clin Invest. 2005; 115(6):1542.
19. Damiano J S, Dalton W S. Integrin-mediated drug resistance in multiple myeloma. Leuk Lymphoma. 2000; 38(1-2):71-81.
20. Peng L, Liu R W, Marik J, Wang X B, Takada Y, Lam K S. Combinatorial chemistry identifies high-affinity peptidomimetics against alpha(4)beta(1) integrin for in vivo tumor imaging. Nat Chem Biol. 2006; 2(7):381-389.
21. Peng L, Liu R, Andrei M, Xiao W, Lam K S. In vivo optical imaging of human lymphoma xenograft using a library-derived peptidomimetic against α4β1 integrin. Mol Cancer Ther. 2008; 7(2):432-437.
22. DeNardo S J, Liu R W, Albrecht H, et al. (111)In-LLP2A-DOTA Polyethylene Glycol-Targeting alpha 4 beta 1 Integrin: Comparative Pharmacokinetics for Imaging and Therapy of Lymphoid Malignancies. J Nucl Med. 2009; 50(4):625-634.
23. Shokeen M, Zheleznyak A, Wilson J M, et al. Molecular Imaging of Very Late Antigen-4 (alpha(4)beta(1) Integrin) in the Premetastatic Niche. J Nucl Med. 2012; 53(5):779-786.
24. Beaino W, Anderson C J. PET Imaging of Very Late Antigen-4 in Melanoma: Comparison of 68Ga- and 64Cu-Labeled NODAGA and CB-TE1A1P-LLP2A Conjugates. J Nucl Med. 2014; 55(11):1856-1863.
25. Soodgupta D, Hurchla M A, Jiang M, et al. Very Late Antigen-4 (alpha(4)beta(1) Integrin) Targeted PET Imaging of Multiple Myeloma. PLoS One. 2013 (Epub 213 February 2013; 8(2).
26. Soodgupta D, Zhou H, Beaino W, et al. Ex Vivo and In Vivo Evaluation of Overexpressed VLA-4 in Multiple Myeloma Using LLP2A Imaging Agents. J Nucl Med. 2016; 57(4):640-645.
27. Jiang M J, Ferdani R, Shokeen M, Anderson C J. Comparison of two cross-bridged macrocyclic chelators for the evaluation of Cu-64-labeled-LLP2A, a peptidomimetic ligand targeting VLA-4-positive tumors. Nucl Med Biol. 2013; 40(2):245-251.
28. Roxin Á, Zhang C, Huh S, et al. Preliminary evaluation of 18F-labeled LLP2A-trifluoroborate conjugates as VLA-4 (α4β1 integrin) specific radiotracers for PET imaging of melanoma. Nucl Med Biol. 2018; 61:11-20.
29. Liu Z B, Pourghiasian M, Radtke M A, et al. An Organotrifluoroborate for Broadly Applicable One-Step F-18-Labeling. Angew Chem-Int Edit. 2014; 53(44):11876-11880.
30. Walker D, Li Y, Roxin A, Schaffer P, Adam M J, Perrin D M. Facile synthesis and F-18-radiolabeling of alpha(4)beta(1)-specific LLP2A-aryltrifluoroborate peptidomimetic conjugates. Bioorg Med Chem Lett. 2016; 26(20):5126-5131.
31. Liu Z B, Amouroux G, Zhang Z X, et al. F-18-Trifluoroborate Derivatives of Des-Arg(10) Kallidin for Imaging Bradykinin 1 Receptor Expression with Positron Emission Tomography. Mol Pharm. 2015; 12(3):974-982.
32. Liu Z B, Lin K S, Benard F, et al. One-step F-18 labeling of biomolecules using organotrifluoroborates. Nat Protoc. 2015; 10(9):1423-1432.
33. Pourghiasian M, Liu Z B, Pan J H, et al. F-18-AmBF3-MJ9: A novel radiofluorinated bombesin derivative for prostate cancer imaging. Biorg Med Chem. 2015; 23(7):1500-1506.
34. Rose D M, Han J, Ginsberg M H. α4 integrins and the immune response. Immunol Rev. 2002; 186(1):118-124.
35. Yusuf-Makagiansar H, Anderson M E, Yakovleva T V, Murray J S, Siahaan T J. Inhibition of LFA-1/ICAM-1 and VLA-4NCAM-1 as a therapeutic approach to inflammation and autoimmune diseases. Medicinal research reviews. 2002; 22(2):146-167.
36. Abe M, Hiura K, Ozaki S, Kido S, Matsumoto T. Vicious cycle between myeloma cell binding to bone marrow stromal cells via VLA-4-VCAM-1 adhesion and macrophage inflammatory protein-1α and MIP-1β production. J Bone Miner Metab. 2009; 27(1):16-23.
37. Imai Y, Shimaoka M, Kurokawa M. Essential roles of VLA-4 in the hematopoietic system. Int J Hematol. 2010; 91(4):569-575.
38. Beaino W, Nedrow J R, Anderson C J. Evaluation of Ga-68- and Lu-177-DOTA-PEG(4)-LLP2A for VLA-4-Targeted PET Imaging and Treatment of Metastatic Melanoma. Mol Pharm. 2015; 12(6):1929-1938.
39. DeNardo S, Sutcliffe J, Anderson C, et al. (111)In-DOTA- and (64)Cu-CB-TE2A-LLP2A targeting alpha 4 beta 1 integrin: Development of imaging directed (67)Cu therapy of lymphoid malignancies. Cancer Biother Radiopharm. 2008; 23(4):515-515.
40. Zwingenberger A L, Kent M S, Liu R W, et al. In-Vivo Biodistribution and Safety of Tc-99m-LLP2A-HYNIC in Canine Non-Hodgkin Lymphoma. PLoS One. 2012; 7(4).

Examples 3 and 4: Synthesis and Characterization of DOTA-Lys(AMBF3)-RM2 (DOTA-Lys-AMBF3-4-amino-1-carboxymethyl-piperidine-D-Phe-Gln-Trp-Ala-Val-Gly-His-Sta-Leu-NH2) and DOTA-Lys (AMBF3)-BK Results and Discussion Synthesis of DTPA

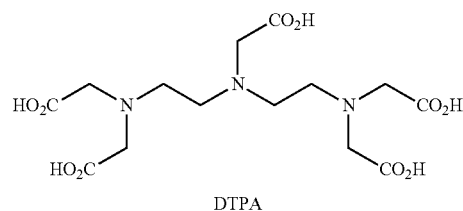 [SMILES: O=C(O)CN(CCN(CC(=O)O)CC(=O)O)CCN(CC(=O)O)CC(=O)O]

DTPA

Diethylenepentaacetic acid (DTPA) is an acidic chelator used in the synthesis of both therapeutic and diagnostic drugs as a chaperone for radioactive metals (e.g. $^{64}Cu$).[25] Because this chelator possesses five arms available for conjugation onto a peptide, the arms themselves must be protected in a design specific to the application. For our purposes, one free arm was desired for solid-phase chemistry, while the other four arms were to be protected by an acid-labile protecting group (compound 4). Then, upon final acidic TFA cleavage of the peptide from the resin, the protecting groups could be removed. This design concept led to synthetic scheme 3 adapted from literature:[26, 27]

Scheme 3. Synthetic scheme for DTPA.

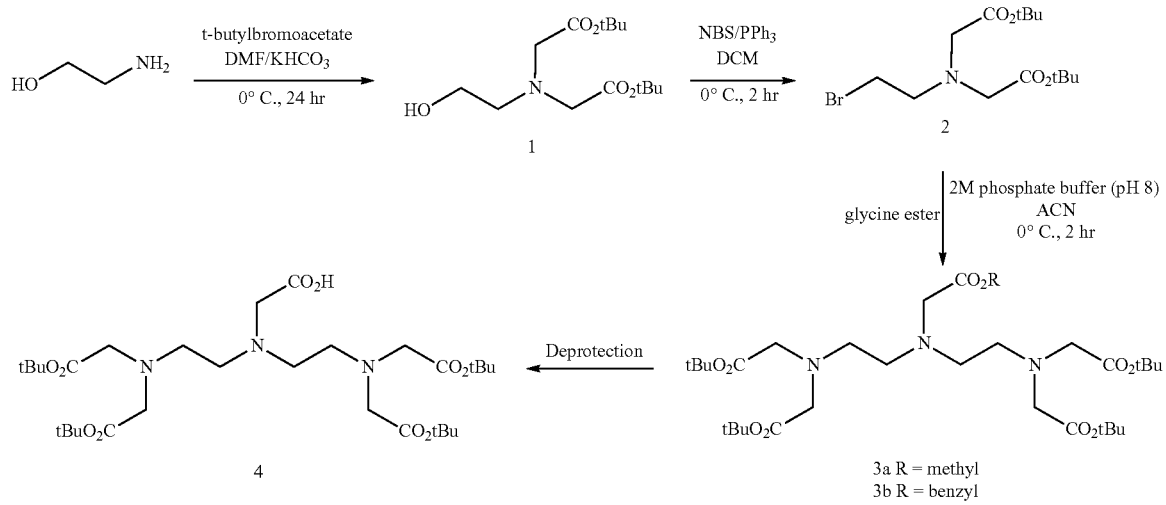

The synthesis of compound 4 was undertaken by mixing commercially available ethanolamine with 2 equivalents of t-butylbromoacetate under basic conditions. Upon extraction with diethyl ether and subsequent sodium bicarbonate and brine washes, the oily residue was purified on a silica column. The purification was amenable to scale-up as almost 3 g of compound 1 was purified in 71% yield. The $^1$H-NMR of this compound indicated high purity, with negligible signals from water and hexane (see Appendix). Compound 1 was subsequently converted to 2 by treating the tertiary aminoalcohol with NBS/PPh$_3$ in DCM under anhydrous conditions and purified in 71% yield. Upon completion of the reaction, the triphenylphospineoxide side product was removed by filtration of the crude reaction mixture over a short silica column, after which the desired product was purified by a second silica column employing 5:1 hexane/diethyl ether. The purity of this compound was confirmed by $^1$H-NMR, and the ESI-MS exhibited the expected bromine isotope pattern (data not shown).

At this point, a suitable glycine ester was double alkylated with 2 to afford DTPA derivate (3). We initially opted for the methyl ester, since we had envisioned a facile removal of the methyl group via saponification, which would leave the tert-butyl protecting groups on the other four arms unaffected. To this end, the synthesis of 3a was conducted in aqueous phosphate-buffered acetonitrile, which was made from the sodium phosphate salts. Unfortunately, the solubility of the phosphate was so low that the salts often precipitated if the ambient temperature dropped. As such, the mono- and di-potassium salts of phosphate were used instead to create the buffer, with the addition of aqueous NaOH or HCl to adjust the pH to 8. This highly concentrated solution formed a biphasic system when mixed with acetonitrile. After 24 hours, the mixture was filtered and the organic layer was removed and evaporated. In order to remove the remaining inorganic salts, the amorphous oil was dissolved in CHCl$_3$ and re-filtered. Chromatographic purification of this compound was problematic due to the three tertiary amino groups that could be easily protonated on acidic silica. To our disappointment, complete purification was still not possible even when the silica was pre-treated with triethylamine and eluted with 1% triethylamine. Nevertheless, we opted to subject the impure 3a to one equivalent of aqueous LiOH to effect the saponification of the methyl ester (4). After completion of the reaction as indicated by TLC, the product was extracted into diethyl ether. Mass spectrometric analysis confirmed the presence of the mono-deprotected DTPA adduct, showing the [M+Na+] signal at m/z=640 (data not shown). Although the saponification resulted in the formation of some desired material, the reaction was neither clean nor high yielding. We hypothesized that saponification conditions were impeding with the purification of the product; indeed, a literature survey indicated that no reported synthesis of the mono-methyl tetra-tert-butyl-protected DTPA (3a). A benzyl-protected glycine ester was employed instead, and for which palladium-catalyzed hydrogenation provided the desired product (3b).[26, 28]

To synthesize 3b, glycine benzyl ester was first isolated from the salt of benzyl glycinate p-toluenesulfonate with ether/carbonate extraction and used immediately. This was reacted with compound 2 in similar conditions (vide supra) to yield benzyl-protected DTPA in 27% crude yield. Again, because of the nature of the functional groups, purification by chromatography proved difficult and was not thoroughly pursued. Other methods of purification (e.g. acidic/basic/neutral alumina, C18 reverse phase, distillation) were not investigated. Rather, crude 3b was deprotected by palladium-catalyzed hydrogenation in MeOH overnight in 81% yield. Upon completion, the Pd/C solid was removed by filtering the mixture over a sintered glass funnel. Interestingly, compound 4 required no further purification as validated by $^1$H-NMR (see Appendix). The overall yield was 11.4% over 4 steps.

Synthesis of a Novel AMBF$_3$

At this point in the project, our focus shifted from synthesizing the DTPA chelator (4) to building a novel trifluoroborate that could be incorporated into any peptide chain. Dimethylammoniomethyltrifluoroborate (AMBF$_3$) (7) was chosen as a precursor because of its high hydrolytic stability, ease of preparation, and usability with copper-assisted azide-alkyne cycloaddition reactions.[19] In fact, even in highly dilute conditions (~5 mM) at pH 7.5, compound 7 lost free fluoride at a very slow, first order rate as shown in FIG. 4.[19] This in vitro stability, coupled with the straightforward synthesis of compound 7, renders the AMBF$_3$ architecture a unique target for PET imaging agents.

Compound 6 was acquired from the equimolar reaction of commercially available iodomethylboronate pinacol ester and N,N-dimethylpropargylamine in diethyl ether (see Scheme 4). Rapid precipitation of the salt followed by filtration yielded the NMR-pure product in >90% yield (see Appendix). Fluorination with KHF$_2$ at pH 2 afforded compound 7 (see Scheme 4). Free fluoride was removed by passage through a short silica plug eluting with the 20% ACN/EtOH. The $^1$H-NMR of the product exhibited δ=1.15 ppm, indicative of the pinacol diol impurities. Moreover, the reaction yield was often 200%-300% due to contaminations such as fluoride salts, KBF$_4$ (seen on $^{19}$F-NMR at −150 ppm), dissolved silicates, and other uncharacterized inorganic impurities. To remedy some of these issues, the crude solid was taken up in diethyl ether and re-filtered. The resulting white powder was $^1$H-NMR and $^{19}$F-NMR pure, excluding the KBF$_4$ impurity that was still not removed.

Scheme 4. Synthetic scheme for AMBF$_3$ (7).

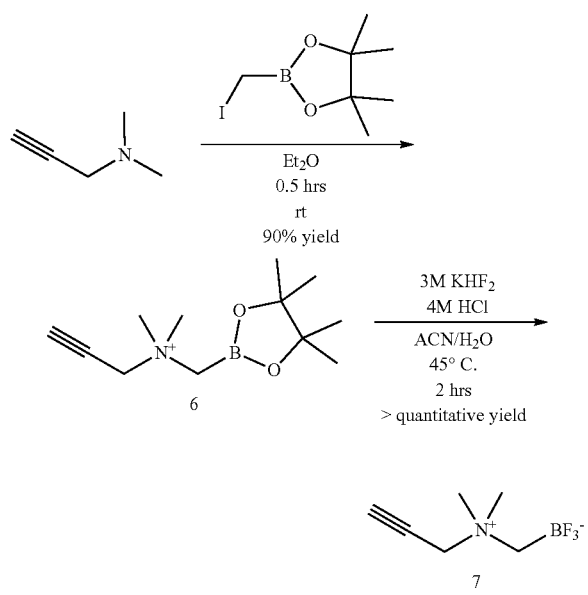

An enlightening discussion on the electronic nature of alkyl trifluoroborates can be made based on the $^1$H-NMR spectra of compounds 6 and 7. Both NMR experiments were conducted in D$_2$O, as it was the only solvent that the two compounds were soluble in that did not interfere with the signals of interest. The signal for the methylene protons between the ammonium group and boron shifts considerably upon fluorination. Specifically, the 2H singlet for 6 is at δ=3.09 ppm, whereas in compound 7, the signal resides at δ=2.55 ppm (see Appendix). While it is evident that the boron in compound 7 has a formal negative charge that should confer a more shielding NMR environment, the presence of three fluorine atoms provides a highly electron-withdrawing (and thereby de-shielding) environment for the methylene protons. This conflicting functionality actually manifests as electron shielding (electron donating), as the upfield shift is observed in both D$_2$O and MeOD (data not shown). In addition to the change in chemical shift of the methylene signal, its appearance changes from a strong singlet to a broad singlet or possibly a multiplet. Coupling to boron-11 can be ruled out because this was not seen in the spectrum for compound 6. Thus, this may be explained by long-range coupling to fluorine-19 or due to some conformational inflexibility that is within the NMR timescale. Validation for either of these theories was not thoroughly pursued.

With regards to the $^{19}$F-NMR of compounds 7 and 8, the 1:1:1:1 quartet expected from $^{11}$B-$^{19}$F coupling is not observed in high resolution. Although $^{11}$B has a nuclear spin of 3/2, its relatively rapid relaxation often inhibits visualization of the splitting pattern with NMR experiments that use standard pulse programs.[29-31] What is seen is a rather broad signal at −140 ppm. As mentioned previously, the diethyl ether wash of compound 7 was not successful in removing the tetrafluoroborate salt impurity and the signal for this appears at −150 ppm for compound 7. However, the modified AMBF$_3$ residue yielded in the next step does not have the signal at −150 ppm. It should be noted that the $^{11}$B-NMR analysis of compounds 6, 7, and 8 did not elucidate any additional information as the peaks were very broad (5 ppm) and thus no splitting patterns could be attained (data not shown).

The azide partner for the Click reaction took the form of a modified lysine residue (5). As shown in Scheme 5, this short synthetic protocol would afford a potentially versatile peptide building block that could be used to incorporate the necessary trifluoroborate functionality using standard solid-phase peptide synthesis. This is an important distinction, because the aryltrifluoroborates previously used by Perrin et al. could only be appended onto the peptide after it was cleaved from the solid support and HPLC purified. In the last two years, several publications have portrayed this technology, primarily focusing on the copper-catalyzed Click reaction between azide-derivates of RGD and alkyne-ArBF$_3$s.[18, 32-35] Difficulties arose in the synthesis and purification of these peptides with alkyne-substituted aryltrifluoroborates because of the instability of these compounds at the low pH required for resin cleavage during SPPS. In fact, even using a 0.1% TFA/H$_2$O solvent system for HPLC resulted in degradation of the aryltrifluoroborate.[19] The discussion in Section 2.3 will outline the stability of two peptides conjugated with the new lysine-AMBF$_3$. To synthesize 5, a mixture of NaN$_3$ and Tf$_2$O in DCM was added to Fmoc-Lys-OH. The mechanism of this reaction proceeds through a trifluoromethanesulfonyl azide (triflic azide) intermediate that serves electrophile for the ε-amino group on lysine. This secondary reaction intermediate is subsequently attacked at the ε-carbon by the recently released azide anion to furnish Fmoc-Lys(N$_3$)—OH (5) in 86% yield.

Scheme 5. Synthetic scheme for Lys(AMBF$_3$) (8).

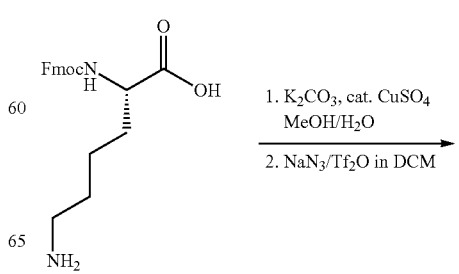

-continued

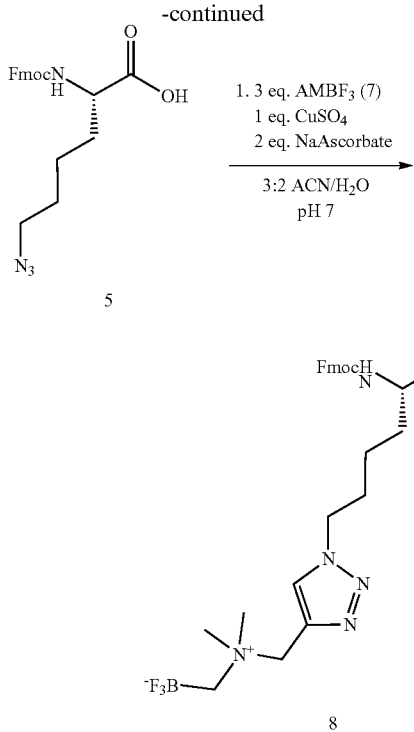

The Click reaction, initially described by Sharpless and coworkers in 2001, is defined as any reaction that is "modular, wide in scope, high yielding, stereospecific, and generating only inoffensive byproducts".[36] Under the ever-growing envelope of Click chemistry falls the most widely used example: the copper-catalyzed azide-alkyne cycloaddition pioneered by Rolf Huisgen in the early '60s.[37] This chemistry was employed for the synthesis of compound 8, using alkyne compound 7 and azide compound 5. The synthesis of 8 was challenging due to the optimization of reaction conditions and issues with reproducibility (Table 8).

Sodium ascorbate was used to reduce the copper from Cu(II) to Cu(I) in situ in order for the alkyne substrate to initially bind. The solvent for all reactions was roughly 3:2 ACN/$1H_2O$. If necessary, this ratio was adjusted to maintain a monophasic system. All reactions were run at 45° C. overnight. The reducing agent, 1M sodium ascorbate, was prepared fresh. The reaction progress was monitored by TLC as Fmoc-Lys-($N_3$)—OH has an $R_f$=0.37 in 9:1 DCM/MeOH while compound 8 runs close to the baseline at $R_f$=0.15. Reactions 1 and 2 did not result in a significant transformation of starting material to product over 24 hours (UV visualization). Similar issues arose in reaction 3, which was not neutralized by 1M sodium bicarbonate. In similar fashion to reactions 1-3, reaction 4 was neutralized, and additionally was column purified. The solvent system resulted in a very slow purification, and the product eluted over many fractions. The crude mixture of reaction 5 was taken up in DCM and washed with brine (3×5 mL) to remove inorganic salts. Although the organic extracts were more amenable to column purification, the overall reaction yield was still low. Reaction 6 employed a simple DCM extraction of the crude reaction mixture to remove inorganic salts from the organic layer. The organic extract was then purified via silica gel column chromatography (yield was 65%). Unfortunately, upon scale-up, the reproducibility of this method was low as reactions 7 and 8 (2× and 4× scale) afforded yields of 45% and <10%, respectively. More insight is required to understand why this Click reaction is not agreeable with gram-scale conditions. The overall yield of compound 8 was calculated to be 56% over 4 steps (convergent synthesis).

Recently, a "dry-down" method was suggested to push the reaction to completion by both concentrating the mixture and degassing the solution to promote a reducing environment for sodium ascorbate. Reactions 9-11 were performed using increasing equivalents of copper and ascorbate. Although the reactions were not purified, visual inspection of TLC plates indicated that there was no discernable improvement with the dry down method. However, it was determined that after 24 hours, significantly more starting

TABLE 8

Reaction conditions for the synthesis of Lys($AMBF_3$).

| | Scale (cmpd5) | pH | Workup | Salt Removal | Chromatography System | Yield | Purity | Dry Down Method | Eq. of 1M $CuSO_4$/ Ascorbate |
|---|---|---|---|---|---|---|---|---|---|
| 1 | 250 µmol | ~7 | No w/u | No wash | Not purified | <10% | Not purified | Not used | 0.1/0.2 |
| 2 | 250 µmol | ~7 | No w/u | No wash | Not purified | <10% | Not purified | Not used | 1/2 |
| 3 | 250 µmol | ~4-5 | No w/u | No wash | Not purified | <10% | Not purified | Not used | 1/2 |
| 4 | 250 µmol | ~7 | No w/u | No wash | 0%-5%-10% MeOH/DCM | <10% | NMR pure | Not used | 1/2 |
| 5 | 250 µmol | ~7 | Brine wash | Aqueous w/u | 0%-5%-10% MeOH/DCM | <10% | NMR pure | Not used | 1/2 |
| 6 | 250 µmol | ~7 | No w/u | DCM wash | 5%-10% MeOH/DCM | 65% | NMR pure | Not used | 3/6 |
| 7 | 500 µmol | ~7 | No w/u | DCM wash | 5%-10% MeOH/DCM | 40% | Not purified | Not used | 3/6 |
| 8 | 1 mmol | ~7 | No w/u | DCM wash | 5%-10% MeOH/DCM | <10% | Not purified | Not used | 3/6 |
| 9 | 125 µmol | ~7 | No w/u | No wash | Not purified | N/A | Not purified | SpeedVac | 0.1/0.2 |
| 10 | 125 µmol | ~7 | No w/u | No wash | Not purified | N/A | Not purified | SpeedVac | 0.5/1 |
| 11 | 125 µmol | ~7 | No w/u | No wash | Not purified | N/A | Not purified | SpeedVac | 1/2 | material remained for reactions 9 and 10 compared to 11. This suggests that using a stoichiometric, or even excess, of copper is essential for this reaction.

Solid-Phase Peptide Synthesis

Figure 47:
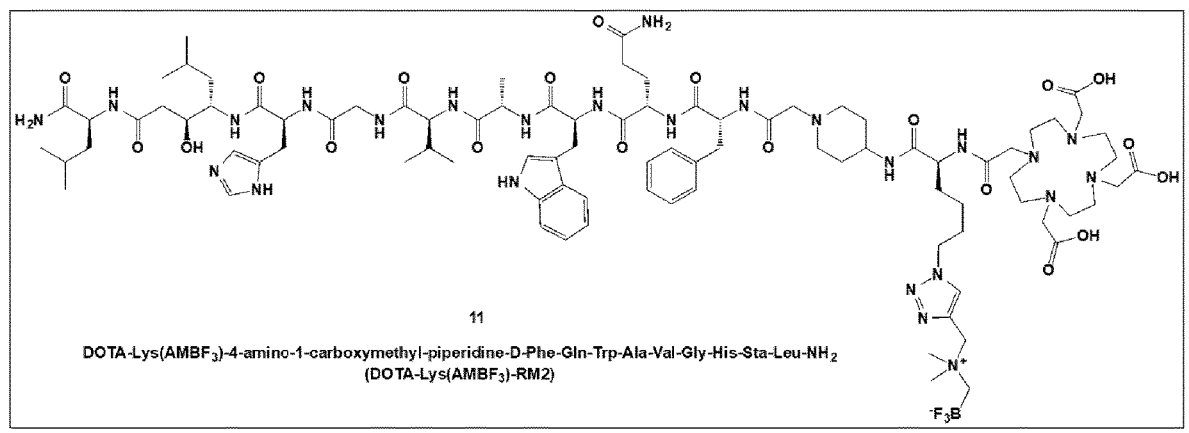
FIG. 47 shows DOTA/AMBF$_3$-conjugated RM2 peptide (11).
Figure 48:
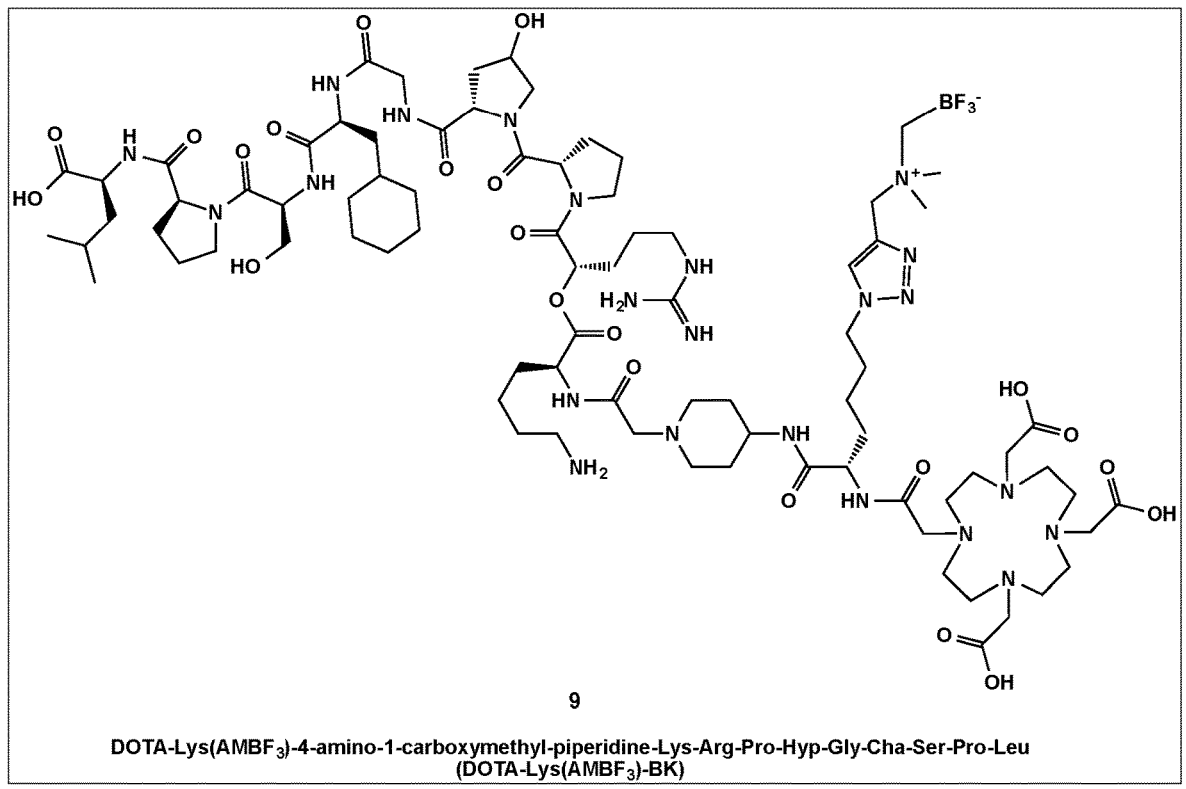
FIG. 48 shows DOTA/AMBF$_3$-conjugated BK peptide (9).
Figure 49:
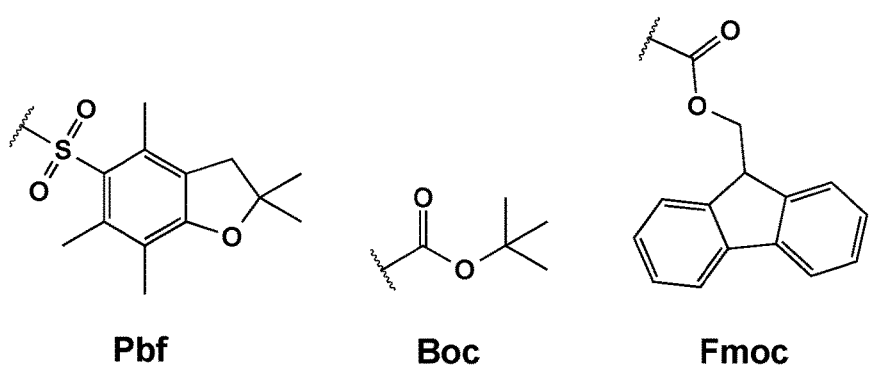
FIG. 49 shows common protecting groups used in solid-phase peptide synthesis.

Recently, two peptides have been synthesized that incorporate the Lys(AMBF$_3$) residue into their sequence. The first peptide, the DOTA- and AMBF$_3$-conjugated RM2 (DOTA-Lys-AMBF$_3$-4-amino-1-carboxymethyl-piperidine-D-Phe-Gln-Trp-Ala-Val-Gly-His-Sta-Leu-NH$_2$), was made using an automated peptide synthesizer and purified by HPLC by Zhibo Liu (FIG. 47).[19] The resin-linked peptide, RM2, was provided to us by the Lin Lab at the BC Cancer Association (BCCA). RM2 is a bombesin antagonist with high affinity for gastrin-releasing peptide receptors (GRPr) found on prostate, breast, and GI tract tumours.[20, 38–42] The following discussion will focus on the synthesis of the second peptide, a bradykinin-derived AMBF$_3$ conjugate (FIG. 48). Scheme 6 was first employed for the synthesis of the RM2 conjugate, and later extrapolated to manual solid-phase peptide synthesis.

Natural bradykinin and its analogues, collectively termed as kinins, are present in the body as signals for pain and normal physiological regulation.[43] These nonapeptides have two types of receptors, B1 and B2.[44] The latter, which are more common than 1 receptors in cells, bind the normal nonamer and similar kinin analogues. Conversely, the B1 receptors only bind kinins that are one amino acid shorter, specifically [des-Arg$^9$]-BK.[44] The primary enzyme that destroys BK in the body is Angiotensin I converting enzyme (ACE), which cleaves at the 7-8 and 5-6 bonds.[45] The role of BK receptors in cancer therapy is evidenced by the fact that B2 receptors, because of their high concentration throughout the body, do not make attractive drug targets. Rather, 1 receptors, which become more prevalent during increased inflammation and tumour growth, are promising drug targets because they are specific to the cancer site.[45] For this reason, we chose to conjugate Lys(AMBF$_3$) onto a B1-receptor-specific [des-Arg$^9$] bradykinin analogue.

The design of these peptides is based on several factors. First, as mentioned in Section 1.5, these naturally lipophilic peptides have been shown to accumulate in the liver and gut in the PET scans of mice.[21] The addition of a pharmacokinetic modifier, such as the chelator DOTA, promotes a decrease in hepatobiliary clearance and improves image contrast.[22, 23] However, this is not the only purpose of appending a chelator. As the name suggests, chelating functionalities such as DOTA and DTPA serve to chelate certain metals (e.g. $^{90}$Y or $^{186}$Re) that can act as either a therapeutic to the disease, or as a diagnostic imaging agent (e.g. $^{68}$Ga) similar to $^{18}$F.[25, 46, 47] This relatively new field of medicine, coined as theranostics by Funkhouser in 2002, is very promising as the targeted therapy can both visualize and attack the disease.[47, 48] It is hypothesized that with our architecture, the AMBF$_3$ will serve as the diagnostic when coupled with $^{18}$F-PET imaging, and the metal, chelated to DOTA, will serve as a potential therapeutic towards the cancer. These two functionalities both rely on high tumour uptake, which makes the cationic linker between Lys (AMBF$_3$) and the native peptide vitally important. Mansi et al. showed that 4-amino-1-carboxymethyl-piperidine, when conjugated to the peptide and protonated at physiological pH, can decrease the K$_d$ of DOTA-RM2 almost 3-fold.[20]

Scheme 6. Synthetic scheme of the DOTA-Lys(AMBF$_3$)-BK peptide (9). (i) Standard Fmoc synthesis. Procedure done in the Lin Lab at BCCA. Resin-coupled BK used in step (ii) was provided for us through collaboration; (ii) 20% piperidine/DMF, rt, 3×5 min, then Fmoc-4-amino-1-carboxymethyl-piperidine, HBTU, DIPEA, DMF, rt, 2 hr; (iii) 20% piperidine/DMF, rt, 3×5 min, then Fmoc-L-Lys-AMBF$_3$—OH (8), HBTU, DIPEA, DMF, rt, 24 hr; (iv) 20% piperidine/DMF, rt, 3×5 min, then DOTA-tri-t-butyl-ester, NHS, DCC, DCM, rt, 24 hr; (v) 95:2.5:2.5 TFA/H$_2$O/TIPS with 30 mM KHF$_2$.

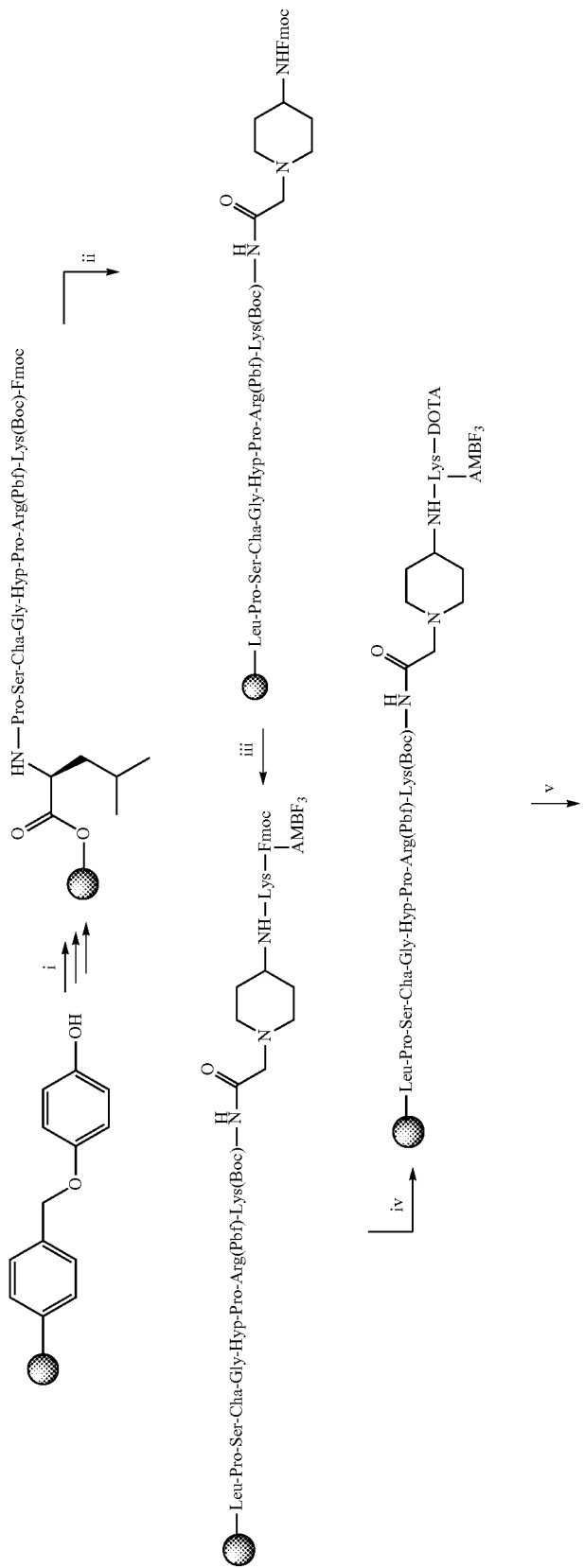

-continued
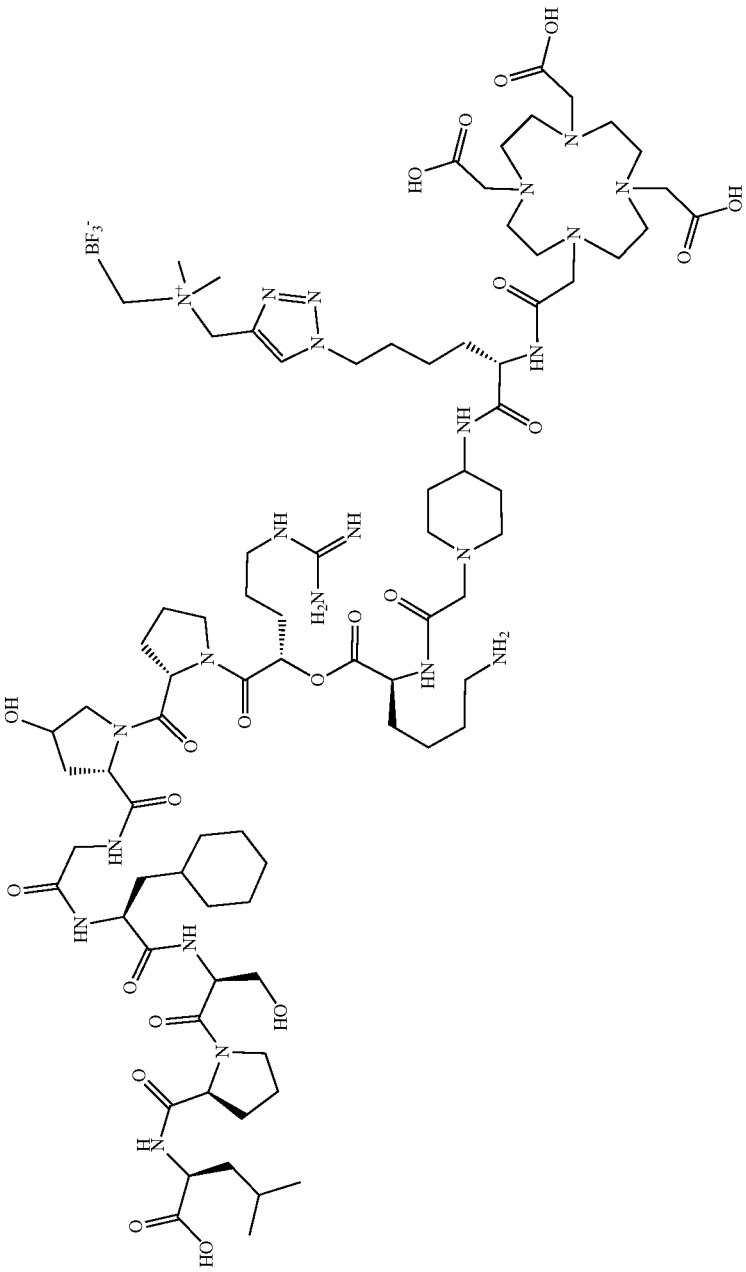

Scheme 6 illustrates the manual solid-phase peptide synthesis protocol used to generate peptide 9. The solid support was a hydroxymethylphenyl functionalized resin (Wang resin) that was coupled to the Fmoc-protected modified bradykinin at BCCA by the Lin lab. In order to afford higher in vivo stability, the BK analogue used in this synthesis is modified at position 3 and position 5, using $Hyp^3$ and $Cha^5$, respectively (FIG. 48). These modifications alter the effects of ACE at these positions, rendering a longer half-life to the peptide which should yield superior PET images.[49] The lysine and arginine residues are protected by Boc (tert-butoxycarbonyl) and Pbf (2,2,4,6,7-pentamethyl-dihydrobenzofuran-5-sulfonyl) groups, respectively. These groups are acid labile and thus come off only in the final TFA resin cleavage. The terminal leucine residue was appended in order to transform the agonist BK to the antagonist form, as natural bradykinin does not contain that residue. All reactions are performed in a 3 mL spin column. Deprotection conditions involved 3 successive washes with 2.5 mL of 20% piperidine/DMF for 5 minutes each. After washing the resin with DMF and DCM, the first coupling reaction (Scheme 6ii) linked the cationic spacer and was done in DMF using HBTU as the activating agent. A Kaiser (ninhydrin) test was used after each deprotection/coupling reaction (Scheme 6ii-6iv) to test for completion. Briefly, this colour test could rapidly discern between a protected peptide and a non-protected peptide due to the presence of a primary amino group.[50] Although this was a semi-quantitative analytical method (as one cannot distinguish exactly how much of the protected amine has been deprotected based solely on the visual inspection of the beads), the use of a positive control helped determine how long the beads should be heated. The test involved taking a few beads of resin and treating them with ninhydrin, phenol dissolved in ethanol, and aqueous KCN in pyridine. One test tube contained a Rink amide resin that had a free amino group (positive control), and the other test tube contained the resin with the peptide in question. Upon heating, a dark blue colour was expected for free terminal amines, while no colour change was observed for Fmoc-protected peptides.

The next coupling reaction (Scheme 6iii) used similar conditions, but was mixed for 24 hours to ensure the maximum possible yield as compound 8 was significantly more valuable than the cationic linker. The coupling of DOTA-tri-t-butyl-ester (Scheme 6iv) was first attempted using NHS/DCC in DMF for 24 hours. After the reaction period, a significant blue colour was still observed with by Kaiser test. A similar result was seen after an additional 24 hours. As such, the solvent was switched to DCM, which gratifyingly yielded a negative Kaiser test after 48 hours. Although HBTU has been shown to work with DOTA for the synthesis of small peptides, previous experience on RM2 and BK analogues had indicated that the synthesis of the NHS ester of DOTA through DCC coupling was a more efficient method.[19, 51]

Figure 50:
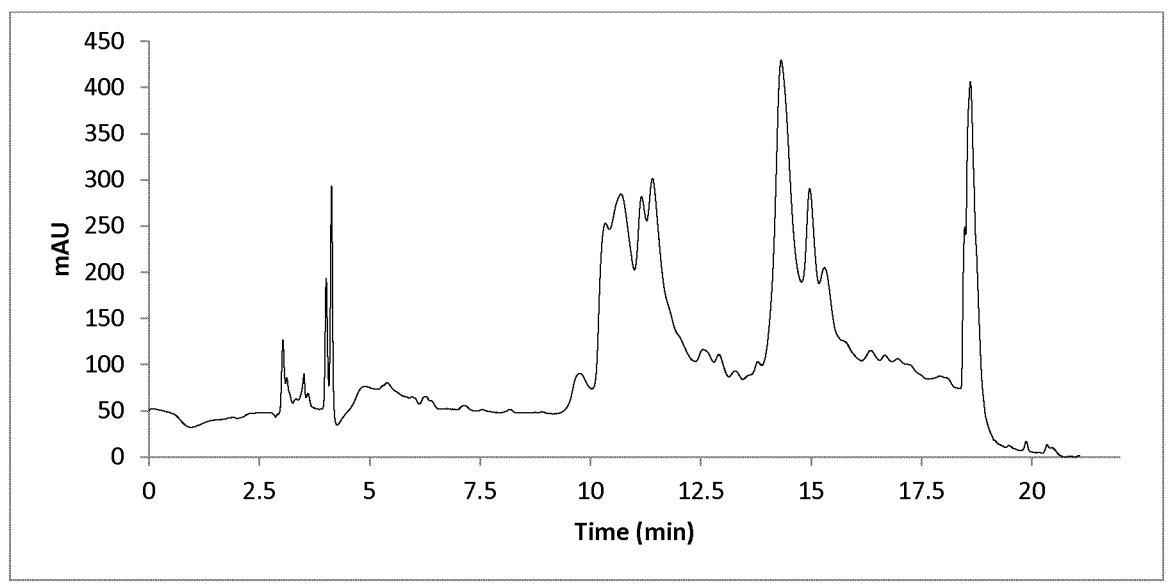
FIG. 50 shows HPLC trace of DOTA-Lys(AMBF$_3$)-BK (compound 9) at 229 nm.
Figure 51:
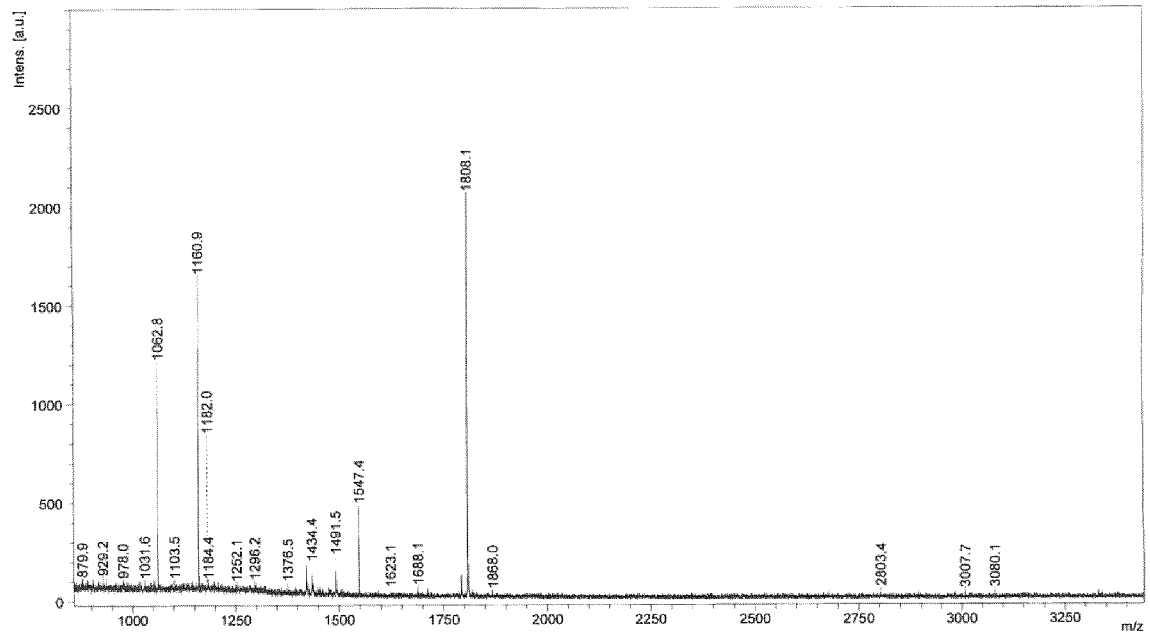
FIG. 51 shows MALDI-TOF for the decomposed peptide (10).

Difficulties arose when we attempted to cleave the peptide from the resin using 95% TFA in water. The HPLC trace of the cleaved peptide showed numerous peaks from 10 to 20 minutes, and no product could be verified by MALDI-TOF analysis (data not shown). It was hypothesized that either the $AMBF_3$ had degraded upon cleavage of the sequence from the resin, or the TFA had potentially cleaved the peptide at multiple locations. This was disheartening, because the purpose of this new technology was its hydrolytic stability. Nevertheless, it was important to realize that these were extremely harsh conditions, and thus it was unlikely that any trifluoroborate could survive. To mediate this problem, it was suggested that an excess of free fluoride should be added to the cleavage mixture to push the equilibrium in the direction of the trifluoroborate, rather than towards the boronic acid. This was based on the kinetic studies performed by Ting et al. shown in Scheme 4. In light of this reasoning, 30 mM of $KHF_2$ was added to 95:2.5:2.5 TFA/$H_2O$/TIPS, and the cleavage reaction was run for a maximum of 2 hours. The solution was filtered and collected, evaporated, and triturated using MeOH/diethyl ether. The precipitated solid was dissolved in 50% aqueous acetonitrile and purified by HPLC as shown in FIG. 50 (see Methods and Materials for detailed HPLC protocol). The peaks at 10-11 mins (peak 1), 11.1-12 mins (peak 2), 14-14.8 mins (peak 3), and 14.9-15.7 mins (peak 4) were collected and analyzed by MALDI-TOF. Only the first two peaks provided useful characterization data (FIG. 51-54).

Figure 52:
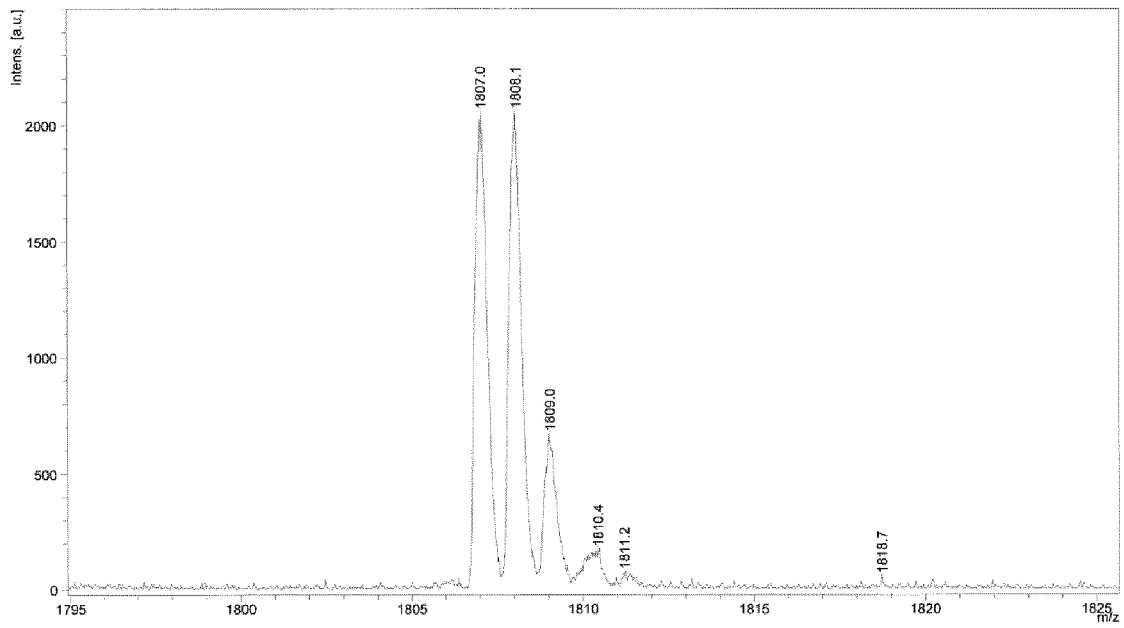
FIG. 52 shows characteristic isotope pattern for the decomposed peptide (10).
Figure 55:
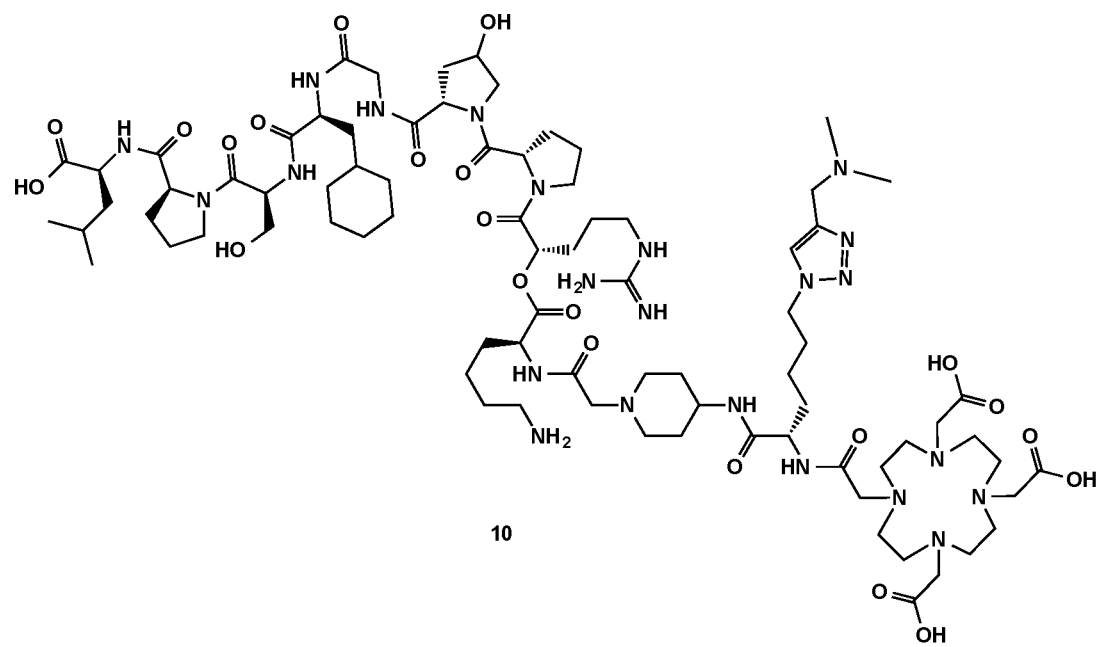
FIG. 55 shows proposed deborylation product of DOTA-Lys(AMBF$_3$)-BK (10) predicted to be the result of the deborylation of peptide 9 during the cleavage procedure (Scheme 6v). The exact mass is 1784.03.

The HPLC purification of bradykinin derivatives has proven to be difficult as the peaks are both similar in retention times broad in nature. Although this may be due to the quality of the synthetic procedure, a similar HPLC trace has been observed before for other BK analogues.[19] An explanation might be that BK peptides tend to have multiple conformations due the Pro and Hyp residues at positions 3/4 and 8, respectively. Thus, even a chemically pure peptide may elute with a broad peak. As seen in FIG. 50, peaks 1 and 2 eluted separately; unfortunately, the separation was not fully effective, as the compound in peak 1 (m/z=1807) can be found in the MALDI-TOF of peak 2, and visa versa. The identity of peak 1 is believed to be the deborylation product of peptide 9 (FIG. 55). The predicted isotope pattern of the structure corresponds very well with the observed MALDI-TOF spectrum (FIG. 52).

Figure 53:
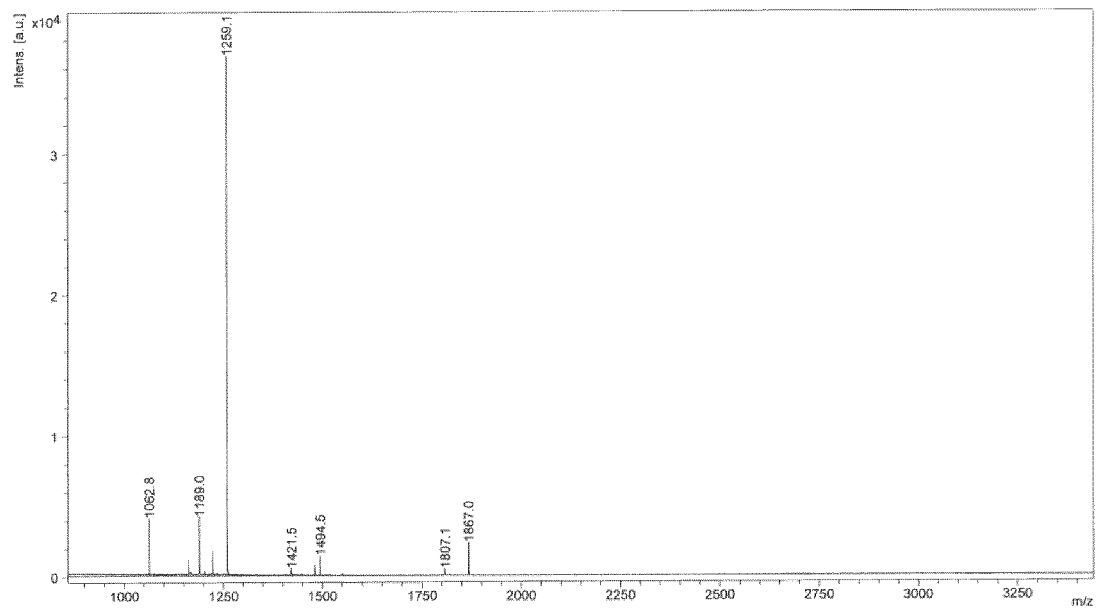
FIG. 53 shows MALDI-TOF for DOTA-Lys(AMBF$_3$)-BK (9).
Figure 54:
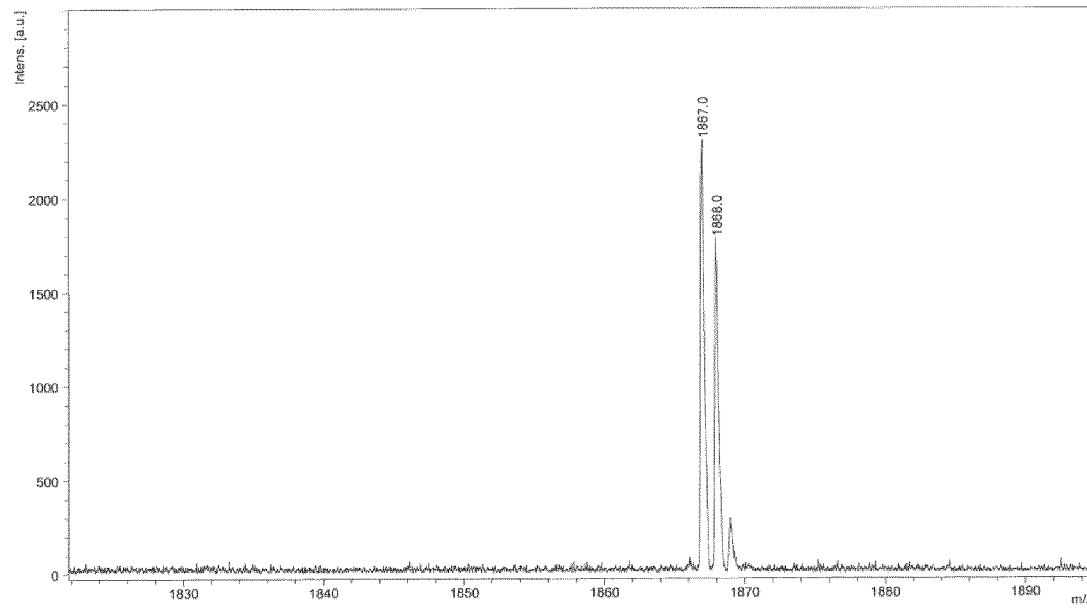
FIG. 54 shows characteristic isotope pattern for DOTA-Lys(AMBF$_3$)-BK (9).
Figure 56:
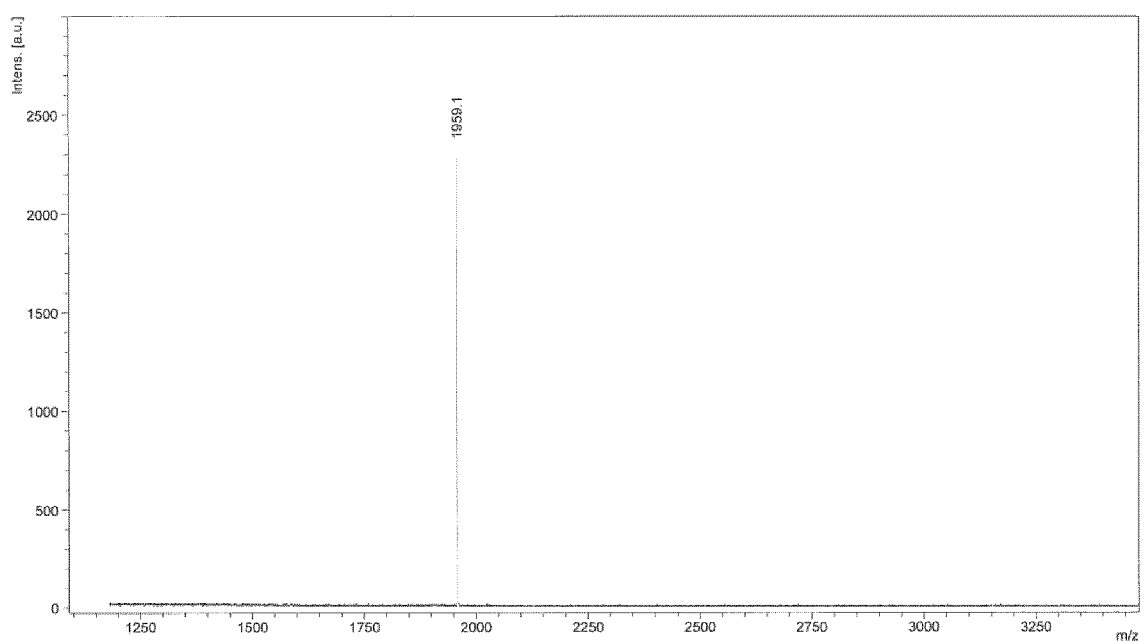
FIG. 56 shows MALDI-TOF for DOTA-Lys(AMBF$_3$)-RM2 (11).
Figure 57:
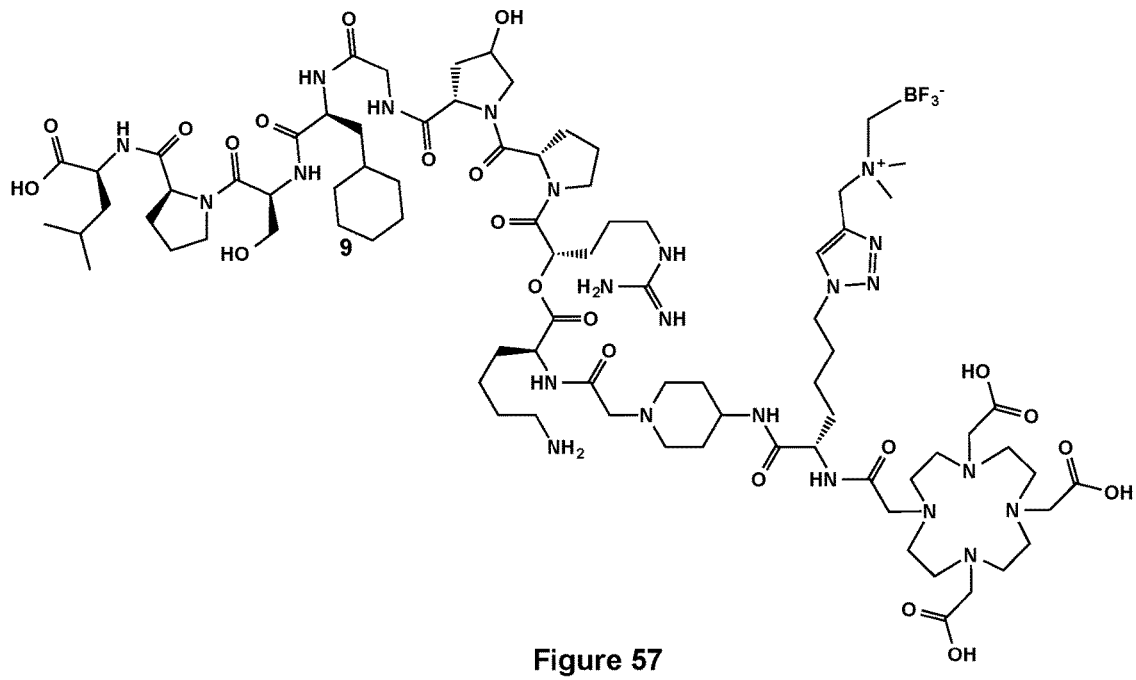
FIG. 57 shows the structure of DOTA-((L)-Lys-c-1,2,3-triazole-N,N-dimethyl-ammoniomethyl-trifluoroborate)-4-amino-1-carboxymethyl-piperidine-Lys-Arg-Pro-Hyp-Gly-Cha-Ser-Pro-Leu-COOH.
Figure 58:
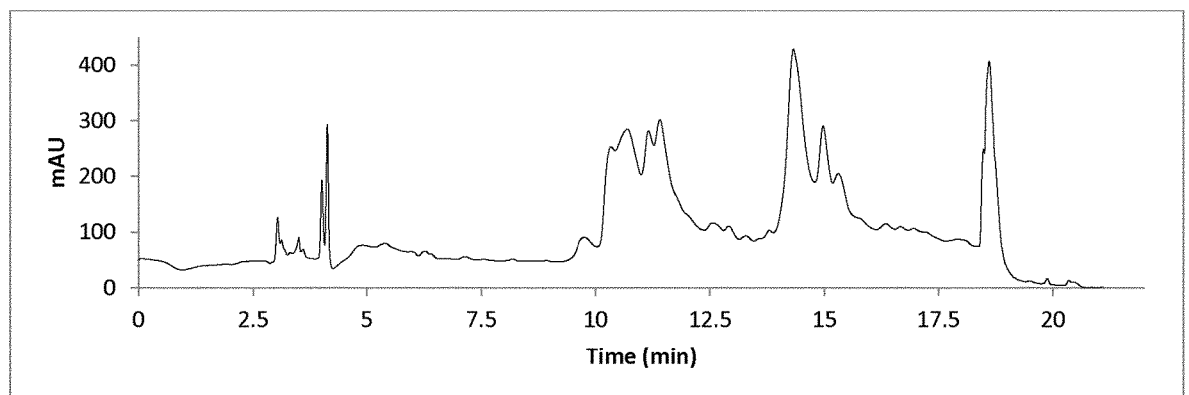
FIG. 58 shows an HPLC trace (229 nm) of crude compound 9.
Figure 59:
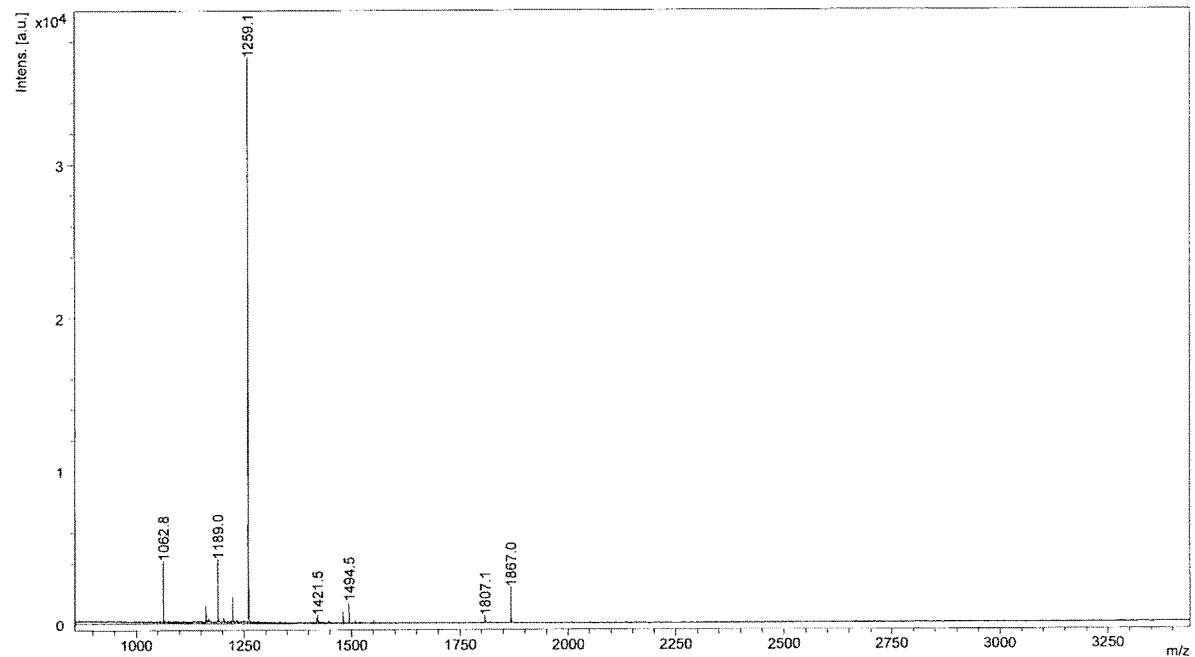
FIG. 59 shows the MALDI-TOF spectrum of compound 9.
Figure 60:
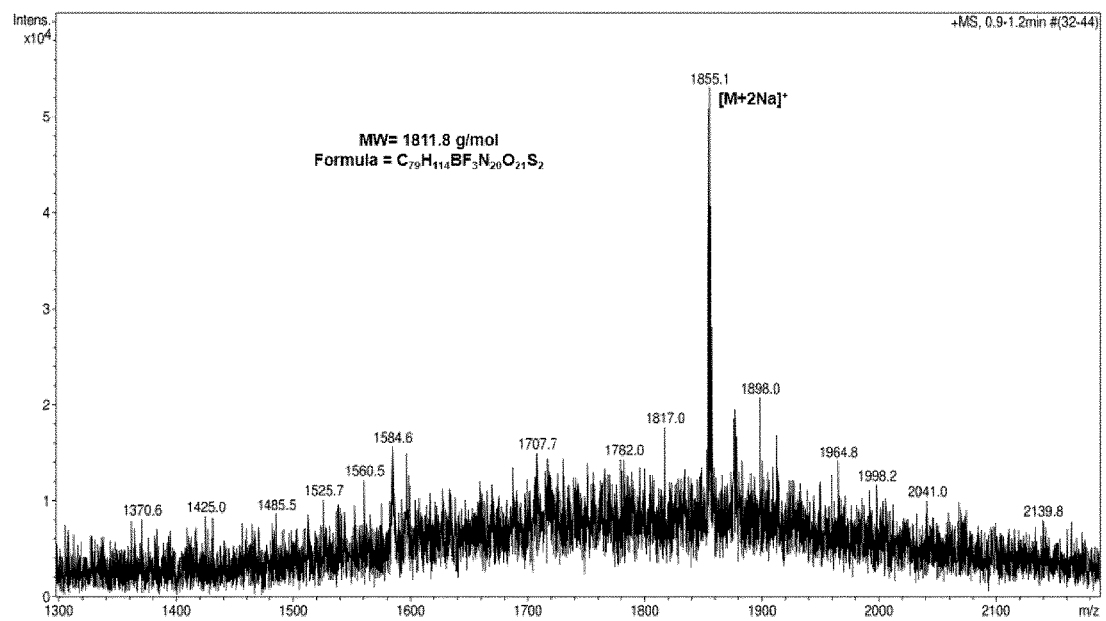
FIG. 60 shows ESI-MS(+) spectrum of DOTA-Lys(AMBF$_3$)-TATE: calculated for $C_{79}H_{114}BF_3N_{20}O_{21}S_2$, 1811.8 m/z; found, [M+2Na]$^+$=1855.1 m/z.

FIG. 53 shows the MALDI-TOF of peak 2, which is the desired product, DOTA-Lys($AMBF_3$)-BK. Unfortunately, as a result of the difficult HPLC purification, the spectrum shows that in addition to a small amount of deboronylated product there are some additional uncharacterized impurities. This is believed to be specific to bradykinin, as the RM2 peptide previously mentioned affords a cleaner HPLC trace and a significantly more agreeable MALDI-TOF spectrum (FIG. 56).

The yield of peptide 9 was only 5.5%, which can be explained due to several reasons. First, the overall scale of the solid-phase synthesis was very low, as only 16.5 µmol of the protected BK was used. Additionally, as discussed above, the HPLC purification of the product was confounded by other peaks that possessed similar retention times as the desired peptide. Lastly, deborylation of DOTA-Lys($AMBF_3$)-BK is partially responsible for the low yield. Nevertheless, we were pleased to see validation that this method was successful even on synthetically challenging peptides such as bradykinin, as confirmed by MADLI-TOF analysis.

The MALDI-TOF of the peptide 11 exhibits a single peak at m/z=$[M+H+]^+$1959.1. This pure spectrum elucidates the relative ease of synthesizing RM2 as compared to BK (peptide 9).

Based on the discussion above, the following question arises: is the proposed technology specific to $AMBF_3$, or can it be used with aryltrifluoroborates? Could an aryltrifluoroborate be conjugated onto an amino acid residue and incorporated into a peptide via solid-phase synthesis? The observations presented herein suggest that it is much easier to synthesize these peptides using the Lys($AMBF_3$) functionality than it is using $ArBF_3$s. The $ArBF_3$ functionality can only be conjugated after SPPS and purification of the clickable peptide, as the cleavage and purification conditions will destroy the trifluoroborate.[21] This is due to the higher hydrolytic stability of a trifluoroborate when it is adjacent to the ammonium group, as compared to the aryl trifluoroborate congeners (FIGS. 3 and 4).[19] Additionally, an inherently useful advantage of $AMBF_3s$ is lower bone uptake of free fluoride as a result of its potential in vivo stability. Although only two peptides have been synthesized with the new $AMBF_3$, we expect to investigate several more, in due course.

Conclusion

The objective of this project was to improve upon several issues plaguing aryltrifluoroborate-derived $^{18}$F-PET imaging agents. Specifically, high lipophilicity and incompatibility with solid-phase peptide synthesis conferred poor image quality and limited synthetic versatility, respectively. To this end, a protected metal chelator was targeted with the goal of conjugation onto a peptide to increase polarity. Tetra-t-butyl protected DTPA (4) was synthesized over 4 steps in 11% overall yield. Issues with the purification of compounds 3a and 3b resulted in this unsatisfactory yield.

A novel alkyltrifluoroborate (8) was synthesized as the result of the Click reaction between $AMBF_3$ (7) and the modified lysine-azide amino acid (5). Based on previous kinetic studies showing improved in vitro stability of $AMBF_3$ to hydrolysis, this residue was hypothesized to be compatible with solid-phase peptide synthesis for small peptides with high tumour affinity.[16] A bradykinin antagonist was chosen as the substrate for appending the Lys ($AMBF_3$) residue. Also coupled to the peptide were DOTA (a metal chelator), and a cationic ammonium linker, which are known to be vital for low lipophilicity and high tumour uptake, respectively.[20] The peptide was purified by HPLC and characterized by MALDI-TOF analysis.

A strength of this new technology is the high versatility in synthesizing trifluoroborate peptide analogues via solid-phase peptide synthesis. The $AMBF_3$ is also inherently useful because of its hydrolytic stability, which should decrease bone uptake of free fluoride. This work enables dual-modal theranostic investigations by coupling the $^{18}$F-labelled peptide with a therapeutic metal chelated to DOTA.

EXPERIMENTAL

All commercial chemicals were purchased from Sigma-Aldrich, Fischer Scientific, Alfa-Aesar, Oakwood Chemicals or Combi-Blocks and were used without further purification. Solvents were purchased from Fischer Scientific or Sigma-Aldrich and used without further purification. Dry THF was obtained via distillation over sodium metal with benzophenone as an indicator. DMF was dried by storing the solvent over activated 4A molecular sieves for at least 24 hours prior to usage. Deuterated solvents were purchased from Cambridge Isotope Laboratories. $^1$H-NMR data was collected on a 300 MHz Bruker Avance Spectrometer and all chemical shifts are reported in ppm on the δ scale with respect to the solvent signal as a reference point: δ 7.26 for $CDCl_3$, δ 1.94 for $CD_3CN$, δ 4.79 for $D_2O$, δ 5.32 for $CD_2Cl_2$, and δ 3.31 for $CD_3OD$. Multiplicity is reported as a singlet (s), doublet (d), triplet (t), quartet (q), multiplet (m), or a broad (br) singlet. Mass spectra were acquired using a Waters ZQ GC-MS coupled with a Waters 2695 HPLC for sample injection. HPLC Silica gel used for flash column chromatography was SiliaFlash F60 (230-400 mesh) silica gel from SiliCycle. HPLC purification was performed using an Agilent 1100 series system through an Agilent Eclipse XDB-C18 column. Detection was done through UV absorbance at 229 nm. The gradient program was the following: Solvent A: acetonitrile, Solvent B: 0.1% $TFA/H_2O$; 0 to 2 minutes: 0% to 5% A, 2 to 15 minutes: 5% to 20% A, 15 to 16 minutes: 20% to 35% A, 16 to 18 minutes: 35% to 100% A, 18 to 19 minutes: 100% to 5% A; flow rate: 3 mL/min; column temperature: 50 to 51° C. Synthetic procedures that were modified from literature have been noted below with a reference.

N,N-Bis[(tert-butyloxycarbonyl)methyl]-2-aminoethanol (1)[26]

In a flame-dried round bottom flask, a mixture of tert-butyl bromoacetate (5.00 mL, 33.9 mmol, 2.5 eq.), anhydrous $KHCO_3$ (3.45 g, 34.5 mmol, 2.5 eq.), and DMF (22 mL) was cooled to 0° C. A solution of ethanolamine (0.826 mL, 13.7 mmol, 1 eq.) in DMF (1.68 mL) was added dropwise to the flask over a period of 5 minutes under inert atmosphere and stirred for 30 minutes. The reaction was further stirred at rt for another 24 hours. The mixture was then filtered, and to the filtrate was added diethyl ether (25 mL) and saturated $NaHCO_3$ (17 mL). The aqueous layer was subsequently extracted with diethyl ether (3×10 mL) and the combined organic extracts were washed with brine (3×10 mL). After drying with $MgSO_4$, the organic mixture was filtered and evaporated under reduced pressure to yield a viscous oil that was purified by flash chromatography on a silica column (petroleum ether/diethyl ether, 2:1; $R_f$=0.17). Yield: 2.79 g, 71%. $^1$H NMR (300 MHz, $CDCl_3$, rt): δ (ppm)=1.51 (s, 18H, tert-butyl $CH_3$), 2.93 (t, 2H, J=5.01, $HOCH_2CH_2N$), 3.47 (s, 4H, $N(CH_2)_2$), 3.57 (m, 2H, $HOCH_2$), 3.81 (t, 1H, J=5.75, OH); ESI-LRMS: $[M+Na+]^+$ 312.4 (100%).

N,N-Bis[tert-butyloxycarbonyl)methyl]-2-bromoethylamine (2)[26]

In a flame-dried round bottom flask, 1 (2.77 g, 9.51 mmol, 1 eq.) was dissolved in DCM (15 mL). To this solution triphenylphosphine (2.17 g, 8.27 mmol, 0.8 eq.) was added and the mixture was cooled to 0° C. N-bromosuccinimide (1.47 g, 8.27 mmol, 0.8 eq.) was then added slowly over the course of 5 minutes. The colourless mixture was stirred for 90 minutes at 0° C. with little observable colour change. The mixture was evaporated under reduced pressure to yield light pink solid. To this was added diethyl ether (28 mL) and the resulting white precipitate was filtered. The filtrate was again evaporated under reduced pressure to afford a yellow oil that was loaded onto a short silica column and eluted with diethyl ether. The crude eluent was evaporated once more and finally purified by flash chromatography on a silica column (hexane/diethyl ether, 5:1; $R_f$=0.65). Yield: 2.38 g, 71%. $^1$H NMR (300 MHz, $CDCl_3$, rt): δ (ppm)=1.51 (s, 18H, tert-butyl $CH_3$), 3.18 (t, 2H, J=7.54, $HOCH_2CH_2N$), 3.48 (dd, 2H, $J_1$=8.16 $J_2$=6.96, $HOCH_2$), 3.52 (s, 4H, $N(CH_2)_2$); ESI-LRMS: $[M+K+]^+$ 390.0 (60%).

N,N,N",N"-Tetrakis[(tert-butyloxycarbonyl)methyl]-N'-[(methyloxycarbonyl) methyl]diethylenetriamine (3a)[52]

A solution was made of glycine methyl ester hydrochloride (32.5 mg, 259 μmol, 1 eq.) and 2 (187 mg, 533 μmol, 2.1 eq.) in acetonitrile (2 mL). Phosphate buffer (1 mL, 2M, pH 8), made by mixing $K_2HPO_4$ (3.26 g, 18.8 mmol) and $KH_2PO_4$ (167 mg, 1.23 mmol) in $H_2O$ (10 mL), was then added and the reaction was stirred at rt for 24 hours. The reaction mixture was filtered and the filtrate was transferred to a separatory funnel. The organic layer was removed from the aqueous layer and dried over MgSO$_4$. Evaporation under reduced pressure yielded a yellow oil that was loaded onto a silica column (CHCl$_3$/MeOH/NEt$_3$ 150:3:1; R$_f$=0.3). This solvent system, among several others attempted (e.g. Hex/Ether/NEt$_3$, Hex/EtOAc/NEt$_3$), could not isolate the target compound in high purity due to the nature of the acidic and basic functional groups and due to solubility issues. ESI-LRMS: [M+K+]$^+$670.5 (100%).

N,N,N",N"-Tetrakis[(tert-butyloxycarbonyl)methyl]-N'-[(benzyloxycarbonyl) methyl]diethylenetriamine (3b)[52,27]

Benzyl glycinate p-toluenesulfonate (200 mg, 592 µmol, 1 eq.) was added to diethyl ether (4 mL), and an aqueous Na$_2$CO$_3$ solution (189 mg, 1.8 mmol, 3 eq., 4 mL of solution) was added. After stirring at rt for 30 minutes, the ether layer was separated, dried over MgSO$_4$, and evaporated under reduced pressure to yield benzyl glycine ester (89 mg, 540 µmol). This intermediate was used without further purification towards the target compound 3b. A phosphate buffer (1 mL, 2M, pH=8) was added to the benzyl glycine ester (60 mg, 364 µmol, 1 eq.) and 2 (280 mg, 795 µmol, 2.2 eq.) dissolved in acetonitrile (2 mL). This biphasic reaction was stirred for 24 hours at rt. The precipitated salts were filtered off and the organic layer was isolated, dried over MgSO$_4$, and evaporated under reduced pressure. The semi-solid residue was then taken up in chloroform, filtered, and again evaporated. The resulting yellow oil was charged onto a silica column for flash chromatography (CHCl$_3$/MeOH/NEt$_3$ 150:3:1; R$_f$=0.35). Similarly to 3a, complete purification via silica chromatography was challenging due to the nature of the basic functional groups. Crude yield: 73.1 mg, 28%. ESI-LRMS: [M+K+]$^+$670.5 (100%).

N,N,N",N"-Tetrakis[(tert-butyloxycarbonyl)methyl]-N'-[acetic acid]diethylenetriamine (4)[52,27]

3b (76 mg, 108 µmol, 1 eq.) was dissolved in methanol (1 mL) and Pd/C 10% (20 mg, cat., 50% wet) was added. The reaction was stirred at rt for 24 hours under hydrogen atmosphere (2 large balloons). The reaction was filtered over a sintered glass funnel and evaporated under reduced pressure to a viscous yellow oil. Yield: 53.5 mg, 81%. $^1$H NMR (300 MHz, CDCl$_3$, rt): δ (ppm)=1.48 (s, 36H, tert-butyl CH$_3$), 3.02 (m, 4H, C(O)OHCH$_2$NCH$_2$CH$_2$N), 3.14 (m, 4H, C(O)OHCH$_2$NCH$_2$CH$_2$N), 3.47 (s, 8H, NCH$_2$C(O)OtBu), 3.59 (s, 2H, NCH$_2$C(O)OH); ESI-LRMS: [M+K+]$^+$654.5 (100%).

Fmoc-(L)-Lys(N$_3$)—OH (5)[24]

At 0° C., NaN$_3$ (7.3 g, 113 mmol) was added to a mixture of H$_2$O (20 mL) and DCM (30 mL). To this was added Tf$_2$O (3.8 mL, 22.45 mmol) dropwise over a period of 30 minutes. This reaction was stirred at 0° C. for 5 hours and subsequently extracted with DCM (2×50 mL). The organic layers were combined and washed with a saturated aqueous solution of Na$_2$CO$_3$ (1×50 mL) and used without further purification. A mixture of K$_2$CO$_3$ (5.6 g, 39.5 mmol), CuSO$_4$☐5H$_2$O (25 mg, cat.), and Fmoc-(L)-Lys-OH (4.78 g, 13 mmol) in 1:1 MeOH/H$_2$O (33 mL) was then created. To this was added the organic extract dropwise over a period of 30 minutes and the mixture was further stirred at rt overnight. 2.5 N HCl (150 mL) was used to quench the reaction, after which the product was extracted with DCM (3×50 mL), washed with brine (2×50 mL), and dried over anhydrous Na$_2$SO$_4$. The mixture was filtered and evaporated under reduced pressure to give the crude oil which was immediately charged onto a silica column for flash chromatography (gradient of MeOH/DCM 0.5:99.5 to 1:99). R$_f$=0.37 (1:9 MeOH/DCM). Yield: 4.4 g, 86%. $^1$H NMR (300 MHz, CD$_2$Cl$_2$, rt): δ (ppm)=1.30-1.60 (m, 6H, β, γ, δ CH$_2$), 3.32 (t, 2H, J=6.38 Hz, c CH$_2$), 4.28 (t, 1H, J=6.60 Hz, a CH), 4.39-4.47 (m, 3H, Fmoc-CHCH$_2$OC(O)), 5.32 (s, 1H, OC(O)NH), 7.36 (t, J=7.11 Hz, Fmoc aryl H), 7.45 (t, J=7.26 Hz, Fmoc aryl H), 7.65 (d, J=7.37 Hz, Fmoc aryl H), 7.82 (d, J=7.37 Hz, Fmoc aryl H); ESI-LRMS: [M+Na+]$^+$417.3 (100%).

N-propargyl-N,N-dimethyl-ammoniomethyl-boronylpinacolate (6)[53]

In a flame-dried round bottom flask, N,N-dimethylpropargylamine (0.67 mL, 6.27 mmol, 1 eq.) was added to diethyl ether (28 mL) and the reaction was heated to 45° C. Iodomethylpinacolboronate (1.144 mL, 6.27 mmol, 1 eq.) was added dropwise to the solution. Immediately upon addition, the mixture became cloudy, with a white solid subsequently precipitating out of solution. The reaction was stirred for a further 15 minutes and the product was filtered and washed with cold diethyl ether. The residue was dried under high vacuum to yield a flaky white solid. Yield: 1.4 g, 100%. $^1$H NMR (300 MHz, D$_2$O, rt): δ (ppm)=1.13 (s, 12H, 2×(CH$_3$)$_2$), 3.09 (s, 2H, N(CH$_3$)$_2$CH$_2$BF$_3$), 3.15 (t, 1H, J=2.53, CH$_2$CCH), 3.19 (s, 6H, N(CH$_3$)$_2$), 4.27 (d, 2H, J=2.51, HCCCH$_2$N(CH$_3$)$_2$); ESI-LRMS: [M]$^+$224.4 (100%).

N-propargyl-N,N-dimethyl-ammoniomethyl-trifluoroborate (7)

6 (1 g, 4.46 mmol, 1 eq.) was dissolved in acetonitrile (12 mL) and was fluorinated by the addition of aqueous KHF$_2$ (3M, 4.25 mL, 12.8 mmol, 2.8 eq.) and HCl (4M, 4.25 mL, 17 mmol, 3.8 eq.) at 45° C. for 2 hours. The clear orange solution was quenched by the addition of concentrated aqueous NH$_4$OH (~1.5 mL) to pH 7. This mixture was transferred to a larger round bottom flask and a 20% acetonitrile/ethanol solution (100 mL) is added. Silica (40 mL) was placed directly to this solution and the mixture is stirred for 20 minutes. The previously brightly yellow solution lost much of its colour and turned into to a clear, colourless mixture. This mixture was loaded onto a short silica column which was set onto a sintered-glass funnel and eluted with 20% acetonitrile/ethanol. After evaporation under reduced pressure and subsequent drying at high vacuum, a pale yellow solid was isolated. This was washed and filtered with cold diethyl ether (20 mL) to produce the NMR-pure zwitterion. The product yield was higher than quantitative due to excess salts remaining in the product, in addition to iodide (as observable by ESI-MS), and KBF$_4$ (as seen on $^{19}$F-NMR). For further reactions, the yield for the synthesis of 7 was assumed to be quantitative. $^1$H NMR (300 MHz, D$_2$O, rt): δ (ppm)=2.55 (m, 2H, N(CH$_3$)$_2$CH$_2$BF$_3$), 3.08 (s, 6H, N(CH$_3$)$_2$), 3.12 (t, 1H, J=2.46, CH$_2$CCH), 4.10 (d, 2H, J=2.41, HCCCH$_2$N(CH$_3$)$_2$); $^{19}$F NMR (282.4 MHz, CD$_3$OD, rt): δ (ppm)=−140 (q, 3F, BF$_3$), −154 (s, BF$_4$); ESI-LRMS: [M−F$^-$]$^+$146.1 (100%).

Fmoc-(L)-Lys-E-1,2,3-triazole-N,N-dimethyl-ammoniomethyl-trifluoroborate [Fmoc-Lys(AMBF$_3$)] (8)

A mixture of aqueous CuSO$_4$ (1M, 0.75 mL, 0.75 mmol) and sodium ascorbate (1M, 1.5 mL, 1.5 mmol) was added to 7 (250 mg, ~0.75 mmol, ~3 eq.) dissolved in acetonitrile/water 3:2 (2.5 mL). 5 (100 mg, 0.25 mmol, 1 eq.) was dissolved in a minimal amount of acetonitrile and added dropwise to the mixture and stirred overnight at 45° C. It was common to see some Cu or ascorbate salts precipitate out throughout the reaction. The reaction was monitored by silica TLC and the starting material disappeared between 20-24 hours of reaction time. Reproducibility was not always achieved upon scale-up, and often more catalyst, reducing agent, or alkyne had to be added to push the reaction to completion. The precipitate was filtered and the reaction mixture was evaporated under reduced pressure. The dark red residue was taken up in 1:1 MeOH/DCM, filtered, and evaporated again. This process was repeated one more time to remove all excess salts and insoluble impurities using 5:95 MeOH/DCM. The final crude oil was completely soluble in 5:95 MeOH/DCM and was subsequently charged onto a silica column and eluted via flash chromatography with a gradient system of MeOH/DCM (5%-10%). R$_f$=0.15 (1:9 MeOH/DCM). Yield: 91.5 mg, 65%. $^1$H NMR (300 MHz, CD$_3$OD, rt): δ (ppm)=1.37-1.93 (m, 6H, β, γ, δ CH$_2$), 3.06 (s, 6H, N(CH$_3$)$_2$), 4.11 (m, 1H, α CH), 4.23 (m, 2H, N(CH$_3$)$_2$CH$_2$BF$_3$), 4.40 (m, 2H, ε CH$_2$), 4.49 (m, 3H, Fmoc-CHCH$_2$OC(O)), 4.55 (s, 2H, CH=CCH$_2$N(CH$_3$)$_2$)), 5.52 (s, 1H, OC(O)NH), 7.34 (t, J=7.00 Hz, Fmoc aryl H), 7.42 (t, J=7.13 Hz, Fmoc aryl H), 7.70 (m, Fmoc aryl H), 7.83 (d, J=7.38 Hz, Fmoc aryl H), 8.27 (s, 1H, CH=CCH$_2$N(CH$_3$)$_2$)); $^{19}$F NMR (282.4 MHz, CD$_3$OD, rt): δ (ppm)=−140 (m, 3F, BF$_3$); ESI-LRMS: [M+Na+]$^+$582.3 (100%).

DOTA-((L)-Lys-E-1,2,3-triazole-N,N-dimethyl-ammoniomethyl-trifluoroborate)-4-amino-1-carboxymethyl-piperidine-Lys-Arg-Pro-Hyp-Gly-Cha-Ser-Pro-Leu-COOH (9)

This linear, modified peptide was prepared using standard Fmoc solid phase peptide synthesis chemistry on a Wang (hydroxymethylphenyl) resin. An unnatural version of bradykinin (Fmoc-Lys-Arg-Pro-Hyp-Gly-Cha-Ser-Pro-Leu-COOH) was pre-loaded onto the resin and used as the scaffold for attaching the cationic spacer, Lys(AMBF$_3$) residue, and DOTA chelator. The resin loading value was pre-calculated at 0.44 mmol/g. The dried resin (37.5 mg, 16.7 μmol) was added to a 3 mL spin column and swollen in DMF (2.5 mL) for 2 hours prior to the first coupling reaction. The DMF was filtered off and Fmoc was removed with 20% piperidine/DMF (3×2.5 mL for 5 minutes each). The resin was washed with DMF (3×2.5 mL), DCM (3×2.5 mL), and DMF (3×2.5 mL). Fmoc-4-amino-1-carboxymethyl-piperidine (25 mg, 65 μmol, 4 eq.), HBTU (25 mg, 65 μmol, 4 eq.), and DIPEA (11.4 μL, 65 μmol, 4 eq.) were dissolved in DMF (2.5 mL) and added to the capped spin column. The reaction was shaken at rt for 2 hours. The solution was filtered through the spin column and washed with DMF (3×2.5 mL), DCM (3×2.5 mL), and DMF (3×2.5 mL) before the next coupling reaction. 8 (14 mg, 25 μmol, 1.5 eq), HBTU (10 mg, 25 μmol, 1.5 eq.), and DIPEA (5.6 μL, 32.5 μmol, 2 eq.) were dissolved in DMF (2.5 mL) and added to the capped spin column. This reaction was shaken at rt overnight. Again the solution was filtered through the spin column and washed with DMF (3×2.5 mL), DCM (3×2.5 mL), and DMF (3×2.5 mL) before the next coupling reaction. DOTA-tri-t-butyl-ester (24 mg, 41.6 μmol, 2.5 eq.), NHS (4.6 mg, 41.6 μmol, 2.5 eq.), and DCC (8.5 mg, 41.6 μmol, 2.5 eq.) were dissolved in DCM (2.5 mL) and added to the capped spin column. This reaction was shaken at rt for 48 hours. As this final appendage had no protecting Fmoc group, the peptide was then cleaved from the resin using a cocktail (2.5 mL) made from a stock solution TFA (9.5 mL), H$_2$O (0.25 mL), TIPS (0.25 mL), and 30 mM KHF$_2$ (10 μL of 3M KHF$_2$). The mixture was shaken at rt for 2 hours, filtered, and evaporated under reduced pressure. The residue was triturated with 1:11 MeOH/Et$_2$O (24 mL) at 0° C. to give a white solid. The mixture was equally separated into 24 1.5 mL Eppendorf tubes and centrifuged to remove the diethyl ether supernatant. Diethyl ether (1 mL) was again added to each tube, centrifuged, and the supernatant was removed. The residual solids were collected with 1:1 H$_2$O/acetonitrile (2 mL total) and purified by HPLC (conditions shown above). Yield: 1.7 mg, 5%. MALDI-TOF LRMS: [M+H]$^+$ 1867.0.

REFERENCES FOR EXAMPLES 3 AND 4

1. Herschman, H. R., Science 2003, 302, 605-608.
2. Willmann, J. K.; Bruggen, N. v.; Dinkelborg, L. M.; Gambhir, S. S., Nat. Rev. Drug Discovery 2008, 7, 591-607.
3. Paans, A. M.; Waarde, A. v.; Elsinga, P. H.; Willemsen, A. T.; Vaalburg, W., Methods 2002, 27, 195-207.
4. Bars, D. L., J. Fluorine Chem. 2006, 127, 1488-1493.
5. Olberg, D.; Hjelstuen, O., Curr. Top. Med. Chem. 2010, 10, 1669-1679.
6. Vallabhajosula, S., Semin. Nuc. Med. 2007, 37, 400-419.
7. Snell, A., Phys. Rev. 1937, 51, 142-150.
8. Ruth, T.; Wolf, A., Radiochimica Acta 1979, 26, 21-24.
9. Cai, L.; Lu, S.; Pike, V. W., Eur. J. Org. Chem. 2008, 2853-2873.
10. Ehrenkaufer, R. E.; Potocki, J. F.; Jewett, D. M., J. Nucl. Med. 1984, 25 (3), 333-337.
11. Hamacher, K.; Coenen, H.; Stöcklin, G., J. Nucl. Med. 1986, 27 (2), 235-338.
12. Ametamey, S. M.; Honer, M.; Schubiger, P. A., Chem. Rev. 2008, 108, 1501-1516.
13. Hummer, G.; Pratt, L. R.; Garcia, A. E., J. Phys. Chem. 1996, 100, 1206-1215.
14. Emsley, J., Chem. Soc. Rev. 1980, 9, 91-124.
15. Ting, R.; Adam, M. J.; Ruth, T. J.; Perrin, D. M., J. Am. Chem. Soc. 2005, 127, 13094-13095.
16. Ting, R.; Harwig, C. W.; Lo, J.; Li, Y.; Adam, M. J.; Ruth, T. J.; Perrin, D. M., J. Org. Chem 2008, 73, 4662-4670.
17. Zhan, C.-G.; Dixon, D. A., J. Phys. Chem. 2004, 108 (11), 2020-2029.
18. Liu, Z.; Li, Y.; Lozada, J.; Wong, M. Q.; Greene, J.; Lin, K.-S.; Yapp, D.; Perrin, D. M., Nuc. Med. Biol 2013, 40, 841-849.
19. Liu, Z.; Perrin, D., University of British Columbia: Vancouver, 2013.
20. Mansi, R.; Wang, X.; Forrer, F.; Waser, B.; Cescato, R.; Graham, K.; Borkowski, S.; Reubi, J. C.; Maecke, H. R., Eur. J. Nucl. Med. Mol. Imaging 2011, 38, 97-107.

21. Li, Y.; Liu, Z.; Harwig, C. W.; Pourghiasian, M.; Lau, J.; Lin, K.-S.; Schaffer, P.; Bernard, F.; Perrin, D. M., Am. J. Nucl. Med. Mol. Imaging. 2013, 3 (1), 57-70.
22. Lin, K.-S.; Luu, A.; Baidoo, K. E.; Hashemzadeh-Gargari, H.; Chen, M.-K.; Pili, R.; Pomper, M.; Carducci, M.; Henry N. Wanger, J., Bioconjugate Chem. 2004, 15, 1416-1423.
23. Lin, K.-S.; Luu, A.; Baidoo, K. E.; Hashemzadeh-Gargari, H.; Chen, M.-K.; Brenneman, K.; Pili, R.; Pomper, M.; Carducci, M. A.; Henry N. Wagner, J., Bioconjugate Chem. 2005, 16, 43-50.
24. Li, Y. Applying Aryltrifluoroborates as PET Imaging Agents. Ph. D. Thesis, University of British Columbia, Vancouver, B C, 2006.
25. Achilefu, S.; Wilhelm, R. R.; Jimenez, H. N.; Schmidt, M. A.; Srinivasan, A., J. Org. Chem. 2000, 65, 1562-1565.
26. Laurent, S.; Elst, L. V.; Botteman, F.; Muller, R. N., Eur. J. Inorg. Chem. 2008, 28, 4369-4379.
27. Anelli, P. L.; Fedeli, F.; Gazzotti, O.; Luttuada, L.; Lux, G.; Rebasti, F., Bioconjugate Chem. 1999, 10, 137-140.
28. Pulido, D.; Albericio, F.; Royo, M., Org. Lett. 2014, 5 (1318-1321).
29. Oliveira, R. A.; Silva, R. O.; Molander, G. A.; Menezes, P. H., Magn. Reson. Chem. 2009, 47, 873-878.
30. Fieldhouse, S. A.; Peat, I. R., J. Phys. Chem. 1969, 73, 275.
31. Metz, K. R.; Lam, M. M.; Webb, A. G., Concepts Mag. Res. 2000, 12, 21.
32. Liu, Z.; Li, Y.; Lozada, J.; Pan, J.; Lin, K.-S.; Schaffer, P.; Perrin, D. M., J. Label. Compd. Radiopharm. 2012, 55 (491-496).
33. Liu, Z.; Hundal-Jabal, N.; Wong, M.; Yapp, D.; Lin, K.-S.; Benard, F.; Perrin, D. M., Med. Chem. Commun. 2014, 5, 171-179.
34. Li, Y.; Liu, Z.; Lozada, J.; Wong, M. Q.; Lin, K.-S.; Yapp, D.; Perrin, D. M., Nuc. Med. Biol. 2013, 40, 959-966.
35. Li, Y.; Guo, J.; Tang, S.; Lang, L.; Chen, X.; Perrin, D. M., Am. J. Nucl. Med. Mol. Imaging 2013, 3 (1), 44-56.
36. Kolb, H. C.; Finn, M. G.; Sharpless, K. B., Angew. Chem. Int. Ed. 2001, 40 (2004-2021).
37. Huisgen, R., Proc. Chem. Soc. 1961, 357-396.
38. Markwalder, R.; Reubi, J., Cancer Res. 1999, 59 (1152-1159).
39. Sun, B.; Halmos, G.; Schally, A.; Wang, X.; Martinez, M., Prostate 2000, 42, 295-303.
40. Gugger, M.; Reubi, J., Am. J. Pathol. 1999, 155, 2067-2076.
41. Halmos, G.; Wittliff, J.; Schally, A., Cancer Res. 1995, 55, 280-287.
42. Reubi, J.; Korner, M.; Waser, B.; Mazzucchelli, L.; Guillou, L., Eur. J. Nucl. Med. Mol. Imaging 2004, 31 (803-810).
43. Bock, M.; Longmore, J., Curr. Opin. Chem. Biol. 2000, 4 (4), 401-406.
44. Stewart, J.; Gera, L.; York, E.; Chan, D.; Bunn, P., Immunopharmacology 1999, 43, 155-161.
45. Stewart, J., Peptides 2004, 25, 527-532.
46. Heppeler, A.; Froidevaux, S.; Macke, H.; Jermann, E.; Behe, M.; Powell, P.; Hennig, M., Chem. Eur. J. 1999, 5 (7), 1974-1981.
47. Funkhouser, J., Curr. Drug Discovery February 2002.
48. Kelkar, S. S.; Reneke, T., Bioconjugate Chem. 2011, 22 (10), 1879-1903.
49. Pan, J.; Mesak, F.; Pourghiasian, M.; Hundal, N.; Lau, J.; Benard, F.; Lin, K.-S., Successful imaging of human bradykinin B1 receptor expression in tumor xenographts in mice with positron emission tomography. J. Nucl. Med. Meeting Abstracts 2013, 54, 61.
50. Kaiser, E.; Colescott, R. L.; Bossinger, C. D.; Cook, P. I., Anal. Biochem. 1970, 34 (2), 595-598.
51. Leon-Rodriguez, L. D.; Kovacs, Z.; Dieckmann, G. R.; Sherry, A., Chem. Eur. J. 2004, 10, 1149-1155.
52. Dehaen, G.; Eliseeva, S. V.; Kimpe, K.; Laurent, S.; Elst, L. V.; Muller, R. N.; Dehaen, W.; Binnemans, K.; Parac-Vogt, T. N., Chem. Eur. J. 2012, 18, 293-302.
53. Matteson, D. S.; Majumdar, D., J. Organomet. Chem. 1979, 170, 259-264.

Example 5: DOTA-Lys(AMBF3)-TATE and DOTA-Bn-NH-Lys-(AMBF3)-NHFmoc

OctreoTATE

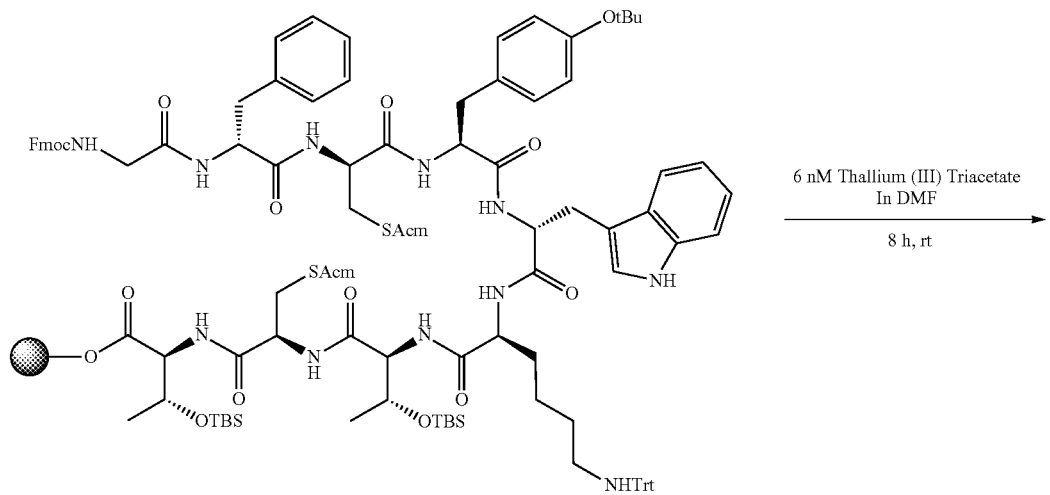

-continued

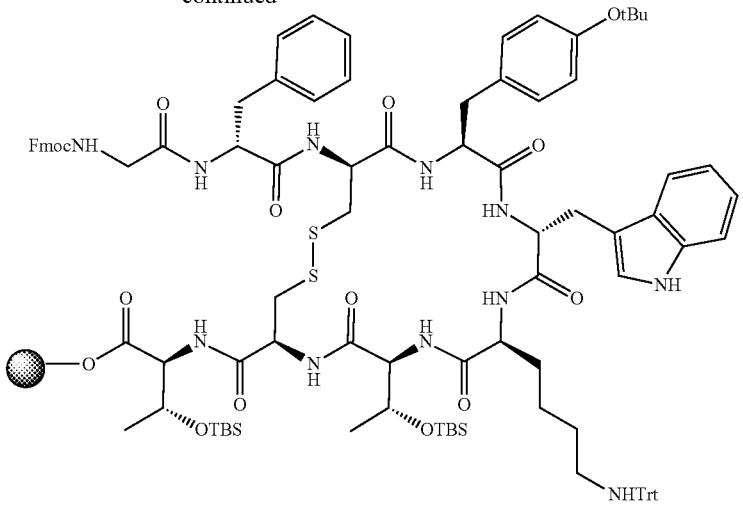

19.9 mg of resin with TATE (4.6 umol, 1 eq.) was swelled with DMF for 30 minutes. The DMF was removed by centrifuging and removing the supernatant. 6 mM of thallium(III) trifluoroacetate (713 μL, 4.28 umol, 0.93 eq.) in DMF was added and the reaction was stirred for 8 hours at room temperature. The resin was centrifuged and supernatant was removed. DMF (200 μL) was used to wash three times. (500 μL) of DCM was then added and centrifuged. The supernatant was removed and the sample was dried down by speed vac. Small sample of the resin was scooped on a micropipette tip and placed on a separate Eppendorf tube where (3:7) HFIP:DCM (100 μL) was used to cleave the product for 10 minutes at room temperature. Mixture was filtered using a filter pipette tip and the filtrate was collected in a separate Eppendorf tube. The mixture was dried down by blowing gentle air and diethyl ether was added to crash out the product. The mixture was centrifuged and the supernatant was removed. MeOH (200 μL) was added to dissolve the product for MS. ESI-MS(+): calculated for $C_{101}H_{127}N_{11}O_{15}S_2Si_2$=1855.5 m/z; found, [M−Trt+2H]$^+$=1615.8 m/z; [M−TBS−tBu]$^+$=1684.9 m/z.

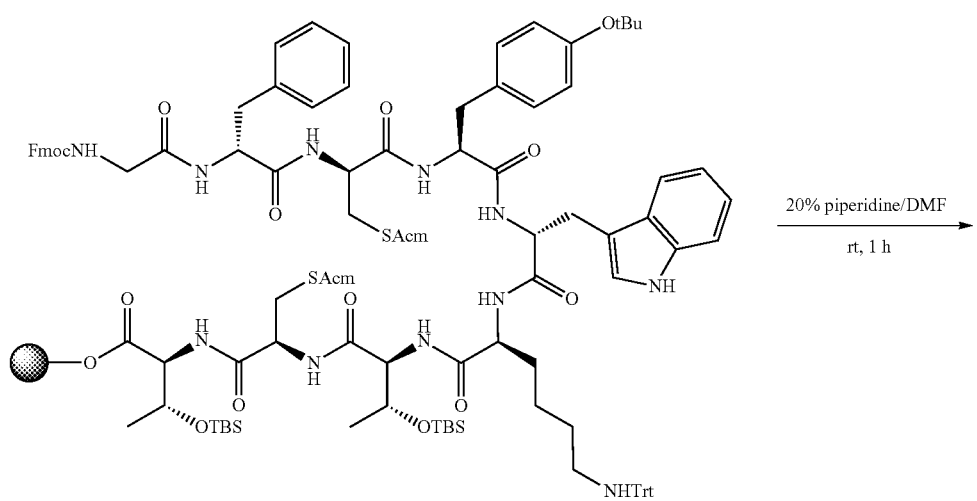

-continued

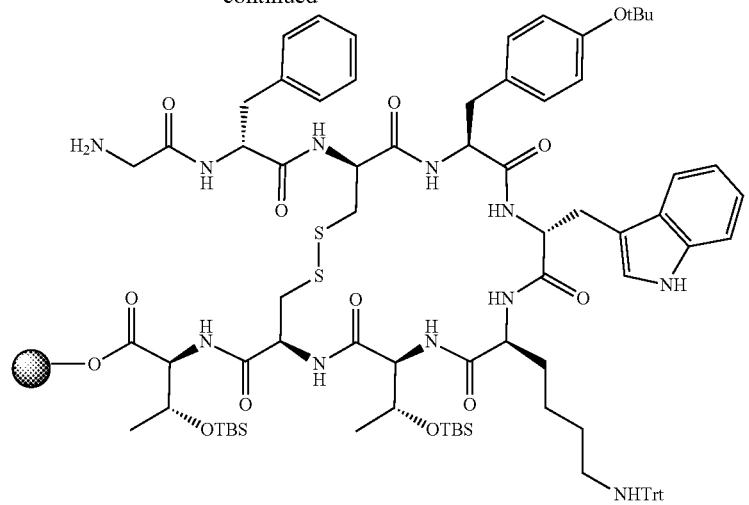

(1:4) Piperidine:DMF (200 μL) was added to resin and the mixture was stirred at rt for 1 hour. The mixture was centrifuged down and supernatant was removed. DMF (3×200 μL) was added to wash the resin. The mixture was vortexed and centrifuged down. The supernatant was removed and the mixture was dried down by speed vac. Small sample of the resin was scooped on a micropipette tip and placed on a separate Eppendorf tube where (3:7) HFIP:DCM (100 μL) was used to cleave the product for 10 minutes at room temperature. Mixture was filtered using a filter pipette tip and the filtrate was collected in a separate Eppendorf tube. The mixture was dried down by blowing gentle air and diethyl ether was added to crash out the product. The mixture was centrifuged and the supernatant was removed. MeOH (200 μL) was added to dissolve the product for MS. ESI-MS(+): calculated for $C_{86}H_{117}N_{11}O_{13}S_2Si_2$, 1633.2 m/z; found, $[M]^+=1663.0$; $[M+2CH_3CN+2H]^+=1390.7$ m/z.

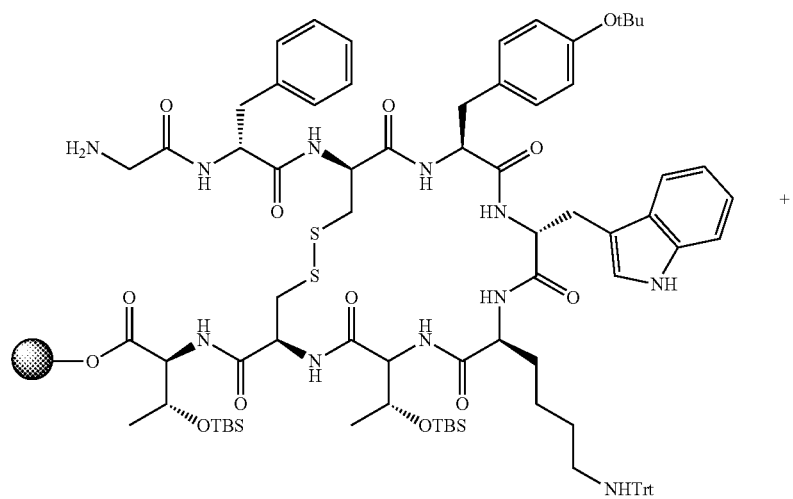

-continued

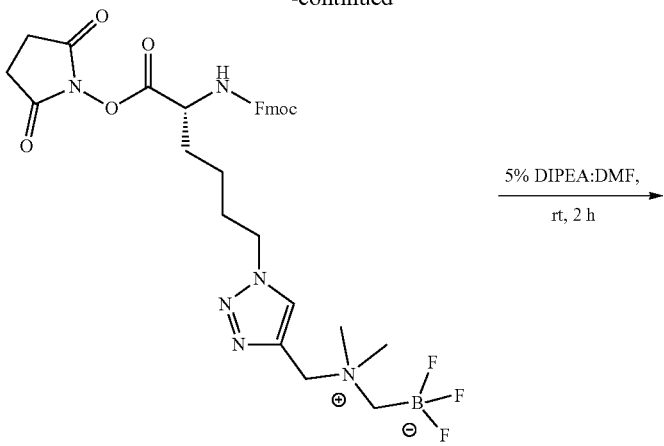

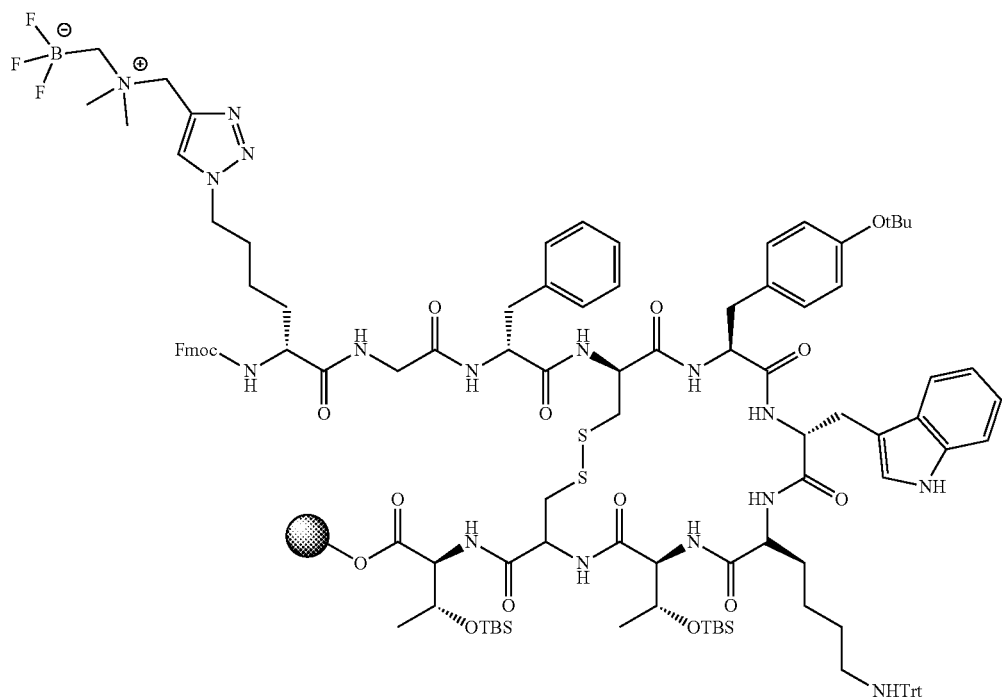

Fmoc-Lys(AMBF3)-NHS (15.1 mg, 23.0 umol, 5 eq.) was weighed out and dissolved in 200 μl of (1:19) DIPEA:DMF. The solution was then added to resin and mixed was stirred for 2 hours at room temperature. The mixture was centrifuged down and supernatant was removed. DMF (3×200 μL) was added to wash the resin. The mixture was vortexed and centrifuged down. The supernatant was removed and the mixture was dried down by speed vac. Small sample of the resin was scooped on a micropipette tip and placed on a separate Eppendorf tube where (3:7) HFIP:DCM (100 μL) was used to cleave the product for 10 minutes at room temperature. Mixture was filtered using a filter pipette tip and the filtrate was collected in a separate Eppendorf tube. The mixture was dried down by blowing gentle air and diethyl ether was added to crash out the product. The mixture was centrifuged and the supernatant was removed. MeOH (200 μL) was added to dissolve the product for MS. ESI-MS(+): calculated for $C_{113}H_{148}BF_3N_{16}O_{16}S_2Si_2$, 2173.03 m/z; found, $[M+CH_3CN+Na]^+$=2236.5 m/z.

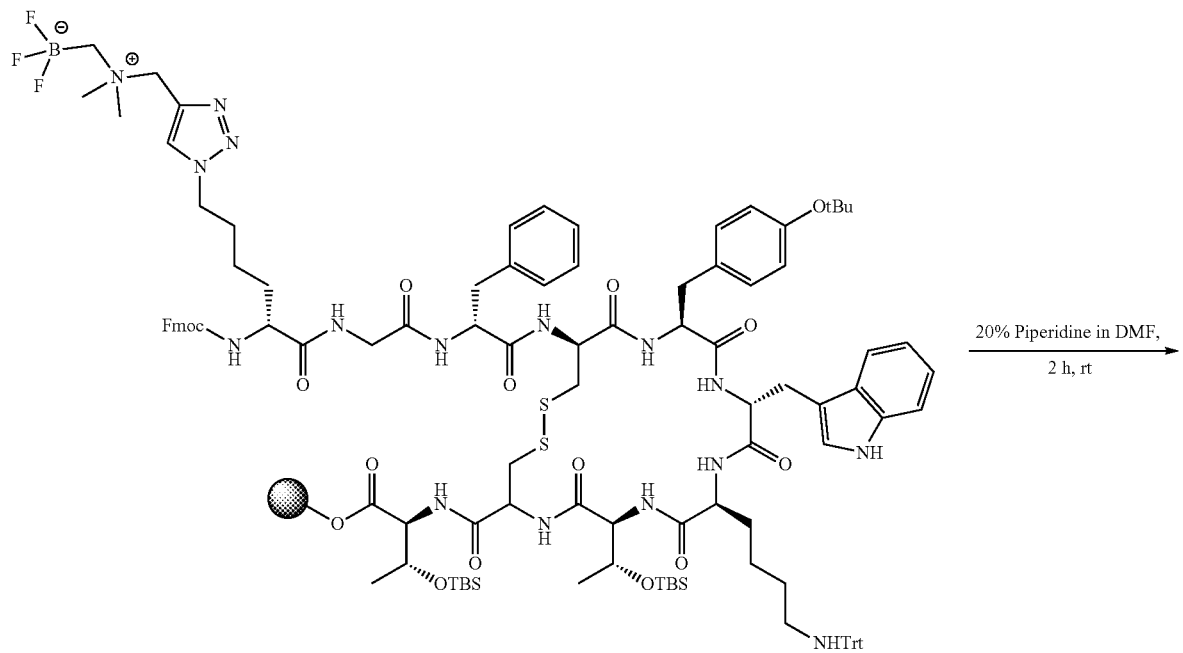

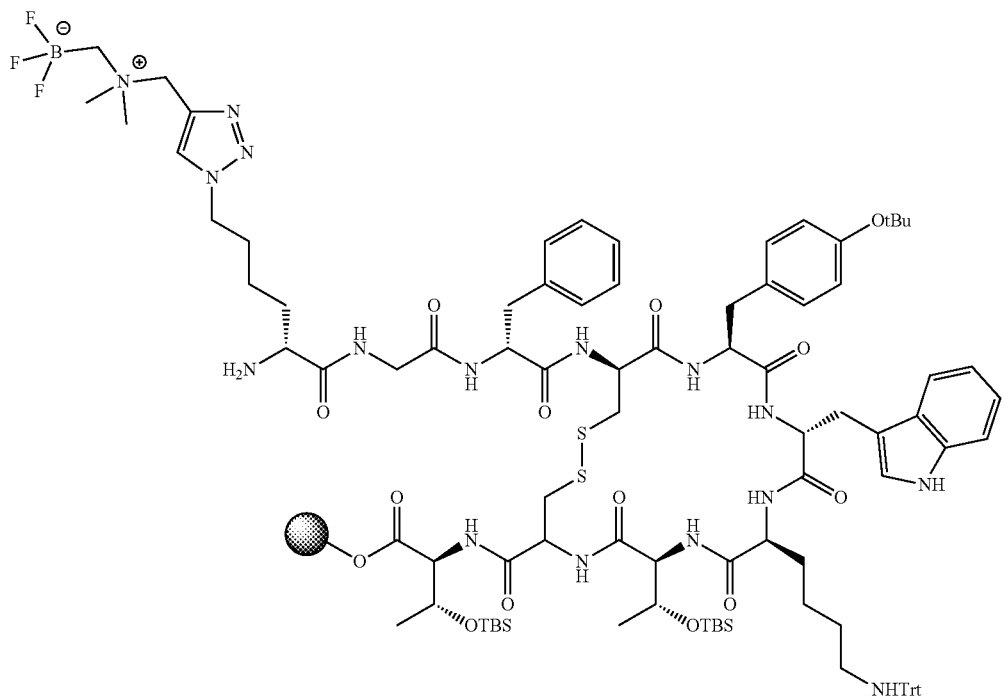

(1:4) piperidine:DMF (200 µL) was added to resin and the mixture was stirred at rt for 1 hour. The mixture was centrifuged down and supernatant was removed. (3×200 µL) DMF was added to wash the resin. (200 µL) of DCM was added and centrifuged. DCM was removed and resin was dried by speed vac. Small sample of the resin was scooped on a micropipette tip and placed on a separate Eppendorf tube where (3:7) HFIP:DCM (100 µL) was used to cleave the product for 10 minutes at room temperature. Mixture was filtered using a filter pipette tip and the filtrate was collected in a separate Eppendorf tube. The mixture was dried down by blowing gentle air and diethyl ether was added to crash out the product. The mixture was centrifuged and the supernatant was removed. MeOH (200 µL) was added to dissolve the product for MS. ESI-MS(+): calculated for $C_{98}H_{138}BF_3N_{16}O_{14}S_2Si_2$, 1952.3 m/z; found, [M+Na]$^+$=1975.4 m/z.

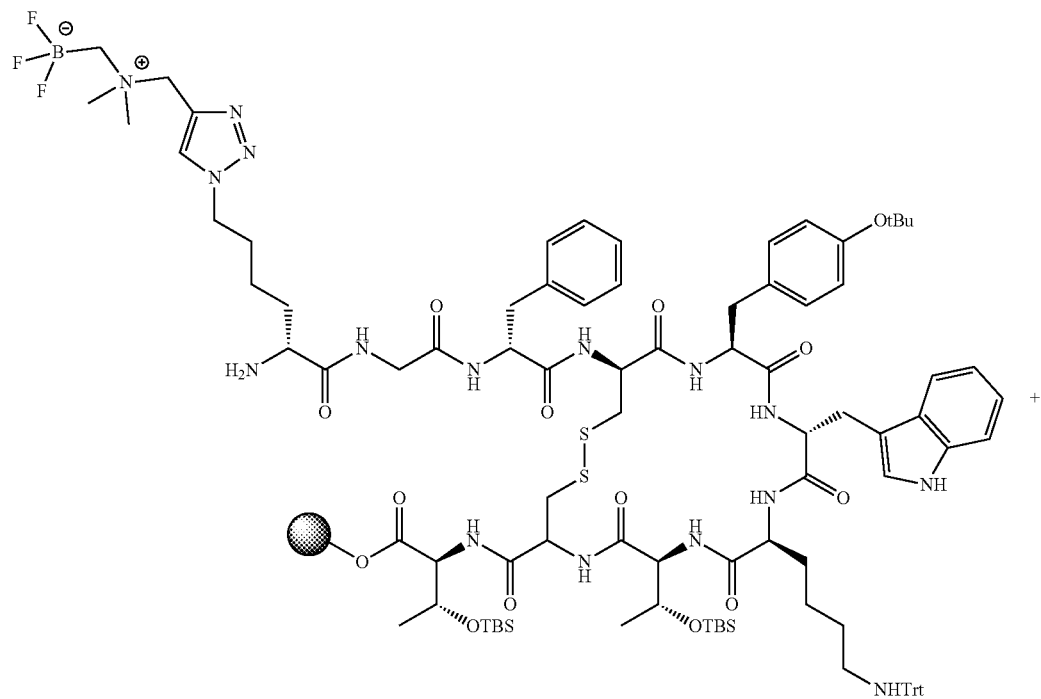
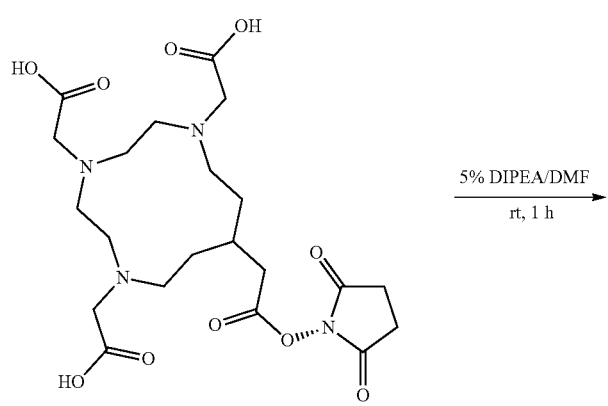
5% DIPEA/DMF
rt, 1 h

-continued

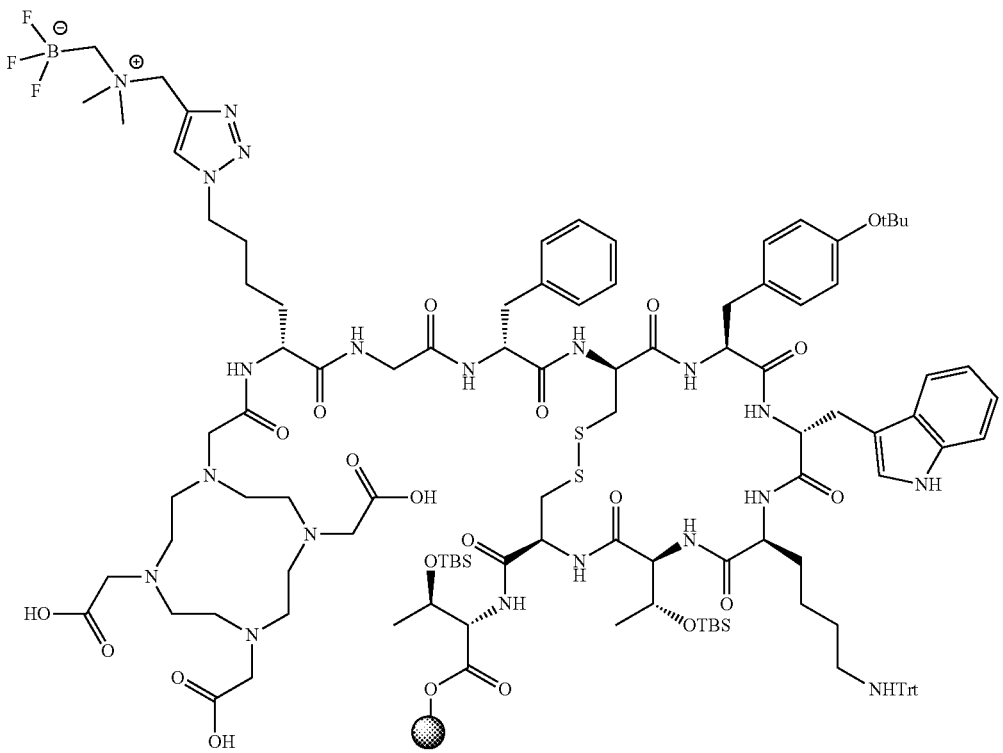

DOTA-NHS·HPF$_6$·TFA (8.75 mg, 11.5 umol, 2.5 eq.) was dissolved in (1:19) DIPEA:DMF (200 μL) and the mixture was added to the resin with H2N-Lys(AMBF3)-TATE and was stirred for 2 hours at room temperature. The resin was washed with DMF (3×200 μL). The mixture was vortexed and centrifuged. The supernatant was removed. The resin was dried down by speed vac. Small sample of the resin was scooped on a micropipette tip and placed on a separate Eppendorf tube where (3:7) HFIP:DCM (100 μL) was used to cleave the product for 10 minutes at room temperature. Mixture was filtered using a filter pipette tip and the filtrate was collected in a separate Eppendorf tube. The mixture was dried down by blowing gentle air and diethyl ether was added to crash out the product. The mixture was centrifuged and the supernatant was removed. MeOH (200 μL) was added to dissolve the product for MS. ESI-MS(+): calculated for $C_{114}H_{164}BF_3N_{20}O_{21}S_2Si_2$, 2337.1 m/z; found, $[M+K]^+=2375.4$ m/z.

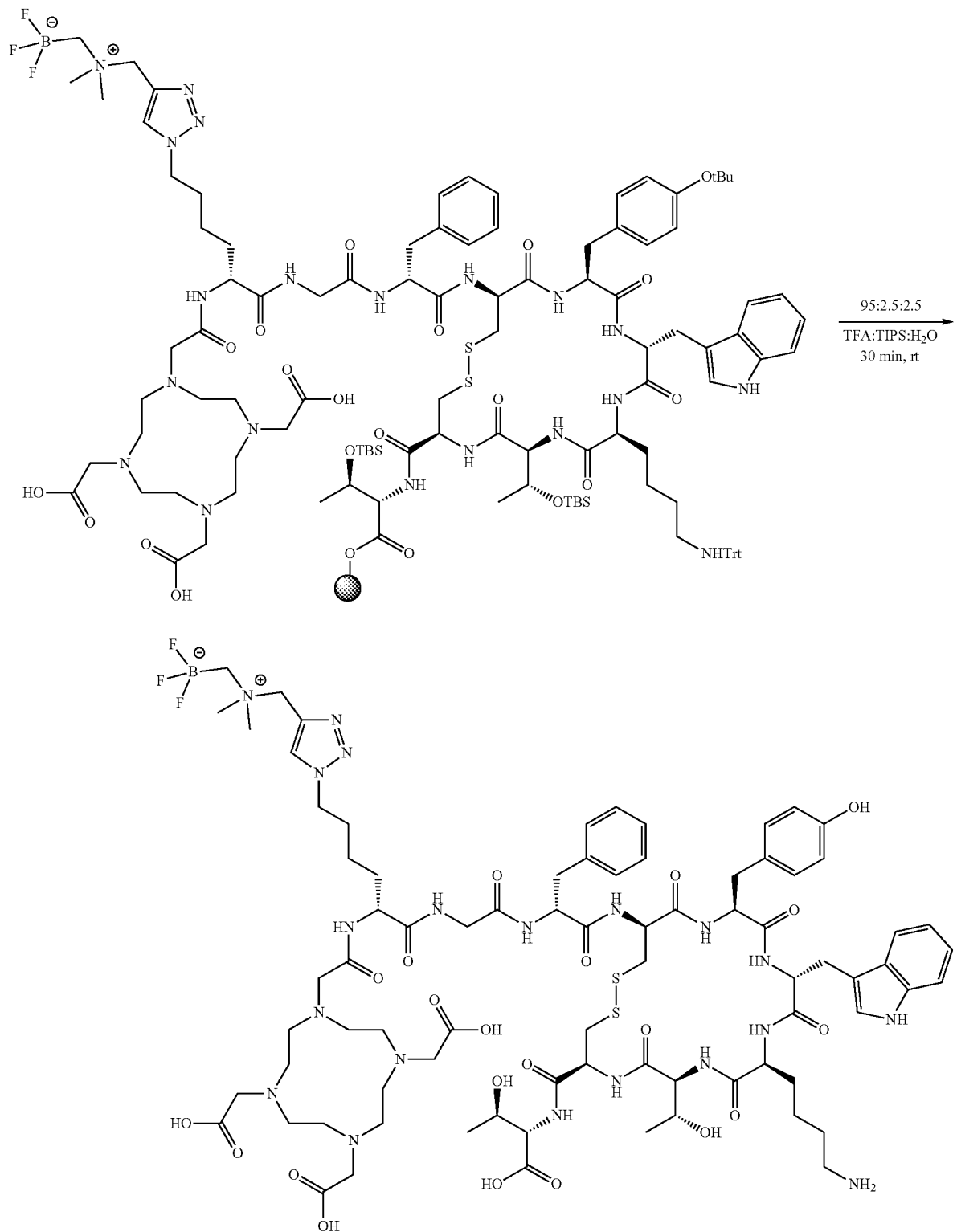

(95:2.5:2.5) TFA:TIPS:H$_2$O (200 μL) was added to the resin to undergo universal deprotection as well as cleaving the DOTA-Lys(AMBF$_3$)-TATE off the resin. The resin was stirred at room temperature for 30 minutes. The filtrate was collected using a pipette tip filter to remove the resin. The filtrate was concentrated down by gently blowing air until volume was ~50 to 100 μL. Diethyl ether (1 mL) was added to crash out the product and the mixture was vortexed and centrifuged. The supernatant was removed and the mixture was dried down by speed vac. The yield was 3.2 mg. ESI-MS(+): calculated for C$_{79}$H$_{114}$BF$_3$N$_{20}$O$_{21}$S$_2$, 1811.8 m/z; found, [M+2Na]$^+$=1855.1 m/z.

Synthesis of DOTA-Bn-NH-Lys-(AMBF3)-NHFmoc:

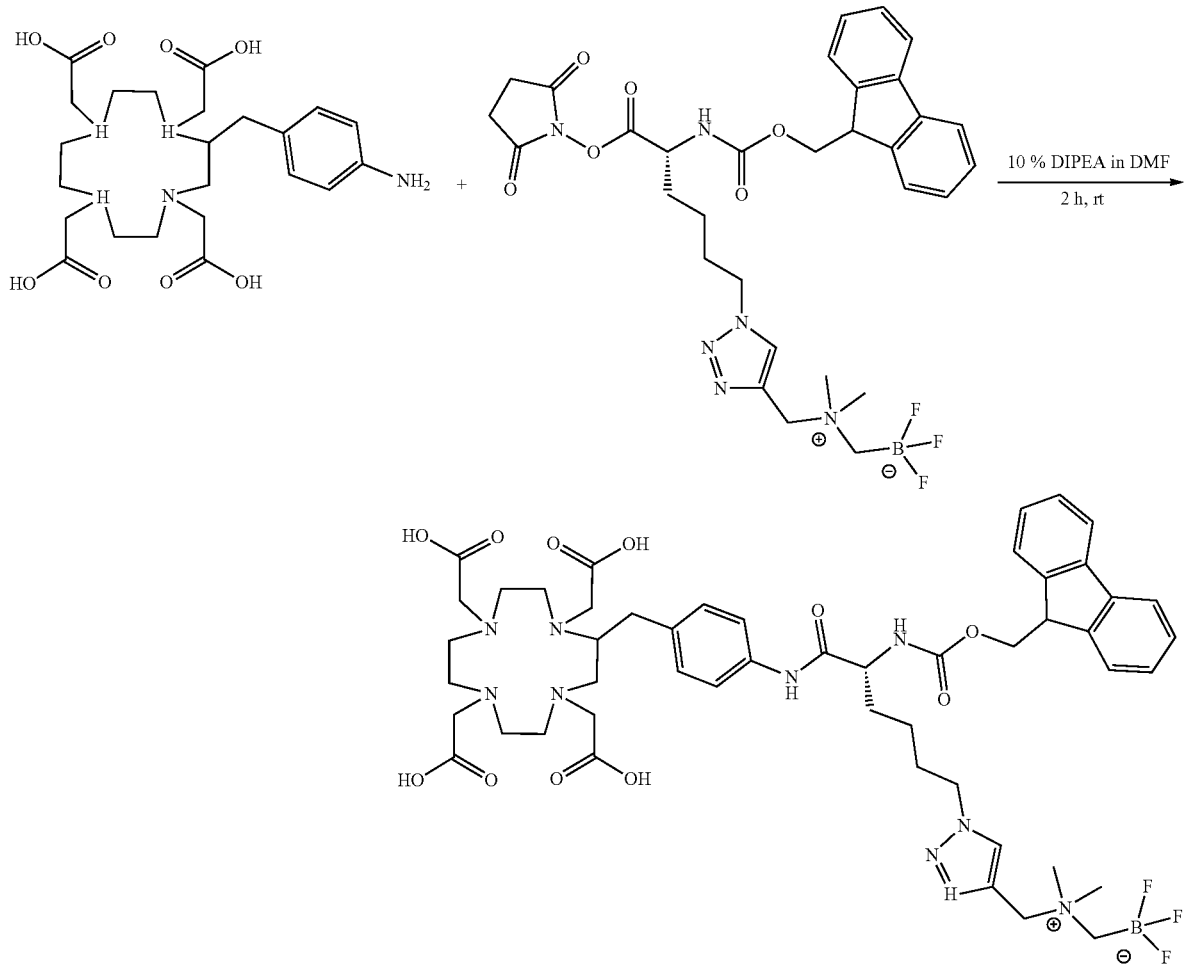

DOTA-Bn-NH$_2$ (10 mg, 0.015 mmol, 1 eq.) in an Eppendorf tube was dissolved in (2:18) DIPEA:DMF (200 μL) and was transferred to a separate Eppendorf tube of Fmoc-Lys (AMBF3)—NHS (14 mg, 0.025 mmol, 1.5 eq.). The mixture was stirred for 2 hours at room temperature using a rotisserie stirrer. Then, 1 mL of cold diethyl ether was added to precipitate the product. This was then vortexed and centrifuged to remove the supernatant. Minimal DMF (~50 μL) was added to the product to redissolve the product and diethyl ether (1 mL) was added to rewash crude. The mixture was vortexed and centrifuged to remove supernatant. The product was then dried and MeCN (~500 μL) was then added to redissolve and remove excess Fmoc-Lys(AMBF3)-NHS. The mixture was centrifuge down and supernatant containing excess reagent was removed. The product was dried once more in speed vac. Small sample of the product was dissolved in MeOH for MS. ESI-MS(+): calculated for $C_{50}H_{66}BF_3N_{00}O_{11}$, 1050.94 m/z; found, $[M+H]^+$=1051.7 m/z, [TLC (1:19 NH$_4$OH:EtOH, R$_f$ of Product=0.2, visible with 254 nm).

It is further appreciated to those trained in the art, that the above DOTA-Lys(AMBF$_3$) could be further conjugated to a fluorescent molecule. An example of such is provided below as one of many that could be considered by those trained in the art of multimodal imaging applications. Such an example would not be limited to DOTA, Cy7 or LysAMBF$_3$ to be found to be practicable.

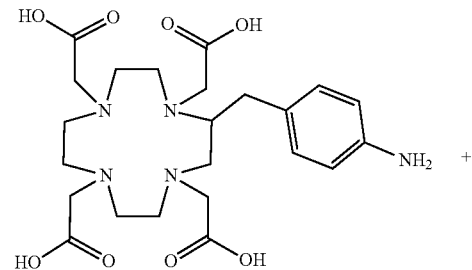

125 126
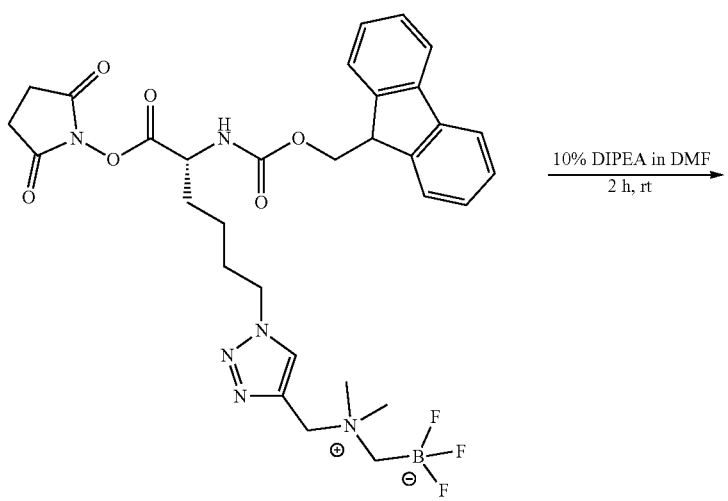
10% DIPEA in DMF
2 h, rt
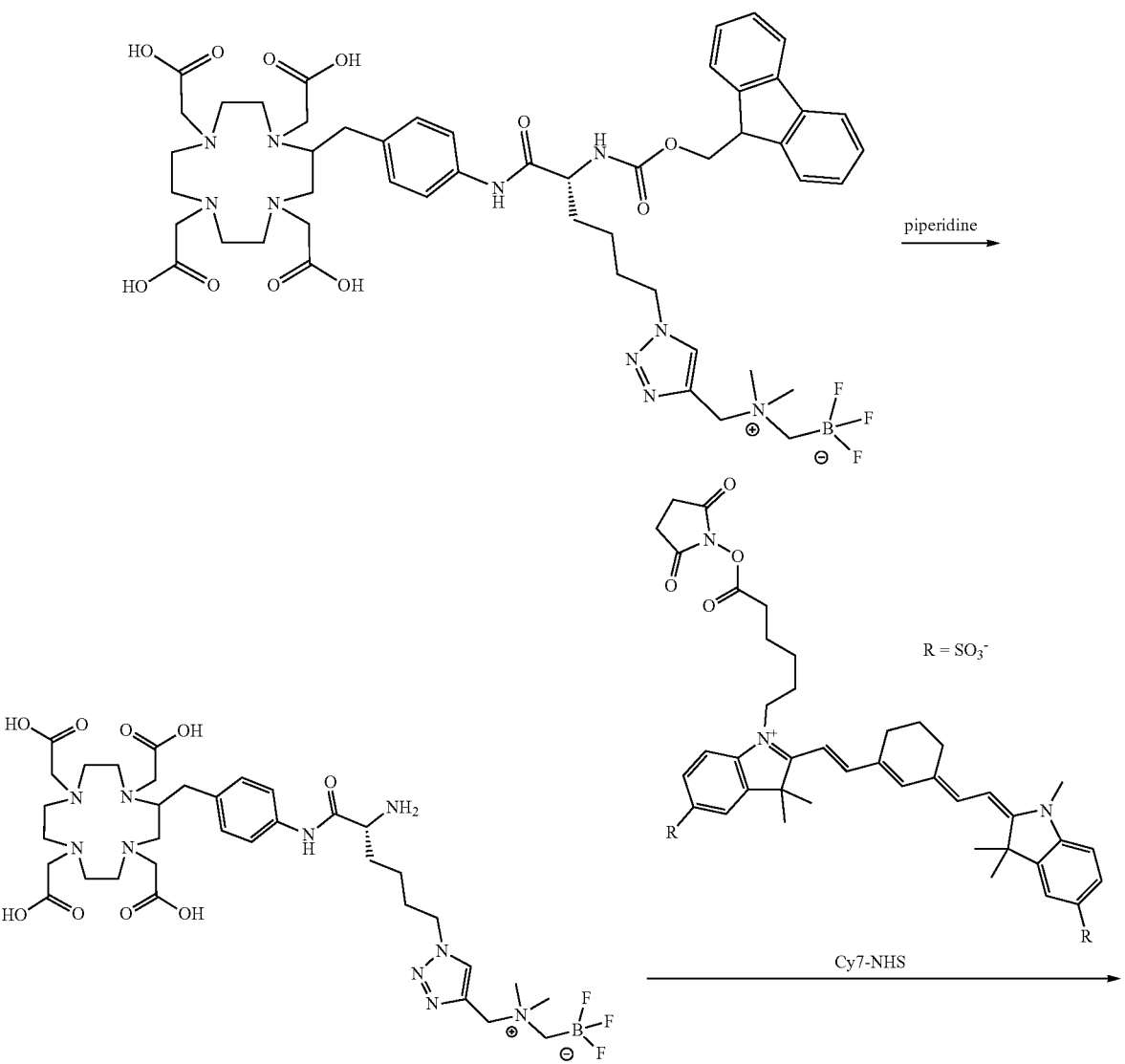
piperidine
R = SO$_3^-$
Cy7-NHS -continued

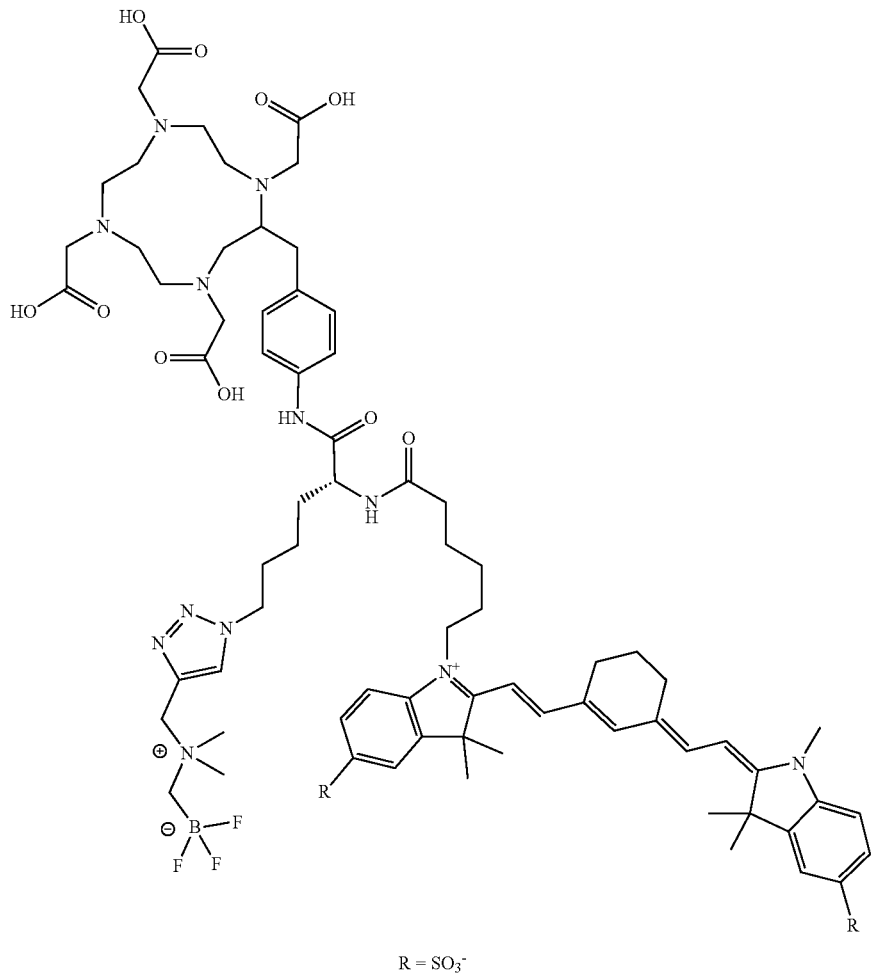

R = SO$_3^-$

The present invention has been described with regard to one or more embodiments. However, it will be apparent to persons skilled in the art that a number of variations and modifications can be made without departing from the scope of the invention. The scope of the invention should not be limited by the preferred embodiments set forth in the examples, but should be given the broadest interpretation consistent with the description as a whole PRIORITY APPLICATION This application claims priority to U.S. 62/781,584, filed on Dec. 18, 2018, which is incorporated by reference in its entirety.

The invention claimed is:
1. A compound or molecular complex comprising:
 a metal chelator configured for chelation with a radioactive metal isotope or a non-radioactive metal isotope;
 a cell-targeting domain; and
 a trifluoroborate ($BF_3$)-containing moiety configured for $^{19}F/^{18}F$ exchange or a boronate precursor that is capable of conversion to an $^{18}F$-labeled trifluoroborate;
 wherein the compound or molecular complex is selected from the group consisting of:

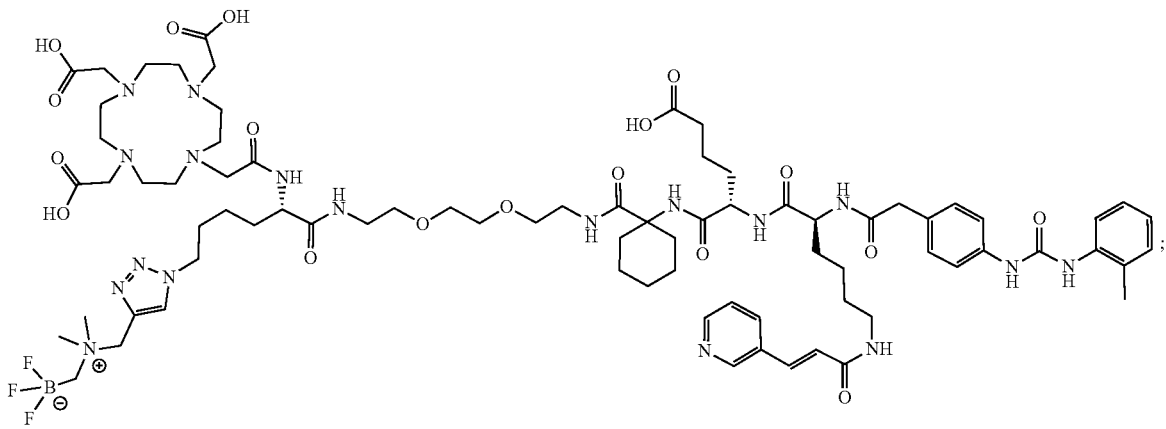

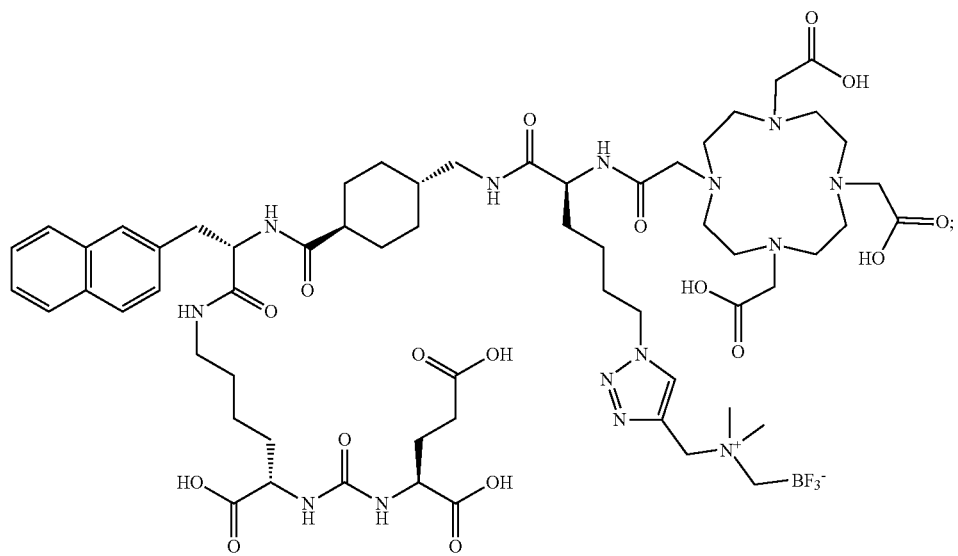

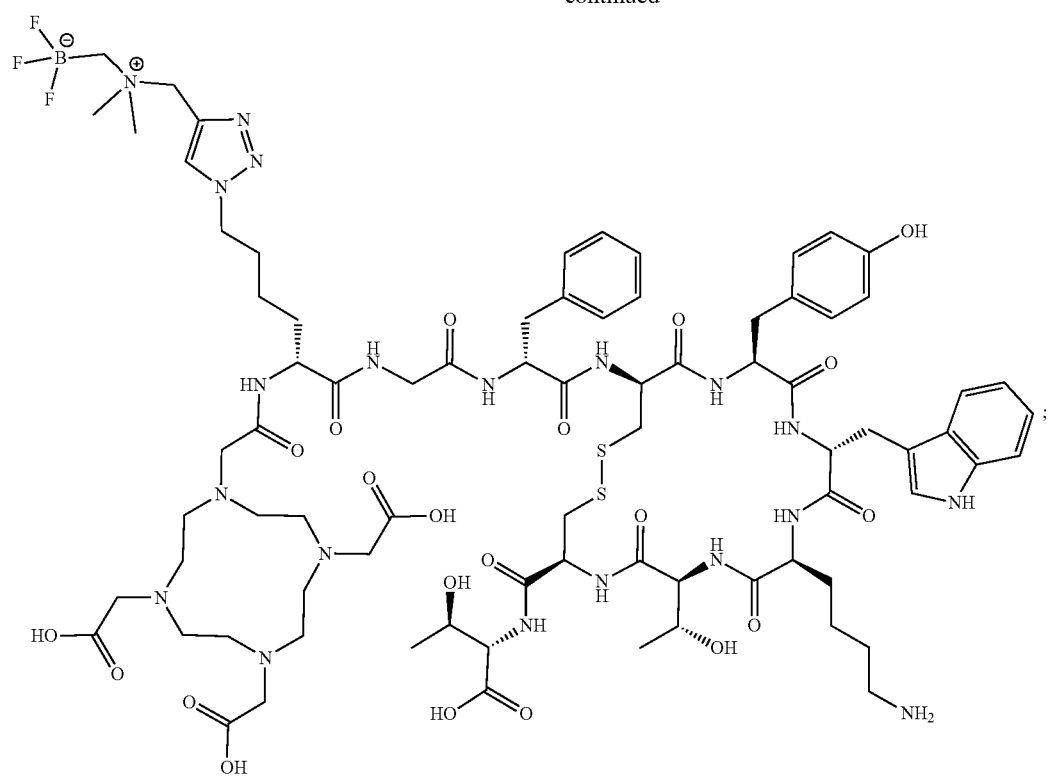
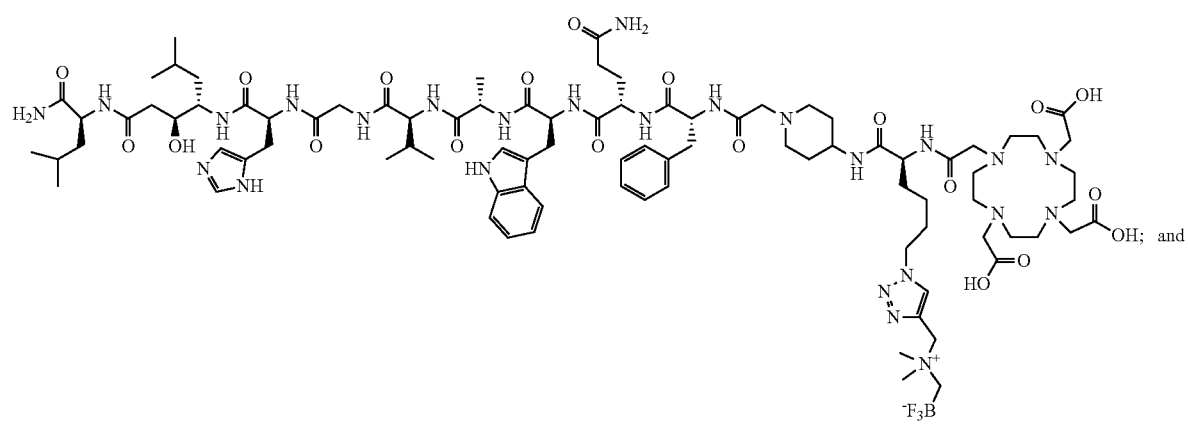

-continued

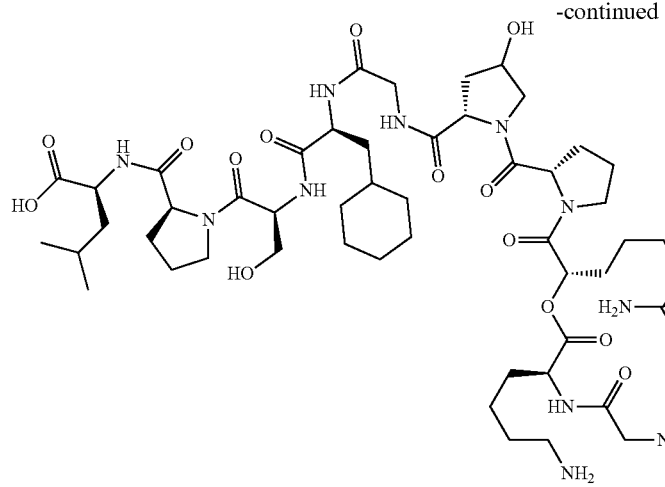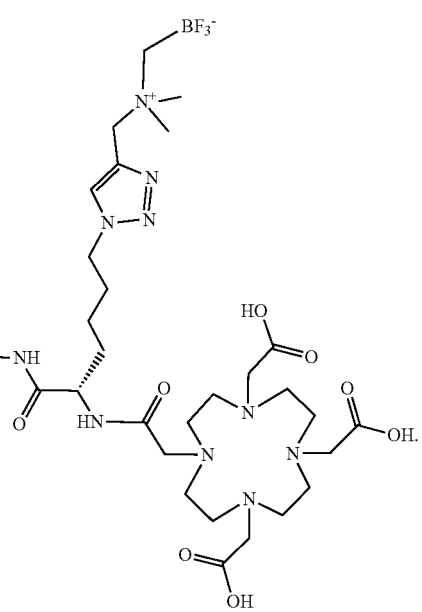

2. A method of imaging and treating a disease or condition in a subject, the method comprising:
   (i) administering a compound or molecular complex according to claim 1 to the subject, wherein the $BF_3$-containing moiety of the compound or molecular complex is labelled with $^{18}F$, the metal chelator of the compound or molecular complex is chelated with a radioactive metal isotope or a non-radioactive metal isotope, and the cell targeting domain targets a cellular marker of the disease or condition, and imaging the subject to confirm the presence of the cellular marker; and
   (ii) administering the compound or molecular complex to the subject, wherein the $BF_3$-containing moiety is labeled with $^{19}F$ and/or $^{18}F$, and the metal chelator is chelated with a therapeutic radioactive isotope.

3. A method of imaging and/or treating a disease or condition in a subject using a compound or molecular complex according to claim 1 in combination with a bispecific antibody, wherein the bispecific antibody is specific for both a cellular marker of the disease or condition and the metal chelator of the compound or molecular complex, the method comprising administering the bispecific antibody to the subject and one or both of the following steps:
   (i) administering the compound or molecular complex to the subject wherein the $BF_3$ containing moiety of the compound or molecular complex is labelled with $^{18}F$, wherein the metal chelator of the compound or molecular complex is chelated with a radioactive metal isotope or a non-radioactive metal isotope, and imaging the subject to confirm the presence of the cellular marker
   (ii) administering the compound or molecular complex to the subject, wherein the $BF_3$-containing moiety is labeled with $^{19}F$ and/or $^{18}F$, and the metal chelator is chelated with a therapeutic radioactive isotope.

4. The method of claim 3, wherein the compound or molecular complex is administered to the subject as a complex with the bispecific antibody.

5. The method of claim 3, wherein the bispecific antibody is administered to the subject prior to administering the compound or molecular complex to the subject in a pretargeting step during which the bispecific antibody binds to the cellular marker.

\* \* \* \* \*